United States Patent
Caradonna et al.

(10) Patent No.: US 10,428,043 B2
(45) Date of Patent: Oct. 1, 2019

(54) GREEN OXIDATION CATALYTIC SYSTEM

(71) Applicant: TRUSTEES OF BOSTON UNIVERSITY, Boston, MA (US)

(72) Inventors: John Philip Caradonna, Boston, MA (US); Paul Christopher Tarves, Boston, MA (US); Joshua McNally, Boston, MA (US); Lauren Gregor Tighe, Boston, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 15/537,746

(22) PCT Filed: Dec. 18, 2015

(86) PCT No.: PCT/US2015/066736
§ 371 (c)(1),
(2) Date: Jun. 19, 2017

(87) PCT Pub. No.: WO2016/100850
PCT Pub. Date: Jun. 23, 2016

(65) Prior Publication Data
US 2018/0297976 A1    Oct. 18, 2018

Related U.S. Application Data

(60) Provisional application No. 62/094,711, filed on Dec. 19, 2014.

(51) Int. Cl.
| | | |
|---|---|---|
| *C07D 401/02* | (2006.01) |
| *B01J 31/18* | (2006.01) |
| *C07C 27/12* | (2006.01) |
| *C07C 29/50* | (2006.01) |
| *C07C 45/33* | (2006.01) |
| *C07C 45/34* | (2006.01) |
| *C07C 45/36* | (2006.01) |
| *C07C 45/38* | (2006.01) |
| *C07C 46/04* | (2006.01) |
| *C07B 41/00* | (2006.01) |
| *C07C 31/02* | (2006.01) |
| *C07C 37/58* | (2006.01) |
| *C07C 45/27* | (2006.01) |
| *C07C 47/02* | (2006.01) |
| *C07C 49/04* | (2006.01) |
| *C07C 51/235* | (2006.01) |
| *C07D 211/22* | (2006.01) |
| *C07D 301/06* | (2006.01) |
| *B01J 31/22* | (2006.01) |

(52) U.S. Cl.
CPC ............ *C07D 401/02* (2013.01); *B01J 31/18* (2013.01); *B01J 31/1815* (2013.01); *B01J 31/2226* (2013.01); *C07B 41/00* (2013.01); *C07C 27/12* (2013.01); *C07C 29/50* (2013.01); *C07C 31/02* (2013.01); *C07C 37/58* (2013.01); *C07C 45/27* (2013.01); *C07C 45/33* (2013.01); *C07C 45/34* (2013.01); *C07C 45/36* (2013.01); *C07C 45/38* (2013.01); *C07C 46/04* (2013.01); *C07C 47/02* (2013.01); *C07C 49/04* (2013.01); *C07C 51/235* (2013.01); *C07D 211/22* (2013.01); *C07D 301/06* (2013.01); *B01J 2231/70* (2013.01); *B01J 2531/0252* (2013.01); *B01J 2531/842* (2013.01); *C07C 2601/16* (2017.05); *C07C 2601/18* (2017.05); *C07C 2603/24* (2017.05)

(58) Field of Classification Search
None
See application file for complete search history.

(56) References Cited

U.S. PATENT DOCUMENTS

| 6,395,904 B1 | 5/2002 | Caradonna et al. |
| 2009/0234121 A1 | 9/2009 | Periana et al. |
| 2011/0015397 A1 | 1/2011 | White et al. |

OTHER PUBLICATIONS

Written Opinion of the International Searching Authority for PCT/US2015/066736 dated Dec. 7 (Year: 2016).*
Borges et al., "Synthesis, Characterization and Mössbauer Studies of Fe(II) and Fe(III) Complexes of 2-Acetylpyridine Thiosemicarbazone", Journal of the Brazilian Chemical Society 8(1):33-38 (1997).
Bruijnincx et al., "Iron(II) Complexes with Bio-Inspired N,N,O Ligands as Oxidation Catalysts: Olefin Epoxidation and cis-Dihydroxylation", Chemistry—A European Journal 14:1228-1237 (2008).
Cappillino et al., "Studies of iron(II) and iron(III) complexes with fac-N2O, cis- N2O2 and N2O3 donor ligands: models for the 2-His 1-carboxylate motif of non-heme iron monooxygenases", Dalton Transactions 41:5662-5677 (2012).

(Continued)

*Primary Examiner* — Zinna Northington Davis
(74) *Attorney, Agent, or Firm* — Nixon Peabody LLP; Ronald I. Eisenstein; Ravinderjit Braich

(57) ABSTRACT

Disclosed herein are reaction compositions comprising an oxidation catalyst, a solvent, and a substrate that is dissolved in the solvent. The oxidation catalyst comprises a metal ion complexed with an α-keto acid and a tridentate N,N,O-ligand. Also disclosed herein are methods for oxidizing a C—H bond of a molecule, the methods comprising contacting the molecule with a metal complex comprising a metal ion complexed with a tridentate N,N,O-ligand in the presence of an α-keto acid and a solvent. In some embodiments, the oxidation catalyst or metal complex is linked to a solid support.

16 Claims, 51 Drawing Sheets

(56) References Cited

OTHER PUBLICATIONS

Cappillino et al., "The effect of varying carboxylate ligation on the electronic environment of N2Ox (x=1-3) nonheme iron: A DFT analysis", Dalton Transactions 41:474-483 (2012).

Gregor L., "Mechanistic Studies of Functional Mononuclear and Binuclear Non-Heme Iron Enzyme Model Complexes Using Variable Temperature Stopped-Flow UV/VIS Spectroscopy: Chapter 4: Low-Temperature Stopped-Flow Kinetic Studies of [FeII(N2O1)Cl2]- with Alpha-Keto Acids and their Subsequent Reactivity with Dioxygen", Doctoral Dissertation, Boston University (2014). (112 pages).

Herrera et al., "Probing TauD Active Site Chemistry with Synthetic Analogues", Austin College Student Scholarship Conference Abstract 27 (2014). (2 pages).

Klopstra et al., "Non-heme iron catalysts for the benzylic oxidation: a parallel ligand screening approach", Tetrahedron Letters 44:4581-4584 (2003).

McNally J., "Synthetic and Density Functional Theory Studies of O2 Activating Non-Heme Iron Model Complexes: Chapter 2: Density Functional Theory (DFT) Study of the Structural Aspects of α-Ketoacid Binding to a Mononuclear Iron(II) Center", Doctoral Dissertation, Boston University (2014). (53 pages).

McNally J., "Synthetic and Density Functional Theory Studies of O2 Activating Non-Heme Iron Model Complexes: Chapter 3: Mechanistic Aspects of Dioxygen Activation by an α-Ketoglutarate Bound Iron(II) Complex: A DFT Analysis", Doctoral Dissertation, Boston University (2014). (97 pages).

McNally J., "Synthetic and Density Functional Theory Studies of O2 Activating Non-Heme Iron Model Complexes: Chapter 4: Synthesis and Characterization of Iron(II) and Iron(III) Compounds with a fac-N2O1-pyridiyl Ligand Motif", Doctoral Dissertation, Boston University (2014). (56 pages).

Paredes-García et al., "Electronic properties of mixed valence iron(II,III) dinuclear complexes with carboxylate bridges", Polyhedron 25 (2006). (7 pages).

Rocks S., "Modeling Ring Cleaving Dioxygenases: Complexes of Iron(II) with Tridentate Ligands and their Reactivity with Catecholates and Phenolates", Doctoral Dissertation, University of Rochester (2009). (248 pages).

Sheet et al., "Enhanced Reactivity of a Biomimetic Iron(II) α-Keto Acid Complex through Immobilization on Functionalized Gold Nanoparticles", Angewandte Chemie International Edition 52:13314-13318 (2013).

Svane et al., "Gas Phase Chemistry of [LFeO]+ complexes", Trends in Inorganic Chemistry (2014). (2 pages).

MOLBASE CAS No. 669083-52-7. http://www.molbase.com/en/cas-669083-52-7.html. From the internet on Aug. 8, 2014.

\* cited by examiner

NO-trans to oxygen    NO-trans to nitrogen

R = CH₃O, CH₃, H, Cl, NO₂

R = Cl, NO₂, OCH₃, CH₃

GREEN OXIDATION CATALYTIC SYSTEM

CROSS-REFERENCE TO RELATED APPLICATIONS

This application is a 371 National Phase Entry of International Patent Application No. PCT/US2015/066736 filed on Dec. 18, 2015 which claims benefit under 35 U.S.C. § 119(e) of the U.S. Provisional Application No. 62/094,711, filed Dec. 19, 2014, the contents of both of which are incorporated herein by reference in their entirety.

GOVERNMENT SUPPORT

This invention was made with government support under grant No. CHE-1300122 awarded by the National Science Foundation (NSF). The government has certain rights in the invention.

TECHNICAL FIELD

The present invention relates to oxidation catalysis and C—H activation.

BACKGROUND

Transition metal catalyzed oxidation of organic molecules is a major class of chemical transformation both in the laboratory synthesis of fine chemicals and in the manufacture of large-volume petrochemical-based feedstocks. While the chemical community has continued to evolve a deeper understanding of the mechanistic aspects of homogeneous catalytic reactions, several significant challenges remain, including the development of catalysts with enhanced selectivity, greater stability, better atom economy, and minimal environment impact (green oxidation chemistry).

An unmet goal of current green oxidation chemistry is the exploitation of dioxygen, as opposed to oxygen atom transfer reagents (i.e. peroxides, oxygen atom donor molecules, etc.), in metal-based catalysis, a direct consequence of the challenges of controlling or eliminating non-selective free-radical chain reactions. Activated oxygen sources require expensive and/or potentially unstable reagents, whereas dioxygen is inexpensive and chemically stable relative to peroxides. However, the necessity of excess reducing agent to perform catalytic chemistry with oxygen frequently results in unwanted radical chemistry or poisoned, inactive catalysts.

SUMMARY

The invention is based, in part, on the discovery of a new oxidation process that directly utilizes dioxygen from air in sustainable metal-based systems that preclude non-selective free-radical oxygen-based chain reactions. Metal-based (e.g. $Fe^{2+}$) catalysts have been developed and shown to catalyze the oxidation of suitable substrates with high turnover numbers.

Accordingly, one aspect of the invention relates to a reaction mixture comprising an oxidation catalyst comprising a metal ion complexed with an α-keto acid and a tridentate N,N,O-ligand; a solvent in contact with the oxidation catalyst; and a substrate dissolved in the solvent, in which the solvent and the substrate are different.

Another aspect of the invention provides an oxidation catalyst. Generally, the catalyst comprises a metal ion complexed with a tridentate N,N,O-ligand. In some embodiments, the catalyst further comprises solvent molecules in contact with the metal ion.

In some embodiments, the catalyst is of structure:

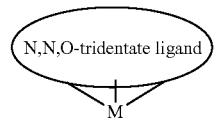

Formula III wherein: M is a metal ion and

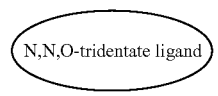

is a N,N,O-tridentate.

Another aspect of the invention relates to a method for oxidizing a C—H bond, the method comprising contacting a molecule having the C—H bond with a metal complex comprising a metal ion complexed with a tridentate N,N,O-ligand in the presence of an α-keto acid and a solvent.

Yet another aspect of the invention relates to a method of catalyzing a reaction, the method comprising contacting a substrate with a metal complex comprising a metal ion complexed with a tridentate N,N,O-ligand in the presence of an α-keto acid and a solvent.

In some embodiments of all aspects of the invention, the metal ion is selected from the group consisting of $Fe^{2+}$, $Ru^{2+}$, $Os^{2+}$, $Mn^{2+}$, $Cr^{2+}$, and $V^{2+}$.

In some embodiments of all aspects of the invention, the tridentate N,N,O-ligand is of Formula (I): $N(R^{11})(R^{12})$—$C(R^{13})(R^{14})$—$(CH_2)_m$—$C(R^{15})(R^{16})$—$N(R^{17})$—$C(R^{18})(R^{19})$—$(CH_2)_n$—X (Formula (I)), wherein: $R^{11}$ and $R^{12}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{11}$ and $R^{12}$ together with the N they are attached to form an optionally substituted heteroaryl or an optionally substituted heterocyclyl; $R^{13}$ and $R^{14}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{11}$ and $R^{13}$ together with the N and C they are attached to form an optionally substituted heteroaryl or an optionally substituted heterocyclyl, or $R^{12}$ and $R^{14}$ together form a double bond between the N and C, or $R^{13}$ and $R^{14}$ together with the C they are attached to form an optionally substituted cyclyl, optionally substituted heterocyclyl, optionally substituted aryl or optionally substituted heteroaryl; $R^{15}$ and $R^{16}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{13}$ and $R^{15}$ together with the carbons they are attached to form an optionally substituted cyclyl, optionally substituted heterocyclyl, optionally substituted aryl or optionally substituted heteroaryl, or $R^{14}$ and $R^{16}$ form a double bond between the carbons they are attached to, or $R^{15}$ and $R^{16}$ together with the C they are attached to form an optionally substituted cyclyl, optionally substituted heterocyclyl, optionally substituted aryl or optionally substituted heteroaryl, or $R^{11}$ and $R^{15}$ together with the N and C they are attached to form an optionally substituted heterocyclyl or optionally substituted heteroaryl; $R^{17}$ is H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{15}$ and $R^{17}$ together with the carbon and nitrogen they are attached to form an optionally substituted heteroaryl or an optionally substituted heterocyclyl, or $R^{16}$ and $R^{17}$ together form a double bond between the N and C, or $R^{13}$ and $R^{17}$ together with the carbon and nitrogen they are attached to form an optionally substituted heteroaryl or an optionally substituted heterocyclyl; $R^{18}$ and $R^{19}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{17}$ and $R^{18}$ together with the N and C they are attached to form an optionally substituted heteroaryl or an optionally substituted heterocyclyl, or $R^{17}$ and $R^{19}$ together form a double bond between the N and C, or $R^{18}$ and $R^{19}$ together with the C they are attached to form an optionally substituted cyclyl, optionally substituted heterocyclyl, optionally substituted aryl or optionally substituted heteroaryl, or $R^{15}$ and $R^{18}$ together with the carbons they are attached to form an optionally substituted heterocyclyl or optionally substituted heteroaryl, or $R^{13}$ and $R^{18}$ together with the carbons they are attached to form an optionally substituted heterocyclyl or optionally substituted heteroaryl, or $R^{11}$ and $R^{18}$ together with the carbons they are attached to form an optionally substituted heterocyclyl or optionally substituted heteroaryl; or one of $R^{11}$, $R^{12}$, $R^{13}$, $R^{14}$, $R^{15}$, $R^{16}$, $R^{17}$, $R^{18}$, $R^{19}$ is a solid support linked to Formula (I) with a linker; X is an oxygen containing moiety; n is 0, 1, 2, 3, or 4; and m is 0, 1, 2, 3, or 4.

In some embodiments of all aspects of the invention, X of Formula (I) comprises a carboxylic acid.

In some embodiments of all aspects of the invention, X of Formula (I) is $CO_2H$ or $CO_2^-$.

In some embodiments of all aspects of the invention, the tridentate N,N,O-ligand is $N(CH_3)_2CH_2CH_2N(CH_3)CH_2C(O)O$; or

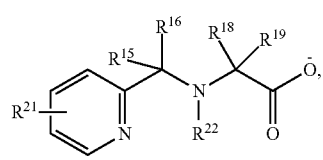
(Formula (IIa))

wherein $R^{21}$ is a solid support linked to the pyridine ring via a linker, an electron-withdrawing group, an electron donating group, or absent; and $R^{22}$ is H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, $OR^{23}$ (where $R^{23}$ is an electron donating group, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or a slid support linked to O via a linker); $R^{15}$ and $R^{16}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{15}$ and $R^{16}$ together with the C they are attached to form an optionally substituted cyclyl, optionally substituted heterocyclyl, optionally substituted aryl or optionally substituted heteroaryl; $R^{18}$ and $R^{19}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{18}$ and $R^{19}$ together with the C they are attached to form an optionally substituted cyclyl, optionally substituted heterocyclyl, optionally substituted aryl or optionally substituted heteroaryl; or

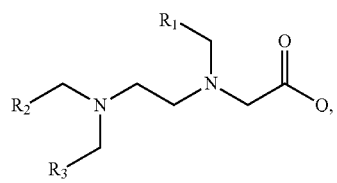

wherein $R_1$, $R_2$, and $R_3$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl.

In some embodiments of all aspects of the invention, the tridentate N,N,O-ligand is

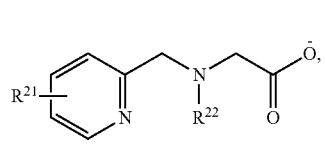
(Formula (II))

wherein $R^{21}$ is a solid support linked to the pyridine ring via a linker, an electron-withdrawing group, an electron donating group, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, $OR^{23}$ (where $R^{23}$ is an electron donating group, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or a slid support linked to O via a linker), or absent; and $R^{22}$ is H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, In some embodiments of all aspects of the invention, $R^{21}$ of Formula (II) or (IIa) is at the para-position to the N.

In some embodiments of all aspects of the invention, the tridentate N,N,O-ligand is linked to a solid support.

In some embodiments of all aspects of the invention, the solid support is selected from the group consisting of a resin, a silica bead, and mesoporous glass.

In some embodiments of all aspects of the invention, the oxidation catalyst has a concentration in the range of 0.1 μM to 10 μM.

In some embodiments of all aspects of the invention, the solvent is a polar solvent.

In some embodiments of all aspects of the invention, the solvent is a polar aprotic solvent.

In some embodiments of all aspects of the invention, the solvent is selected from the group consisting of supercritical $CO_2$, dichloromethane, tetrahydrofuran, ethyl acetate, acetone, dimethylformamide, acetonitrile, dimethyl sulfoxide, propylene, toluene, 1,4-dioxane, chloroform, diethyl ether, formic acid, n-butanoel, isopropanol, n-propanol, ethanol, methanole, acetic acid, nitromethane, carbon tetrachloride, and dimethoxyethane.

In some embodiments of all aspects of the invention, the α-keto acid is selected from the group consisting of α-ketoglutarate, benzoylformate, and pyruvate.

In some embodiments of all aspects of the invention, the substrate comprises a C—H bond.

In some embodiments of all aspects of the invention, the substrate is selected from the group consisting of alkanes, alkenes, alcohols, aldehydes, ketones, amines, cyano-containing compounds, cyclyls, heterocycles, sulfides, and sulfoxides.

In some embodiments of all aspects of the invention, the reaction is selected from the group consisting of hydrocarbon hydroxylation, alkene epoxidation/alkyne oxygenation, arene epoxidation, aromatic hydroxylation, NIH shift, N-dealkylation, S-dealkylation, O-dealkylation, N-hydroxylation, N-oxidation, S-oxidation, oxidative deamination, oxidative dehalogenation, alcohol and aldehyde oxidations, dehydrogenation, dehydrations, reductive dehalogenation, N-oxide reduction, epoxide reduction, reductive (β-scission of alkyl peroxides, NO reduction, isomerizations, and oxidative C-C bond cleavage.

BRIEF DESCRIPTION OF THE DRAWINGS

(FIG. 9A) Fit to one exponential and (FIG. 9B) Fit to two exponentials. Data collected at −85° C. Insets: Residuals to fit.

FIG. 10 is a diagram that illustrates a possible mechanism for the binding α-KA to 17a.

DETAILED DESCRIPTION

Figure 1:
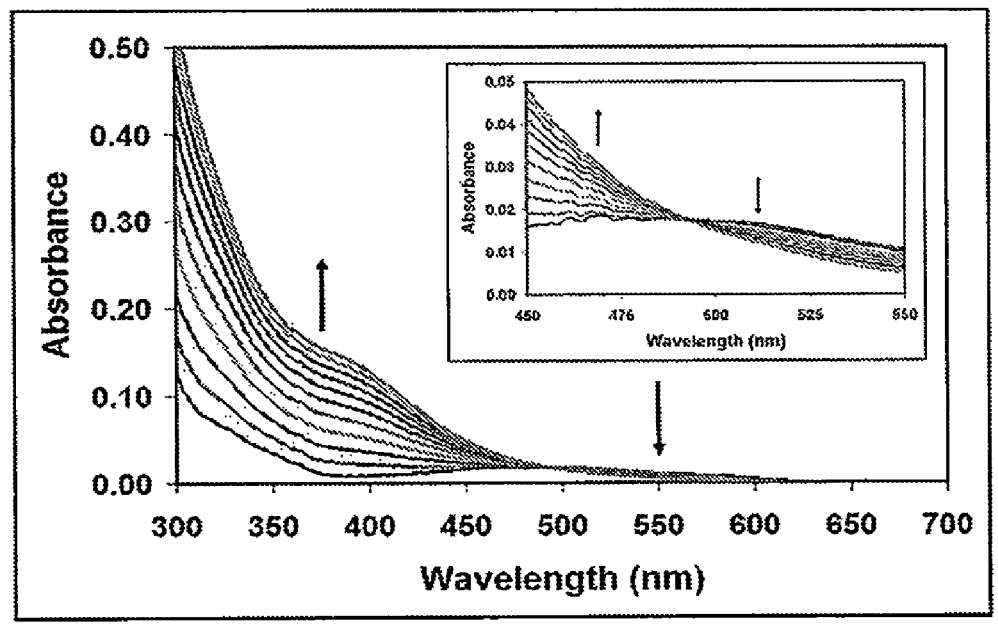
FIG. 1 is a graph that demonstrates reactivity of $[Fe^{II}(N_2O_1)(\alpha\text{-}KG)(CH_3OH)]$ (18) and dioxygen in methanol at room temperature.

The invention is based, in part, on the discovery of a new oxidation process that directly utilizes dioxygen from air in sustainable metal-based systems that preclude non-selective free-radical oxygen-based chain reactions. Specifically, the inventors have developed biologically inspired mononuclear iron complexes that utilize air in the production of an iron-based reactive species that can catalytically oxidize carbon-hydrogen (C—H) bonds in the presence of sacrificial two-electron donor ligands such as α-keto acids at ambient temperatures and pressures. The inventors have used a cyclical combination of state-of-the-art experimental, spectroscopic, and modern computational simulations to characterize the intimate mechanistic steps in order to develop catalysts with enhanced and selective reactivity properties. The use of iron in these catalytic systems is particularly attractive as this metal is earth-abundant and non-toxic, and thus this effort opens new avenues in inexpensive and sustainable catalytic transformations of interest to the industry community.

However, two factors have been identified that contributed to the low turnover number using the catalyst described herein in an oxidation reaction. First, monomers of the catalyst described herein could undergo dimerization as a result of autoxidation, which deactivates the catalyst. Second, certain solvents can be oxidized in the presence of the catalyst, thus effectively competing with the substrate for binding sites.

Solutions to address this problem of low turnover number are provided herein. Specifically, it was discovered that dimerization could be prevented or significantly reduced by linking the monomer of the catalyst to a solid support. Alternatively, dimerization can be significantly reduced by decreasing the concentration of the catalyst. In addition, the solvent can be judiciously selected so that it minimally competes with the substrate for binding sites. These solutions are exploited herein, either alone or in combination, to increase the turnover number. In some embodiments, the turnover number is at least 1, at least 1.5, at least 2, at least 2.5, at least 3, at least 4, at least 5, at least 6, at least 7, at least 8, at least 9, or at least 10. In some embodiments, the turnover number is at least 100, at least 200, at least 300, at least 400, at least 500, at least 600, at least 700, at least 800, or at least 900. And thus aspects and embodiments of the present invention are related to reaction compositions comprising mononuclear metal complexes described herein and methods of use thereof.

The catalytic system disclosed herein is an easily modifiable, bio-inspired catalytic system that is highly effective and represents an economic approach for converting common petroleum and biomass feedstock into advanced oxidized chemicals (e.g., alcohols). The reactivity properties of the system (e.g., utilizing oxygen from air, functional at ambient temperatures and pressures) permit the facile generation of essential advanced feedstocks required for the production of high-value chemicals. The involvement of environmentally and biologically friendly reagents (e.g., air, α-ketoglutarate/α-ketoacids, substrate) and products (e.g., carbon dioxide, succinate/carboxylate) and the use of inexpensive and physiologically benign base metals such as iron can minimize the use and/or production of toxic chemicals during catalysis. In short, the inventors have developed a synthetic system that functions with air and α-keto acid (e.g., α-ketoglutarate) to generate a metal-based oxidant that is thermodynamically and kinetically competent to oxidize unreactive alkane, alkene, and arene molecules to their more economically important products such as alcohol and epoxide. The observed oxidation chemistry is rapid, e.g., 1-10 turnovers/second at room temperature, and can operate at near thermoneutral conditions, indicating that the system does not generate excessive thermal energy. Finally, the process uses renewable feedstocks (air, biogenerated a-ketoglutarate), eliminates the production, transport, and waste removal costs associated with the industrial use of activated forms of oxygen (peroxides, oxygen atom donor molecules), and is inherently more safe to perform than standard oxidation reactions.

The catalytic system disclosed herein can significantly alter synthetic strategies for many highly valued end products used in multiple key industrial sectors including the pharmaceutical industry. The various aspects disclosed herein, based on a demonstrated understanding how biological systems tightly couple thermodynamically favorable reactions with an initial thermodynamically unfavorable reaction in order to drive challenging processes of interest in a near thermo-neutral manner, are a significant enhancement over current oxidation processes from both an economic (less expensive reagents) and chemical process (the absence of the need for dangerous activated forms of oxygen) perspective. In addition, lower operational costs can be expected from (i) the use of base metal catalysts, (ii) the use of air rather than more expensive forms of activated oxygen (e.g., peroxides, peracids, oxygen atom donor molecules), (iii) the lower costs of storage of air versus activated oxygen reagents, (iv) the absence of hidden costs to a chemical manufacturing process resulting from the production, transport, and proper use of more reactive reagents than air, and (v) the generation of environmentally safe or more easily trapped chemical byproducts.

The oxidation catalyst and method disclosed herein can be used to oxidize any desired molecule. For example, the oxidation catalyst and method disclosed herein can be used to oxidze a molecule selected from the group consisting of alkanes, alkenes, alcohols, aldehydes, ketones, amines, cyano-containing compounds, cyclyls, heterocycles, sulfides, and sulfoxides.

Accordingly, in one aspect, the disclosure provides an oxidation catalyst comprising a metal ion complexed with an α-keto acid and a tridentate N,N,O-ligand. The oxidation catalyst can be used in a catalytic reaction to oxidize one or more bonds in a substrate.

In some embodiments, the catalyst disclosed herein comprises further ligands. Thus, in some embodiments, the catalyst is of structure:

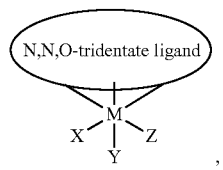

Formula IV wherein:
M is a metal ion;

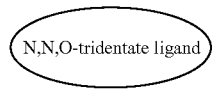

is a N,N,O-tridentate ligand; and X, Y and Z are same or different and independently selected from halogen, alkoxy or ROH, where R is alkyl, alkenyl, alkynyl, cyclyl, heterocylyl, aryl or heteroaryl, each of which can be optionally substituted with 1, 2, 3, 4 or 5 independently selected substituents.

In some embodiments of the catalyst of Formula IV, the N,N,O tridentate ligand is not $N(CH_3)_2CH_2CH_2N(CH_3)CH_2C(O)O$.

In some embodiments of the catalyst of Formula IV, the N,N,O tridentate ligand is not

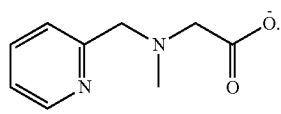

In some embodiments of the catalyst of Formula IV, the N,N,O tridentate ligand is not

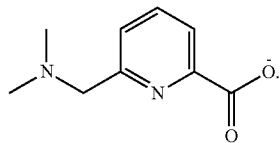

Figure 55:
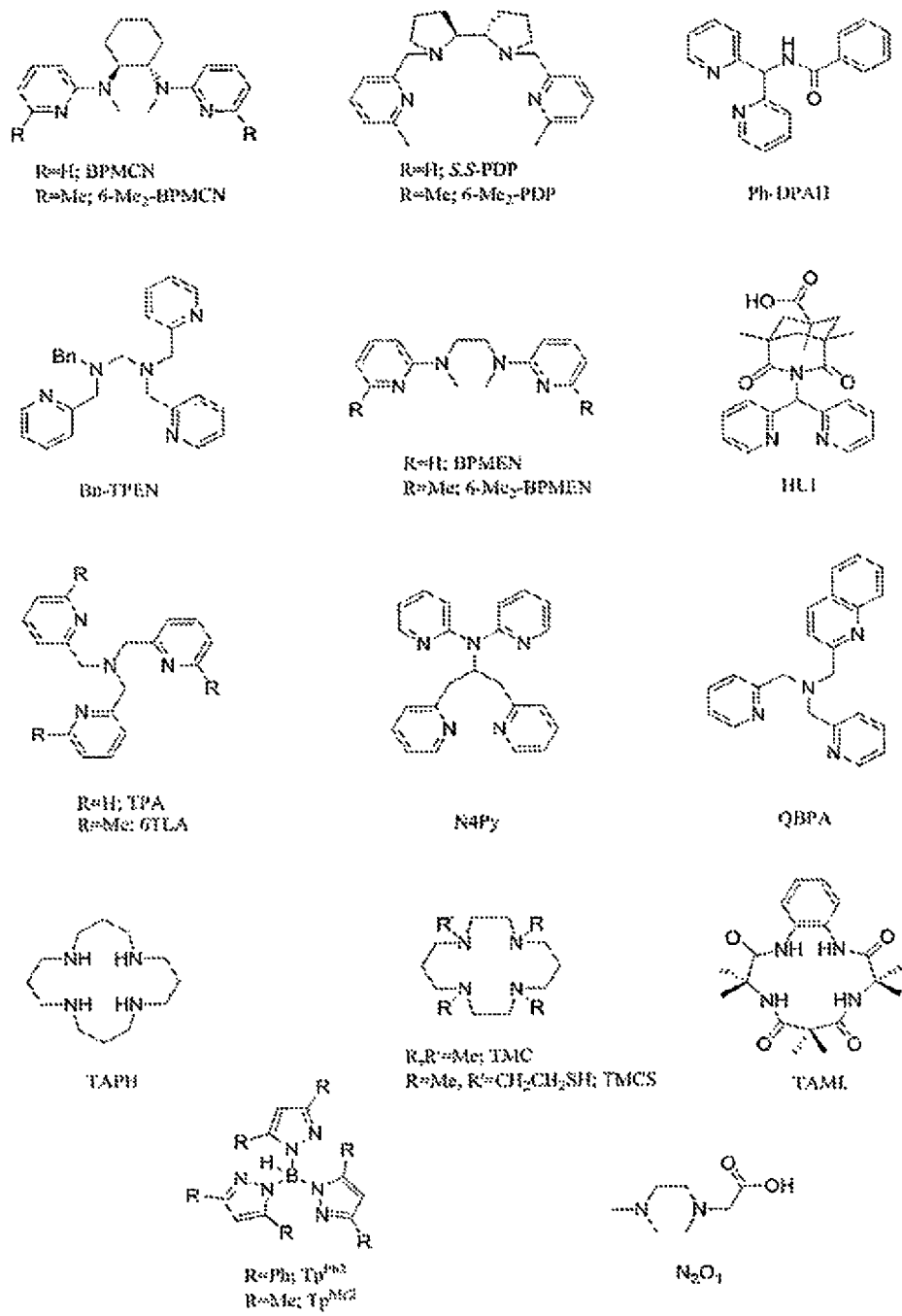
FIG. 55 is a set of chemical structures of ligands used in modeling studies.
Figure 56:
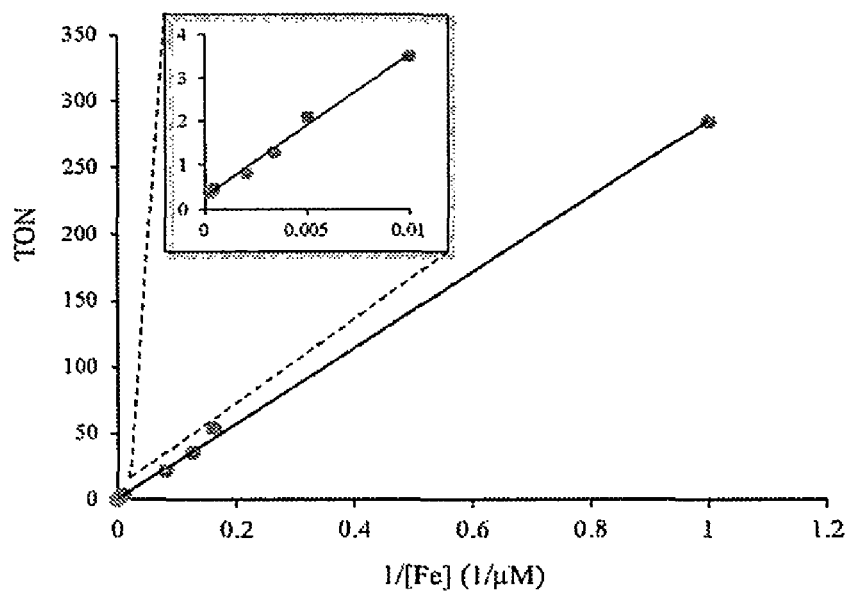
FIG. 56 is a graph that demonstrates the dependence of turnover number on complex concentration in the catalytic oxidation of MeOH by [Fe$^{II}$(N$_2$O$_1$)(αKG)] with O$_2$.

In some embodiments of the catalyst of Formula IV, the N,N,O tridentate ligand is not a ligand shown in FIG. 55

In some embodiments, M is $Fe^{2+}$.

In some embodiments, the

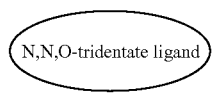

is a N,N,O-tridentate ligand of Formula I.

In some embodiments, the

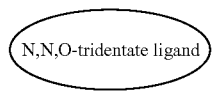

is a N,N,O-tridentate ligand of Formula II.

In some embodiments, X, Y, Z are halogen. For example, X, Y and Z are independently Cl, Br, or I. In one embodiment, X, Y, Z are Cl.

In some embodiments, two of X, Y and Z are halogen and the other is an alkoxide or ROH. In one embodiment, two of X, Y and Z are Cl and the other is methanol or methoxy.

In one embodiment, the catalyst is of structure:

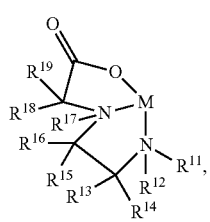

Formula V wherein:
$R^{11}, R^{12}, R^{13}, R^{14}, R^{15}, R^{16}, R^{17}, R^{18}, R^{19}$ are as defined in Formula (I).

In one embodiment, the catalyst is of structure:

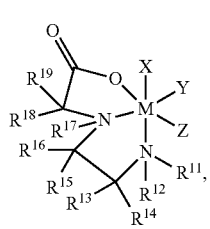

Formula Va wherein:

$R^{11}$, $R^{12}$, $R^{13}$, $R^{14}$, $R^{15}$, $R^{16}$, $R^{17}$, $R^{18}$, $R^{19}$ are as defined in Formula (I); and X, Y and Z are same or different and independently selected from halogen, alkoxy or ROH, where R is alkyl, alkenyl, alkynyl, cyclyl, heterocylyl, aryl or heteroaryl, each of which can be optionally substituted with 1, 2, 3, 4 or 5 independently selected substituents.

In some embodiments, the catalyst is of structure:

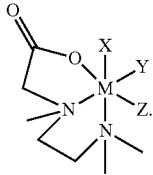

Formula VI

In some embodiments, the catalyst is of structure:

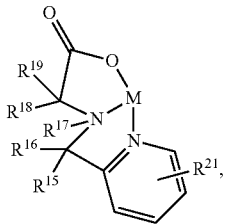

Formula VII wherein:

$R^{15}$, $R^{16}$, $R^{17}$, $R^{18}$, and $R^{19}$ are as defined in Formula (I); and $R^{21}$ is as defined in Formula (II[In some embodiments, the catalyst is of structure:

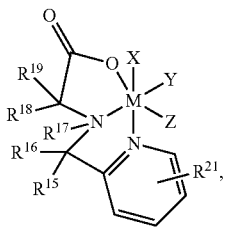

Formula VIIa wherein:

$R^{15}$, $R^{16}$, $R^{17}$, $R^{18}$ and $R^{19}$ are as defined in Formula (I); $R^{21}$ is as defined in Formula (II); and X, Y and Z are same or different and independently selected from halogen, alkoxy or ROH, where R is alkyl, alkenyl, alkynyl, cyclyl, heterocylyl, aryl or heteroaryl, each of which can be optionally substituted with 1, 2, 3, 4 or 5 independently selected substituents In some embodiments, the catalyst is of structure:

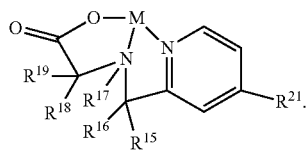

Formula VIII

In some embodiments, the catalyst is of structure:

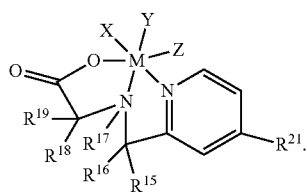

Formula VIIIa

In some embodiments, the catalyst is of structure:

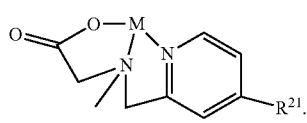

Formula IX

In some embodiments, the catalyst is of structure:

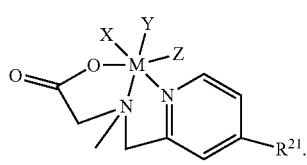

Formula IXa

It is noted that each of the substituents (such as M, $R^1$-$R^{19}$, X, Y and Z) and variables (such as m and n) recited in Formulas (I)-(IXa), as appropriate, can be varied independently or in any combinations with the others. Thus, the specific groups or values listed for substituents such as M, $R^1$-$R^{19}$, X, Y and Z) and variables (such as m and n) in Formulas (I)-(IXa) can be combined with each other in any combinations. In other words, each and every combination of specific groups listed for substituents (such as M, $R^1$-$R^{19}$, X, Y and Z) and variables (such as m and n) in Formulas (I)-(IXa) is part of the disclosure. Furthermore, the disclosure also contemplates selecting any and each specific combination and/or subset of the specific groups or values listed for substituents such as M, $R^1$-$R^{19}$, X, Y and Z) and variables (such as m and n) in Formulas (I)-(IXa).

By way of example only, $R^{11}$ being H or methyl can be combined with any combinations or subset of the specific groups listed for the other substituents or variables. In another example, $R^{12}$ being H or methyl can be combined with any combinations or subset of the specific groups listed for the other substituents or variables. In yet another example, $R^{11}$ and $R^{12}$ forming an optionally substituted heteroaryl or heterocyclyl can be combined with any combinations or subset of the specific groups listed for the other substituents or variables. In still another example, $R^{13}$ and $R^{14}$ being H can be combined with any combinations or subset of the specific groups listed for the other substituents or variables. In still another example, $R^{15}$ and $R^{16}$ being H can be combined with any combinations or subset of the specific groups listed for the other substituents or variables. In yet another example, $R^{15}$ and $R^{16}$ being H can be combined with any combinations or subset of the specific groups listed for the other substituents or variables. In another example, $R^{17}$ being a H, methyl or solid support linked via a linker to the N can be combined with any combinations or subset of the specific groups listed for the other substituents or variables. In yet another example, X being $—C(O)O^-$ can be combined with any combinations or subset of the specific groups listed for the other substituents or variables.

In a further example, $R^{21}$ being absent, a solid support linked via a linker to the pyridine ring, $OR^{23}$, an electron-withdrawing group or an electron donating group can be combined with any combinations or subset of the specific groups listed for the other substituents or variables. In another example, $R^{15}$ being H can be combined with any combinations or subset of the specific groups listed for the other substituents or variables. In yet another example, $R^{16}$ being H can be combined with any combinations or subset of the specific groups listed for the other substituents or variables. In still another example, $R^{18}$ being H can be combined with any combinations or subset of the specific groups listed for the other substituents or variables. In yet still another example, $R^{19}$ being H can be combined with any combinations or subset of the specific groups listed for the other substituents or variables. In another example, $R^{22}$ being H, methyl or a solid support linked via a linker to the N can be combined with any combinations or subset of the specific groups listed for the other substituents or variables.

In one example, M being $Fe^{2+}$ can be combined with any combinations or subset of the specific groups listed for the other substituents or variables. In another example, X being a halogen, methanol or methoxy can be combined with any combinations or subset of the specific groups listed for the other substituents or variables. In one example, X being Cl can be combined with any combinations or subset of the specific groups listed for the other substituents or variables. In another example, Y being a halogen, methanol or methoxy can be combined with any combinations or subset of the specific groups listed for the other substituents or variables. In one example, Y being Cl can be combined with any combinations or subset of the specific groups listed for the other substituents or variables. In another example, Z being a halogen, methanol or methoxy can be combined with any combinations or subset of the specific groups listed for the other substituents or variables. In one example, Z being Cl can be combined with any combinations or subset of the specific groups listed for the other substituents or variables.

In another aspect, the disclosure provides a reaction mixture comprising the oxidation catalyst described herein, a solvent, and a substrate that is dissolved in the solvent.

In yet still another aspect, the disclosure provides a method for oxidizing a C—H bond in a molecule, the method comprising contacting the molecule having the C—H bond with an metal complex comprising a metal ion complexed with a tridentate N,N,O-ligand. In some embodiments, said contacting is in the presence of an α-keto acid. The α-keto acid molecule can bind the metal complex to form an oxidation catalyst in situ. In some embodiments, said contacting is in the presence of a solvent.

The metal ion can be any metal ion that can reduce dioxygen by one electron to form a $M^{3+}$-superoxide adduct. In some embodiments of the various aspects disclosed herein, the metal ion is $Fe^{2+}$. In some embodiments of the various aspects disclosed herein, the metal ion is $Ru^{2+}$. In some embodiments of the various aspects disclosed herein, the metal ion is $Os^{2+}$. In some embodiments of the various aspects disclosed herein, the metal ion is $Mn^{2+}$. In some embodiments of the various aspects disclosed herein, the metal ion is $Cr^{2+}$. In some embodiments of the various aspects disclosed herein, the metal ion is $V^{2+}$.

In some embodiments of the various aspects disclosed herein, the tridentate N,N,O-ligand is of Formula (I):

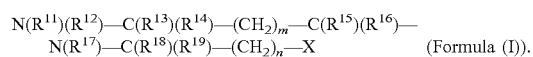

$$N(R^{11})(R^{12})—C(R^{13})(R^{14})—(CH_2)_m—C(R^{15})(R^{16})—$$
$$N(R^{17})—C(R^{18})(R^{19})—(CH_2)_n—X \quad \text{(Formula (I))}.$$

In the tridentate N,N,O-ligands of Formula (I), $R^{11}$ and $R^{12}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or and le together with the N they are attached to form an optionally substituted heteroaryl or an optionally substituted heterocyclyl.

In the tridentate N,N,O-ligands of Formula (I), $R^{13}$ and $R^{14}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{13}$ and $R^{14}$ together with the carbon they are attached to form an optionally substituted cyclyl, optionally substituted heterocyclyl, optionally substituted aryl or optionally substituted heteroaryl.

In some embodiments, $R^{11}$ and $R^{13}$ together with the N and C they are attached to form an optionally substituted heteroaryl or an optionally substituted heterocycly. In some embodiments, $R^{12}$ and $R^{14}$ together form a double bond between the N and C.

In the tridentate N,N,O-ligands of Formula (I), $R^{15}$ and $R^{16}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{15}$ and $R^{16}$ together with the carbon they are attached to form an optionally substituted cyclyl, optionally substituted heterocyclyl, optionally substituted aryl or optionally substituted heteroaryl.

In some embodiments, $R^{13}$ and $R^{15}$ together with the carbons they are attached to form an optionally substituted cyclyl, optionally substituted heterocyclyl, optionally substituted aryl or optionally substituted heteroaryl. In some embodiments, $R^{14}$ and $R^{16}$ form a double bond between the carbons they are attached to. In some embodiments, $R^{11}$ and $R^{15}$ together with the N and C they are attached to form an optionally substituted heterocyclyl or optionally substituted heteroaryl;

In the tridentate N,N,O-ligands of Formula (I), $R^{17}$ is H optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl.

In some embodiments, $R^{15}$ and $R^{17}$ together with the carbon and nitrogen they are attached to form an optionally substituted heteroaryl or an optionally substituted heterocyclyl. In some embodiments, $R^{16}$ and $R^{17}$ together form a double bond between the N and C. In some embodiments, $R^{13}$ and $R^{17}$ together with the carbon and nitrogen they are attached to form an optionally substituted heteroaryl or an optionally substituted heterocyclyl;

In the tridentate N,N,O-ligands of Formula (I), $R^{18}$ and $R^{19}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{18}$ and $R^{19}$ together with the C they are attached to form an optionally substituted cyclyl, optionally substituted heterocyclyl, optionally substituted aryl or optionally substituted heteroaryl.

In some embodiments, $R^{17}$ and $R^{18}$ together with the N and C they are attached to form an optionally substituted heteroaryl or an optionally substituted heterocyclyl. In some embodiments, $R^{17}$ and $R^{19}$ together form a double bond between the N and C. In some embodiments, $R^{18}$ and $R^{19}$ together with the C they are attached to form an optionally substituted cyclyl, optionally substituted heterocyclyl, optionally substituted aryl or optionally substituted heteroaryl. In some embodiments, $R^{15}$ and $R^{18}$ together with the carbons they are attached to form an optionally substituted heterocyclyl or optionally substituted heteroaryl. In some embodiments, $R^{13}$ and $R^{18}$ together with the carbons they are attached to form an optionally substituted heterocyclyl or optionally substituted heteroaryl. In some embodiments, $R^{13}$ and $R^{18}$ together with the carbons they are attached to form an optionally substituted heterocyclyl or optionally substituted heteroaryl In the tridentate N,N,O-ligands of Formula (I), X is an oxygen containing moiety. In some embodiments, X comprises a carboxylic acid. In one embodiment, X is $CO_2H$ or $CO_2^-$.

In the tridentate N,N,O-ligands of Formula (I), variables m and n are independently 0, 1, 2, 3, or 4. Without limitations, the ligands of Formula (I) can comprise m and n in any combination. For example, m can be 0 and n can be 0, m can be 0 and n can 1, m can be 0 and n can 2, m can be 0 and n can 2, m can be 0 and n can 3, m can be 0 and n can 4, m can be 1 and n can be 0, m can be 1 and n can be 1, m can be 1 and n can be 2, m can be 1 and n can be 3, m can be 1 and n can be 4, m can be 2 and n can 0, m can be 2 and n can be 1, m can be 2 and n can be 2, m can be 2 and n can be 3, m can be 2 and n can be 4, m can be 3 and n can 0, m can be 3 and n can be 1, m can be 3 and n can be 2, m can be 3 and n can be 3, m can be 3 and n can be 4, m can be 4 and n can be 0, m can be 4 and n can be 1, m can be 4 and n can be 2, m can be 4 and n can be 3, or m can be 4 and n can be 4.

In one embodiment, m and n are both 0.

In some embodiments, at least one of $R^{11}$, $R^{12}$, $R^{13}$, $R^{14}$, $R^{15}$, $R^{16}$, $R^{17}$, $R^{18}$, and $R^{19}$ is a bulky group. As used herein, the term "bulky group" is meant a substituent that produces steric hindrance about the space to which it is attached. Generally, a bulky group has a steric parameter -Es' value of 1.5 or more. Note that the term "steric parameter -Es' value" is a parameter that represents a steric bulkiness of a substituent. The -Es' values listed in the literature can be used. See, for example, J. A. Macphee, et al, Tetrahedron, Vol. 34, pp 3553-3562, and Kagaku Zokan "Kozo kassei Sokan to Doraggu Dezain (Structure Activity Correlation and Drug Design)" compiled and edited by Toshio Fujita, published on Feb. 20, 1986 (KAGAKU-DOJIN PUBLISHING CO., LTD.), content of both of which is incorporated herein by reference. Generally, the bulky group can be any suitable moiety that limits the extent of dimer formation of the metal complex. In some embodiments, the bulky group is t-butyl, isopropyl, cyclohexyl, neopentyl, adamantyl, mesityl, or 3,5-diisopropylbenzene.

Examples of tridentate N,N,O-ligands of Formula (I) can be found, for example, in the thesis of Paul Tarves; Cappillino et al., Dalton Trans., 2012, 41, 5662; and Cappillino et al., Dalton Trans., 2012, 41, 474-483, the contents of each of which can be incorporated by references in their entireties.

The homogeneous form of the catalyst can become inactivated via a dimerization pathway, a deleterious pathway that can be minimized/eliminated, for example, through the transformation of the solution-based catalyst to an insoluble, heterogeneous version. Accordingly, in some embodiments of the various aspects disclosed herein, the tridentate N,N,O-ligand can be linked to a solid support. As used herein, the term "solid support" refers to solid material which can be bonded to the oxidation catalyst or metal complex described herein and which is not soluble in a solvent where a desired oxidation reaction occurs. In some embodiments, the tridentate N,N,O-ligand can be linked to a solid support via a linker. The complex or catalyst can be linked to a variety of solid supports such that the migration or interaction of adjacent active monomers of the complex or catalyst is prevented, thereby eliminating the inactivation process (i.e., dimerization) in the solution. In some embodiments, the solid support is porous (e.g., macroporous). In some embodiments, the solid support is non-porous. Non-limiting examples of solid supports include inorganic oxide support materials, such as: talcs, silicas, titania, silica/chromia, silica/chromia/titania, silica/alumina, zirconia, aluminum phosphate gels, silanized silica, silica hydrogels, silica xerogels, silica aerogels, montmorillonite clay and silica co-gels as well as organic solid supports such as polystyrene and functionalized polystyrene. In some embodiments, the solid support is a resin. Many types of resin are commercially available. In some embodiments, the resin is a polystyrene resin. Standard organic chemistry methodology can be used to link the tridentate N,N,O-ligand to the solid support. In some embodiments, click chemistry can be used. In some embodiments, standard azide-alkyne cycloaddition coupling methodology can be used, for example, see Ladouceur et al., Synthesis, 2011, 22, 3604-3611; Kolb et al., Angew. Chem. Inter. Ed., 2001, 40, 2004-2021; and Hoyle et al., Angew. Chem. Inter. Ed., 2010, 49, 1540-1573. For catalysts linked to a resin, the resin can be used in a flow condition such that the reaction products are continuously removed from the reaction mixture.

A variety of locations on the tridentate N,N,O-ligand can be used to link the ligand to the solid support. These locations include $R^{11}$, $R^{12}$, $R^{13}$, $R^{14}$, $R^{15}$, $R^{16}$, $R^{17}$, $R^{18}$, and $R^{19}$ of Formula (I), $R^{21}$ and $R^{22}$ of Formula (II). In some embodiments, the location is $R^{17}$ of Formula (I). In some embodiments, the location is $R^{21}$ or $R^{22}$ of Formula (II).

The dimerization pathway also can be minimized/eliminated by having a relatively low concentration of the oxidation catalyst or metal complex. In some embodiments of the various aspects disclosed herein, the oxidation catalyst or metal complex can have a concentration in the range of 0.01 µM to 50 µM, 0.01 µM to 40 µM, 0.01 µM to 30 µM, 0.01 µM to 20 µM, 0.01 µM to 15 µM, 0.01 µM to 10 µM, 0.01 µM to 5 µM, 0.05 µM to 50 µM, 0.05 µM to 40 µM, 0.05 µM to 30 µM, 0.05 µM to 20 µM, 0.05 µM to 15 µM, 0.05 µM to 10 µM, 0.05 µM to 5 µM, 0.1 µM to 50 µM, 0.1 µM to 40 µM, 0.1 µM to 30 µM, 0.1 µM to 20 µM, 0.1 µM to 15 µM, 0.1 µM to 10 µM, or 0.1 µM to 5 µM. It should be noted that the concentration should be high enough to provide oxidation of a sufficient amount of substrate to be commercially viable.

In some embodiments of the various aspects disclosed herein, the tridentate N,N,O-ligand is $N(CH_3)_2CH_2CH_2N(CH_3)CH_2C(O)O^-$.

In some embodiments of the various aspects disclosed herein, the tridentate N,N,O-ligand is

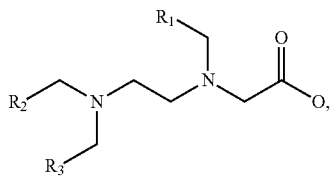

wherein $R_1$, $R_2$, and $R_3$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl. In some embodiments, $R_1$ is a solid support linked to the ligand via a linker, and $R_2$ and $R_3$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl.

In some embodiments of the various aspects disclosed herein, the tridentate N,N,O-ligand is

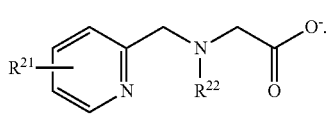

(Formula (II))

The pyridine ring permits the addition of substituents that can tailor the solubility properties of the metal complex or catalyst described herein and offers the ability to immobilize the metal complex or catalyst to a solid support.

In the tridentate N,N,O-ligands of Formula (II), $R^{21}$ is a solid support linked to the pyridine ring via a linker, an electron-withdrawing group, an electron-donating group, $OR^{23}$ (where $R^{23}$ is an electron donating group, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or a slid support linked to O via a linker), or absent. While only one $R^{21}$ is shown, the pyridine ring can be substituted with 1, 2, 3, or 4 $R^{21}$, each of which can be independently selected. In some embodiments, $R^{21}$ can be at the para-position to the N. In some embodiments, $R^{21}$ can be at the meta-position to the N. In some embodiments, $R^{21}$ can be at the ortho-position to the N. When there is more than one $R^{21}$, the $R^{21}$ can be at any combination of available positions on the pyridine ring.

In the tridentate N,N,O-ligands of Formula (II), $R^{22}$ is H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl.

In some embodiments, $R^{21}$ is absent and $R^{22}$ is H.

In some embodiments, $R^{21}$ is absent and $R^{22}$ is a linear or branched $C_1$-$C_{10}$ alkyl which can be optionally substituted. In some embodiments, $R^{21}$ is absent and $R^{22}$ is a linear or branched $C_1$-$C_6$ alkyl which can be optionally substituted. In some embodiments, $R^{21}$ is absent and $R^{22}$ is a linear or branched $C_1$-$C_5$ alkyl which can be optionally substituted. In some embodiments, $R^{21}$ is absent and $R^{22}$ is a linear or branched $C_1$-$C_4$ alkyl which can be optionally substituted. In some embodiments, $R^{21}$ is absent and $R^{22}$ is selected from the group consisting of methyl, ethyl, propyl, and isopropyl, each of which can be optionally substituted.

In some embodiments, $R^{21}$ is absent and $R^{22}$ is linear or branched $C_2$-$C_{10}$ alkenyl which can be optionally substituted. In some embodiments, $R^{21}$ is absent and $R^{22}$ is linear or branched $C_2$-$C_6$ alkenyl which can be optionally substituted. In some embodiments, $R^{21}$ is absent and $R^{22}$ is linear or branched $C_2$-$C_5$ alkenyl which can be optionally substituted. In some embodiments, $R^{21}$ is absent and $R^{22}$ is linear or branched $C_2$-$C_4$ alkenyl which can be optionally substituted. In some embodiments, $R^{21}$ is absent and $R^{22}$ is selected from the group consisting of vinyl, allyl, propenyl, and isopropenyl, each of which can be optionally substituted.

In some embodiments, $R^{21}$ is absent and $R^{22}$ is linear or branched $C_2$-$C_{10}$ alkynyl which can be optionally substituted. In some embodiments, $R^{21}$ is absent and $R^{22}$ is linear or branched $C_2$-$C_6$ alkynyl which can be optionally substituted. In some embodiments, $R^{21}$ is absent and $R^{22}$ is linear or branched $C_2$-$C_5$ alkynyl which can be optionally substituted. In some embodiments, $R^{21}$ is absent and $R^{22}$ is linear or branched $C_2$-$C_4$ alkynyl which can be optionally substituted. In some embodiments, $R^{21}$ is absent and $R^{22}$ is selected from the group consisting of ethynyl, 1-propynyl, and 2-propynyl, each of which can be optionally substituted In some embodiments, $R^{21}$ is absent and $R^{22}$ is optionally substituted cyclyl.

In some embodiments, $R^{21}$ is absent and $R^{22}$ is optionally substituted heterocyclyl.

In some embodiments, $R^{21}$ is absent and $R^{22}$ is optionally substituted aryl.

In some embodiments, $R^{21}$ is absent and $R^{22}$ is optionally substituted heteroaryl.

In some embodiments, $R^{21}$ is a solid support linked to the pyridine ring via a linker and $R^{22}$ is H.

In some embodiments, $R^{21}$ is a solid support linked to the pyridine ring via a linker and $R^{22}$ is a linear or branched $C_1$-$C_{10}$ alkyl which can be optionally substituted. In some embodiments, $R^{21}$ is a solid support linked to the pyridine ring via a linker and $R^{22}$ is a linear or branched $C_1$-$C_6$ alkyl which can be optionally substituted. In some embodiments, $R^{21}$ is a solid support linked to the pyridine ring via a linker and $R^{22}$ is a linear or branched $C_1$-$C_5$ alkyl which can be optionally substituted. In some embodiments, $R^{21}$ is a solid support linked to the pyridine ring via a linker and $R^{22}$ is a linear or branched $C_1$-$C_4$ alkyl which can be optionally substituted. In some embodiments, $R^{21}$ is a solid support linked to the pyridine ring via a linker and $R^{22}$ is selected from the group consisting of methyl, ethyl, propyl, and isopropyl, each of which can be optionally substituted.

In some embodiments, $R^{21}$ is a solid support linked to the pyridine ring via a linker and $R^{22}$ is linear or branched $C_2$-$C_{10}$ alkenyl which can be optionally substituted. In some embodiments, $R^{21}$ is a solid support linked to the pyridine ring via a linker and $R^{22}$ is linear or branched $C_2$-$C_6$ alkenyl which can be optionally substituted. In some embodiments, $R^{21}$ is a solid support linked to the pyridine ring via a linker and $R^{22}$ is linear or branched $C_2$-$C_5$ alkenyl which can be optionally substituted. In some embodiments, $R^{21}$ is a solid support linked to the pyridine ring via a linker and $R^{22}$ is linear or branched $C_2$-$C_4$ alkenyl which can be optionally substituted. In some embodiments, $R^{21}$ is a solid support linked to the pyridine ring via a linker and $R^{22}$ is selected from the group consisting of vinyl, allyl, propenyl, and isopropenyl, each of which can be optionally substituted.

In some embodiments, $R^{21}$ is a solid support linked to the pyridine ring via a linker and $R^{22}$ is linear or branched $C_2$-$C_{10}$ alkynyl which can be optionally substituted. In some embodiments, $R^{21}$ is a solid support linked to the pyridine ring via a linker and $R^{22}$ is linear or branched $C_2$-$C_6$ alkynyl which can be optionally substituted. In some embodiments, $R^{21}$ is a solid support linked to the pyridine ring via a linker and $R^{22}$ is linear or branched $C_2$-$C_5$ alkynyl which can be optionally substituted. In some embodiments, $R^{21}$ is a solid support linked to the pyridine ring via a linker and $R^{22}$ is linear or branched $C_2$-$C_4$ alkynyl which can be optionally substituted. In some embodiments, $R^{21}$ is a solid support linked to the pyridine ring via a linker and $R^{22}$ is selected from the group consisting of ethynyl, 1-propynyl, and 2-propynyl, each of which can be optionally substituted In some embodiments, $R^{21}$ is a solid support linked to the pyridine ring via a linker and $R^{22}$ is optionally substituted cyclyl.

In some embodiments, $R^{21}$ is a solid support linked to the pyridine ring via a linker and $R^{22}$ is optionally substituted heterocyclyl.

In some embodiments, $R^{21}$ is a solid support linked to the pyridine ring via a linker and $R^{22}$ is optionally substituted aryl.

In some embodiments, $R^{21}$ is a solid support linked to the pyridine ring via a linker and $R^{22}$ is optionally substituted heteroaryl.

In some embodiments, $R^{21}$ is an electron-withdrawing group and $R^{22}$ is H. Examples of electron-withdrawing group include, but are not limited to, halogen (e.g., F, Cl, Br, or I), nitro, cyano, carboxy, carboalkoxy, acyl, acetyl, trimethyl ammonium, sulfonic acid, and carbamido groups. In some embodiments, $R^{21}$ is a halogen.

In some embodiments, $R^{21}$ is an electron-withdrawing group and $R^{22}$ is a linear or branched $C_1$-$C_{10}$ alkyl which can be optionally substituted. In some embodiments, $R^{21}$ is an electron-withdrawing group and $R^{22}$ is a linear or branched $C_1$-$C_6$ alkyl which can be optionally substituted. In some embodiments, $R^{21}$ is an electron-withdrawing group and $R^{22}$ is a linear or branched $C_1$-$C_5$ alkyl which can be optionally substituted. In some embodiments, $R^{21}$ is an electron-withdrawing group and $R^{22}$ is a linear or branched $C_1$-$C_4$ alkyl which can be optionally substituted. In some embodiments, $R^{21}$ is an electron-withdrawing group and $R^{22}$ is selected from the group consisting of methyl, ethyl, propyl, and isopropyl, each of which can be optionally substituted.

In some embodiments, $R^{21}$ is an electron-withdrawing group and $R^{22}$ is linear or branched $C_2$-$C_{10}$ alkenyl which can be optionally substituted. In some embodiments, $R^{21}$ is an electron-withdrawing group and $R^{22}$ is linear or branched $C_2$-$C_6$ alkenyl which can be optionally substituted. In some embodiments, $R^{21}$ is an electron-withdrawing group and $R^{22}$ is linear or branched $C_2$-$C_5$ alkenyl which can be optionally substituted. In some embodiments, $R^{21}$ is an electron-withdrawing group and $R^{22}$ is linear or branched $C_2$-$C_4$ alkenyl which can be optionally substituted. In some embodiments, $R^{21}$ is an electron-withdrawing group and $R^{22}$ is selected from the group consisting of vinyl, allyl, propenyl, and isopropenyl, each of which can be optionally substituted.

In some embodiments, $R^{21}$ is an electron-withdrawing group and $R^{22}$ is linear or branched $C_2$-$C_{10}$ alkynyl which can be optionally substituted. In some embodiments, $R^{21}$ is an electron-withdrawing group and $R^{22}$ is linear or branched $C_2$-$C_6$ alkynyl which can be optionally substituted. In some embodiments, $R^{21}$ is an electron-withdrawing group and $R^{22}$ is linear or branched $C_2$-$O_5$ alkynyl which can be optionally substituted. In some embodiments, $R^{21}$ is an electron-withdrawing group and $R^{22}$ is linear or branched $C_2$-$C_4$ alkynyl which can be optionally substituted. In some embodiments, $R^{21}$ is an electron-withdrawing group and $R^{22}$ is selected from the group consisting of ethynyl, 1-propynyl, and 2-propynyl, each of which can be optionally substituted In some embodiments, $R^{21}$ is an electron-withdrawing group and $R^{22}$ is optionally substituted cyclyl.

In some embodiments, $R^{21}$ is an electron-withdrawing group and $R^{22}$ is optionally substituted heterocyclyl.

In some embodiments, $R^{21}$ is an electron-withdrawing group and $R^{22}$ is optionally substituted aryl.

In some embodiments, $R^{21}$ is an electron-withdrawing group and $R^{22}$ is optionally substituted heteroaryl.

In some embodiments, $R^{21}$ is an electron-donating group and $R^{22}$ is H. Examples of electron-donating group include, but are not limited to, hydroxy, alkyl, alkoxy, amino, aryl, and heterocyclyl.

In some embodiments, $R^{21}$ is an electron-donating group and $R^{22}$ is a linear or branched $C_1$-$C_{10}$ alkyl which can be optionally substituted. In some embodiments, $R^{21}$ is an electron-donating group and $R^{22}$ is a linear or branched $C_1$-$C_6$ alkyl which can be optionally substituted. In some embodiments, $R^{21}$ is an electron-donating group and $R^{22}$ is a linear or branched $C_1$-$C_5$ alkyl which can be optionally substituted. In some embodiments, $R^{21}$ is an electron-donating group and $R^{22}$ is a linear or branched $C_1$-$C_4$ alkyl which can be optionally substituted. In some embodiments, $R^{21}$ is an electron-donating group and $R^{22}$ is selected from the group consisting of methyl, ethyl, propyl, and isopropyl, each of which can be optionally substituted.

In some embodiments, $R^{21}$ is an electron-donating group and $R^{22}$ is linear or branched $C_2$-$C_{10}$ alkenyl which can be optionally substituted. In some embodiments, $R^{21}$ is an electron-donating group and $R^{22}$ is linear or branched $C_2$-$C_6$ alkenyl which can be optionally substituted. In some embodiments, $R^{21}$ is an electron-donating group and $R^{22}$ is linear or branched $C_2$-$C_5$ alkenyl which can be optionally substituted. In some embodiments, $R^{21}$ is an electron-donating group and $R^{22}$ is linear or branched $C_2$-$C_4$ alkenyl which can be optionally substituted. In some embodiments, $R^{21}$ is an electron-donating group and $R^{22}$ is selected from the group consisting of vinyl, allyl, propenyl, and isopropenyl, each of which can be optionally substituted.

In some embodiments, $R^{21}$ is an electron-donating group and $R^{22}$ is linear or branched $C_2$-$C_{10}$ alkynyl which can be optionally substituted. In some embodiments, $R^{21}$ is an electron-donating group and $R^{22}$ is linear or branched $C_2$-$C_6$ alkynyl which can be optionally substituted. In some embodiments, $R^{21}$ is an electron-donating group and $R^{22}$ is linear or branched $C_2$-$C_5$ alkynyl which can be optionally substituted. In some embodiments, $R^{21}$ is an electron-donating group and $R^{22}$ is linear or branched $C_2$-$C_4$ alkynyl which can be optionally substituted. In some embodiments, $R^{21}$ is an electron-donating group and $R^{22}$ is selected from the group consisting of ethynyl, 1-propynyl, and 2-propynyl, each of which can be optionally substituted In some embodiments, $R^{21}$ is an electron-donating group and $R^{22}$ is optionally substituted cyclyl.

In some embodiments, $R^{21}$ is an electron-donating group and $R^{22}$ is optionally substituted heterocyclyl.

In some embodiments, $R^{21}$ is an electron-donating group and $R^{22}$ is optionally substituted aryl.

In some embodiments, $R^{21}$ is an electron-donating group and $R^{22}$ is optionally substituted heteroaryl.

The invention also provides the tridentate N,N,O-ligands described herein, i.e., a N,N,O-tridentate ligand disclosed herein without being in complex with a metal ion.

The ligands, oxidation catalysts, and metal complexes can be synthesized using conventional synthetic methodology. Exemplary synthetic methodology can be found in the Examples section.

The substrate should be soluble in the solvent. Preferably, the solvent is not oxidized or minimally oxidized by dioxygen in the presence of the oxidation catalyst. Without limitations, the solvent can a non-polar or polar solvent. Further, the solvent can be aprotic or protic solvent. In some embodiments, the solvent is a polar aprotic solvent. In some other embodiments, the solvent is a polar protic solvent. Solvent can be selected from the group consisting of supercritical $CO_2$, dichloromethane, tetrahydrofuran, ethyl acetate, acetone, dimethylformamide, acetonitrile, dimethyl sulfoxide, propylene, toluene, 1,4-dioxane, chloroform, diethyl ether, formic acid, n-butanol, isopropanol, n-propanol, ethanol, methanol, acetic acid, nitromethane, carbon tetrachloride, dimethoxyethane, and any combinations thereof. In some embodiments of the various aspects disclosed herein, the solvent can be supercritical $CO_2$.

Reactions that can be catalyzed by the oxidation catalysts described herein include, but are not limited to, hydrocarbon hydroxylation, alkene epoxidation/alkyne oxygenation, arene epoxidation, aromatic hydroxylation, NIH shift, N-dealkylation, S-dealkylation, O-dealkylation, N-hydroxylation, N-oxidation, S-oxidation, oxidative deamination, oxidative dehalogenation, alcohol and aldehyde oxidations, dehydrogenation, dehydrations, reductive dehalogenation, N-oxide reduction, epoxide reduction, reductive β-scission of alkyl peroxides, NO reduction, isomerizations, and oxidative C—C bond cleavage. Detailed description of the applicable reaction types can be found, for example, in Chemical Reviews, 1996, 96, 2841-2887. In some embodiments, the oxidation catalysts describe herein can catalyze the oxidation of any alkane. In some embodiments, the oxidation catalysts describe herein can catalyze the oxidation of alcohol to aldehyde/ketone.

Without limitations, the oxidation can be carried out at any desired temperature. For example, the oxidation can be carried out at a temperature between 0° C. to 100° C. In some embodiment, the oxidation is conducted at room temperature. As used herein, the terms "room temperature" and "RT" refer to temperatures greater than 4° C. Generally, room temperature is a temperature from 15° C. to 40° C., 15° C. to 30° C., 15° C. to 24° C., and 16° C. to 21° C. Such temperatures will include, 14° C., 15° C., 16° C., 17° C., 18° C., 19°, 20° C., and 21° C. The oxidation can also be carried out at temperatures below 0° C. (e.g., −40° C. to 0° C.).

Without limitations, the oxidation can be carried out at any desired pressure. For example, the oxidation can be carried out at a pressure below, at, or above sea level standard atmospheric pressure (i.e. 101325 Pa). In some embodiments, the oxidation is conducted at the local atmospheric pressure. Depending on the location, atmospheric pressure varies widely on Earth. The pressure can depend on the solvent being used. For example, when supercritical $CO_2$ is used, the pressure can be equal to or exceed 7.39 MPa. In some embodiments, the oxidation is carried out at a sufficiently high pressure to enhance the solubility of gaseous substrates (e.g., methane, ethane, propane, but not limited to just these examples).

In some embodiments of the various aspects disclosed herein, the α-keto acid is α-ketoglutarate. In some embodiments of the various aspects disclosed herein, the α-keto acid is benzoylformate. In some embodiments of the various aspects disclosed herein, the α-keto acid is pyruvate. Other non-limiting examples of α-keto acids that can be applicable include 3-methyl-2-oxobutanoic acid, 2-oxopropanoic acid, 2-oxohexanoic acid, and 2-oxohexanedioic acid, and substituted benzoylformates.

In some embodiments, to catalyze the oxidation of a substrate, an oxidation catalyst comprising a metal ion complexed with an α-keto acid and a tridentate N,N,O-ligand, as described herein, can be added to a reaction mixture comprising the substrate and a suitable solvent.

In some embodiments, to catalyze the oxidation of a substrate, a metal complex comprising a metal ion complexed with a tridentate N,N,O-ligand, as described herein, can be added to a reaction mixture comprising the substrate, a suitable solvent, and an α-keto acid. The α-keto acid can bind the metal complex in situ to form the oxidation catalyst as described herein. Without wishing to be bound by theory, each α-keto acid can generate an intermediate that can oxidize one substrate molecule to its product (referred to as 1:1 coupling herein). This 1:1 coupling indicates that the chemistry does not arise from a free-radical chain process after an initiation step. In some embodiments, the molar ratio of the α-keto acid to the metal complex is at least 1:1, at least 2:1, at least 3:1, at least 4:1, at least 5:1, at least 6:1, at least 7:1, at least 8:1, at least 9:1, or at least 10:1. In some embodiments, the molar ratio of the α-keto acid to the substrate is at least 1:1, at least 2:1, at least 3:1, at least 4:1, at least 5:1, at least 6:1, at least 7:1, at least 8:1, at least 9:1, or at least 10:1.

In some embodiments, a gaseous composition comprising oxygen is added to the reaction mixture to catalyze the oxidation of a substrate. The gaseous composition can comprise at least 5%, at least 10%, at least 15%, at least 20%, at least 25%, at least 30%, at least 40%, at least 50%, at least 60%, at least 70%, at least 80%, or at least 90% by weight of oxygen. Examples of a gaseous composition comprising oxygen include, but are not limited to, air and oxygen gas. In some embodiments, the method further comprises purifying or isolating the desired product (e.g., oxidized substrate or molecule) from the reaction. Methods for purifying reaction products are well known in the art and available to one of ordinary skill in the art. Exemplary purification/isolation methods include, but are not limited to, chromatography (e.g., column, HPLC, Gas, etc . . . ), distillation, filtration, extraction, crystallization and the like.

As used herein, the term "substrate" refers to a molecule that is capable of being oxidized into a product molecule by at least one catalyst molecule described herein. A variety of substrates can be oxidized using the compositions and methods described herein. In some embodiments, the substrate is a small organic molecule. As used herein, the term "small organic molecule" refers to a natural or synthetic organic molecule having a molecular mass of less than about 5 kD, organic or inorganic compounds having a molecular mass of less than about 5 kD, less than about 2 kD, or less than about 1 kD. In some embodiments, the substrate comprises one or more C—H bonds. In some embodiment, the substrate is a compound present in petroleum. In some embodiment, the substrate is a compound present in biomass feedstock.

Figure 45:
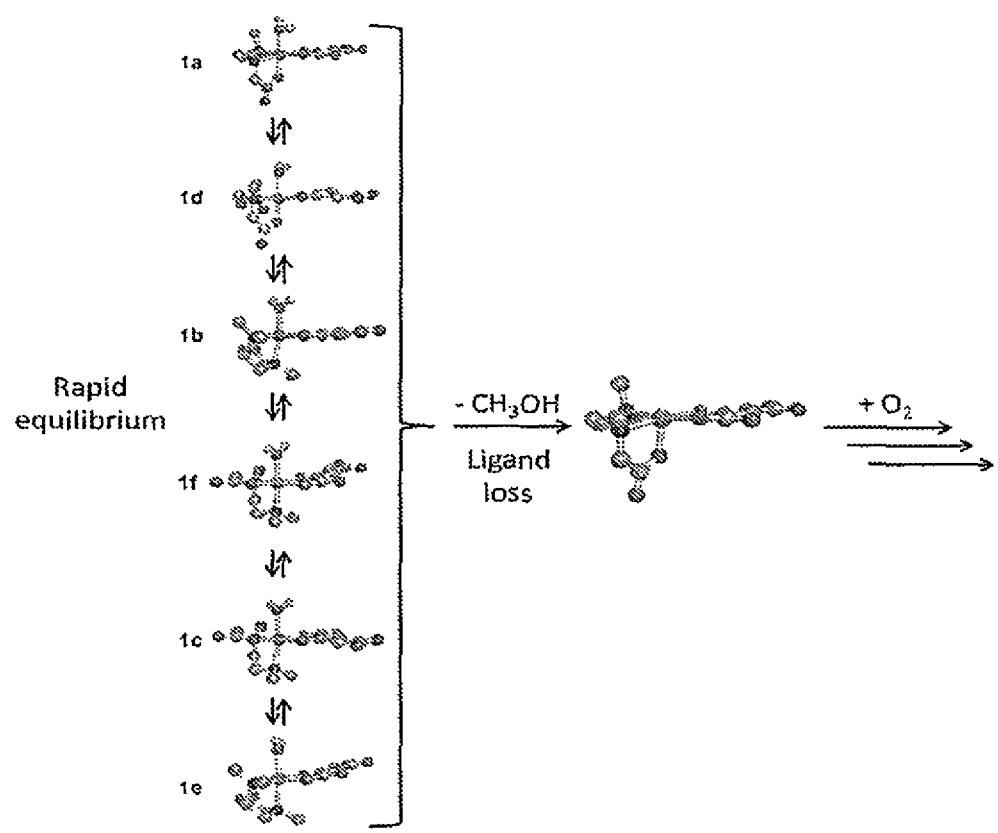
FIG. 45 presents representation of the six possible configurations present in solution in a rapid equilibrium.
Figure 46:
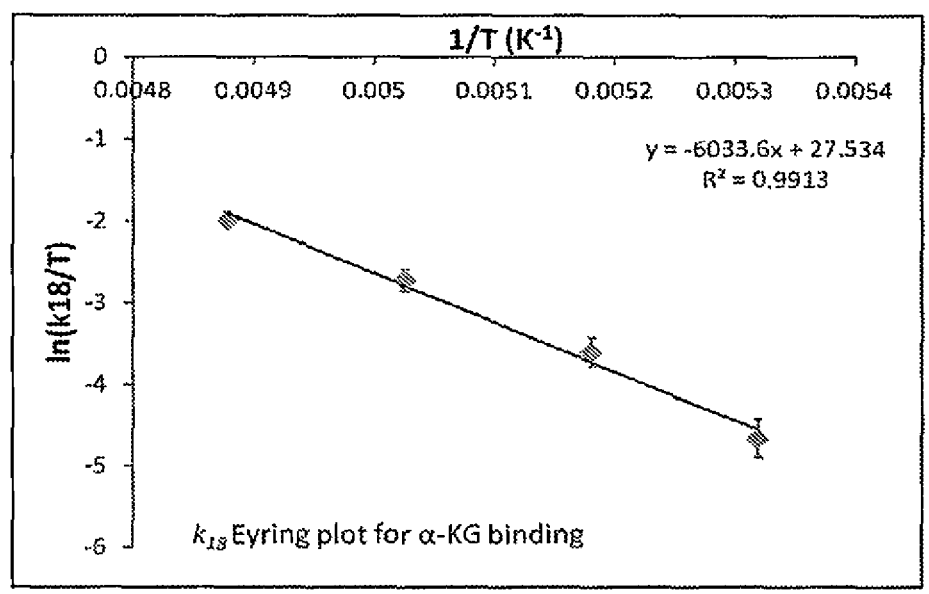
FIG. 46 is a graph of Eyring process of k$_{18}$ for the binding of α-KG to 17. Data collected over a temperature range of −85 to −70° C. Each data point is the average of at least three data scans.
Figure 47:
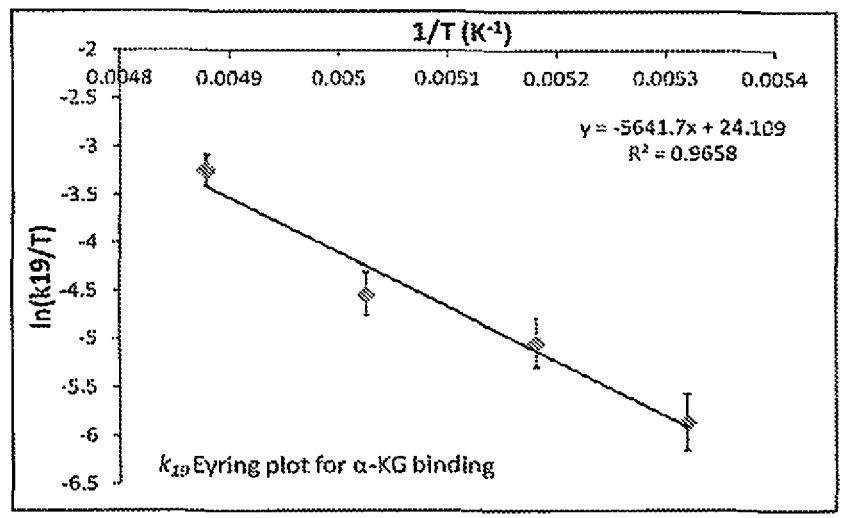
FIG. 47 is a graph of Eyring process of k$_{19}$ for the binding of α-KG to 17. Data collected over a temperature range of −85 to −70° C. Each data point is the average of at least three data scans.
Figure 48:
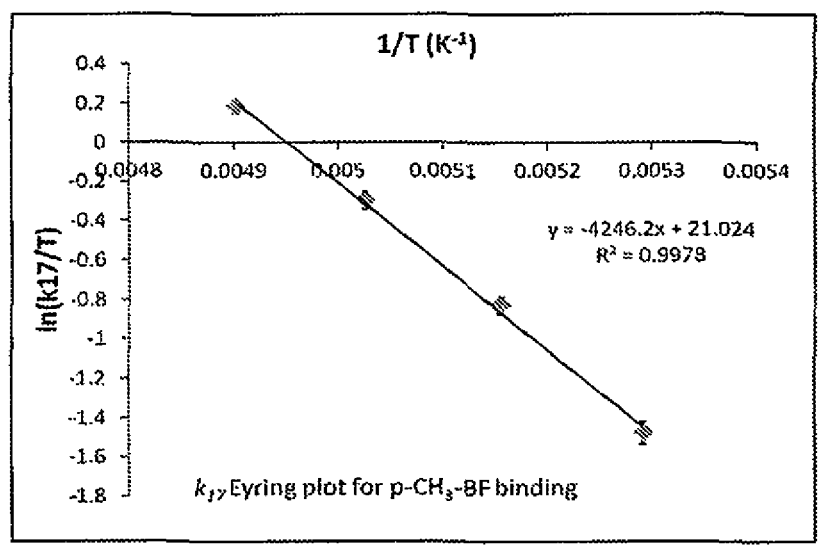
FIG. 48 is a graph of Eyring process of k$_{17}$ for the binding of p-CH$_3$-BF to 17. Data collected over a temperature range of −85 to −70° C. Each data point is the average of at least three data scans.
Figure 49:
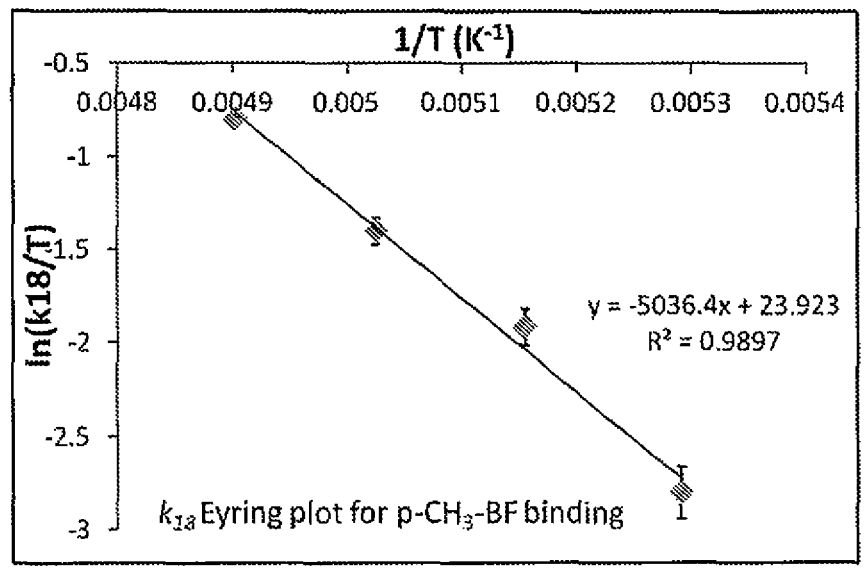
FIG. 49 is a graph of Eyring process of k$_{18}$ for the binding of p-CH$_3$-BF to 17. Data collected over a temperature range of −85 to −70° C. Each data point is the average of at least three data scans.
Figure 50:
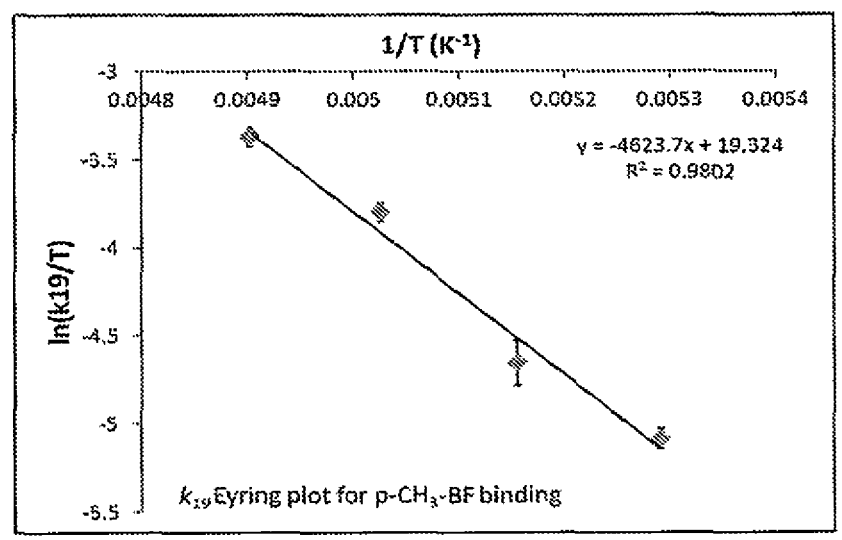
FIG. 50 is a graph of Eyring process of k$_{19}$ for the binding of p-CH$_3$-BF to 17. Data collected over a temperature range of −85 to −70° C. Each data point is the average of at least three data scans.
Figure 51:
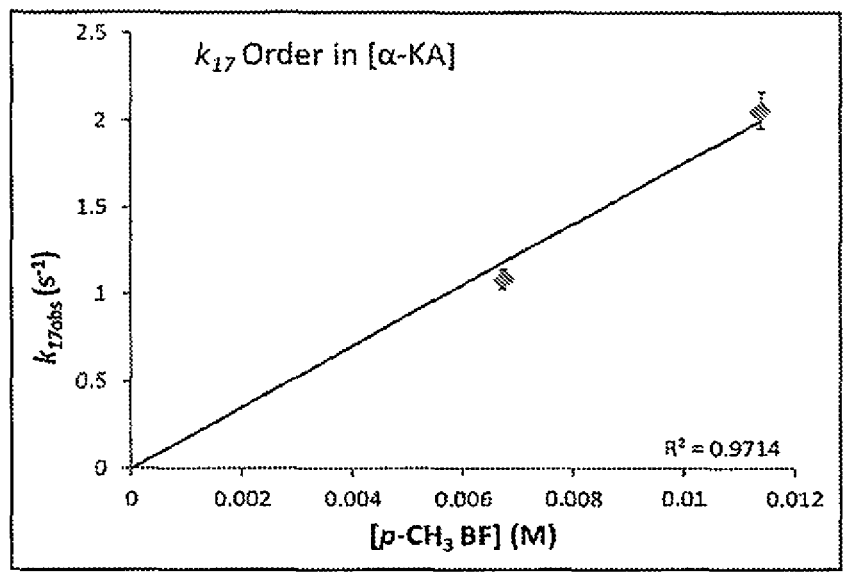
FIG. 51 is a graph of order determination of the k$_{17}$ reaction in α-KA. At least 4 data points collected at each concentration.
Figure 52:
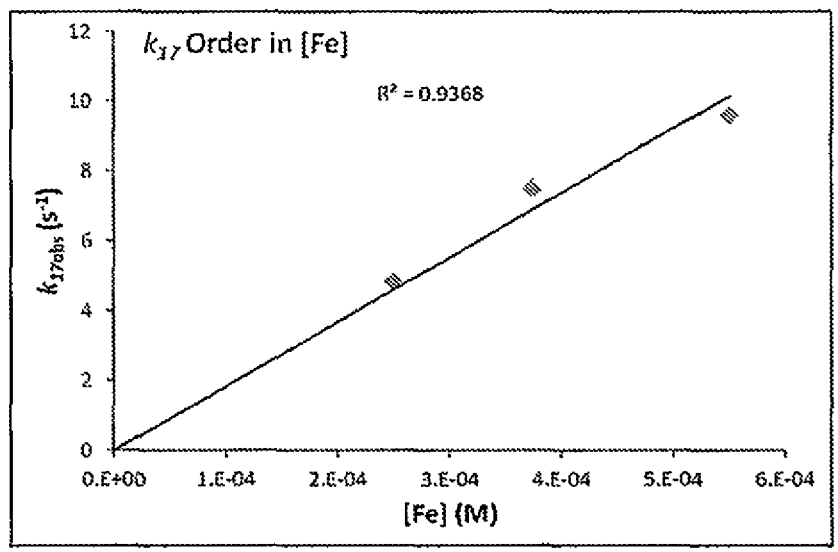
FIG. 52 is a graph of order determination of the k$_{17}$ reaction in 17. At least 4 data points collected at each concentration.
Figure 53:
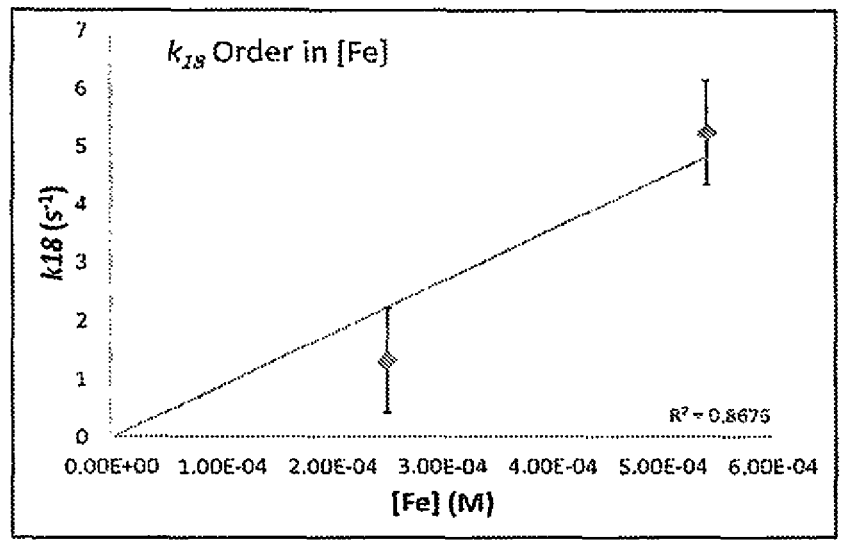
FIG. 53 is a graph of order determination of the k$_{18}$ reaction in 17. At least 4 data points collected at each concentration.
Figure 54:
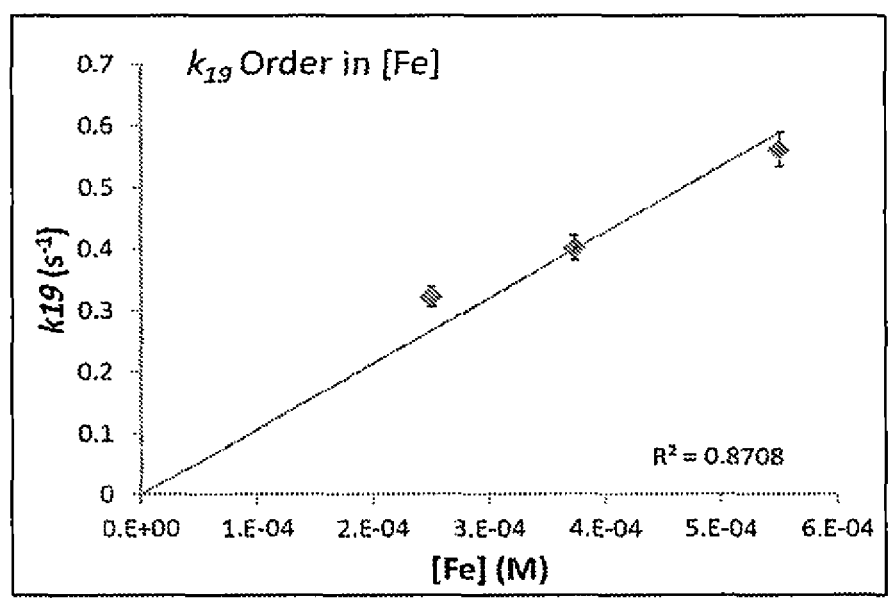
FIG. 54 is a graph of order determination of the k$_{19}$ reaction in 17. At least 4 data points collected at each concentration.

In all aspects of the invention described herein, it should be noted that a set of isomers may exist for the catalysts described herein, e.g. see FIG. 45. The use of a single isomer or a combination of isomers is contemplated. DFT calculations can be used to predict the relative reactivity of these isomers. Experimentally, multidimensional EPR spectroscopic methods using isotopically labeled ligand can be used to determine the relative reactivity of these isomers. In one embodiment, the isomer used to catalyze a reaction has a configuration substantially similar to 1a in FIG. 45. In one embodiment, the isomer used to catalyze a reaction has a configuration substantially similar to 1b in FIG. 45. In one embodiment, the isomer used to catalyze a reaction has a configuration substantially similar to 1c in FIG. 45. In one embodiment, the isomer used to catalyze a reaction has a configuration substantially similar to 1d in FIG. 45. In one embodiment, the isomer used to catalyze a reaction has a configuration substantially similar to 1e in FIG. 45. In one embodiment, the isomer used to catalyze a reaction has a configuration substantially similar to 1f in FIG. 45. For enantioselective oxidation reactions, a particular isomer may be used.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although any known methods, devices, and materials may be used in the practice or testing of the invention, the methods, devices, and materials in this regard are described herein.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment of the invention.

As used herein, the term "monomer" refers to a mononuclear metal complex molecule.

As used herein, the terms "turnover number" or "turnover" are used interchangeably to refer to the number of moles of substrate that a mole of catalyst can convert before becoming deactivated.

As used herein, the term "ligand" refers to a set of atoms, ions, or molecules in contact with a metal ion.

As used herein, the term "tridentate N,N,O-ligand" refers to a ligand which binds a metal ion using two nitrogen atoms and an oxygen atom.

As used herein, the term "alkyl" means a straight or branched, saturated aliphatic radical having a chain of carbon atoms. The term "alkyl" includes cycloalkyl or cyclic alkyl. $C_x$ alkyl and $C_x$-$C_y$ alkyl are typically used where X and Y indicate the number of carbon atoms in the chain. For example, $C_1$-$C_6$ alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$)aryl($C_0$-$C_3$)alkyl includes phenyl, benzyl, phenethyl, 1-phenylethyl 3-phenylpropyl, and the like. Backbone of the alkyl can be optionally inserted with one or more heteroatoms, such as N, O, or S. Examples of alkyl radicals include, but are not limited to, methyl, ethyl, propyl, isopropyl, n-butyl, tert-butyl, neopentyl, n-hexyl, and n-octyl radicals.

In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkynls that have a chain of between 1 and 6 carbons and at least one triple bond, e.g., ethynyl, 1-propynyl, 2-propynyl, 1-butynyl, iso-pentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine. A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl (—CF3), 2,2,2-trifluoroethyl, perfluoroethyl, 2,2,2-trifluoro-1,1-dichloroethyl, and the like).

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$-$C_y$cylcyl are typically used where X and Y indicate the number of carbon atoms in the ring system. The cycloalkyl group additionally can be optionally substituted, e.g., with 1, 2, 3, or 4 substituents. Examples of cyclyl groups include, without limitation, cyclopropyl, cyclobutyl, cyclopentyl, cyclopentenyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo [2.2.1]hept-1-yl, and the like The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, 0, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

The terms "bicyclic" and "tricyclic" refers to fused, bridged, or joined by a single bond polycyclic ring assemblies. As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

The term "aryl" refers to monocyclic, bicyclic, or tricyclic fused aromatic ring system. $C_x$ aryl and $C_x$-$C_y$aryl are typically used where X and Y indicate the number of carbon atoms in the ring system. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3,1-6, or 1-9 heteroatoms of N, O, or S if monocyclic, bicyclic, or tricyclic, respectively. $C_x$ heteroaryl and $C_x$-$C_y$heteroaryl are typically used where X and Y indicate the number of carbon atoms in the ring system. Heteroaryls include, but are not limited to, those derived from benzo[b]furan, benzo[b] thiophene, benzimidazole, imidazo[4,5-c]pyridine, quinazoline, thieno[2,3-c]pyridine, thieno[3,2-b]pyridine, thienop, 3-blpyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazol[1,5-a]pyridine, pyrazolol[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3c]pyridine, pyrrolo[3,2-c]pyridine, pyrrolo[3,2-b]pyridine, pyrrolo[2,3-d]pyrimidine, pyrrolo[3,2-d]pyrimidine, pyrrolo [2,3-b]pyrazine, pyrazolo[1,2-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, $CF_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, isopropyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —$SO_2$—. It is noted that the sulfonyl radical can be further substituted with a variety of substituents to form different sulfonyl groups including sulfonic acids (—$SO_3H$), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —NH$_2$. The term "alkylamino" means a nitrogen moiety having at least one straight or branched unsaturated aliphatic, cyclyl, or heterocyclyl radicals attached to the nitrogen. For example, representative amino groups include —NH$_2$, —NHCH$_3$, —N(CH$_3$)$_2$, —NH(C$_1$-C$_{10}$alkyl), —N(C$_1$-C$_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NH(heteroaryl), and —N(heteroaryl)$_2$. Optionally, two substituents together with the nitrogen can also form a ring. Unless indicated otherwise, the compounds described herein containing amino moieties can include protected derivatives thereof Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an (C$_2$-C$_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —OCH$_2$CH$_2$OCH$_3$, and the like. The term "alkoxycarbonyl" means —C(O)O-(alkyl), such as —C(=O)OCH$_3$, —C(=O)OCH$_2$CH$_3$, and the like. The term "alkoxyalkyl" means -(alkyl)-O-(alkyl), such as —CH$_2$OCH$_3$, —CH$_2$OCH$_2$CH$_3$, and the like. The term "aryloxy" means —O-(aryl), such as —O-phenyl, —O-pyridinyl, and the like. The term "arylalkyl" means -(alkyl)-(aryl), such as benzyl (i.e., —CH$_2$phenyl), —CH$_2$-pyrindinyl, and the like. The term "arylalkyloxy" means —O-(alkyl)-(aryl), such as —O-benzyl, —O—CH$_2$-pyridinyl, and the like. The term "cycloalkyloxy" means —O-(cycloalkyl), such as —O-cyclohexyl, and the like. The term "cycloalkylalkyloxy" means —O-(alkyl)-(cycloalkyl), such as —OCH$_2$cyclohexyl, and the like. The term "aminoalkoxy" means —O-(alkyl)-NH$_2$, such as —OCH$_2$NH$_2$, —OCH$_2$CH$_2$NH$_2$, and the like. The term "mono- or di-alkylamino" means —NH(alkyl) or —N(alkyl)(alkyl), respectively, such as —NHCH$_3$, —N(CH$_3$)$_2$, and the like. The term "mono- or di-alkylaminoalkoxy" means—O-(alkyl)-NH(alkyl) or —O-(alkyl)-N(alkyl)(alkyl), respectively, such as —OCH$_2$NHCH$_3$, —OCH$_2$CH$_2$N(CH$_3$)$_2$, and the like. The term "arylamino" means —NH(aryl), such as —NH-phenyl, —NH-pyridinyl, and the like. The term "arylalkylamino" means —NH-(alkyl)-(aryl), such as —NH-benzyl, —NHCH$_2$-pyridinyl, and the like. The term "alkylamino" means —NH(alkyl), such as —NHCH$_3$, —NHCH$_2$CH$_3$, and the like. The term "cycloalkylamino" means —NH-(cycloalkyl), such as —NH-cyclohexyl, and the like. The term "cycloalkylalkylamino" —NH-(alkyl)-(cycloalkyl), such as —NHCH$_2$-cyclohexyl, and the like.

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a C$_1$ alkyl comprises methyl (i.e., —CH$_3$) as well as —CR$_a$R$_b$R$_c$ where R$_a$, R$_b$, and R$_c$ can each independently be hydrogen or any other substituent where the atom alpha to the carbon is a heteroatom or cyano. Hence, CF$_3$, CH$_2$OH and CH$_2$CN are all C$_1$ alkyls.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

As used herein, the term "linker" means an organic moiety that connects two parts of a compound. Linkers typically comprise a direct bond or an atom such as oxygen or sulfur, a unit such as NH, C(O), C(O)NH, SO, SO$_2$, SO$_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), SO$_2$, NH, C(O). The terms linker and spacer are used interchangeably herein.

As used here in the term "isomer" refers to compounds having the same molecular formula but differing in structure. Isomers which differ only in configuration and/or conformation are referred to as "stereoisomers." The term "isomer" is also used to refer to an enantiomer.

Other than in the operating examples, or where otherwise indicated, all numbers expressing quantities of ingredients or reaction conditions used herein should be understood as modified in all instances by the term "about." The term "about" when used in connection with percentages may mean ±1% of the value being referred to. For example, about 100 means from 99 to 101.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology described herein is further illustrated by the following examples which in no way should be construed as being further limiting.

Example 1

Low-Temperature Stopped-Flow Kinetic Studies of $[Fe^{II}(N_2O_1)Cl_2]^-$ with Alpha-Keto Acids and their Subsequent Reactivity with Dioxygen Materials and Methods General Experimental Considerations. The 2-((2-dimethylamino)ethyl) (methyl)amino)acetic acid ($N_2O_1$) ligand and $[C_{14}H_{19}N_2][Fe^{II}(N_2O_1)(Cl_2)]$ complex were prepared according to previously published procedures (Cappillino, P. J.; et al., *Dalton Transactions* 2012, 41, 5662). $K[Ru^{III}(Hedta)Cl].2H_2O$ was synthesized according to the previously published procedure (Diamantis, A. A.; Dubrawski, J. V. *Inorganic Chemistry* 1981, 20, 1142; Mercer, E. E.; Buckley, R. R. *Inorganic Chemistry* 1965, 4, 1692). Thallium triflate and thallium hexafluorophosphate were used inside an inert atmosphere glovebox with extreme care due to the high toxicity of thallium salts. Tetraethylammonium hydroxide 25% in methanol was purchased from Sigma and the exact concentration was determined by titration prior to use. Prior to use, methanol (Pharmaco-Aaper) was distilled over magnesium metal. The dimethylformamide was processed through a PureSolv solvent purification system from Innovative Technologies and then distilled over phosphorus pentoxide (Acros Organics, ACS grade). Tetrahydrofuran was processed through a PureSolv solvent purification system from Innovative Technologies. α-Ketoglutaric acid and the mono-sodium salt of α-ketoglutarate were purchased from Sigma and used as received. Unstabilized dichloromethane was obtained from Fisher and was distilled over calcium hydride before use. All of the solvents used in air-sensitive work were thoroughly degassed by subjecting them to at least seven successive freeze-pump-thaw cycles, after which they were transferred to an inert atmosphere glove box, in which all of the solution preparations were carried out. Non-stopped-flow UV/vis spectra were collected on a Hewlett-Packard (Agilent) 8453 spectrophotometer using the HP UV/vis Chemstation software package. NO gas was passed through a column of moist KOH prior to use. Warning: NO is a toxic, powerful physiological reagent (toxicity limit 25 ppm at 25° C.). Additionally, the reaction of superoxides (formation of Fe(II) reaction with dioxygen) with NO results in the formation of redox-related species including peroxy-nitirite anion ($OONO^-$) is extremely reactive and toxic (Feelisch, M. S.; John Whiley & Sons: Chichester, 1996). Ensuring the complete absence of $O_2$ when working with NO is imperative.

Synthesis of $[Fe^{II}(N_2O_1)Cl_2][Na]$ (17). Dried $N_2O_1$ (158 mg) ligand was dissolved in approximately 30 mL of THF in an inert atmosphere glovebox. In a separate vial, $NaOCH_3$ (50 mg) was dissolved in minimal (>1 mL) of methanol and added to the solution of $N_2O_1$ and was allowed to stir which resulted in a yellow solution. Separately, $Fe^{II}Cl_2$ (105 mg) was dissolved in minimal methanol and added to the solution of the $N_2O_1$ and $NaOCH_3$. Immediately a white precipitate was observed and the solution was allowed to stir overnight. The solution was then filtered in the glovebox and washed with THF and ether which yielded a while solid (150 mg, 75% yield). Characterization described in reference (Cappillino, P. J.; et al., Dalton Transactions 2012, 41, 5662.;Thesis of Tarves, P. C., Boston University, 2012).

General synthesis of [α-keto acid] [NEt$_4$] salts. The desired α-keto acid (200-300 mg) is dissolved in about 5 mL of methanol under a flow of $N_2$. Then 0.98 equivalents of tetraethylammonium hydroxide (25% in methanol) is added and allowed to stir for 1-2 hours also under $N_2$. The methanol is then removed under reduced pressure yielding an oily solid. The oil is then triturated with THF several times until a dry solid is apparent. The flask is then transferred to an inert atmosphere glovebox and stored in a vial until use.

Stopped-flow Spectroscopy and Data analysis. Stopped-flow time-resolved spectra were acquired using a Hi-Tech Scientific KinetAsyst SF-61DX2 CryoStopped-Flow system (TgK Scientific Ltd.) equipped with a quartz tungsten halogen light source, a J&M TIDAS diode array detector and a Brandenburg 4479 Series PMT monochromator. The 1.00 cm³ quartz mixing cell is submerged within an ethanol cooling bath and low-temperatures of ±0.1° C. are maintained using a CAL 3200 automatic temperature controller. Data acquisition was performed using TIDAS-DAQ and/or Kinetic Studio software programs with mixing times of 2-3 ms. Data analysis was performed using Kinetic Studio, IGOR Pro 5.0 (Wavemetrics, Inc.) and ReactLab Kinetics Global Analysis software (JPlus Consulting, Pty. Ltd.) or utilizing nonlinear least-squares fitting methods contained in Specht/32 version 3.0.36. All concentrations in kinetic experiments are reported as the final observed concentration after mixing in the stopped-flow cell.

Sample Preparation. The following is the procedure followed when prepping samples for use in the stopped-flow UV/vis spectrometer. In an inert atmosphere glovebox a sample of $[Fe^{II}(N_2O_1)Cl_2][Na]$ (17) was dissolved in about 5 mL of distilled and degassed methanol forming a colorless solution. The concentration was determined by removing an aliquot and adding [α-KG] [Na] and using the intensity of the peak at 500 nm in the UV/vis spectrum ($\varepsilon 125=M^{-1}$ $cm^{-1}$) for 18. The solution was then diluted with excess methanol to the desired concentration. The solution was placed in a 200 mL Wheaton bottle with a butyl-rubber stopped, crimped with an aluminum seal, and placed in the freezer within the glovebox at −30° C. until ready to use. Solutions of iron complex were prepared no more than two days in advance. All adduct complexes are prepared on-site to prevent decomposition or reaction with trace $O_2$ in solution. Solid samples (α-ketoglutarate or benzoylformate salts) were weighed out into Wheaton bottles, transferred to the glove box where they were capped with butyl-rubber stoppers and crimped with aluminum seals. Pure degassed and distilled methanol was also used for washing the stopped-flow system to ensure it was completely air-free before beginning the experiment. Solutions of NO and $O_2$ were also prepared by using a gas-tight syringe of methanol and purging it with either gas using a long needle. The gas-tight syringe was purged for about 10-15 minutes to ensure complete saturation of the gases in methanol. Initial concentrations are assumed to that of fully saturated concentrations in methanol for NO (14.5 mM) (*Methods in Enzymology*; Packer, L.; Cadenas, E., Eds., 2005; Vol. 396) and $O_2$(10 mM) (Battino, R.; et al., *Journal of Physical Chemistry Reference Data* 1983, 12, 163) at room temperature. Variable concentrations of the gasses were obtained from dilution of the concentrated solution into another gas-tight syringe of solvent by attaching the two syringed by their three-way stopcocks.

Reactivity Studies. Gas chromatography studies were performed on a Hewlett Packard 5980 Series II GC equipped with an analytical methyl silicon capillary column (30 m×0.25 mm i.d.) and interfaced to a HP3396 Series II Integrator with the exception of cyclooctane performed on Agilent GC-MS 6890N is a gas chromatography instrument equipped with a MS detector up to 800 m/z. The ionization is electron impact (EI) and software is ChemStation. Gradient temperature programs were used for baseline resolution. Quantification of the products was done using either 1-bromo-4-t-butyl-phenol or chlorobenzene as an internal standard. For each reaction, two samples were prepared and then each reaction was analyzed a minimum of three times to provide reproducibility as well. For all reactions, products were verified by the addition of authentic samples. In a typical reaction, a stock solution of $[FeN_2O_1(Cl_2)][Na]$ (17) was dissolved in DMF and the concentration was determined by adding some [α-KG][Na] and using UV/vis ($\lambda_{max}$ 525 and $\varepsilon=175$ $M^{-1}$ $cm^{-1}$). The original solution of 17 was diluted down to the desired final concentration (1-20 μM) into 1 mL of DCM (in the case of liquid substrates only 0.5 mL DCM was utilized with 0.5 mL substrate) and 0.01 mL DMF. The substrate was also added (1-4 M) followed by [α-KG][NEt₄] (10-20 mM). The vial was removed from the glovebox and equipped with a balloon of $O_2$ and allowed to react for one hour followed by the addition of the internal standard prior to GC analysis.

Reactivity of $[Fe^{II}(N_2O_1)(CH_3OH)Cl_2][Na]$ (17) with α-KG, $O_2$, and 9,10-dihydroanthracene. In a vial in an inert atmosphere glovebox, 192 mg of 9,10-dihydroanthrancene and 18.2 mg of α-ketoglutarate tetraethylammonium salt was dissolved in 1 mL of DCM and 0.01 mL DMF. Then 2 μL of a 5.1 mM $[Fe^{II}(N_2O_1)(CH_3OH)Cl_2][Na]$ solution in DMF was added to the reaction mixture. The vial was equipped with a butyl-rubber stopper and crimped with an aluminum seal. The reaction was brought out of the glovebox and equipped with a balloon of $O_2$ and allowed to stir at room temperature for two hours. After the reaction, 50 μL of an external standard, 1-bromo-4-t-butyl phenol was added and the reaction mixture was run through GC-FID and product amounts were quantified by utilizing $R_f$ values of standard reactions. For the anthracene product, a small amount of anthracene was found in the pure sample 9,10-DHA and the amount of this background anthracene was determined and accounted for.

Final concentrations: [Fe]=10.1 μM, [α-KG]=65 mM, [9,10-DHA]=1.05 M.

Reactivity of $[Fe^{II}(N_2O_1)(CH_3OH)Cl_2][Na]$ with α-KG, $O_2$, and 2,4-di-tert-butyl phenol. In a vial in an inert atmosphere glovebox, 230 mg of 2-4-di-tent-butyl phenol and 29.6 mg of α-ketoglutarate tetraethylammonium salt was dissolved in 1 mL of DCM and 0.01 mL DMF. Then 2 μL of a 5.1 mM $[Fe^{II}(N_2O_1)(CH_3OH)Cl_2][Na]$ solution in DMF was added to the reaction mixture. The vial was equipped with a butyl-rubber stopper and crimped with an aluminum seal. The reaction was brought out of the glovebox and equipped with a balloon of $O_2$ and allowed to stir at room temperature for two hours. After the reaction, 50 μL of an external standard, 1-bromo-4-t-butyl phenol was added and the reaction mixture was run through GC-FID and product amounts were quantified by utilizing $R_f$ values of standard reactions. Final concentrations: [Fe]=9.6 μM, [α-KG]=96 mM, [DBPH]=1.1 M.

Reactivity of $[Fe^{II}(N_2O_1)(CH_3OH)Cl_2][Na]$ with α-KG, $O_2$, and cyclohexene. In a vial in an inert atmosphere glovebox, 0.5 mL of cyclohexene 16.9 mg of α-ketoglutarate tetraethylammonium salt was dissolved in 0.5 mL of DCM and 0.01 mL DMF. Then, 2 μL of a 5.1 mM $[Fe^{II}(N_2O_1)(CH_3OH)Cl_2][Na]$ solution in DMF was added to the reaction mixture. The vial was equipped with a butyl-rubber stopper and crimped with an aluminum seal. The reaction was brought out of the glovebox and equipped with a balloon of $O_2$ and allowed to stir at room temperature for two hours. After the reaction, 50 μL of an external standard, 1-bromo-4-t-butyl phenol was added and the reaction mixture was run through GC-FID and product amounts were quantified by utilizing $R_f$ values of standard reactions. Final concentrations: [Fe]=9.6 μM, [α-KG]=58 mM, [cyclohexene]=4.6 M.

$[Fe^{II}(N_2O_1)(CH_3OH)Cl_2][Na]$ with α-KG, $O_2$, and cyclooctane. In a vial in an inert atmosphere glovebox, 0.5 mL of cyclooctane 26.5 mg of α-ketoglutarate tetraethylammonium salt was dissolved in 0.5 mL of DCM and 0.01 mL DMF. Then either 8.4 or 1.0 μL of a 1.18 mM $[Fe^{II}$ ($N_2O_1$)($CH_3OH$)$Cl_2$][Na] solution in DMF was added to the reaction mixture to obtain the desired concentration. The vial was equipped with a butyl-rubber stopper and crimped with an aluminum seal. The reaction was brought out of the glovebox and equipped with a balloon of $O_2$ and allowed to stir at room temperature for two hours. After the reaction, 50 μL of an external standard, 1-bromo-4-t-butyl phenol was added and the reaction mixture was run through GC-MS 6890N and product amounts were quantified by utilizing $R_f$ values of standard reactions. For the product, a small amount of cyclooctanol and cyclooctanone was found in when the pure sample was run through the GC-MS 6890N and this amount of products was determined and subtracted from the reactivity trials. Final concentrations: [Fe]=9.7 or 1.1 μM, [α-KG]=93 mM, [cyclooctane]=4.6 M.

Reactivity of [$Fe^{II}$($N_2O_1$)($CH_3OH$)$Cl_2$][Na] with α-KG, $O_2$ and cyclohexane. In a vial in an inert atmosphere glovebox, 0.5 mL of cyclohexane 22 mg of α-ketoglutarate tetraethylammonium salt was dissolved in 0.5 mL of DCM and 0.01 mL DMF. Then, 2 μL of a 5.1 mM [$Fe^{II}$($N_2O_1$) ($CH_3OH$)$Cl_2$][Na] solution in DMF was added to the reaction mixture. The vial was equipped with a butyl-rubber stopper and crimped with an aluminum seal. The reaction was brought out of the glovebox and equipped with a balloon of $O_2$ and allowed to stir at room temperature for two hours. After the reaction, 50 μL of an external standard, 1-bromo-4-t-butyl phenol was added and the reaction mixture was run through GC-FID and product amounts were quantified by utilizing $R_f$ values of standard reactions. Issues in quantifying the products (cyclohexanol and cyclohexanone) arose from the inability to separate the products from the DMF in the reaction due to their comparable boiling points (160° C., 155° C., and 153° C. for cyclohexanol, cyclohexanone, and DMF, respectively).

Computational Studies. DFT calculations were carried out using the Gaussian 09 software package (Revision B.01). To allow for comparison to previous calculations (Cappillino, P. J.; et al., *Dalton Trans* 2012, 41, 474), the unrestricted B3LYP method of hybrid DFT, which includes Becke's three-parameter exchange functional (B3) and the Lee, Yang and Parr (LYP) correlation functional (Becke, A. D. *Physical Review A* 1988, 38, 3098; Becke, A. D. *Journal of Chemical Physics* 1992, 96, 2155; Becke, A. D. *Journal of Chemical Physics* 1992, 97, 9173; Becke, A. D. *Journal of Chemical Physics* 1993, 98, 5648; Lee, C. T.; Yang, W. T.; Parr, R. G. *Physical Review B* 1988, 37, 785; Vosko, S. H.; et al., *Canadian Journal of Physics* 1980, 58, 1200), was used for the geometry optimization and frequency calculation. The valence triple-ζ-311+G(d,p) (Krishnan, R.; et al., *Journal of Chemical Physics* 1980, 72, 650) basis set was used, which includes polarization functions on all atoms and diffuse functions on non-hydrogen atoms. The energy minimized geometry was obtained by removal of two $H_2O$ ligands and addition of benzoylformate to the optimized [$Fe^{II}$($N_2O_1$) ($H_2O$)$_3$]$^+$ geometry obtained in previous studies (Cappillino, P. J.; et al., *Dalton Trans* 2012, 41, 474) using Gaussview 5.0, followed by re-optimization. Solvation effects were handled using the self-consistent reaction field (SCRF) approach as implemented by Gaussian 09 using the default IEF-PCM method. Dimethylsulfoxide, with a dielectric constant of 46.8, was used as the solvent. A frequency calculation verified the geometry as being energy minimized by the absence of imaginary frequencies.

Results and Discussion

Figure 8:
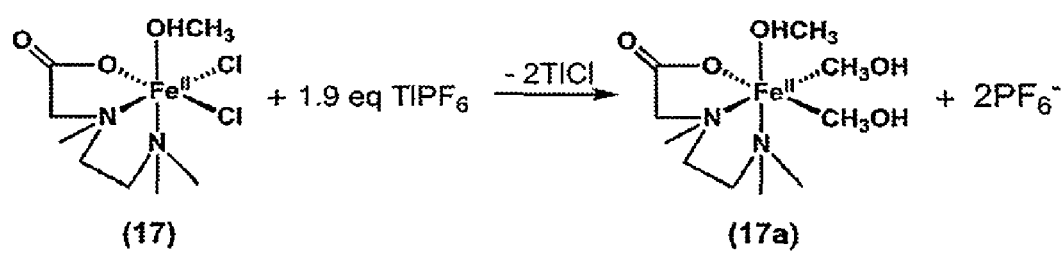
FIG. 8 is a diagram that illustrates the synthesis of 17a, $[Fe^{II}(N_2O_1)(CH_3OH)_3)]$.

Binding studies of alpha-keto acids to [$Fe^{II}$($N_2O_1$)($Cl$)$_2$ (MeOH)]$^-$ (17). The binding of alpha-keto acids to 17 was investigated at low-temperatures by stopped-flow kinetic analysis. Initial studies were performed on the completely solvated form of complex 17, [$Fe^{II}$($N_2O_1$)($CH_3OH$)$_3$)] (17a). This was done by chemically removing the coordinated chlorides and replacing them with non-coordinating ligands such a hexafluorophosphate, $PF_6^-$. This would than result in a solvated complex (complex 17 coordinated to three methanol ligands) in solution (17a, FIG. 8). This was achieved by reacting 17 with 1.9 equivalents of thallium hexafluorophosphate (TlPF$_6$), and filtering off the insoluble thallium chloride to synthesize 17a, where the iron center is presumed to be coordinated by three solvent molecules (methanol).

Figure 9A:
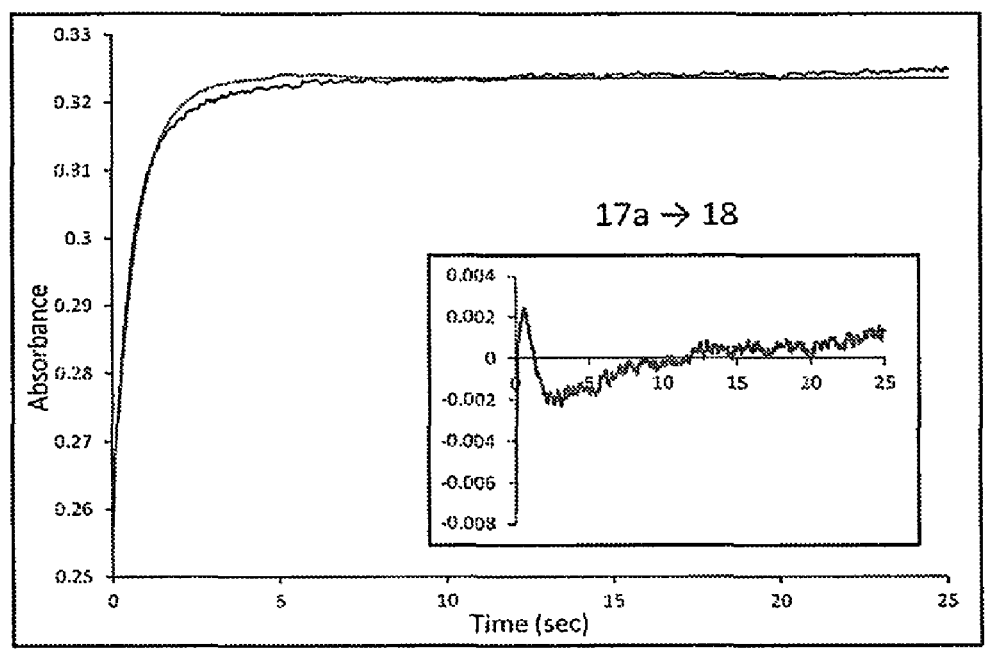
FIGS. 9A-9B is a set of graphs of single wavelength data of 17a (0.49 mM) with α-KG (4.9 mM) fit to equations 4.9 and 4.10.
Figure 9B:
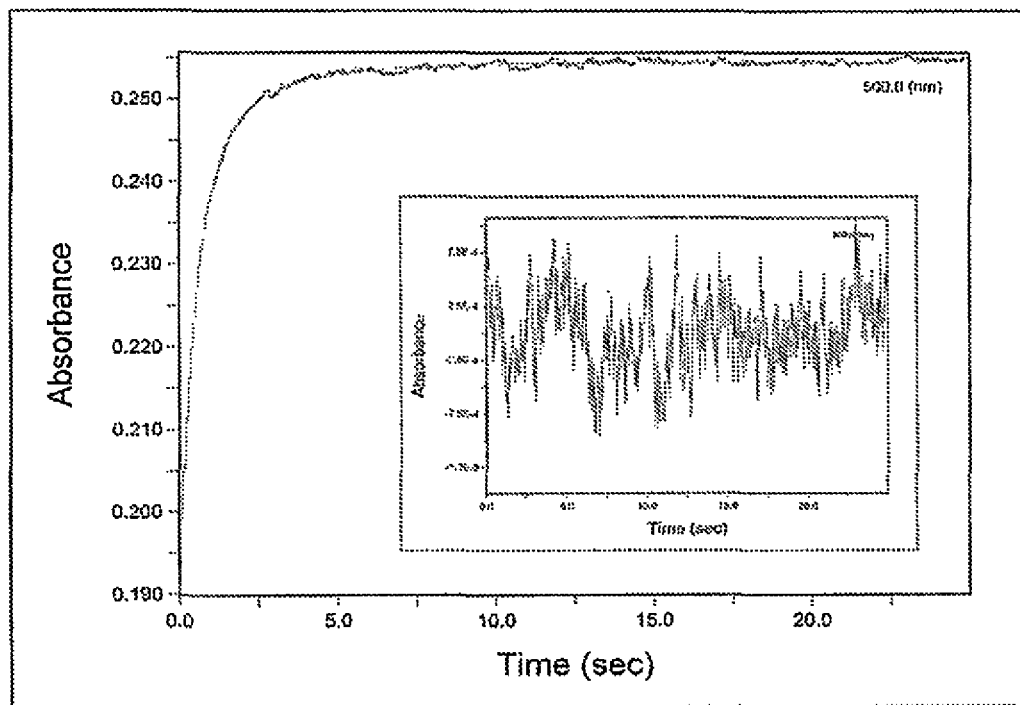

The same single-mixing experiment was performed with α-KG; the single mixing data is shown in FIGS. 9A-9B. These data were initially fit to a simple one step exponential (17a→18) in FIG. 9A however the residuals clearly show a poor fit to the data and therefore a second mechanistic step was added. The data was then best fit to a simplified two-step process according to the stoichiometry in equations 4.1 and 4.2 and fit according to the rate laws in equation 4.3 and 4.4.

$$17a \xrightarrow{k_{18obs}} 17b \quad (4.1)$$

$$17b \xrightarrow{k_{19}} 18 \quad (4.2)$$

$$\frac{-d[17a]}{dt} = \frac{d[17b]}{dt} = k_{18obs}[17a] = k_{18}[17a][\alpha KG] \quad (4.3)$$

$$\frac{-d[17b]}{dt} = \frac{d[18]}{dt} = k_{19}[17b] \quad (4.4)$$

Figure 10:
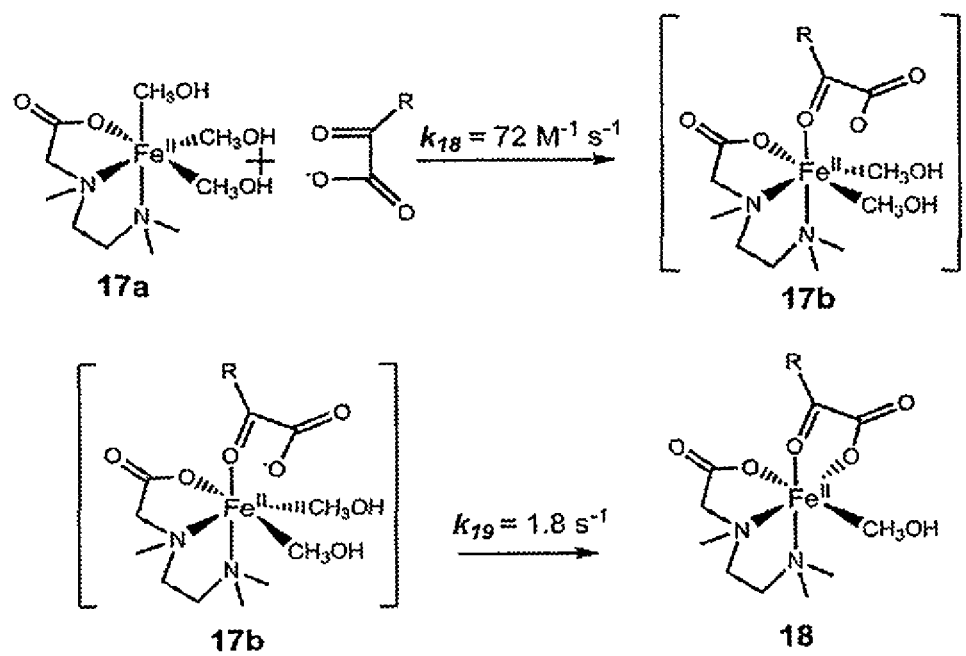

The rates for the proposed steps in the mechanism shown in FIG. 10. This pathway assumes a rapid first step for the initial binding of α-KG and a slower second step similar and has been tentatively assigned to the mechanism in FIG. 10. These kinetic models establish a time scale for spectroscopic characterization of each of the proposed intermediates and structures by rapid freeze-quench EPR and Mössbauer. Flow Resonance Raman spectroscopy can be used to characterize the many proposed intermediates.

Figure 11:
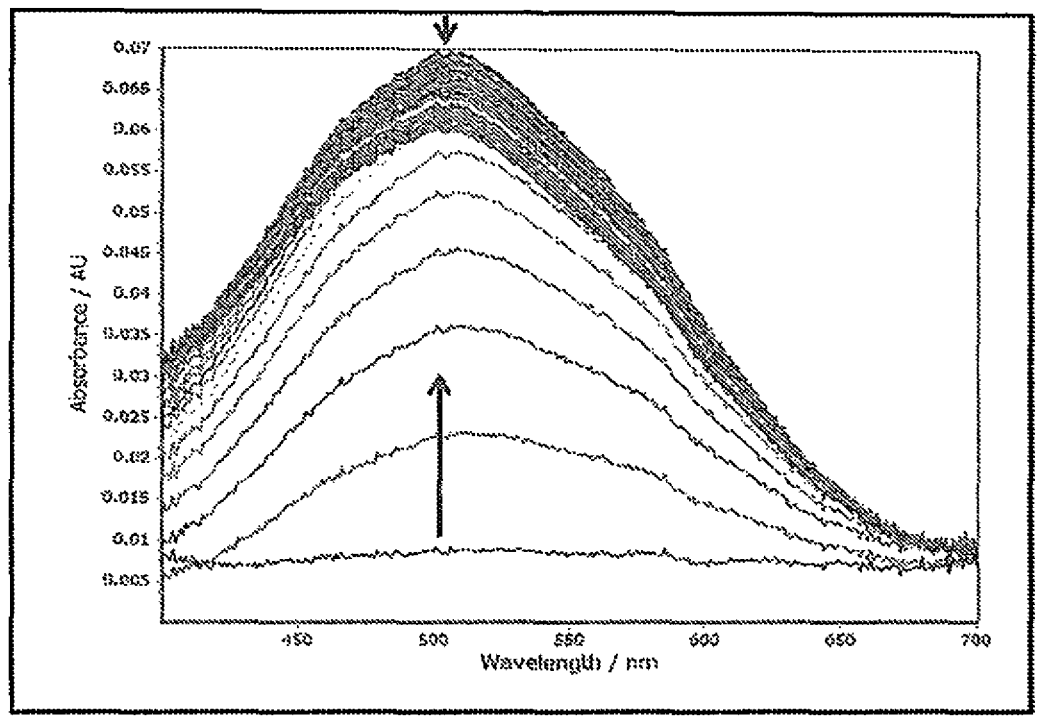
FIG. 11 is a graph of diode array data for the binding of α-KG (0.38 mM) to 17 (5.7 mM) at −85° C. in methanol showing the first 10 seconds of the reaction.

The same analysis was then performed with [$Fe^{II}$($N_2O_1$) ($Cl$)$_2$(MeOH)]$^-$ (17) which contains two bound chloride ions to see if these ions have any effect on the reaction. Single-mixing studies were performed where a methanol solution of 17 was mixed with a second methanol solution of α-KG salt at −85° C. and the reaction was followed at 500 nm which corresponds to observed $\lambda_{max}$ of 18. The diode array data for the reaction is shown in FIG. 11 where there is a large increase in the chromophore of approximately 500 nm, for the formation of the α-KG adduct complex. Also, there is no observed formation of the μ-oxo species or isosbestic point as seen in the reaction of 18 with $O_2$ (FIG. 1) suggesting the mixing cell is air-free and the only processes being observed is the binding of α-KG.

Figure 12A:
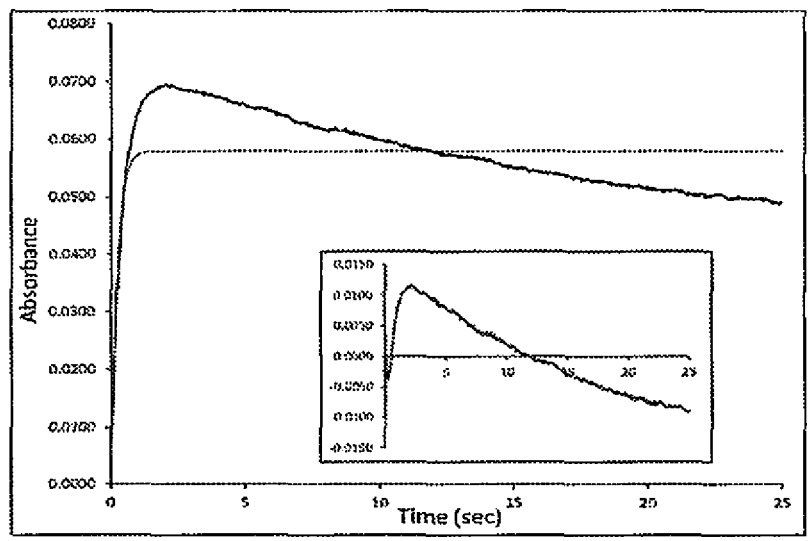
FIGS. 12A-12B is a set of graphs demonstrating mechanistic models that led to poor fits in the data for the binding of α-KG to 17.
Figure 12B:
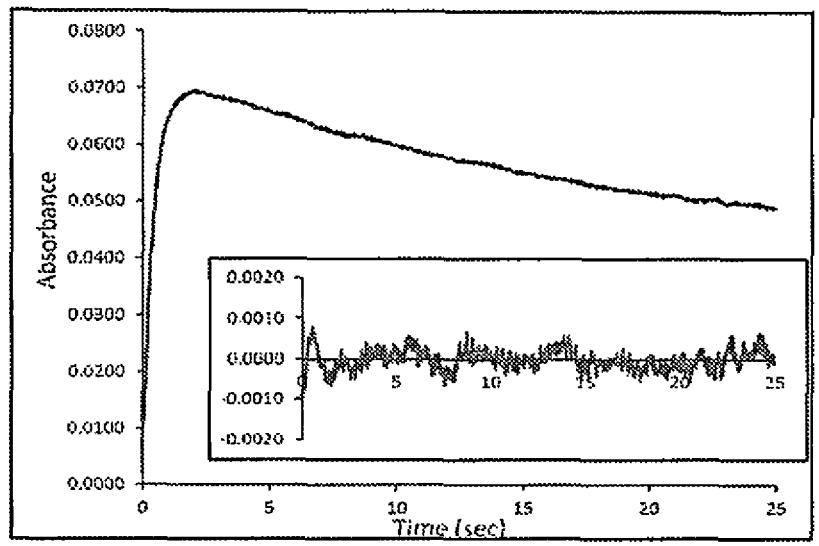

Next, the single wavelength data was collected at 500 nm which affords a better signal-to-noise ratio which is required for species with weak extinction coefficients. More simplified mechanisms of either a concerted bidentate binding in a single step (A→B, FIG. 12A) or a two step process (A→B→C, FIG. 12B) where one oxygen atom of α-KG. The case of the single exponential clearly does not fit to the data, however, a two-step processes appears to fit quite well. But the calculated rates for a two-step process (FIG. 12B) have physically unrealistic standard deviations, particularly for the second step, which suggest a local minimum in the fit analysis and therefore can be ruled out.

Figure 13:
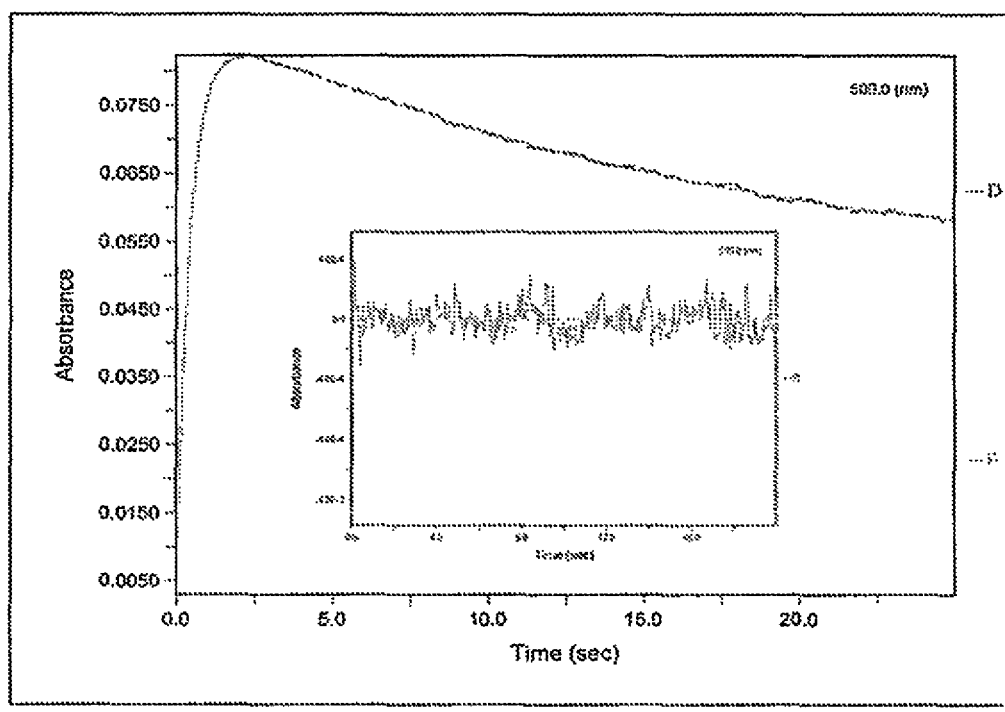
FIG. 13 is a graph of single wavelength data (green) at 500 nm for the binding of α-KG (5.54 mM) to $[Fe^{II}(N_2O_1)Cl_2(MeOH)]^-$ (0.55 mM) (17) collected at −85° C. Fit (red) according to equations 4.8-4.10. Inset: Residuals to fit.

The data in FIG. 13 fit best to a three-step mechanism according to the stoichiometry shown in equations 4.5-4.7. The single wavelength data at 500 nm in FIG. 13 best fit to a three step process with the stoichiometry described by equations 4.5-4.7. Attempts to obtain an order dependence for this process were unsuccessful due the low solubility of the [α-KG][Na] salt in methanol (~10 mM) and the low extinction coefficient of 18 (125 $M^{-1}$ $cm^{-1}$). The challenges were trying to stay close to pseudo first order in α-KG (10 fold excess) and having a high enough absorbance of 18 to be observed (signal to noise). Therefore the order dependence (FIGS. 51-54) here is based off the observed order dependence for the reaction of 17 with p-$CH_3$-benzoylformate such that $k_{15}$ is first order in iron complex and α-keto acid and the subsequent steps ($k_{16}$ and $k_{17}$) are first order in iron and independent of α-keto acid (vide infra).

   (4.5)

   (4.6)

   (4.7)

Figure 14:
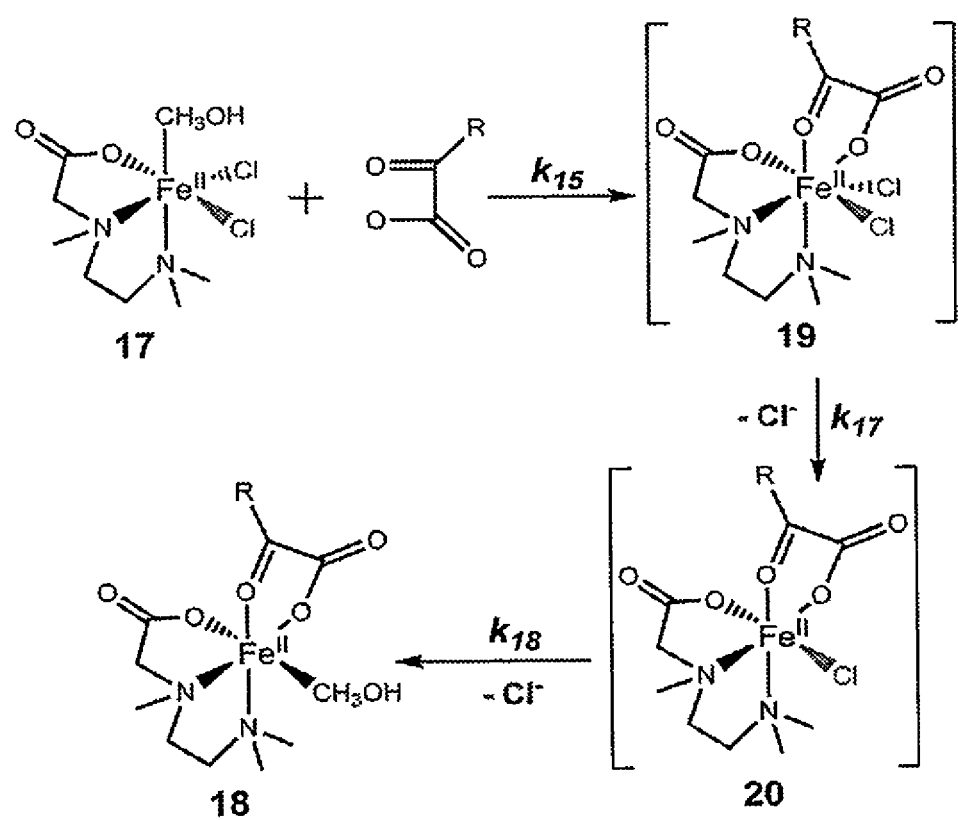
FIG. 14 is a diagram that illustrates a proposed mechanism for the mechanism of binding of α-ketoacids to 17.

FIG. 13 was fit according to the rate law equations 4.8 through 4.10 and the rates are given in Table 1 where the first step is a rapid second order process ($k_{15}$=9.6 $M^{-1}$ $s^{-1}$) which is initially proposed to correspond to the concerted bidentate binding of α-KG to form a 7-coordinate iron species, followed by two slower steps ($k_{16}$=1.7 $s^{-1}$ and $k_{17}$=0.53 $s^{-1}$) which are proposed to be subsequent loss of the two bound chloride ligands. Although these rates are similar in value and may be difficult to accurately determine the absolute values here it is clear the data fits better to a three step-process than a two exponential fit. The result of interest here is the process that is occurring and what contribution the chloride ligands may have which will ultimately require spectroscopic characterization of these intermediates. This initial mechanism is shown in FIG. 14 which shows the three step process that arrives in the final observed product, 18.

$$\frac{-d[17]}{dt} = \frac{d[19]}{dt} = k_{15obs}[17] = k_{15}[17][\alpha KA] \quad (4.8)$$

$$\frac{-d[19]}{dt} = \frac{d[20]}{dt} = k_{16}[19] \quad (4.9)$$

$$\frac{-d[20]}{dt} = \frac{d[18]}{dt} = k_{17}[20] \quad (4.10)$$

TABLE 1

Rate and activation parameters for the binding of α-KAs to 17.

| | $k_{15}$ ($M^{-1}$ $s^{-1}$) | $k_{16}$ ($s^{-1}$) | $k_{17}$ ($s^{-1}$) |
|---|---|---|---|
| 17 + α-KG | 10 ± 0.2 | 1.7 ± 0.5 | 0.5 ± 0.1 |
| ΔH‡ (kJ $mol^{-1}$) | 36 ± 2 | 50 ± 5 | 47 ± 6 |
| ΔS‡ (J $mol^{-1}$ $K^{-1}$) | −30 ± 9 | 31 ± 23 | 3 ± 1 |
| 17 + p-$CH_3$-BF | 45 ± 5 | 12 ± 1 | 1.2 ± 0.1 |
| ΔH‡ (kJ $mol^{-1}$) | 35 ± 2 | 42 ± 9 | 38 ± 1 |
| ΔS‡ (J $mol^{-1}$ $K^{-1}$) | −23 ± 12 | 1.5 ± 0.9 | 37 ± 15 |

Supporting data for the mechanism in FIG. 14 arises from the predicted extinction coefficients that are generated from the fits using the global fitting software SpecFit/32. These predicted extinction coefficients are given in FIG. 15A. The final species, 18, is predicted to have an $\varepsilon_{18}$=150 $M^{-1}$ $cm^{-1}$ which is effectively equivalent to that experimentally observed at room temperature by UV/vis spectroscopy (18 ε=125 $M^{-1}$ $cm^{-1}$.) In addition, the starting material, 17, has essentially no absorbance in the visible spectrum (ε=15 $M^{-1}$$cm^{-1}$), which corresponds well to the predicted extinction coefficient of $\varepsilon_{17}$=24 $M^{-1}$ $cm^{-1}$. This small predicted extinction coefficient could also be attributed to the "dead time" of the stopped-flow apparatus of 2-5 ms, since by the time the detection has begun, some of species 17 has already reacted with α-KG to form intermediate 19 which is predicted to have an unusually large extinction coefficient of $\varepsilon_{19}$≈9700 $M^{-1}$ $cm^{-1}$. The speciation plot for each reactive intermediate in FIG. 15B shows a significant contribution to the overall change in concentration of each intermediate showing that their inclusion in the proposed mechanism is justified.

Figures 16A, 16B:
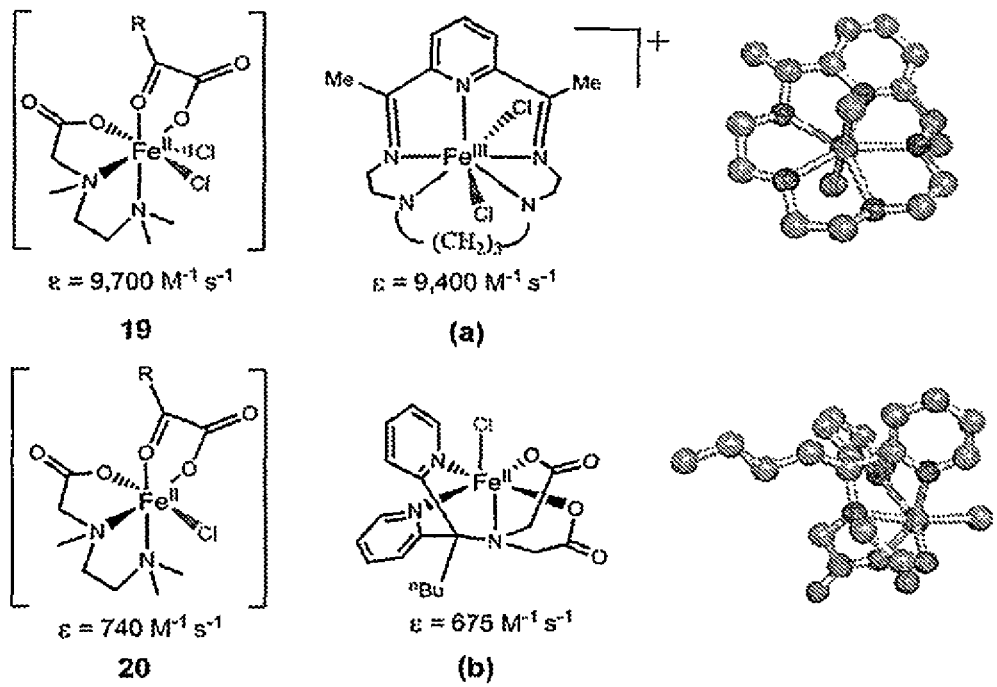
FIGS. 16A-16B show literature comparisons for the extinction coefficients of the intermediates in the binding of α-KG to 17.

The large projected extinction coefficient for 19 in the visible range of the spectrum is consistent with a MLCT band in a non-centrosymmetric complex. A search of the literature for well characterized N,O ligand containing complexes with two Cl-ligands indicated the possibility that 19 is a 7-coordinate iron species (with two Cl-ligands) while 20 may be a 6-coordinate iron species (with one $Cl^-$ ligand, FIGS. 16A-16B). Intermediate 19 displays a similar extinction coefficient to the fully characterized 7-coordinate Fe(III) species (FIG. 16A) (Drew, M. G.; bin Othman, A. H. *Journal of the Chemical Society, Dalton Transactions* 1975, 23, 2507), however, this may not be totally due to an Fe(II)-to-pyridine charge transfer band as an alternative ligand has been synthesized which contains a pyridine moiety on the $N_2O_1$ ligand backbone and this has a $\lambda_{max}$~300 nm. Similarly 20 displays a similar extinction coefficient for the 6-coordinate, single chloride bound species (FIG. 16B) (McDonald, A. R.; et al., Chemical Science 2012, 3, 1680).

Figure 15A:
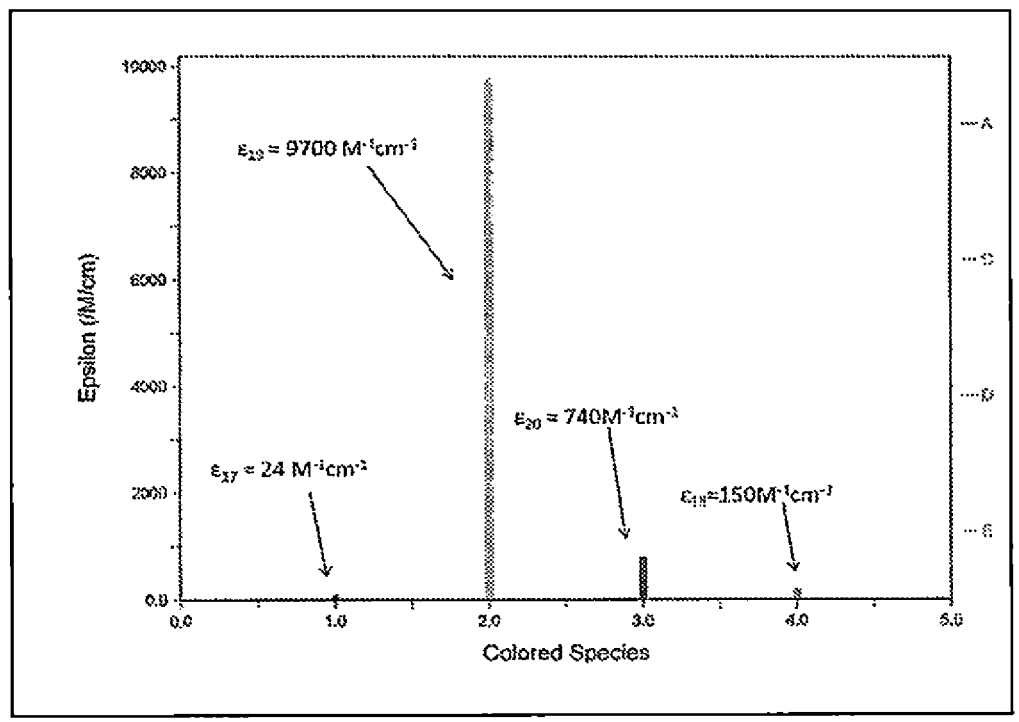
FIG. 15A is a graph of predicted extinction coefficients for the binding of α-KG to 17. Colors corresponding to 17 (red), 19 (green), 20 (pink), 18 (orange).
Figure 15B:
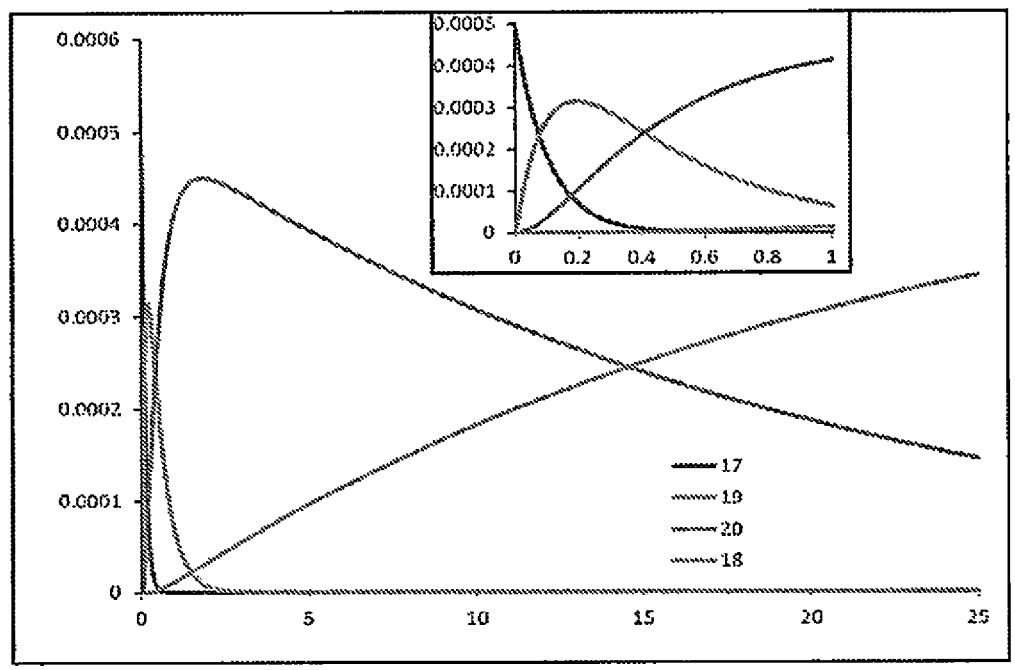
FIG. 15B is a speciation plot for each intermediate at −85° C.

A calculation was performed to analyze the contribution of the observed large extinction coefficients in FIG. 15A by using the speciation plots obtained (FIG. 15B). This was done by calculating the mole fraction of each species at t=0.2 seconds which represents the time that the greatest amount of intermediate 19 present in solution. The max absorbance at t=0.2 seconds in FIG. 13 is 0.0308 and Table 2 shows the absorbencies calculated based on the predicted extinction coefficient and the value of 9700 for intermediate 19 greatly over estimates the observed absorbance. By altering the extinction coefficients to a more reasonable values for intermediates 19 and 20 results in an accurate prediction of the observed absorbance at t=0.2 seconds (Table 3). This suggests that these intermediates may not have such a dramatic extinction coefficient but are still responsible for the majority of the observed absorbance value.

TABLE 2

Predicted absorbance values based on extinction coefficients obtained from SpecFit.

| Species | Concentration (M) | Extinction coefficient ($M^{-1}$ $cm^{-1}$) | Predicted observed absorbance |
|---|---|---|---|
| 17 | 0.00031 | 25 | 0.0049 |
| 19 | 0.00011 | 9700 | 0.23 |
| 20 | 0.000068 | 740 | 0.0068 |
| | | Total absorbance | 0.24 |

TABLE 3

Predicted absorbance values based on more reasonable values.

| Species | Concentration (M) | Extinction coefficient ($M^{-1}$ $cm^{-1}$) | Predicted observed absorbance |
|---|---|---|---|
| 17 | 0.00031 | 25 | 0.0049 |
| 19 | 0.00011 | 1000 | 0.0242 |
| 20 | 0.000068 | 3000 | 0.0027 |
| | | Total absorbance | 0.031 |

Figure 17:
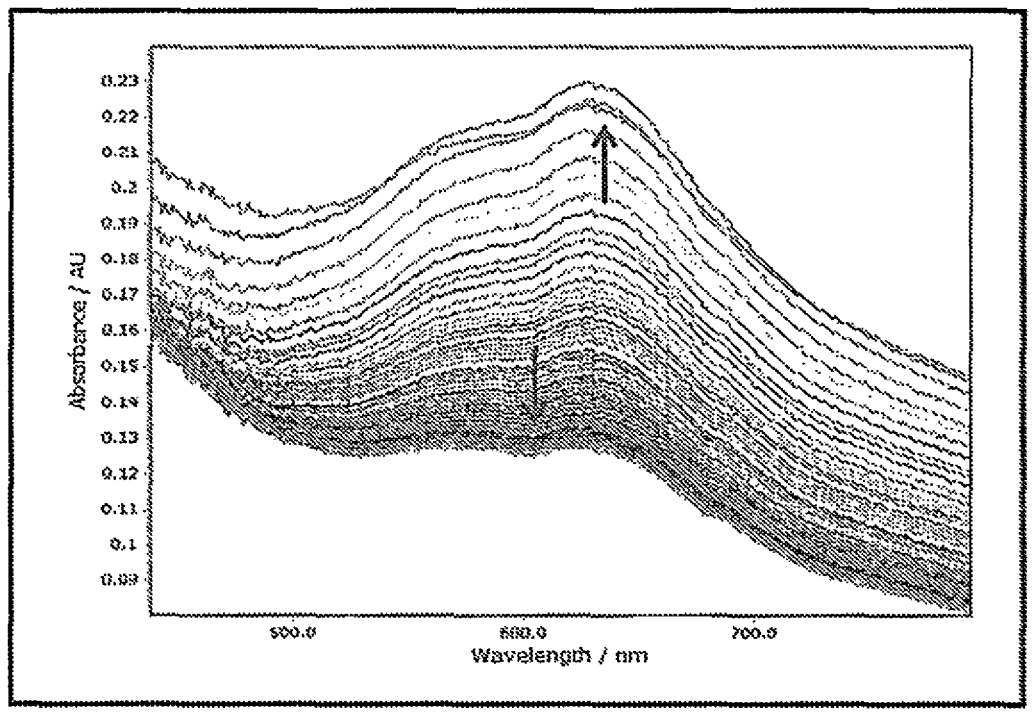
FIG. 17 is a graph of diode array data for the binding of p-CH3-BF (11 mM) to 17 (0.66 mM) at −85° C. in methanol, figure showing the first 5 seconds of the reaction.

As previously discussed, attempts to determine the order dependence for the binding of α-KG to 17 were inconclusive. These issues led to performing the same analysis with p-CH$_3$-benzoylformate (p-CH$_3$-BF) which is more soluble at low temperatures. Also useful was the characteristic that the benzoylformate adduct complex, [Fe$^{II}$(N$_2$O$_1$)(p-CH$_3$-BF)(MeOH)] (21), has a greater extinction coefficient ($\varepsilon_{615}$=390 $M^{-1}$ $cm^{-1}$), allowing for better signal to noise ratios in the spectroscopic studies. The same single-mixing set of experiments was performed with p-CH$_3$-benzoylformate (p-CH$_3$-BF). FIG. 17 shows the diode array data, which again shows a large increase in the chromophore corresponding to the adduct complex with no subsequent O$_2$ reactivity under the experimental conditions.

Figure 18A:
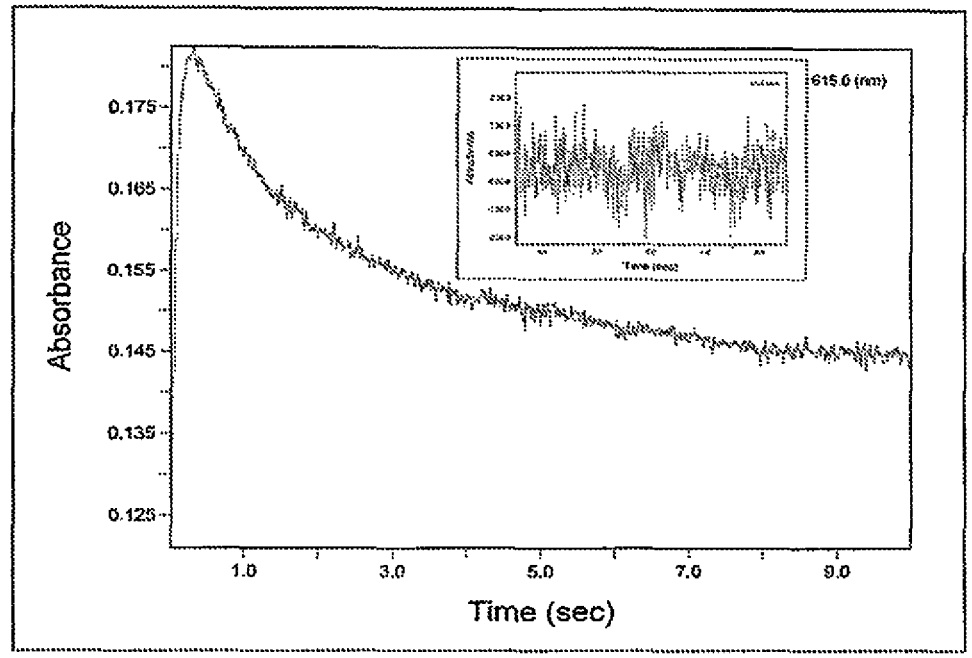
FIG. 18A is a graph of single wavelength data at 615 nm for the binding of p-$CH_3$-BF (23.4 mM) to $[Fe^{II}(N_2O_1)Cl_2(MeOH)]^-$ (0.66 mM) (17).
Figure 18B:
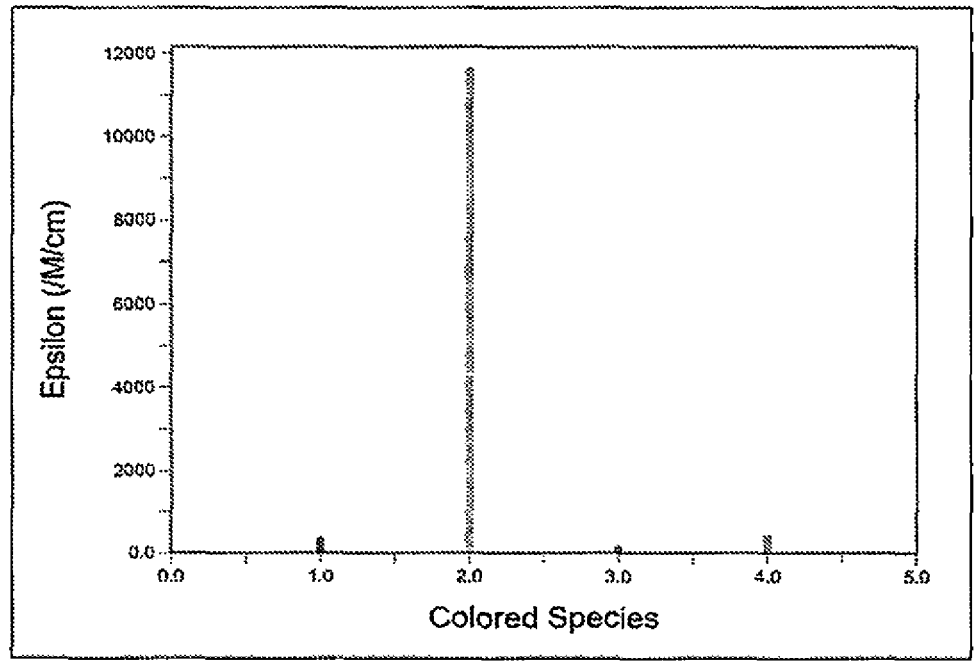
FIG. 18B is a graph demonstrating similar trend observed for the predicted extinction coefficients.

The single-wavelength data at 625 nm, which was fit to the same mechanism shown in FIG. 18A and also used the same rate law equations 4.8-4.10. The rates of p-CH$_3$-BF binding are given in Table 1. The same pattern in extinction coefficients is observed as predicted by SpecFit/32 suggesting a similar mechanism of binding (FIG. 18B). The use of p-CH$_3$-BF also allowed for the determination of an order dependence which showed that k$_{17}$ was first order in iron complex and p-CH$_3$-BF while k$_{18}$ and k$_{19}$ were independent of the p-CH$_3$-BF concentration. The order dependence figures are given in FIGS. 51-54.

Interestingly the p-CH$_3$-BF ligand binds to 17 almost 5 times faster than α-KG (k$_{15}$=45.3 $M^{-1}$ $s^{-1}$ versus k$_{15}$=9.6 $M^{-1}$ $s^{-1}$, respectively) and for each ligand, the subsequent steps approximately an order of magnitude slower than the previous step which is consistent with the same reaction pathway for both α-keto acids (Table 1). The binding affinity for α-KG was measured to be K$_d$=50±10 μM while for p-CH$_2$-BF, the binding affinity was determined to be K$_d$ 193±11 μM (Thesis of Tarves, P. C., Boston University, 2012). This observed pattern for the difference in rates parallels the known ligand affinities that benzoate-like α-keto acids are inherently better ligands than alkyl-like.

In comparing the spectra for complex 17 versus 17a it is clear that the chloride ligands have an effect on the observed spectrum. In the absence of chlorides only a single growth is observed in forming the α-KG adduct complex (18), however when chlorides are present the result is significantly different where there is a large increase followed by a decrease in absorbance. This change in spectrum is also independent of the type of α-keto acid used therefore supporting the proposed 7-coordinate iron species with two bound chloride ligands and simply cannot be the same mechanistic pathway was in the absence of chlorides.

Figure 19:
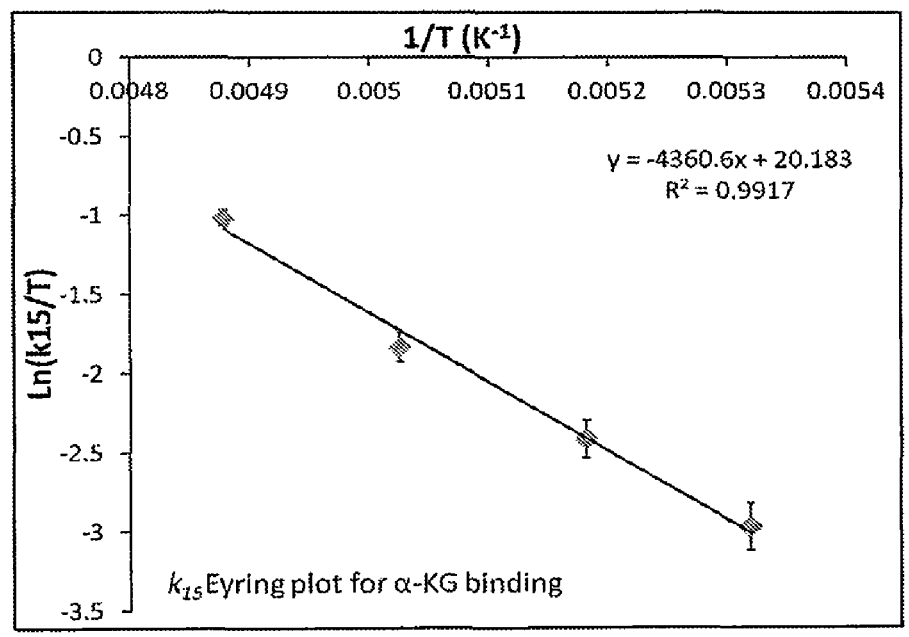
FIG. 19 is a graph demonstrating Eyring process of $k_{15}$ for the binding of α-KG to 17. Data collected over a temperature range of −85 to −70° C. Each data point is the average of at least three data scans.

To further probe the mechanism of α-keto acid binding, a temperature dependence was determined for both p-CH$_3$-BF and α-KG (results are also given in Table 1). A sample of the Eyring plot used to determine the activation parameters for each mechanistic step is shown in FIG. 19. Owing to the rapid rate of the reaction, the only accessible temperature range was between −85 to −70° C. (the remaining Eyring plots are given in FIGS. 46-50) which led to the large standard deviations for these values, however it is limit of detection for this process. The values in Table 1 for the activation parameters show very little dependence on the enthalpy of activation (ΔH$^{\ddagger}$) of the reaction for either p-CH$_3$-BF or α-KG, however there is a very clear dependence on the entropy of activation (ΔS$^{\ddagger}$) for each process.

For both α-keto acids there is a very negative ΔS$^{\ddagger}$ value for the initial binding of these coenzymes to 17 for process k$_{15}$ (ΔS$^{\ddagger}_{\alpha KG}$=−29.7±9 J mol$^{-1}$ K$^{-1}$ and ΔS$^{\ddagger}_{BF}$=−22.7±12 J mol$^{-1}$ K$^{-1}$), which is consistent with a more ordering process of two molecular equivalents forming one equivalent (associative type mechanism), particularly one that is as sterically hindered as a 7-coordinate iron species. In the case of the α-KG for the next process (k$_{16}$) shows a large positive entropy is observed (ΔS$^{\ddagger}$=31.3±23 J mol$^{-1}$ K$^{-1}$) which is consistent with the loss of a ligand from a sterically crowded 7-coordinate molecule to a 6-coordinate iron center and the final step (k$_{17}$) displays essentially no dependence on the entropy of activation of the final step where the last chloride ligand is exchanged with the solvent (methanol) and there is no observed change in coordination number. This large change in entropy value may also have some contribution from solvent reorganization effects.

Figure 20:
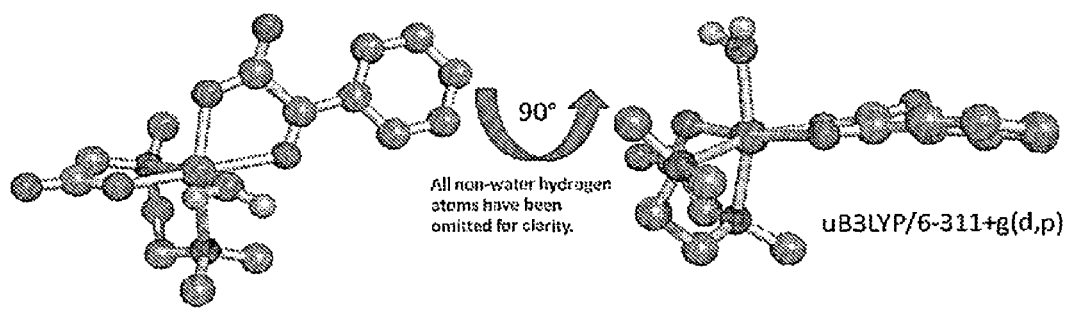
FIG. 20 is a schematic illustrating optimized geometry of $[FeII(N_2O_1)(BF)]$ showing forced planar configuration of the aromatic ring of the benzoylformate coenzyme.
Figure 21:
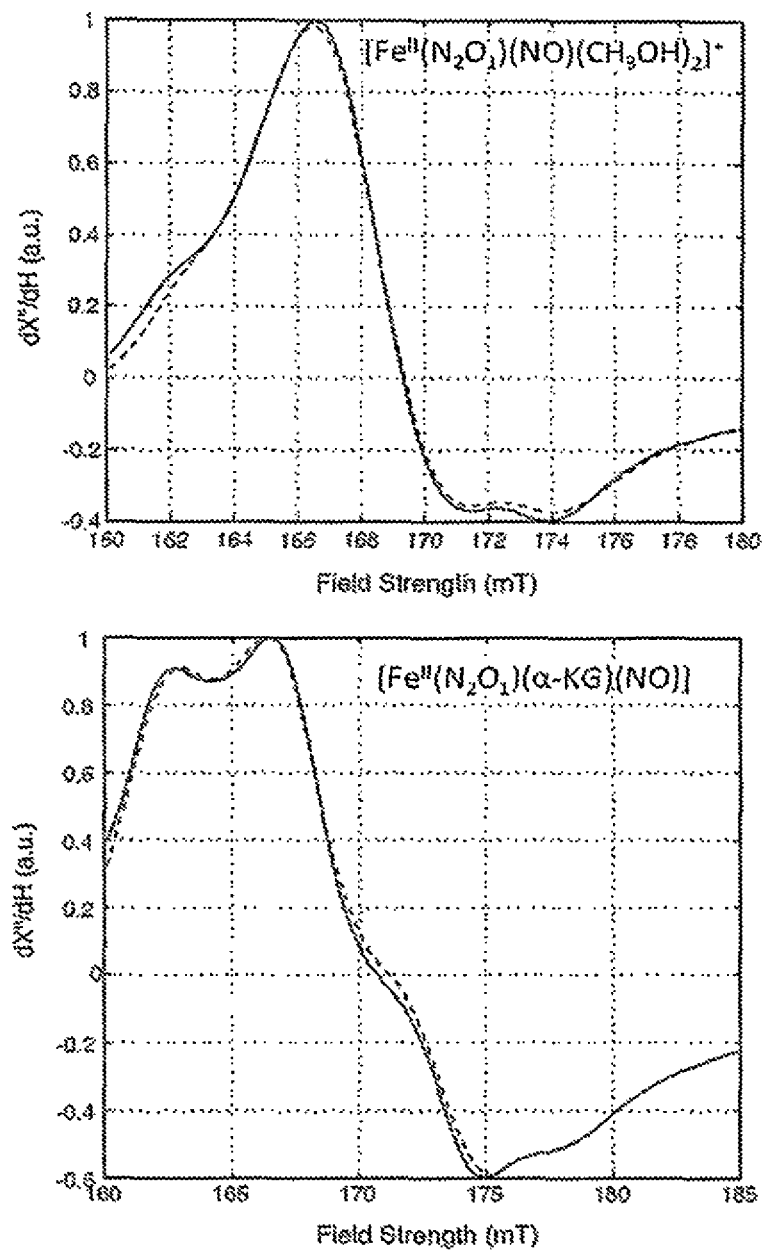
FIG. 21 is a graph of EPR spectra (solid line) and simulations (dashed line) of the NO adduct complexes.

The last two steps for p-CH$_3$-BF are significantly different where a small change in entropy is observed for k$_{16}$ (ΔS$^{\ddagger}$=1.35±0.9 J mol$^{-1}$ K$^{-1}$) followed by a large change in entropy for the last step k$_{19}$ (ΔS$^{\ddagger}$=36.9±15 J mol$^{-1}$ K$^{-1}$). For k$_{16}$ which corresponds to the loss of a chloride ligand and a change in coordination number (7 to 6) there is a very small observed change in entropy which could be attributed to the size of the coenzyme. Benzoylformate is a much bulkier ligand then α-KG therefore the change in coordination number may not have as much of an effect because the complex still contains a large amount of steric bulk. It was postulated that the last step (k$_{17}$) which has a large observed entropy of activation could possibly be due to the aromatic ring of the benzoylformate being locked into an unfavorable position due the bidentate binding to the iron center. DFT studies were utilized and the geometry optimization of the adduct species is shown in FIG. 20. It is clear that the aromatic ring of the benzoylformate is being forced into a planar configuration which may explain a part of the large entropy of activation for the final step of the binding mechanism. Each species in this reaction is charged and therefore there is some dipole ordering of solvent around both 17 and α-KG or p-CH$_3$-BF and therefore the binding will lead to a reorganization of the first solvent shell. Although the extent of this effect cannot be measured from these data alone, it is another factor that may contribute to the observed large negative entropy of binding.

NO binding studies to [Fe$^{II}$(N$_2$O$_1$)(α-KG)(MeOH)]$^-$ (18). Prior to initiating any detailed stopped-flow studies investigating the interaction of O$_2$ with 18, UV/vis spectroscopy was used to determine the type of speciation in solution at low-temperatures. Based on previous work with this complex at room temperature, it is clear that there is only one species differentiated by UV/vis spectroscopy (FIG. 1). However, EPR data obtained for the [Fe(N$_2$O$_1$)(Cl)$_2$(NO)] and [Fe(N$_2$O$_1$)(α-KG)(NO] showed the presence of multiple species in the frozen samples. The parent complex, 17, resulted in a best fit of two species with an approximate ratio of 65:35 where as the adduct complex, 18, also fit best to two species but with a slightly different ratio of 80:20. This result correlates well to the DFT studies previously discussed and also to previous data obtained for the NO adduct of the TauD/Fe$^{II}$/α-KG (75:25) in the absence of the substrate (taurine).

Figure 22:
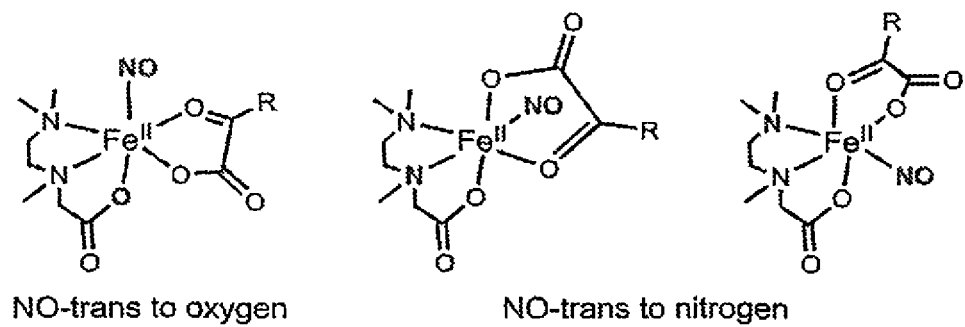
FIG. 22 shows possible binding modes of NO to 18.

Therefore initial stopped-flow studies were designed to investigate the binding of nitric oxide (NO) to 18 and analyze how many kinetically distinct species were present in solution. There are two possible binding modes for NO to 18 depending on the different configurations and what type of atom (nitrogen vs. oxygen) is trans to the bound NO. FIG. 22 shows the possibility of having NO trans to the oxygen of the ligand carboxylate moiety as well as being trans to either of the nitrogen centers.

There is precedence for multiple modes of NO binding to an Fe(II) center. Previous work by Gülbenk Anarat-Cappillino studied the NO binding with phenylalanine hydroxylase (PAH) which contains an Fe(II) with the 2-his-1-carboxylate ligation. NO binding studies using stopped-flow visible spectroscopy with the truncated form of the enzyme (Δ1-117 PAH) was found that the data best fit to two parallel reactions occurring at the same time (A→B and A→C) and analysis of the speciation plot found the relative percentages of B to C to be approximately 63% to 37%, respectively (Thesis of Anarat-Cappillino, G., Boston University, 2010). A similar reaction manifold has also been observed for [Fe$^{II}$(N$_2$O$_1$)Cl$_2$(MeOH)]$^-$ (17) and its interaction with NO which was also best fit to two parallel processes (A→B and A→C) in aqueous solutions at 4° C. and resulted in a speciation ratio 94% to 6%. These results are important when developing a kinetic model for the NO binding to 18 as there is precedence for the observation of multiple final species in solution under stopped-flow conditions.

Figure 23A:
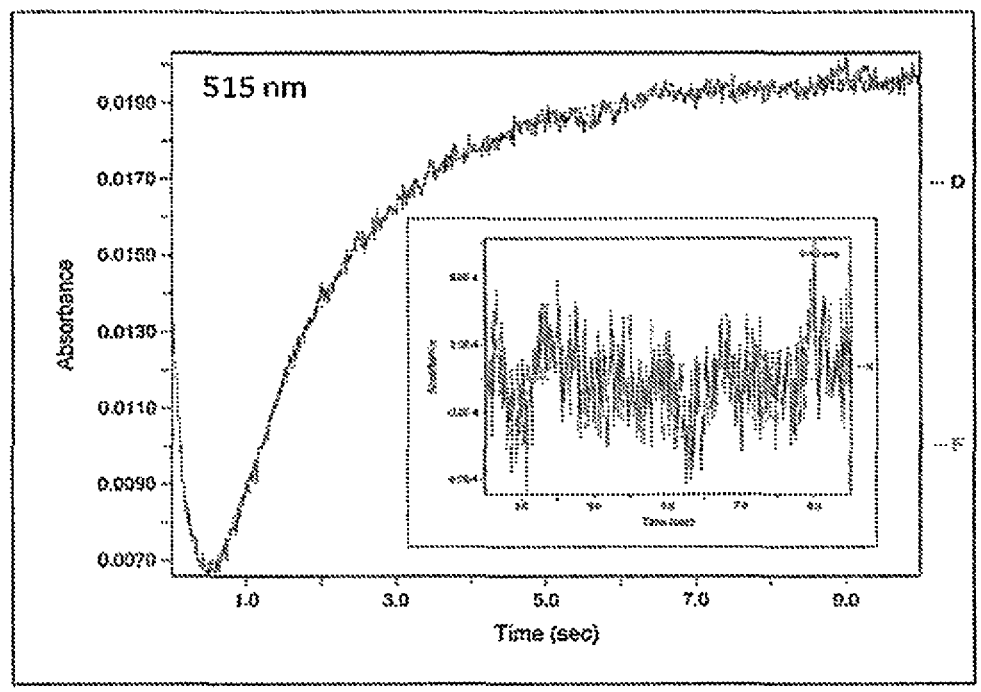
FIG. 23A is a graph of single wavelength stopped-flow data for the reaction of 18 (0.35 mM) with NO (6.4 mM).

Single-mixing reactions were performed at −85° C. where 18 (0.35 mM) was mixed with a saturated solution of NO (6.4 mM) in methanol. The single-wavelength data, is shown in FIG. 23A, indicates a change in chromophore at 515 nm. Initial analysis of the data found that it fit best to a two-step process under pseudo-first order conditions in NO (equations 4.11 and 4.12). However, based on EPR and DFT studies there is the possibility of multiple species in solution so attempts were made to also model the data in FIG. 23A with parallel reactions as previously used successfully by Gülbenk Anarat-Cappillino (equations 4.13 and 4.14). This resulted in poor kinetic fits to the data even with varying the initial amount of 18 in the kinetic simulations.

(4.11)

(4.13)

(4.12)

(4.14)

Figure 24:
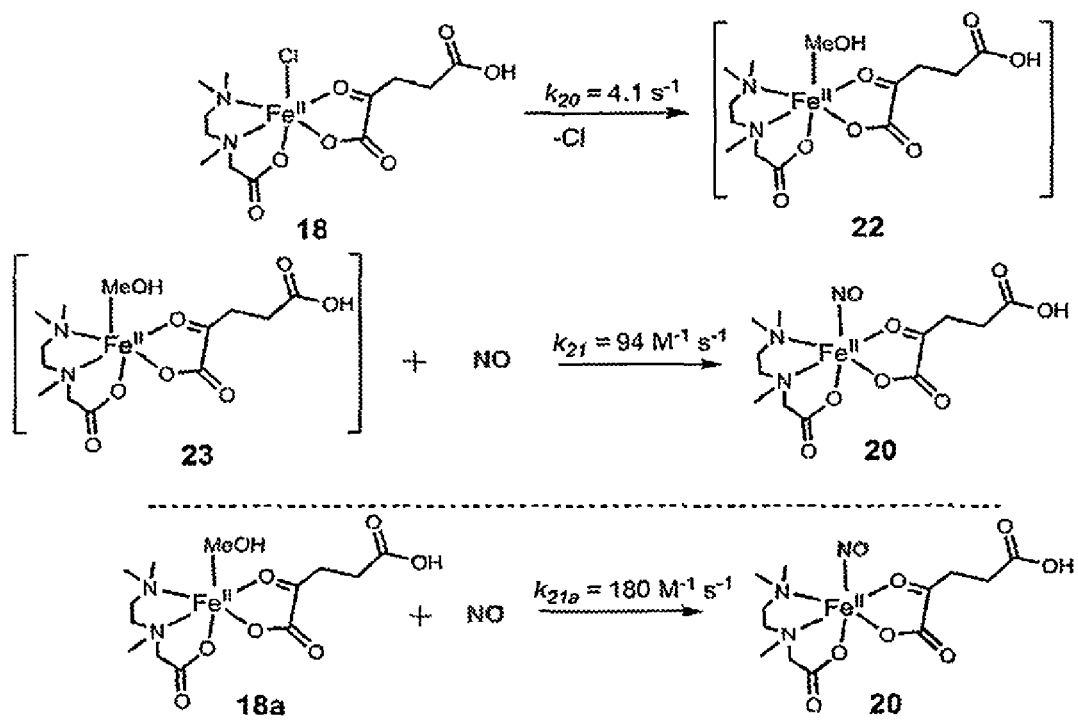
FIG. 24 is a diagram that illustrates a proposed mechanism for the binding of NO to $[Fe^{II}(N_2O_1)(\alpha\text{-}KG)(Cl)]^-$ (18) in the presence (top) and absence (bottom) of a bound chlorides.

The data in FIG. 23A was fit to the rate law equations 4.15 and 4.16 under pseudo-first order conditions, which resulted in a first order rate constant of $k_{20}$=4.1 s$^{-1}$ and a rapid second order rate constant of $k_{21}$=95 M$^{-1}$ s$^{-1}$. A proposed mechanism consistent with these processes is shown in FIG. 24. The steps were mechanistically assigned as $k_{20}$ corresponding the loss of a solvated ligand (methanol) to go from a 6-coordinate to 5-coordinate iron complex to allow for the binding of the NO ligand. This is followed by a rapid second order process that corresponds to the binding of NO to the iron complex.

(4.15)

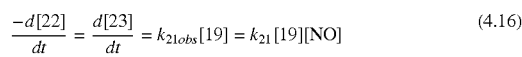
(4.16)

Figure 23B:
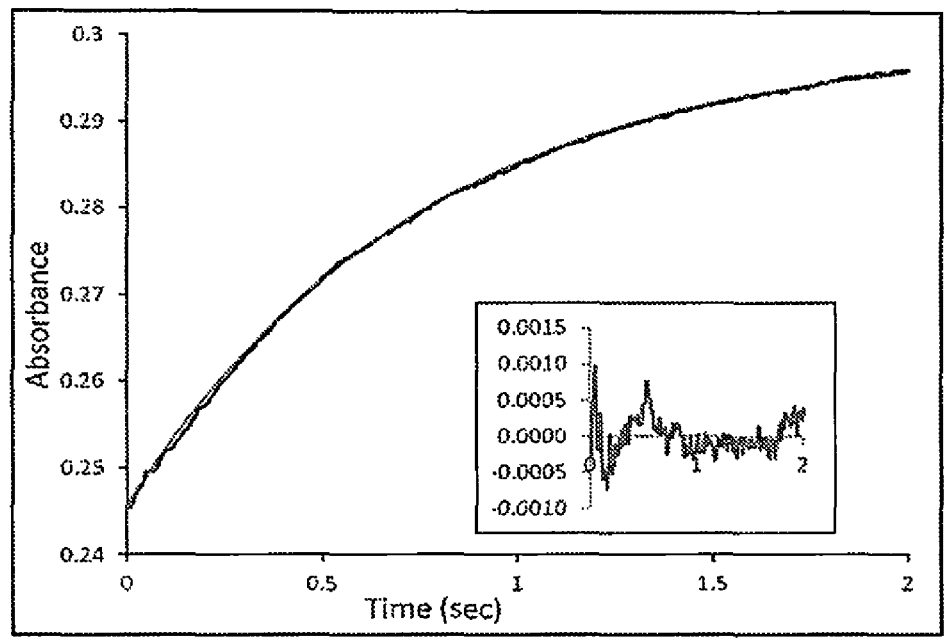
FIG. 23B is a graph of single wavelength data of 18a with no chlorides (0.22 mM) with NO (7.2 mM). Insets: Residuals to fit. Data collected at −85° C.

The same reaction was performed starting with species 17a, [Fe$^{II}$(N$_2$O$_1$)(CH$_3$OH)$_3$)], which does not have any bound chlorides since they have been removed by the treatment of TIPF$_6$. The adduct complex was made with α-KG forming species 18a (FIG. 24). The subsequent binding with NO (FIG. 23B) resulted in a loss of the decrease in absorbance as seen with species 18 (FIG. 23A). This supports the proposed dissociative mechanism where a bound chloride leaves before the binding of NO. In the absence of chlorides there is presumably still a methanol coordinated to the iron complex but the resolution of the bound solvent would be too rapid to be observed under these conditions.

To further support the proposed mechanism for NO binding, in particular the feature in the first second of the spectrum in FIG. 23A where a clear drop in absorbance is observed followed by the growth of the chromophore. To probe this feature the classic ruthenium complex, K[Ru$^{III}$(Hedta)Cl].2H$_2$O, was utilized since it's interaction with NO has been highly studied and is widely used as a NO scavenger. In reactions at room temperature in aqueous solution K[Ru$^{III}$(Hedta)Cl].2H$_2$O reacts with NO at a rate of k=3.8×10$^4$ to 1.2×10$^5$ M$^{-1}$ s$^{-1}$ depending on pH (Wanat, A.; et al., *Dalton Transactions* 2002, 6, 941). The same single mixing reaction was performed with K[Ru$^{III}$(Hedta)Cl].2H$_2$O (0.15 mM) in methanol with a solution of NO (6.4 mM). The single wavelength data following the chromophore for the growth of K[Ru$^{III}$(Hedta)NO] 360 nm is shown in FIG. 24.

Figure 25:
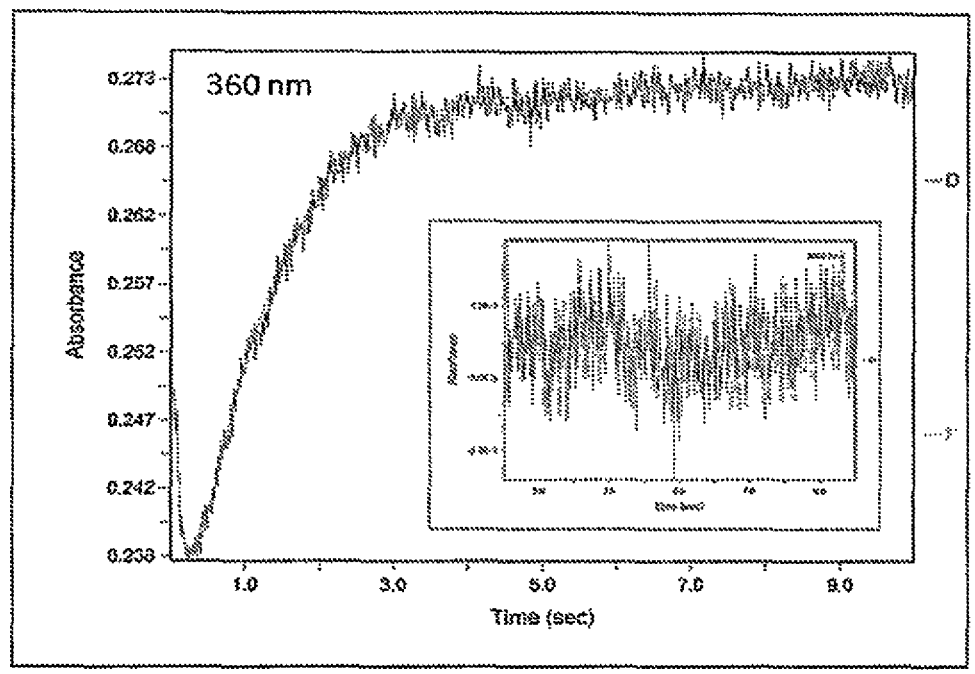
FIG. 25 is a graph of single wavelength stopped-flow data for the reaction of $[Ru^{III}(Hedta)Cl]^-$ (0.15 mM) with NO (6.4 mM) at −85° C. Inset: Residuals to fit.

The data in FIG. 25 was also fit to equations 4.15 and 4.16 and the fit (green line) shows good correlation to the data based on the residuals (FIG. 25, Inset). The values for the rates were calculated to be $k_{20}$=8.2 s$^{-1}$ and a rapid second order rate constant of $k_{21}$=127 M$^{-1}$ s$^{-1}$. The similar order of magnitude for $k_{20}$, which possibly corresponds to the loss of a coordinated ligand suggests that this mechanistic assignment is reasonable. The faster rate observed for the binding of NO for the Ru(III) species is consistent with its ability to be a strong radical scavenger. Attempts to remove the bound chloride and with TIPF$_6$ and repeat the NO binding in the absence of chlorides were unsuccessful likely due to the much tighter bond of Ru(III)-Cl as opposed to Fe(II)-Cl.

The literature examples that studies NO binding to this Ru(III) complex do not propose a loss of a ligand prior to NO binding, however, these are performed in aqueous solutions and such low temperatures are not accessible and therefore may not be possible to observe this rapid ligand loss. Nonetheless, an order dependence of NO is still required to confirm that $k_{21}$ corresponds to NO binding.

There are numerous examples of NO binding to mononuclear non-heme Fe(II) centers in the literature. One example from van Eldik et al. utilized an [Fe$^{II}$(dca)$_5$Cl]$^{4-}$ complex (dca=dicyanamide) rapidly reacted with NO at 20° C. with a second order rate constant of k=1.7×10$^7$ M$^{-1}$ s$^{-1}$ following a proposed dissociative mechanism with the loss of the chloride ligand prior to NO binding (Begel, S.; et al., *Inorganic Chemistry* 2011, 50, 3946). However, the rates of ligand loss are not reported likely due to the fact that binding of NO is reported to be completed in 4.8 μsec. On the other hand, an example of an NO binding trans to solely an oxygen atom can be found in the reaction of [Fe(H$_2$O)$_6$)]$^{2+}$ with NO.

The rate for this binding is also extremely fast at (k=1.42× $10^6$ $M^{-1}$ $s^{-1}$). In both cases these reactions were performed using stopped-flow spectroscopy coupled to laser flash photolysis at 20° C. and increased pressure (Wanat, A.; et al., *Inorganic Chemistry* 2002, 41, 4). Other examples that utilized a mixed N/O ligand set similar to the $N_2O_1$-α-KG coordination environment such as EDTA or other chelating ligands were also found to rapidly bind NO (k>$10^6$ $M^{-1}$ $s^{-1}$) however; the authors do not discuss or make any distinction as to whether the NO is binding trans to an nitrogen or an oxygen atom (Malgut, J.; et al., *Inorganic Chemistry* 2008, 47, 6314; Schneppensieper, T.; et al., *Inorganic Chemistry* 2002, 41, 2565). Therefore, in the case where there are multiple possible binding sites, it may not be possible to distinguish which is the more favorable based on UV/vis spectroscopy solely, suggesting the potential that multiple species in solution. It is also possible that multiple species are reacting in solution but their rates are similar they are indistinguishable under the stopped-flow conditions.

Figure 26:
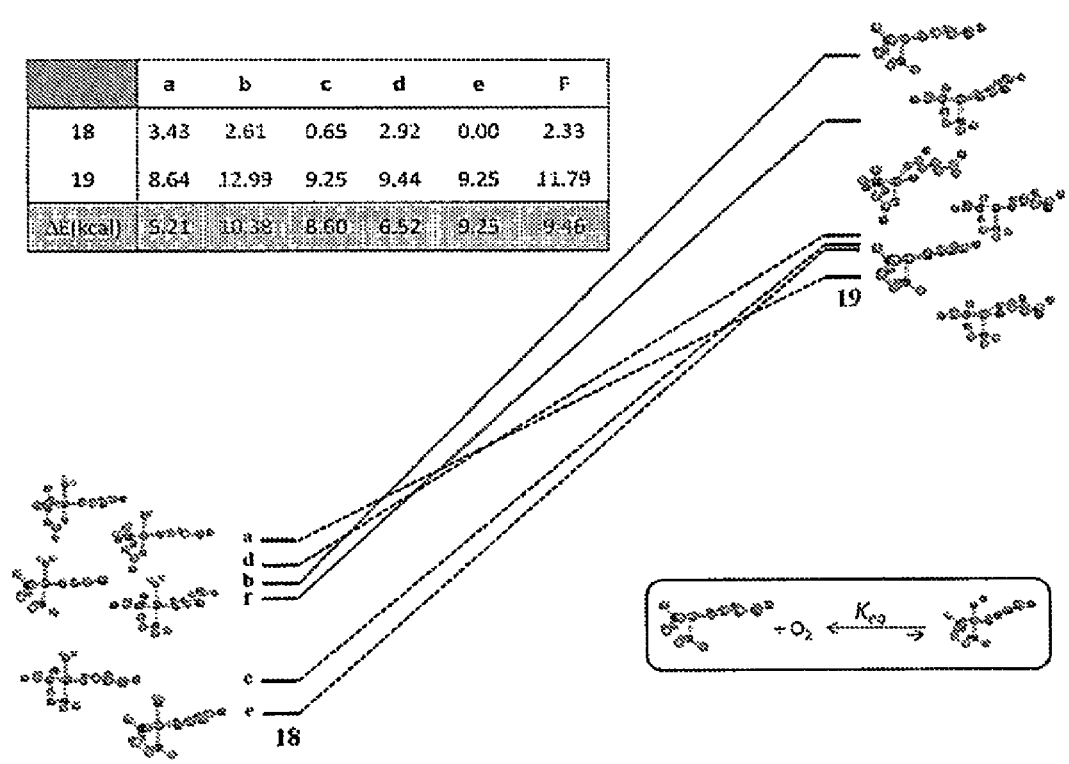
FIG. 26 is a graph demonstrating energy change associated with the loss of $H_2O$ ligand from (18) to give (19) for the six isomers of the α-KG adduct complexes.

DFT simulations have been performed on the interaction of dioxygen with 18 following the reaction profile of all six configurations from the ground state structures and can be used as a comparison to what may be happening in solution. The comparison of the first step in the proposed mechanism for the binding of NO to 18 (modeled as a loss of a ligand) can be compared to the DFT simulations that have modeled this same step in preparation for the reaction with $O_2$. The computational studies model the 6 to 5 coordination change modeled by the loss of a bound water ligand, which induces energy changes for each of the six configurations (FIG. 26). However, DFT analysis unable to find a reasonable transition state during the loss of the water ligand, which strongly suggests a dissociative process. The majority of ligand reactions for octahedral complexes occur via a dissociative process and octahedral Fe(II) species are thought to undergo rapid $S_N1$-like substitution reactions (Basolo, F.; Pearson, R. G. *Mechanisms of inorganic reaction*; John Wiley & Sons, Inc.: London, 1958). These results infer that at such low temperatures for the kinetic studies (−85° C.) it may be possible to observe the loss of a ligand by stopped-flow UV/vis spectroscopy. This dissociative reaction pathway has also been observed in mononuclear non-heme iron enzymes and the formation of a 5-coordinate Fe(II) species has been spectroscopically observed prior to $O_2$ activation (Zhou, J.; et al., *Journal of the American Chemical Society* 2001, 123, 7388).

Figure 27:
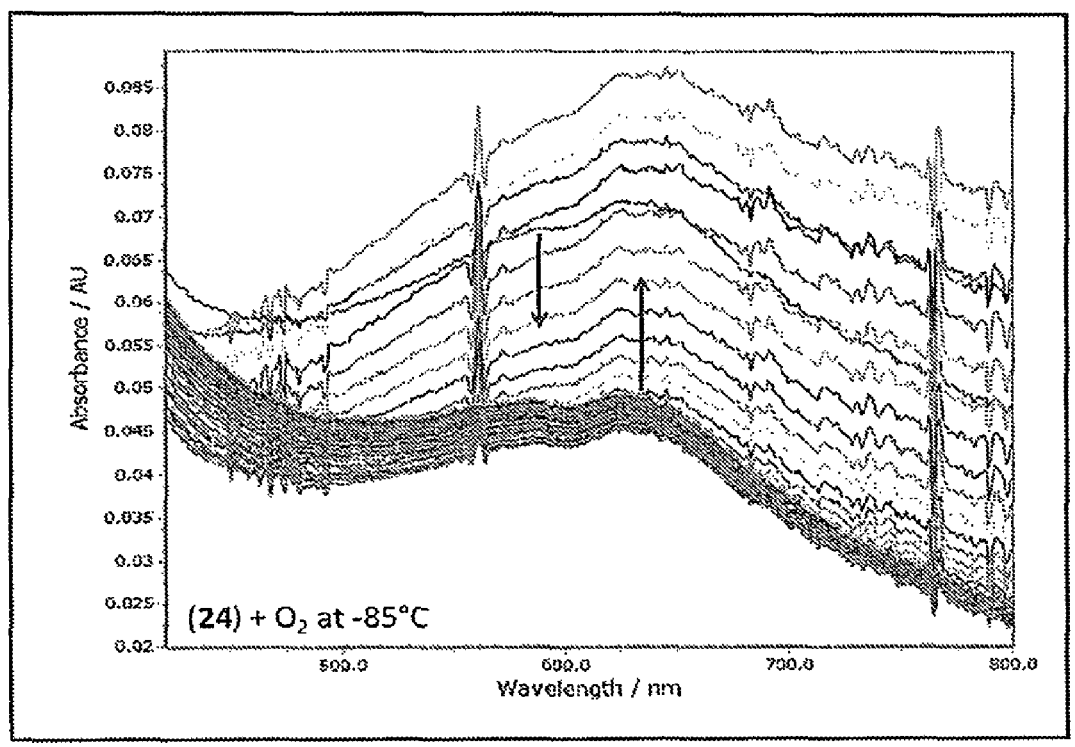
FIG. 27 is a graph of diode array data for the reaction of [Fe$^{II}$(N$_2$O$_1$)(p-H-BF)] (24) (0.74 mM) and O$_2$ (4.2 mM) at −85° C. Data shows the first 10 seconds of the reaction.

Kinetic studies of $[Fe^{II}(N_2O_1)(\alpha\text{-KG})(CH_3OH)]^-$ and $[Fe^{II}(N_2O_1)(p\text{-X-BF})(CH_3OH)]^-$ adduct complexes with dioxygen. Low-temperature stopped flow studies of this reaction were performed. Initial efforts focused on investigating both $[Fe^{II}(N_2O_1s)(p\ H\text{-BF})]$ (24) as (i) it has a higher extinction coefficient (ε=225 $M^{-1}$ $cm^{-1}$) vs. 18 (ε=125 $M^{-1}$ $cm^{-1}$) and (ii) in this reaction the limiting factor is the saturated concentration of dioxygen in methanol (10 mM). Therefore, at low concentrations of the iron complex, a better signal to noise resolution is obtained with a higher absorbance. Reactions were designed to be as close to pseudo first order (10 fold excess) as possible in dioxygen but the low extinction coefficients required experiments to be performed slightly below (4 fold excess). The data were still able to be simulated using second order rate laws with an excess of $O_2$ or greater (4≤5.3≤10). FIG. 27 shows the diode array data for the reaction of 24 with $O_2$ at −85° C., which shows a fast decrease followed by an increase in the change in absorbance of the chromophore at 625 nm.

As seen in FIG. 26 the data is very noisy because of the low extinction coefficients so the switch was made to single-wavelength mode and the data was collected at 625 nm. Because the data presented here is an initial investigation into the mechanism of dioxygen reactivity, the reactive intermediate species will be labeled beginning with the letter 'A' and while the rate constants discussed will be labeled with primes such a $k'_1$, $k'_2$, etc. with the aim of simplifying the discussion.

Figure 28:
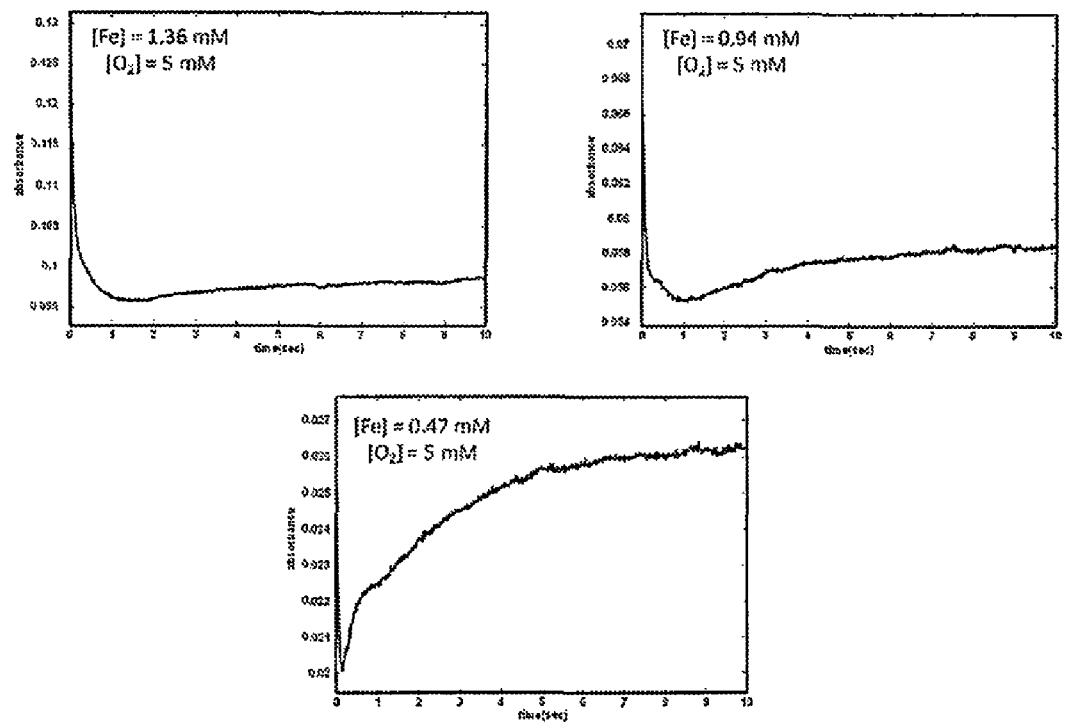
FIG. 28 is a set of graphs of single wavelength data at 625 nm of the reaction of [Fe$^{II}$(N$_2$O$_1$)(p-H-BF)(CH$_3$OH)] with O$_2$ at varying iron concentrations showing the higher concentrations show a slower reaction.

Order dependence analysis. The single-wavelength data at varying concentration 24 (1.36, 0.94. and 0.47 mM) are given in FIG. 28 reacting with the same concentration of $O_2$ (5 mM) and already the data presents a unique challenge. As can be seen from left to right as the reaction is run with lower iron concentrations, the reaction visibly occurring faster on the same time scale (10 seconds). This contrary observation is indicative of iron concentration dependent processes that are effectively reducing the [Fe] available for the reaction thereby decreasing the spectroscopically observed excursion of the composite absorbance changes.

Figure 29:
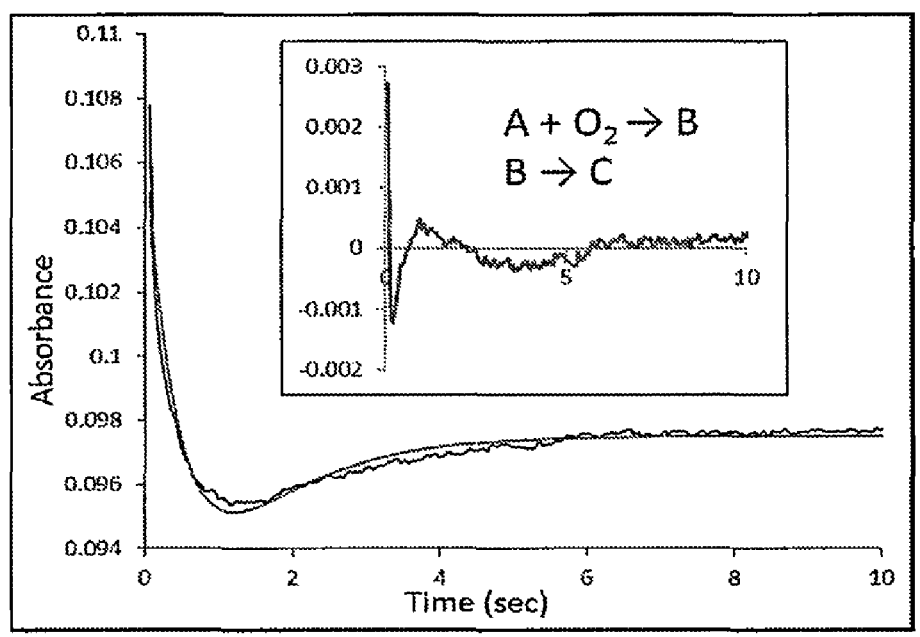
FIG. 29 is a graph demonstrating attempt to fit the reaction of 24 with O$_2$ to a two-exponential processes.

The preliminary model that resulted in the best fits to the data is described by the stoichiometry in equations 4.17 to 4.20. Initial data were fit using the most concentrated experiment in FIG. 28 of 1.36 mM because it provided the best signal to noise ratio. The kinetic model was built by starting from simple two- and three-exponential processes. First a two exponential process was considered (FIG. 29) which clearly does not result in good residuals to the fits and therefore an additional kinetic step was added.

Figure 30A:
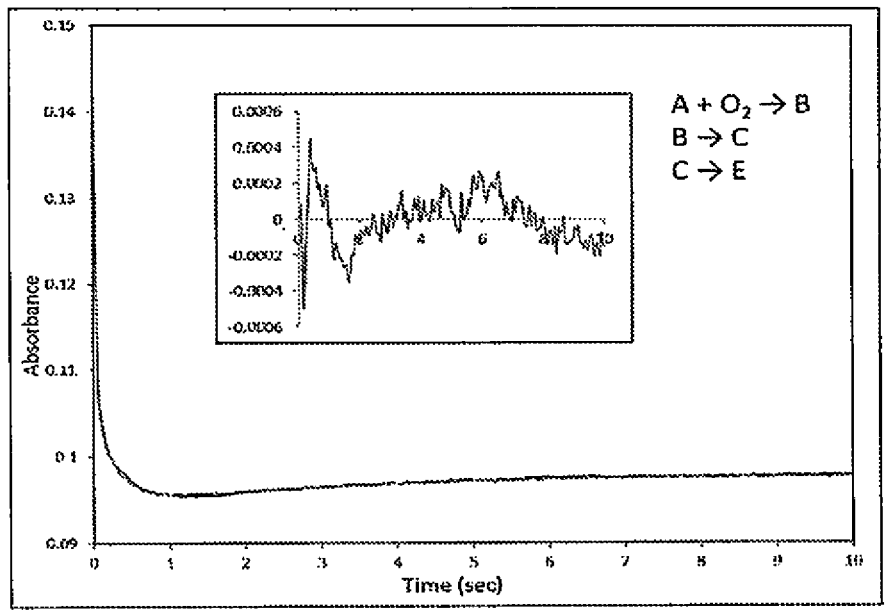
FIGS. 30A-30B is a set of graphs demonstrating attempts to fit the reaction with 24 and O$_2$ to a three step process.
Figure 30B:
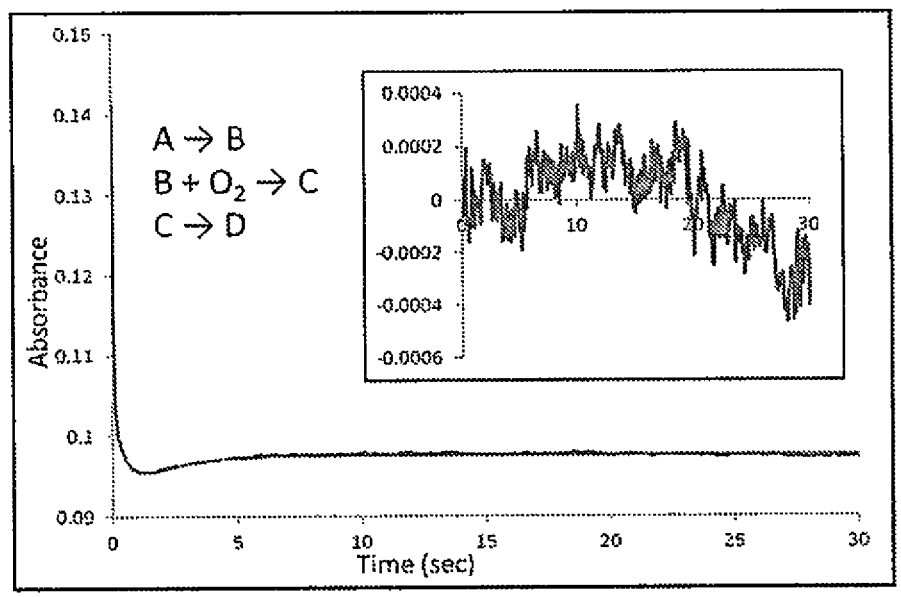

Next, an additional step was added and attempts were made to fit either the reaction with $O_2$ in the first step (FIG. 30A) or have it included in the second step in the model based on the reaction previously discussed with NO (i.e. a loss of a ligand prior to $O_2$ activation (FIG. 30B). Neither of these models resulted in adequate fits to the data. Finally, a fourth step was added (FIG. 31) which resulted in good fits to the data. It is known in kinetic simulations, the more steps added to the data simulations will almost always result in a better fit, however the following analysis will challenge each of the proposed four steps and support their inclusion in the model.

Figure 31:
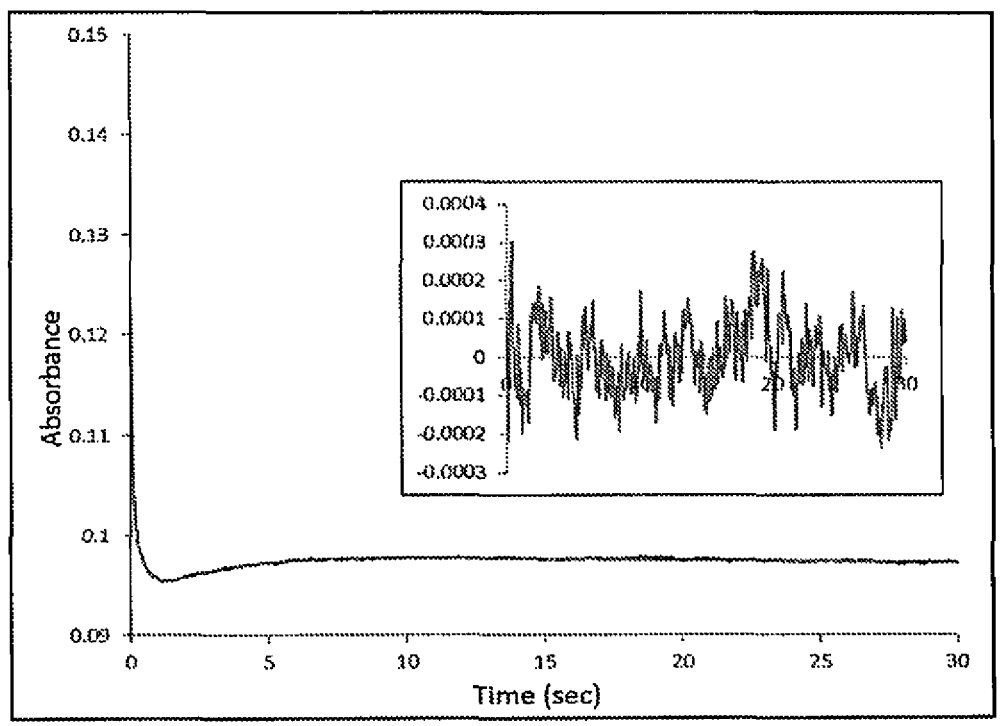
FIG. 31 is a graph of single-wavelength data (black) and kinetic fit to the data (red) for the reaction of [Fe$^{II}$(N$_2$O$_1$)(p-H-BF)(CH$_3$OH)] (1.37 mM) with O$_2$ (5 mM) at −85° C. Inset: Residuals to fit.
Figure 32A:
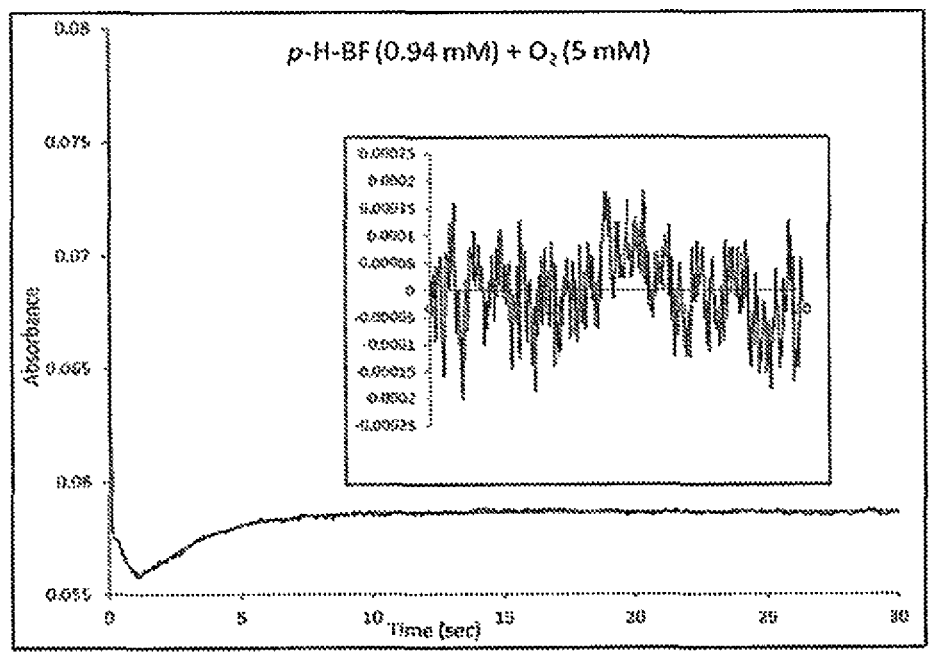
FIG. 32A is a graph of single-wavelength data (black) and kinetic fit to the data (red) for the reaction of [Fe$^{II}$(N$_2$O$_1$)(p-H-BF)(CH$_3$OH)] (0.94 mM) with O$_2$ (5 mM) at −85° C. Inset: Residuals to fit.
Figure 32B:
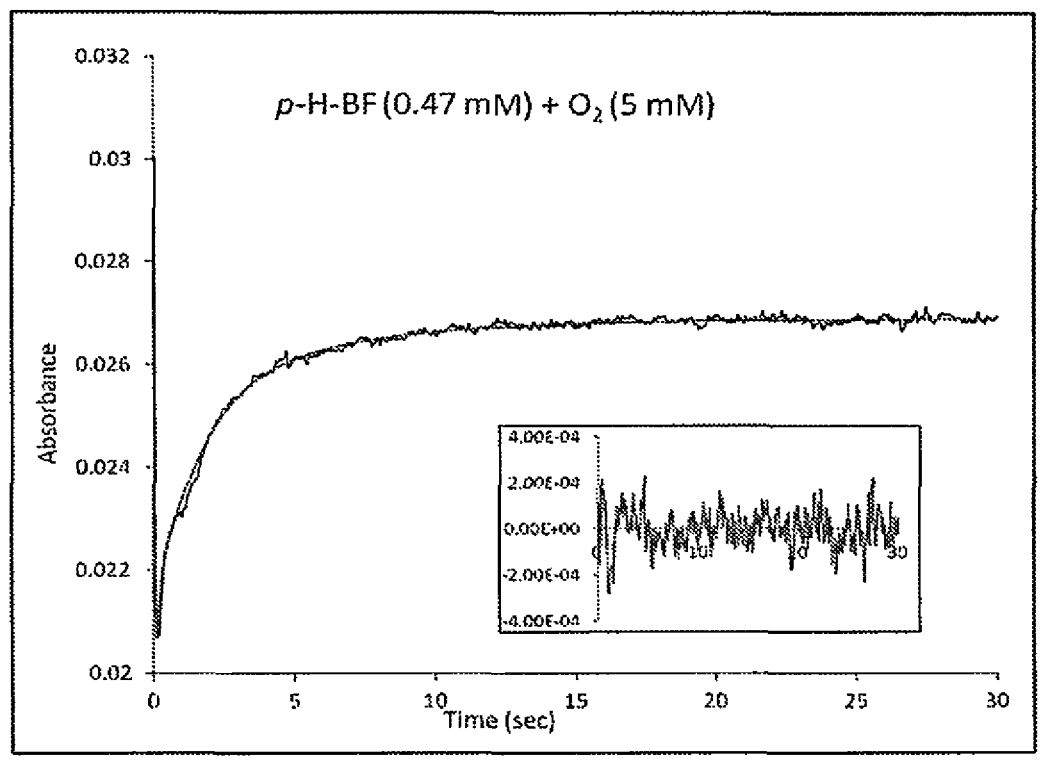
FIG. 32B is a graph of single-wavelength data (black) and kinetic fit to the data (red) for the reaction of [Fe$^{II}$(N$_2$O$_1$)(p-H-BF)(CH$_3$OH)] (0.47 mM) with O$_2$ (5 mM) at −85° C. Inset: Residuals to fit.
Figure 33:
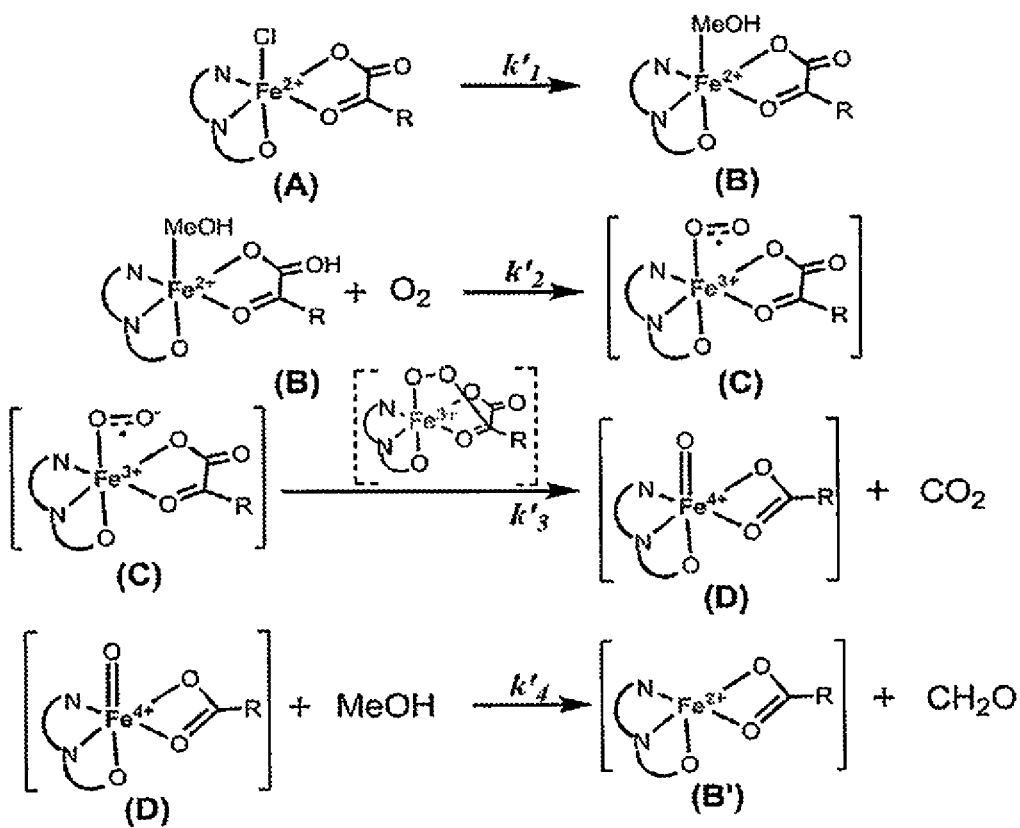
FIG. 33 is a diagram that illustrates a working hypothesis for the mechanism of α-KG model complexes with O$_2$ at −85° C.

The data in FIG. 31 was fit according to equations 4.21 and 4.24. The proposed intermediates, given in FIG. 33, represent an initial assignment of the species with the goal of providing a visual too for the kinetically assigned processes (equations 4.17 to 4.23). It is possible there may be a re-ordering of the mechanistic assignment of the species with further spectroscopic analysis. The single wavelength data for the lower concentration of 18 analyzed are shown in FIGS. 32A-32B (0.47 mM) and FIGS. 30A-30B (0.94 mM) which were fit using the rate laws described in equations 4.24-4.30. As seen from the residuals, the data presents a reasonable kinetic fit to the model, with the values for the rates (Table 4) giving rise to narrow standard deviations. The following discussion will build on the kinetic model and give reference to those that did not result in good mechanistic fits to these data. Stoichiometry of the equations for the proposed model in FIG. 29:

$$24 \xrightarrow{k'_1} B \quad (4.17)$$

$$B + O_2 \xrightarrow{k'_2} C \quad (4.18)$$

$$C \xrightarrow{k'_3} D \quad (4.19)$$

$$D \xrightarrow{k'_4} E \quad (4.20)$$

TABLE 4

Data for the analysis of reaction with 24 and $O_2$ (5 mM) at $-85°$ C.

| Step (units) | 0.47 mM | 0.94 mM | 1.34 mM |
|---|---|---|---|
| $k'_1$ ($s^{-1}$) | 8.5 ± 0.2 | 7.8 ± 1.0 | 6.1 ± 0.9 |
| $k'_{2obs}$ ($s^{-1}$) | 0.9 ± 0.04 | 0.13 ± 0.02 | 0.08 ± 0.01 |
| $k'_2$ ($M^{-1} s^{-1}$) | 170 ± 8 | 240 ± 4 | 150 ± 5 |
| $k'_3$ ($s^{-1}$) | 21 ± 0.06 | 20 ± 0.9 | 20 ± 1.1 |
| $k'_4$ ($s^{-1}$) | 0.2 ± 0.01 | 0.4 ± 0.03 | 0.002 ± 0.001 |
| $TON^a$: | 0.9 | 0.6 | 0.3 | a. TON value predicted based on the line of best fit in FIG. 2 for the α-KG adduct complex.

Rate laws used to analyze the kinetic data:

$$\frac{-d[A]}{dt} = \frac{d[B]}{dt} = k'_1[A] \quad (4.21)$$

$$\frac{-d[B]}{dt} = \frac{-d[O_2]}{dt} = \frac{d[C]}{dt} = k'_2[B][O_2] \quad (4.22)$$

$$\frac{-d[C]}{dt} = \frac{d[D]}{dt} = k'_3[C] \quad (4.23)$$

$$\frac{-d[D]}{dt} = \frac{d[B']}{dt} = k'_{4obs}[D] = k'_4[D][MeOH] \quad (4.24)$$

Figure 2:
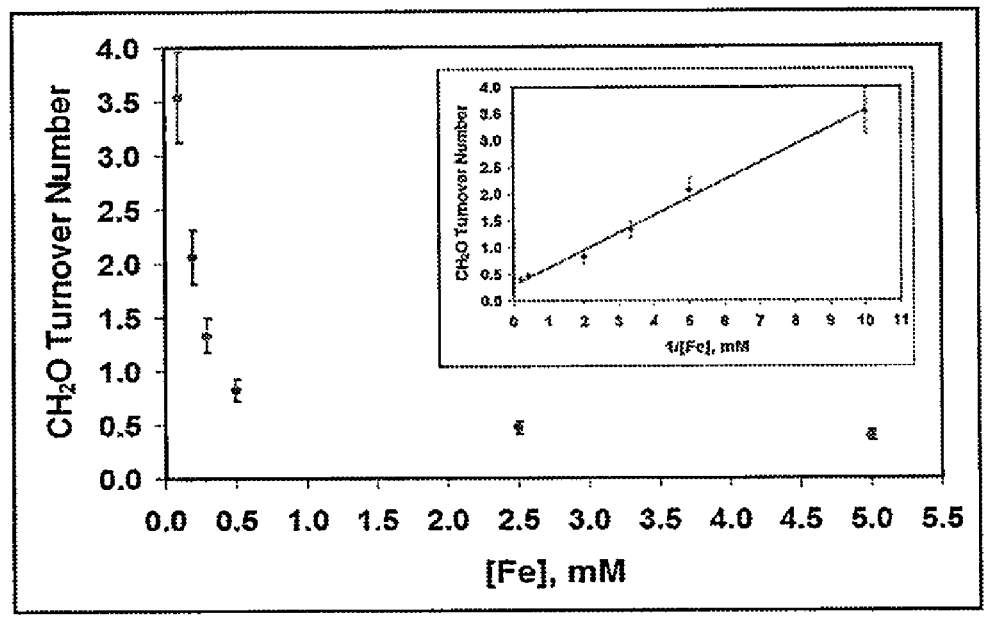
FIG. 2 is a graph that demonstrates methanol to formaldehyde oxidation at various iron concentrations. Inset: Plot of 1/[Fe] vs. TON (turnover number).
Figure 3:
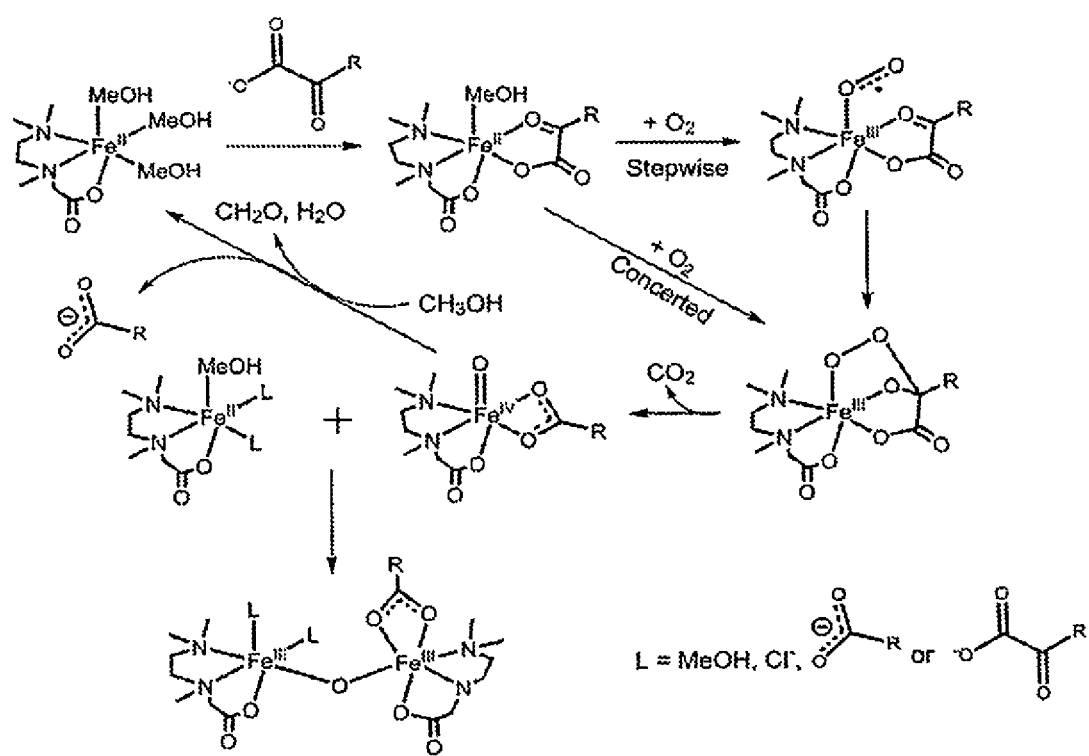
FIG. 3 is a diagram that illustrates a proposed room temperature mechanism of $[FeII(N_2O_1)(\alpha\text{-}KG)]$ (18) dioxygen reactivity in methanol at room temperature.
Figure 4:
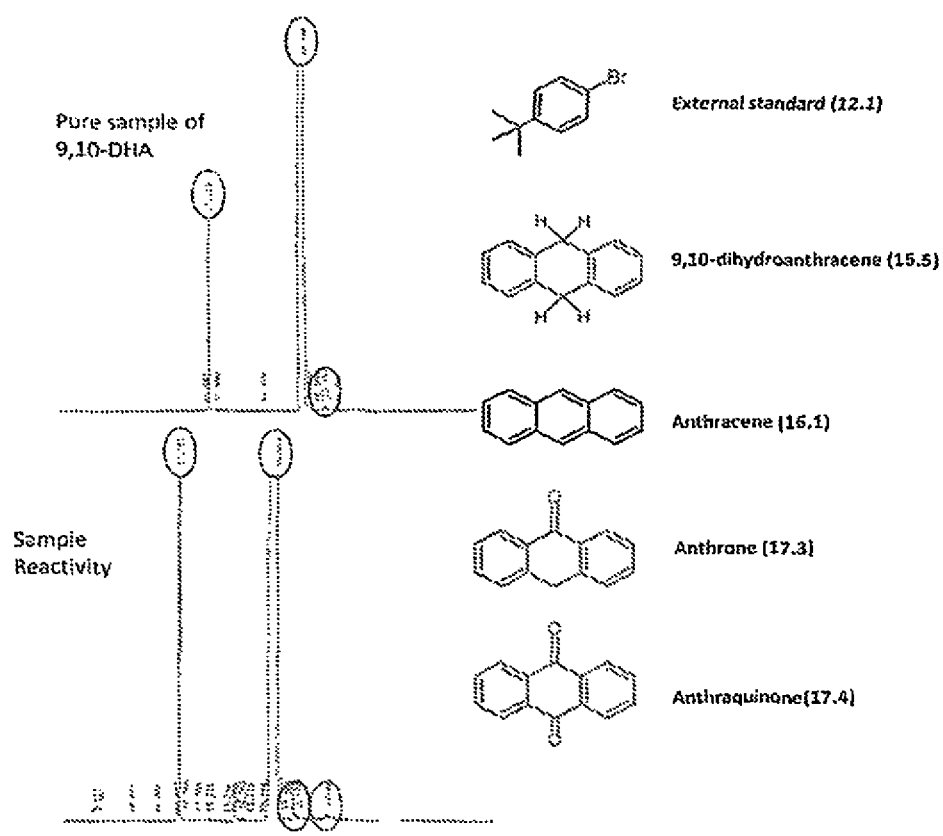
FIG. 4 is a graph of GC-FID traces for the reactivity of 9,10-dihydroanthracene with (17), α-KG, and $O_2$.
Figure 5:
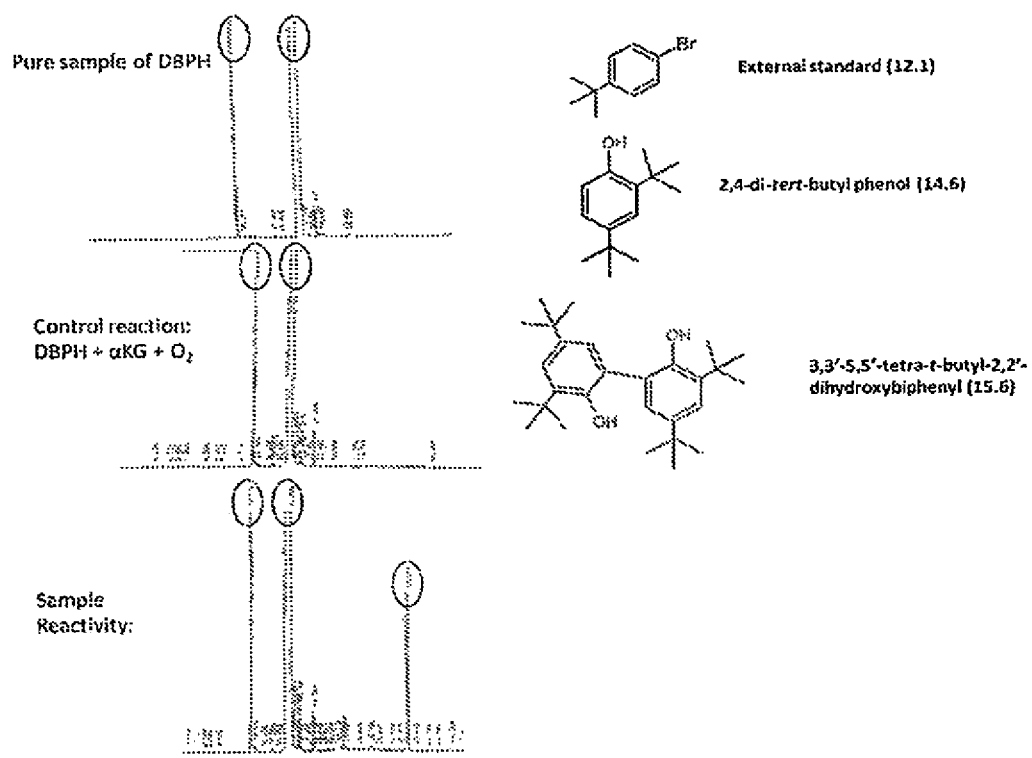
FIG. 5 is a graph of GC-FID traces for the reactivity of 2-4-di-tert-butyl phenol with (17), α-KG, and $O_2$.
Figure 34:
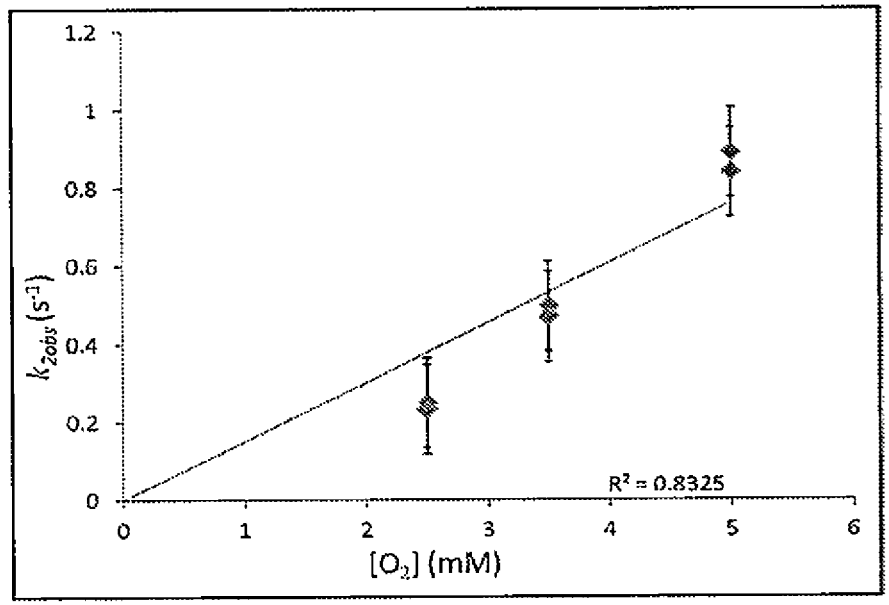
FIG. 34 is a graph that demonstrates order dependence of k'2 on O$_2$. Each data point the average of at least two trials.

As seen from the data, a complete order dependence analysis is not available in this chemistry owing to the observation that doubling the concentration of iron species causes the rate to decrease. This observation is dominated by inverse relationship between the catalyst concentration and observed turnover numbers (FIG. 2). The higher the concentration of the iron complex, the lower the number of turnovers is observed (Table 4). However, an order dependence for dioxygen sensitive steps (doubling the oxygen concentration while keeping the concentration of iron constant) resulted only $k'_2$ being affected (Table 5), showing a first order dependence in $O_2$ (FIG. 34). The remaining steps in the mechanism in FIG. 33 appear independent of $O_2$ concentration. Therefore, based on what is known from the NO binding studies we mechanistically assigned $k'_1$ as the loss of a ligand to go from a 6-coordinate iron species to a 5-coordinate species, followed by the reaction of $O_2$ ($k'_2$) to the five-coordinate Fe(II) species.

TABLE 5

Rate values for the order dependence of $O_2$ with 24 (1.34 mM) at $-85°$ C.

| [$O_2$] (mM) | $k'_1$ ($s^{-1}$) | $k'_{2obs}$ ($s^{-1}$) | $k'_3$ ($s^{-1}$) | $k'_4$ ($s^{-1}$) |
|---|---|---|---|---|
| 5 | 8 ± 0.9 | 0.9 ± 0.1 | 21 ± 5 | 0.3 ± 0.1 |
| 3.5 | 9 ± 1.1 | 0.5 ± 0.2 | 16 ± 4 | 0.3 ± 0.09 |
| 2.5 | 7 ± 1.2 | 0.2 ± 0.1 | 14 ± 6 | 0.2 ± 0.03 |

Figure 35:
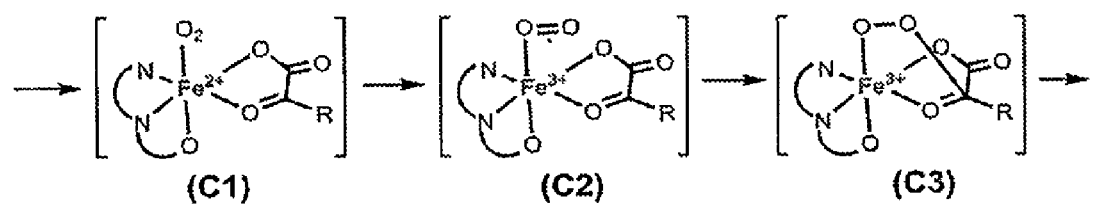
FIG. 35 illustrates chemical structure of possible intermediates of C: an Fe(II)-dioxygen adduct complex (C1), Fe(III)-superoxide species (C2), or a Fe(III)-bridging peroxide species (C3).

Next, the mechanistic steps were added for the species formed after the reaction with dioxygen. The data were fit best to two steps where only a single intermediate (C) is observed ($k'_3$) between the reaction steps involved in the interaction with $O_2$. There are several species that have been proposed to occur on the reaction pathway with ferrous metal center and $O_2$ with a bound α-keto acid (FIG. 35). The first is the formation of an Fe(II)-dioxygen adduct (C1) which is followed by electron transfer and subsequent activation of dioxygen to form a possible Fe(III)-superoxide species (C2). This superoxide species is then capable of nucleophilic attack on the C2 position of the bound α-KG coenzyme to form a bridging peroxide species, C3.

Identification of the exact nature of intermediate C will undoubtedly require either rapid freeze quench or flow spectroscopy studies to identify but some possible structure are given in FIG. 35. Computational studies following this same mechanism have been performed to investigate the relative energies of these activated oxygen species. The DFT simulations suggest that the different in energy between the 5-coordinate species (B) and the proposed [$Fe^{IV}$=O] intermediate (D) are relatively small. The largest energy barrier was calculated for the conversion of C2-C3 (~3.5 kcal) which suggests that C2 is a reasonable assignment of intermediate C in FIG. 33 based on computational studies. The different in energy between C3 and D is estimated at ~0.5 kcal which suggest the formation and decay of the bridging peroxide species (C3) may not be observable. These DFT observations parallel the mechanistic analysis such that only a single intermediate is observed kinetically prior to formation of the [$Fe^{IV}$=O] moiety. Species D then reacts with solvent (methanol) to form formaldehyde ($k'_4$) which must occur at some point during the reaction based on previous room temperature studies to form the final species E, proposed to be the Fe(II) species with succinate bound. This proposed mechanistic step will be further challenged by a Hammett analysis (vida supra).

Stopped-flow analysis with the addition of benzoate in solution. Owing to the technical and mechanistic challenges to perform an order dependence analysis for iron complex, we looked to other experiments that may affect different rates of the reaction in order continue to assess the proposed mechanism in FIG. 33. The first experiment was the addition of sodium benzoate (the product of decarboxylation of the bound benzoylformate) to the reaction in order to see if there are any observed effects of the rates. A solution of 24 (1.0 mM) was reacted with a saturated solution of $O_2$ (5 mM) with an excess of sodium benzoate (3.1 mM) dissolved in the oxygenated solvent. The single-wavelength data at 625 nm is shown in FIG. 36 and fit according to the mechanism in FIG. 33 and with the rate law equations 4.21-4.34 and the residuals show a very good fit to the data.

Figure 36:
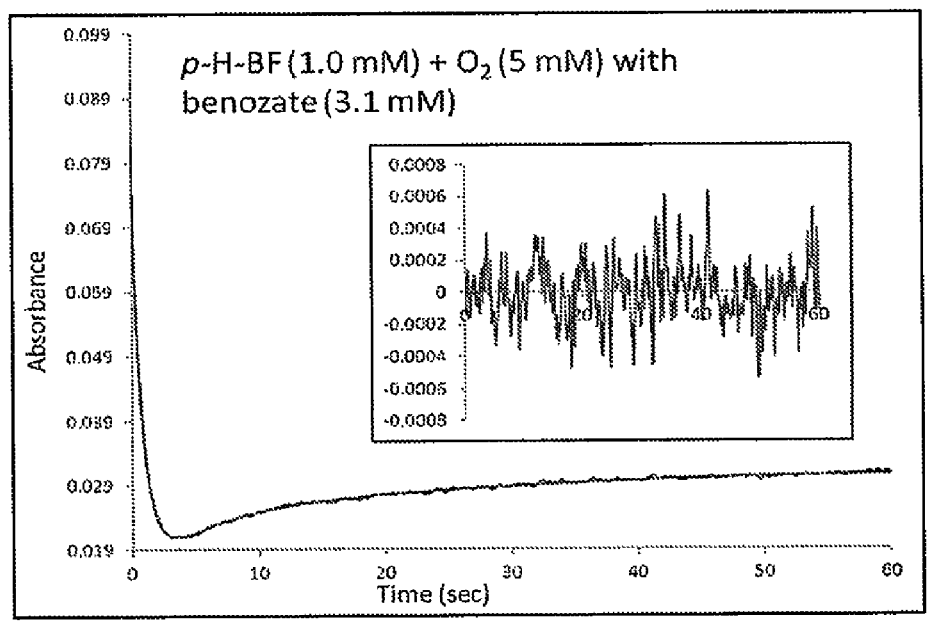
FIG. 36 is a graph of single-wavelength data (black) and kinetic fit to the data (red) for the reaction of [Fe$^{II}$(N$_2$O$_1$)(p-H-BF)(CH$_3$OH)] (1.0 mM) with O$_2$ (5 mM) with benzoate (3.1 mM) at −85° C. Top: Residuals to fit.

The rates obtained from the fits in FIG. 36 are given in Table 6 and shown in comparison to the reaction of 24 with $O_2$. The addition of benzoate appears to have an effect on several steps of the reaction. In particular it has decreased the rate of the first step in the reaction by slowing down the loss of a methanol ligand to go from a 6-coordinate species to a 5-coordinate species. Such a dissociative step is thought to be required for the reaction with dioxygen, and may reflect the inhibition with an extra coordinating species in solution.

TABLE 6

Rate comparison for the reaction of 24 with $O_2$ with the addition of benzoate to the reaction.

| Step (units) | p-H (24)$^a$ | p-H (24) + benzoate$^b$ |
|---|---|---|
| $k'_1$ ($s^{-1}$) | 7.8 ± 1.0 | 0.04 ± 0.01 |
| $k'_2$ ($M^{-1} s^{-1}$) | 24 ± 4 | 2900 ± 500 |
| $k'_3$ ($s^{-1}$) | 20 ± 0.9 | 0.25 ± 0.05 |
| $k'_{4obs}$ ($s^{-1}$) | 0.4 ± 0.03 | 1.1 ± 0.2 |

$^a$[24] = 0.94 mM, [$O_2$] = 5 mM
$^b$[24] = 1.0 mM, [$O_2$] = 5 mM, [benzoate] = 3.1 mM There is also a small effect on $k'_3$ (reduced by a factor of 100 in the presence of benzoate) which is modeled at the attack of the superoxide species and subsequent decarboxylation of benzoylformate. It is likely the benzoate is exchanging with bound benzoylformate and inhibiting the reaction. However, the presence of benzoate greatly enhanced the reaction with $O_2$ ($k'_2$) and only slightly for the reaction of the proposed [$Fe^{IV}=O$] species (D) with the methanol solvent ($k'_4$).

Low-temperature Hammett Analysis. The next control experiment was to utilize the Hammett constants for substituted benzoylformates and look at the rates of different substituted benzoylformates under stopped-flow conditions. This was based upon previously established Hammett analyses of the dioxygen reactivity of an α-keto acid model system. The nucleophilic nature of the C2 α-keto carbonyl carbon is involved in the rate determining step of the reaction and has a direct effect on the rate of decarboxylation (Chiou, Y.-M.; Que, L. J. *Journal of the American Chemical Society* 1995, 117, 3999). Previous work by Paul Tarves investigated the room temperature oxidation of a series of p-substituted benzoylformates where the observed rates of reaction were determined by the release of the p-X-benzoate species by GC analysis over a time period of minutes.

The rates show a clear dependence on the Hammett constants and the rate increases as the trend shifts from electron donating to electron withdrawing groups in the para position, suggesting the involvement of a nucleophilic attack (FIG. 37) (Thesis of Tarves, P. C., Boston University, 2012). There are two outliers in the plot (FIG. 37) corresponding to the p-N(Me)$_2$ and p-N(Et)$_2$ benzoylformates which may be due to the para group being protonated on the amino group as a result of the synthesis of these substituted benzoylformates. If these are protonated then they would switch from electron donating to electron withdrawing and with a positive Hammett coefficient they may fall along the line. A re-examination of the p-N(Me)$_2$ and p-N(Et)$_2$ benzoylformates at room temperature is required.

Figure 37:
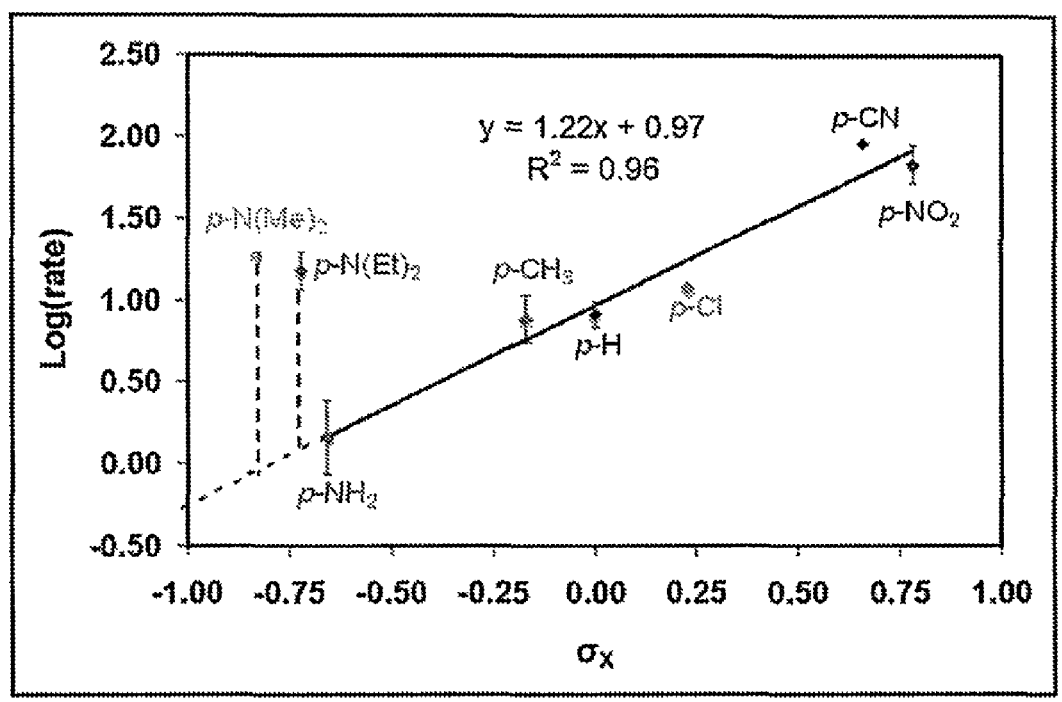
FIG. 37 is a Hammett plot for the decarboxylation of [Fe$^{II}$(N$_2$O$_1$)(p-X-BF)] adduct complexes at room temperature.
Figure 38:
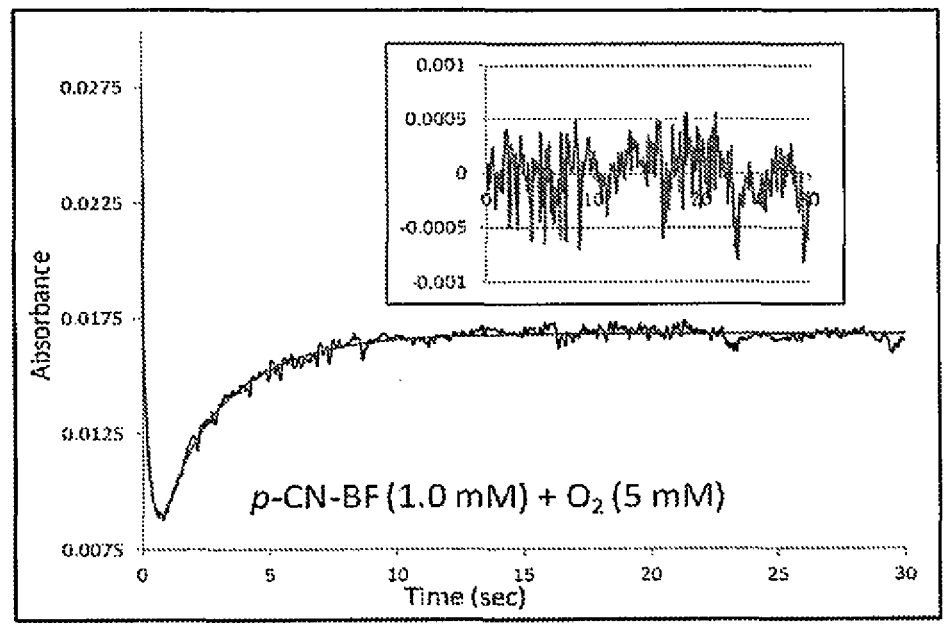
FIG. 38 is a graph of single-wavelength data at 660 nm (black) and kinetic fit to the data (red) for the reaction of [Fe$^{II}$(N$_2$O$_1$)(p-CN-BF)(CH$_3$OH)] (25) (1.0 mM) with O$_2$ (5 mM) at −85° C. Top: Residuals to fit.
Figure 39:
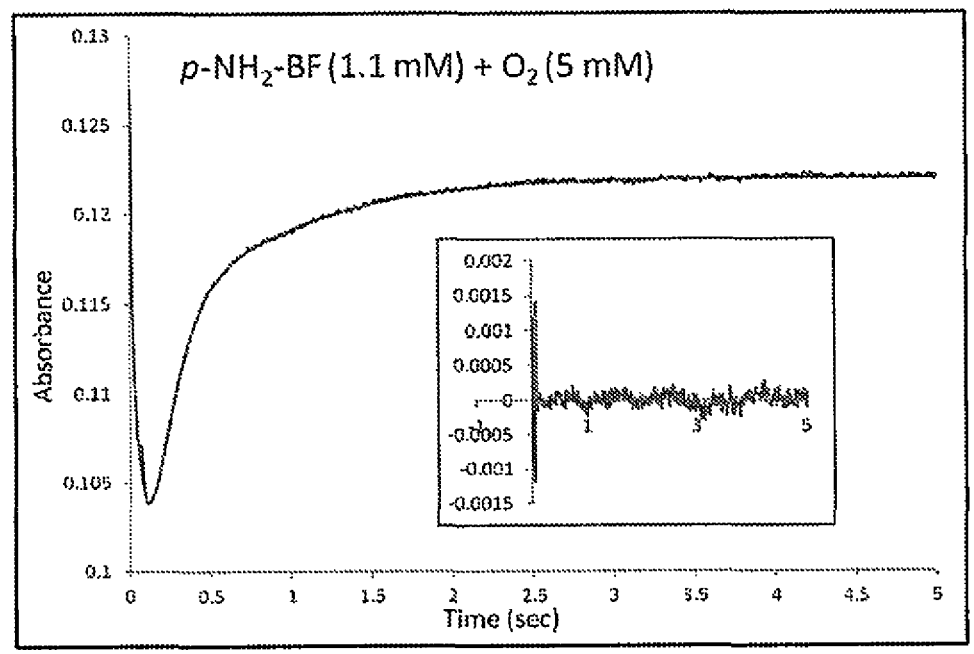
FIG. 39 is a graph of single-wavelength data at 615 nm (black) and kinetic fit to the data (red) for the reaction of [Fe$^{II}$(N$_2$O$_1$)(p-NH$_2$-BF)(CH$_3$OH)] (1.0 mM) with O$_2$ (5 mM) at −85° C. Top: Residuals to fit.

Using the results in FIG. 37, experiments were designed to analyze several substituted benzoylformates and see what changes are observed in the rates with the presence of an electron withdrawing and electron donating group. For starters, a benzoylformate from each extreme of the Hammett plot was chosen for the initial studies. The adduct complexes of p-CN-BF (25) and p-NH$_2$-BF (26) were reacted at −85° C. under cryogenic stopped-flow conditions with dioxygen. The single-wavelength (660 nm) data for the reaction of [$Fe^{II}(N_2O_1s)(p\text{-CN-BF})(CH_3OH)$] (25) with $O_2$ is given in FIG. 36 and was fit according to FIG. 38 and equations 4.21 to 4.44 and the calculated rates are given in Table 7. The same reaction was performed with [$Fe^{II}(N_2O_1)$(p-NH$_2$-BF)(CH$_3$OH)] (26) at 615 nm (FIG. 39) and also fit to equations 4.21 and 4.24.

TABLE 7

Reactions of different benzoylformate adduct complexes of 17. All rates reported at −85° C. in methanol.

| Step (units) | p-NH$_2$ (26)$^a$ | p-H (24)$^b$ | p-CN (25)$^c$ |
|---|---|---|---|
| $k'_1$ (s$^{-1}$) | 8.5 ± 1.8 | 7.8 ± 1.0 | 8.7 ± 1.2 |
| $k'_2$ (M$^{-1}$ s$^{-1}$) | 2700 ± 300 | 240 ± 4 | 140 ± 12 |
| $k'_3$ (s$^{-1}$) | 1.0 ± 0.2 | 20 ± 0.9 | 60 ± 5 |
| $k'_{4obs}$ (s$^{-1}$) | 1.7 ± 0.4 | 0.4 ± 0.03 | 0.2 ± 0.02 |
| Hammett constant (σx) | −0.66 | 0.00 | +0.66 |
| $K_D$ (μM) | 22 ± 7 | 410 ± 13 | 138 ± 14 |

$^a$[26] = 1.1 mM, [O$_2$] = 5 mM
$^b$[24] = 0.94 mM, [O$_2$] = 5 mM
$^c$[25] = 1.0 mM, [O$_2$] = mM

The rates for p-CN, p-NH$_2$, and p-H for comparison are given in Table 7. There are several steps that appear to have little effect from the electron donating and electron withdrawing groups ($k'_1$, $k'_4$). However, there is a clear trend $k'_2$ which corresponds to the reaction with O$_2$ such that p-NH$_2$-BF (26) reacts significantly faster than p-CN-BF (25) by a factor of 1000. This may suggest that the electron donating nature can help stabilize the high-valent iron center therefore facilitating a faster reaction with dioxygen. More importantly, the rates of $k'_3$, which is modeled as the step that corresponds to the decarboxylation of the benzoylformate to benzoate shows a very clear trend in observed rates in comparison to the Hammett constants.

Figure 40:
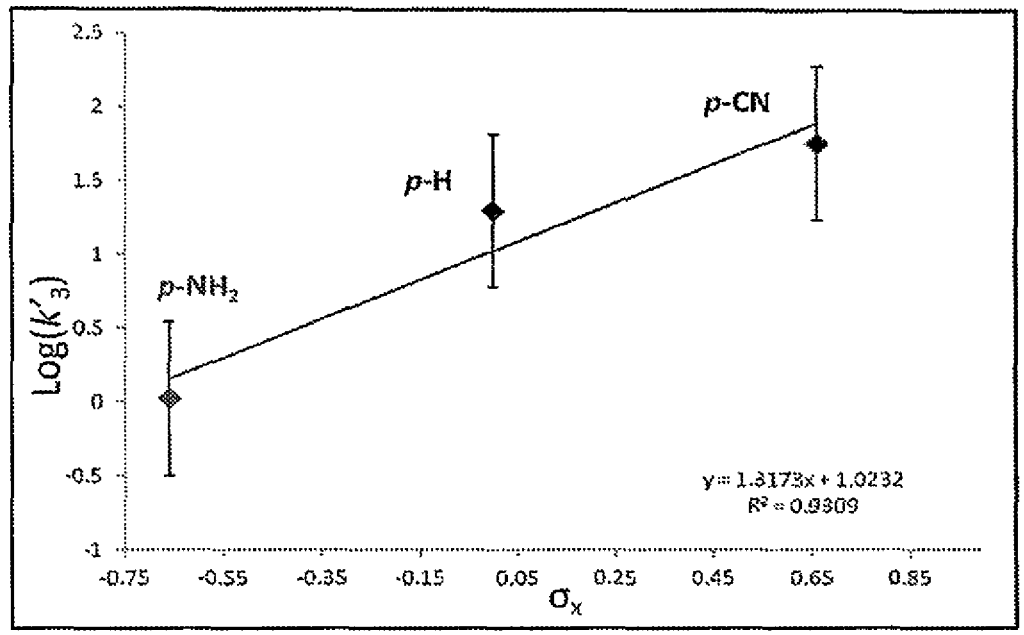
FIG. 40 is a Hammett plot for the rate k'3 which is proposed to correspond to the decarboxylation of the [Fe$^{II}$(N$_2$O$_1$)(p-X-BF)] adduct complexes at −85° C.

A plot of the log($k'_3$) vs. the Hammett constant ($σ_x$) is shown in FIG. 40 and shows excellent linearity in the data. This supports the inclusion of this step in the proposed mechanism in FIG. 29 and that $k'_3$ involves the attack of the C2 carbon of the α-keto acid by a nucleophilic attack of the Fe(III)-superoxide intermediate which is consistent with mechanistic influence of a para-substituent on the benzoate group. This is reinforced by the optimized DFT structure of the benzoylformate adduct complex, 18, that shows the delocalization effects (FIG. 20). It is interesting to note that the line of best fit in FIG. 40 is comparable to the room temperature Hammett plot in FIG. 38 (1.06x+1.18 vs. 1.22x+0.97, respectively).

Figure 41:
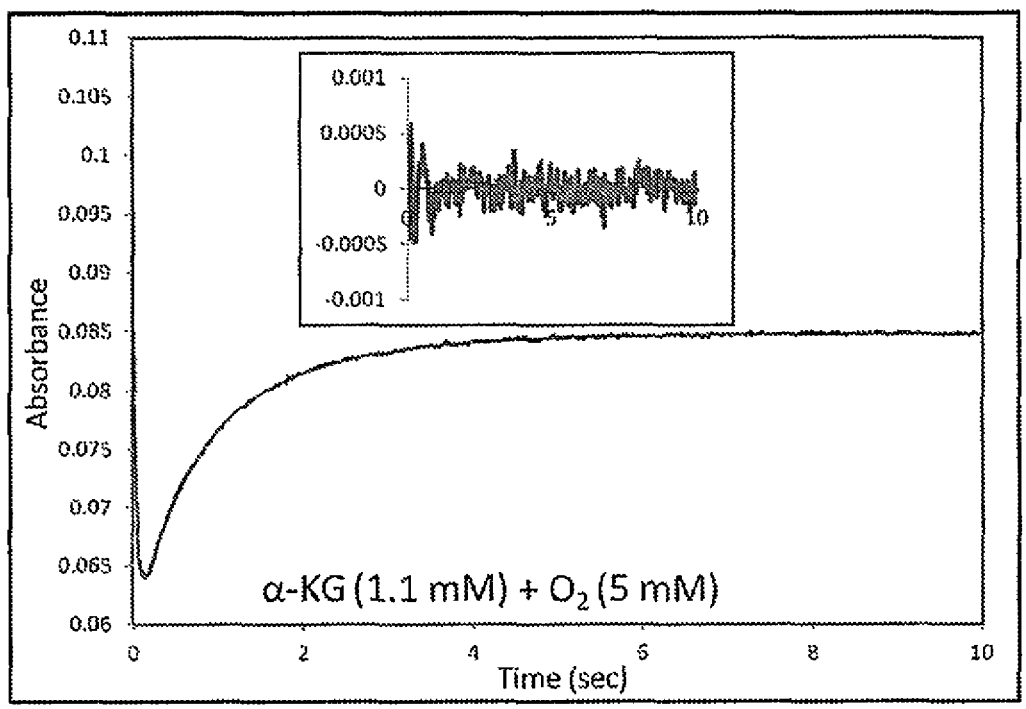
FIG. 41 is a graph of single-wavelength data at 500 nm (black) and kinetic fit to the data (red) for the reaction of [Fe$^{II}$(N$_2$O$_1$)(α-KG)(CH$_3$OH)] (18) (1.1 mM) with O$_2$ (5 mM) at −85° C. Top: Residuals to fit.

Low-temperature stopped-flow analysis of [$Fe^{II}(N_2O_1)$(α-KG)] (18) with O$_2$. With a good idea on the low-temperature mechanism of the reaction of [$Fe^{II}(N_2O_1)$(p-X-BF] adduct complexes with O$_2$, the reaction with the α-KG coenzyme was analyzed. The single-wavelength data were collected at 500 nm (FIG. 41) and were fit to the same mechanism used for the benzoylformate complexes and equations 4.21 to 4.34. The residuals show a good fit to the data as well as the small standard deviations in the calculated rate constants (Table 8).

TABLE 8

Calculated rate constant for the reaction of 18 (1.1 mM) with O$_2$ (5 mM) in methanol. All rates reported at −85° C.

| Step (units) | α-KG (18) | p-H (24)$^a$ |
|---|---|---|
| $k'_1$ (s$^{-1}$) | 7.6 ± 1.1 | 7.8 ± 1.0 |
| $k'_2$ (M$^{-1}$ s$^{-1}$) | 3100 ± 300 | 240 ± 4 |
| $k'_3$ (s$^{-1}$) | 0.8 ± 0.1 | 20 ± 0.9 |
| $k'_{4obs}$ (s$^{-1}$) | 11 ± 1 | 0.4 ± 0.03 |

First, the value for the loss of the a methanol ligand to allow for the reaction with O$_2$ ($k'_1$=7.6 s$^{-1}$) is comparable to the same process in the binding of NO to 18 ($k_{20}$=4.1 s$^{-1}$) which shows a good internal control of the proposed mechanism. The rates in Table 8 parallel what is already known about the room temperature reactivity of 18 in comparison to the benzoylformate analog (24). Also, the rates for the reaction with dioxygen ($k'_2$) as well with substrates (methanol, $k'_4$) are greatly accelerated which parallels the rate of room temperature reactivity of 18 of 2 minutes versus nearly 200 minutes for 24. Previous electrochemical studies suggest that the α-KG adduct complex is significantly less stable. This is based off electrochemical studies where 18 displayed irreversible electrochemical behavior ($E_{ox}$=225 mV vs. NHE) upon a one-electron oxidation where as 24 displayed a quasi-reversible electrochemical process under identical experimental conditions ($E_{1/2}$=60 mV vs. NHE) (Thesis of Tarves, P. C., Boston University, 2012).

Figure 42:
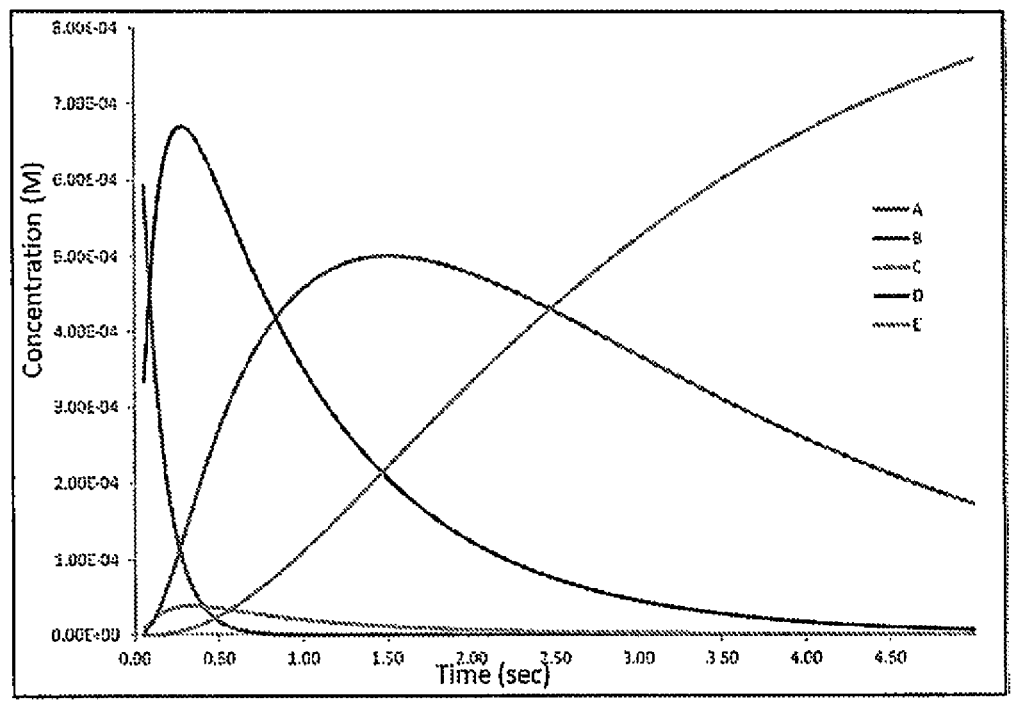
FIG. 42 is a speciation plot for the reaction of 24 with O$_2$ at −85° C.
Figure 43:
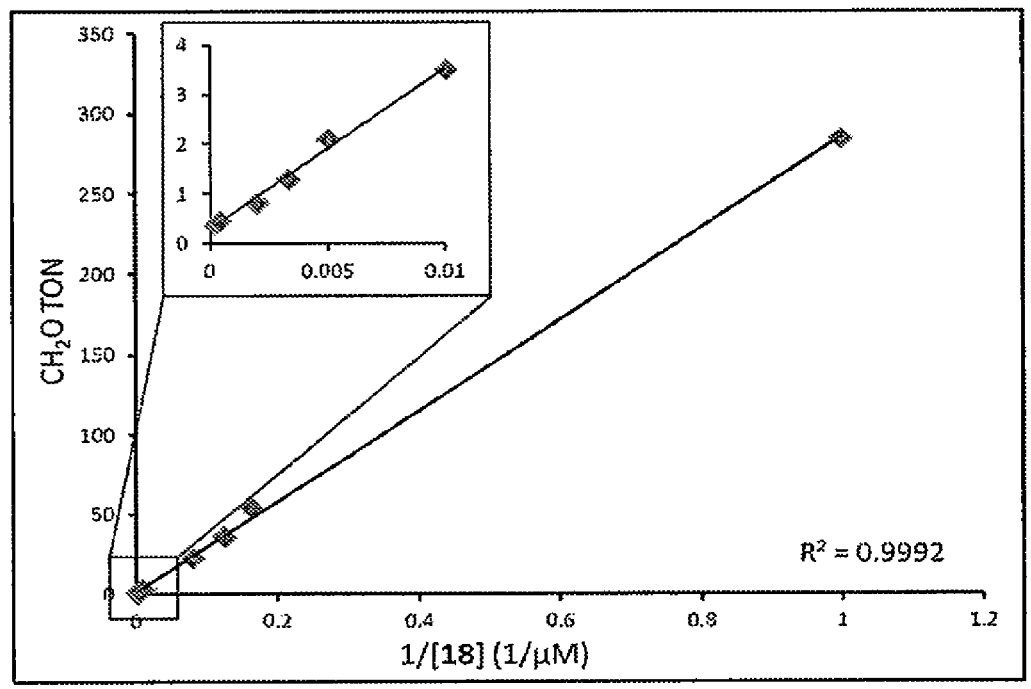
FIG. 43 is a plot of 1/[18] vs. formaldehyde TON, data from Table 6.

The mechanistic analysis of this reaction and the calculated rate constants result in the formation of speciation plots which will be vital in the spectroscopic characterization of the reactive intermediates. The speciation plot of the reaction of 18 with $O_2$ is shown in FIG. 42 which shows the concentration of each species versus the time of the reaction. The speciation plots will be used to help simulate the different populations of each species at different time points in the reaction. This will be mainly accomplished by the use of flow Resonance Raman studies and $^{18}O_2$ labeling studies. Intermediate C, the proposed [$Fe^{III}$-superoxide] complex will have characteristic O—O and Fe—O stretching frequencies that will easily distinguishable with $^{16}O_2/^{18}O_2$ isotopic labeling studies. The proposed reactive species, a putative [$Fe^{IV}$=O] species will also show a Fe—O stretching frequency.

Figure 6:
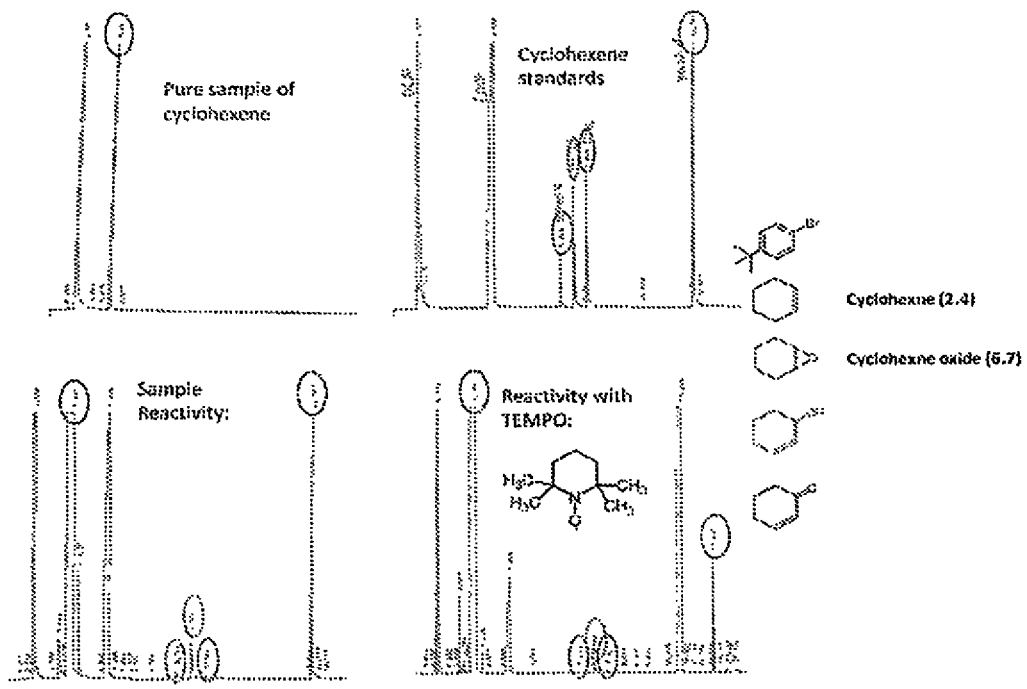
FIG. 6 is a graph of GC-FID traces of the reactivity of cyclohexene with (17), α-KG, and $O_2$ with/without the free radical scavenger TEMPO.
Figure 7:
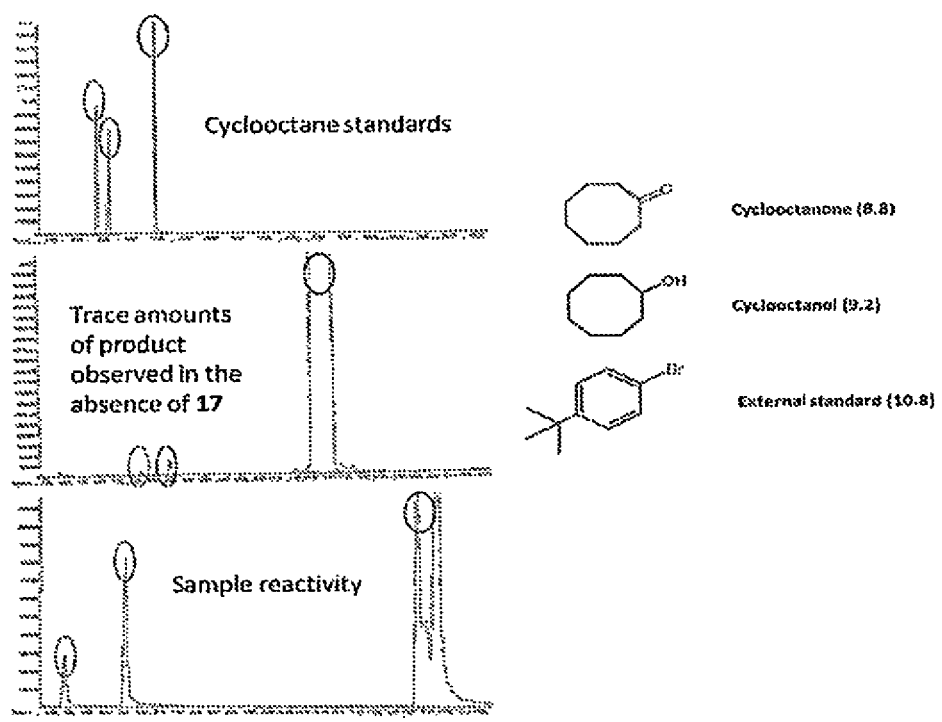
FIG. 7 is a graph of GC-FID traces for the reactivity of cyclooctane with (17), α-KG, and $P_2$.

Reactivity studies with [$Fe^{II}(N_2O_1)(\alpha$-KG)(MeOH)]$^-$ (18) and substrates. Based on the apparent catalytic solvent reactivity previously found, efforts were directed towards testing the limit of the catalysis at lower iron concentrations. First, the plot in FIG. 2 was extended beyond 0.1 mM of 18 all the way down to 1 μM (Table 9). This data were added to the plot of 1/[18] versus turnover number (FIG. 6) and retains excellent linearity at low-concentrations.

The results of methanol oxidation 18 was capable of oxidizing the strong bond of methanol ($BDE_{C—H}$=96 kcal mol$^{-1}$) which prompted the investigation of other substrates. First, this required the use of a non-reactive solvent to direct the oxidation towards an external substrate. A 90:10 DCM:DMF (v/v) solvent mixture was used.

Multiple substrates were considered and a summary of the reactivity studies is shown in Table 9. These results show that 18 is capable of oxidizing a wide variety of substrates such as the weak bond of 9,10-DHA, the O—H bond of phenols as well as alkenes and alkanes at very high turnovers (TON). Additionally, the reaction with cyclooctane can be done with $O_2$ or with air with relatively the same activity (305 and 317 TON, respectively). The presence of 6×10$^4$ excess of the radical scavenger TEMPO ((2,2,6,6-tetramethyl-piperidin-1-yl)oxyl) also led to very little difference in the total turnover number observed for cyclohexene oxidation which suggests that the catalytic activity is a result of a metal based oxidant as opposed to freely diffusing radicals in solution. Table 6 shows the great versatility of this complex and this catalyst can be mobilized on a solid support to inhibit the formation for the μ-oxo species which is the thermodynamic sink of this reaction. Reactions were also performed analyzing the oxidation of cyclohexane ($BDE_{C—H}$=99.5 kcal mol$^{-1}$) and there was some cyclohexanol and cyclohexanol formed. The amount of α-keto acid decomposition to its acid is tightly coupled to substrate to product conversion; that is, one product molecule is generated for each α-keto acid decomposition. Shown here are NMR spectra of the before and after reaction solution for 5 turnovers. This 1:1 coupling indicates that the chemistry does not arise from a free-radical chain process after an initiation step, but requires the decomposition of one α-keto acid to generate the reactive iron-based intermediate.

Figure 44:
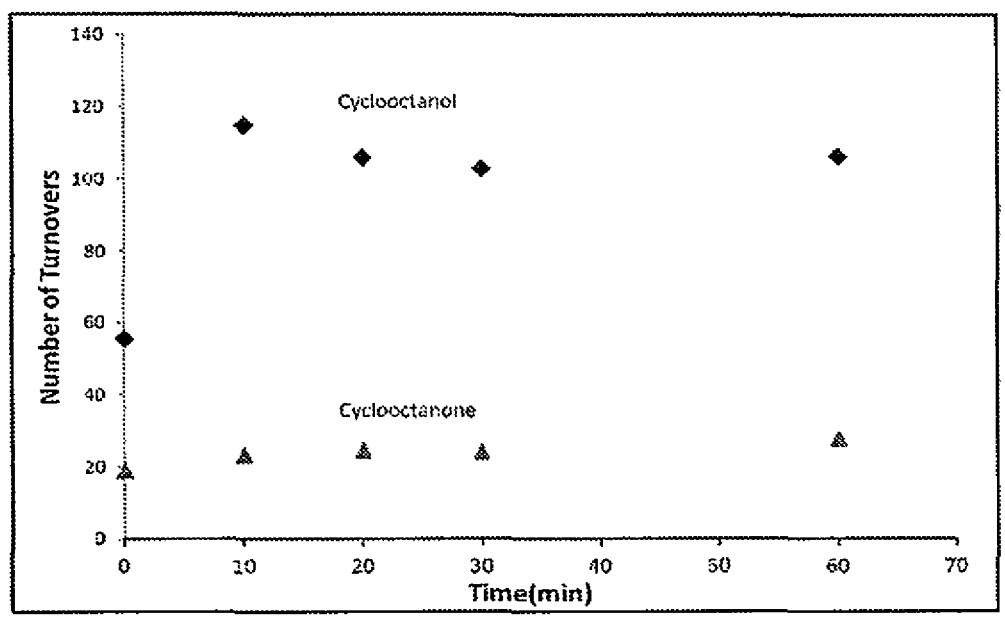
FIG. 44 is a graph of time course for the reaction of 18 (1.02 μM) with α-KG (24 mM) and cyclooctane (4.6 M).

FIG. 44 shows a time course reaction. The initial time point (t=0) was about 15 seconds after first exposing the solution to dioxygen (the amount of time it takes to inject into the GC column) and there are already approximately 60 observed turnovers which is effectively two turnovers per second. Next, a method for quenching the reaction is required so that smaller time points can be obtained and not be dependent on the timing of the GC system but FIG. 44 shows the real potency of these complexes and their ability to catalyze challenging reactions.

Conclusions

This model system is a prime example of greatly enhanced $O_2$ reactivity observed with the addition of α-KG to an Fe(II) metal center. This α-KG model system represents the first example of a model system capable of utilizing the native coenzyme and performing tightly coupled biomimetic oxidative decarboxylation of α-KG utilizing dioxygen. This complex has also been shown to oxidize a wide variety of substrates with high catalytic activity at low iron concentrations. The low-temperature kinetic studies presented here have identified and mechanistically assigned multiple intermediates of the reaction profile of a well definite functional mononuclear model complex starting with the binding of α-KA's to 17. This was then extended to the reaction of the adduct complexes (18, 24-26) with dioxygen which resulted in a proposed mechanism for this process with multiple control reactions in support of the mechanism.

TABLE 9

Summary of reactivity studies of 17 with substrates.

| Substrate[a] | BDE (kcal/mol) | Oxidant | [Fe] (μM) | Product[b] | TON | Total TON |
|---|---|---|---|---|---|---|
| Methanol | 96 | $O_2$ | 5000 | Formaldehyde | 0.39 (0.6) | 0.39 (0.6) |
| | | | 2500 | Formaldehyde | 0.46 (0.2) | 0.46 (0.2) |
| | | | 500 | Formaldehyde | 0.82 (0.1) | 0.82 (0.1) |
| | | | 300 | Formaldehyde | 1.3 (0.3) | 1.3 (0.3) |
| | | | 200 | Formaldehyde | 2.1 (0.3) | 2.1 (0.3) |
| | | | 100 | Formaldehyde | 3.5 (0.5) | 3.5 (0.5) |
| | | | 12.5 | Formaldehyde | 22 (5) | 22 (5) |
| | | | 8.0 | Formaldehyde | 36 (2) | 36 (2) |
| | | | 6.2 | Formaldehyde | 54 (6) | 54 (6) |
| | | | 1.0 | Formaldehyde | 285 (10) | 285 (10) |
| Cyclooctane | 95 | $O_2$ | 9.7 | Cyclooctanol | 24 (4) | 40 (4) |
| | | | | Cyclooctanone | 7.8 (0.8) | |
| | | | 1.1 | Cyclooctanol | 182 (17) | 305 (28) |
| | | | | Cyclooctanone | 62 (5) | |
| | | Air[c] | 1.1 | Cyclooctanol | 189 (5) | 317 (9) |
| | | | | Cyclooctanone | 64 (2) | |

TABLE 9-continued

Summary of reactivity studies of 17 with substrates.

| Substrate[a] | BDE (kcal/mol) | Oxidant | [Fe] (μM) | Product[b] | TON | Total TON |
|---|---|---|---|---|---|---|
| Cyclohexene | 85 | $O_2$ | 9.6 | Cyclohexene oxide | 132 (35) | 520 (16) |
| | | | | 2-Cyclohexen-1-ol | 249 (22) | |
| | | | | 2-Cyclohexen-1-one | 70 (3) | |
| | | $O_2$ | 9.6 + TEMPO[d] | Cyclohexene oxide | 53 (2) | 414 (33) |
| | | | | 2-Cyclohexen-1-ol | 240 (19) | |
| | | | | 2-Cyclohexen-1-one | 60 (6) | |
| 2,4-di-tert-butyl-phenol | 83 | $O_2$ | 9.6 | 3,3'-5,5'-terta-t-butyl-2,2'-dihydroxybiphenyl | 619 (77) | 619 (77) |
| 9,10-Dihydroanthracene | 78 | $O_2$ | 10.1 | Anthracene | 54 (16) | 128 (12) |
| | | | | Anthrone | 21 (10) | |
| | | | | Anthraquinone | 26 (6) | |

In Table 9,
[a]all reactions performed with 55-75 mM [α-KG][NEt$_4$] salt with balloon of ultra high purity $O_2$ and 1-5M substrate concentration;
[b]formaldehyde product determined by Nash assay, all other products determined by GC/MS;
[c]reaction vial opened to air during the reaction;
[d]presence of radical scavenger in 6 × 10$^4$ excess TEMPO = (2,2,6,6-Tetramethyl-piperidin-1-yl)oxyl.

Example 2

Synthesis and Characterization of Iron(II) and Iron(III) Compounds with a fac-$N_2O_1$-pyridiyl Ligand Motif Described herein are the preparation, characterization and reactivity studies of a catalyst that contains a pyridine functional group in place of the terminal dimethyl amine group of $N_2O_1$. The incorporation of this aromatic functionality provides a ligand system with greater synthetic potential for multiple purposes: (1) A variety of electron donating/withdrawing substituents in the para position may alter the electronics of the metal center, which can in turn allow for the tuning of the reactivity properties of the complex. (2) The solubility of the complex in organic solvents, inert to oxidation, may be increased by the addition of 'solubility friendly' substituents. (3) The functionalization of the ligand with a terminal alkyne provides the ability to immobilize the complex using azido-functionalized supports via 'click' chemistry.

General Methods

All reagents and solvents used were purchased from commercial sources and used as received unless otherwise noted. Prior to use, methanol (Pharmco-Aaper) was distilled over magnesium metal, dimethyl sulfoxide (Fisher Scientific) was distilled over calcium hydride, triethylamine was distilled over sodium metal and unstabilized dichloromethane (Fisher Scientific) was distilled over calcium hydride. Ferrocene was purified by sublimation for use as a reference for electrochemical analyses. All manipulations involving ferrous complexes were carried out in an inert atmosphere glovebox (M. Braun, Stratham, N.H.) with distilled and thoroughly degassed solvents. UV/Vis spectra were collected using a Hewlett Packard Spectrometer (8453). IR spectra were collected using a Thermo Nicolet AVATAR 330-FT-IR. Cyclic voltammetry experiments were performed using a Princeton Applied Research model 273 potentiostat with a glassy carbon working electrode, a silver wire reference electrode and a platinum wire counter electrode. Electron Paramagnetic Resonance (EPR) spectra were collected on a Bruker ESP-300E spectrometer operating at 9.460 GHz. NMR spectra were recorded at 25° C. using a Varian spectrometer operating at 400 MHz with all chemical shifts referenced to SiMe4. Iron concentrations were determined using a Varian AA240Z Atomic Absorption Spectrometer.

Scheme 1: Synthesis of $N_2O_1$-py ligand

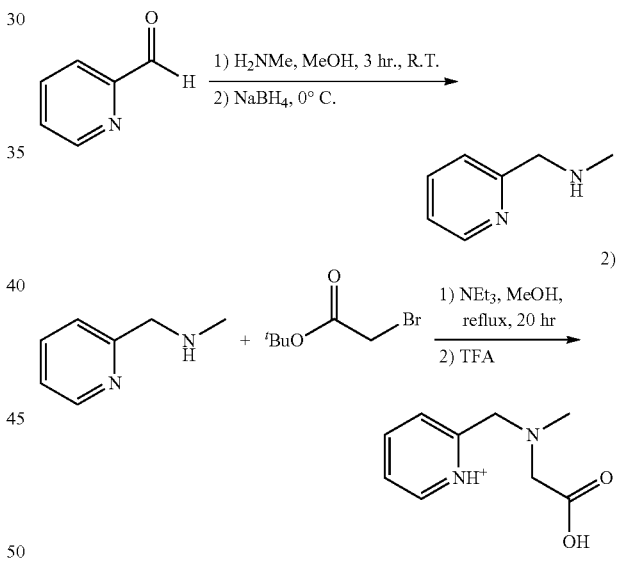

Synthesis of N-methyl-1-(pyridine-2-yl)methanamine: In a purged three neck flask, pyridinecarboxyladehyde (5.0 g, 46.7 mmol) was dissolved in 25 mL of freshly distilled methanol. To the stirring solution, methylamine (17.26 mL, 140 mmol, 33% solution in ethanol) was added. The reaction stirred for 3 hours before being cooled to 0° C. NaBH$_4$ (2.28 g, 60 mmol) was added and the reaction was allowed to warm to room temperature and stir for 20 hours. The reaction was quenched with NaHCO$_3$, and the product was extracted with 3×50 mL CH$_2$Cl$_2$. The organic phases were collected and dried over NaSO$_4$ and then reduced via a rotary evaporator to yield the product as a yellow oil, which was used without any further purification (5.54 g, 45.3 mmol, 90% yield); $^1$H NMR (400 MHz, DMSO) δ 8.50 (d, J=5.6 Hz, 1H), 7.75 (dd, J=8.0 Hz, 1H), 7.41 (d, J=8.0 Hz, 1H), 7.25 (dd, J=7.6 Hz, 1H), 3.80 (s, 2H), 2.33 (s, 3H). $^{13}$C NMR (400 MHz, DMSO) δ 159.58 ($^{Ar}C$), 149.20 ($^{Ar}C$), 136.93 ($^{Ar}C$), 122.47 ($^{Ar}C$), 122.32 ($^{Ar}C$), 56.41 ($CH_2$), 35.75 ($CH_3$).

Synthesis of 2-(methyl(pyridine-1-ium-2-ylmethyl)ammonio)acetate ([$H_2N_2O_1py$]-[$C_2O_2F_3$]): In a round bottom flask, N-methyl-1-(pyridine-2-yl)methanamine (1.01 g, 8.2 mmol) was added to a solution of triethylamine (10.0 g, 98.8 mmol) and freshly distilled MeCN (23 mL). The solution was refluxed at 80° C. for 45 minutes before being cooled to 0° C., at which point t-butyl bromoacetate (3.65 mL, 24.7 mmol) was added slowly via pipet over a period of five min. A white precipitate ($NH_4Br$) formed that dissolved back into solution as the reaction was returned to reflux and allowed to stir at 80° C. for 20 hours. The reaction was cooled to 0° C. and the precipitate was removed via vacuum filtration through a fritted glass funnel. The filtrate was reduced via a rotary evaporator yielding an orange solid that was dissolved in 50 mL $CH_2Cl_2$ and extracted with 4×50 mL portions of 2M HCl. Each 50 mL fraction of HCl was immediately collected into a flask cooled to 0° C. containing 100 mL of 7M KOH to prevent unwanted hydrolysis of the t-butyl group. The aqueous phases were collected and the product was extracted with 4×50 mL of ethyl acetate. The organic phases were collected and washed twice with 2×40 mL of sat. $K_2CO_3$, dried over $MgSO_4$ and then reduced via a rotary evaporator to yield the t-butyl protected form of the ligand as a brown oil. DE protection was performed by dissolving the oil in 50 mL of concentrated trifluoroacetic acid and stirring for 3 hours. The trifluoroacetic acid was removed under high vacuum, and the remaining oil was triturated six times with THF. The product was dissolved in a minimal amount of THF and recrystallized by the addition of diethyl ether as a white solid (1.19 g, 4.05 mmol, 49% yield). Electro spray MS ($CH_3OH$, positive ion mode, m/z): $C_9H_{13}N_2O_2$, expected 181.1 (100%); found: 181.1 (100%). $^1$H NMR (400 MHz, DMSO) δ 8.66 (d, J=5.2 Hz, 1H), 7.92 (dd, J=9.6 Hz, 1H), 7.55 (d, J=8.0 Hz, 1H), 7.47 (dd, J=7.6 Hz, 1H), 4.48 (s, 2H), 4.09 (s, 2H), 2.82 (s, 3H). $^{13}$C NMR (400 MHz, DMSO) δ 168.11 (C=O), 151.33 ($^{Ar}C$), 149.70 ($^{Ar}C$), 138.16 ($^{Ar}C$), 125.29 ($^{Ar}C$), 124.53 ($^{Ar}C$), 59.63 ($CH_2$), 55.83 ($CH_2$), 41.93 ($CH_3$). Selected IR bands (KBr, $cm^{-1}$): 1640 (Py), 1730 (C=O), 3080 (O—H).

Synthesis of [PSH][$Fe^{II}(N_2O_1py)(Cl)_2$]: In an inert atmosphere ($N_2$) glovebox, the $H_2N_2O_1py$ ligand (0.258 g, 0.877 mmol) was dissolved along with two equivalents of proton sponge (0.379 g, 1.77 mmol) in 5 mL 1:4 methanol/THF, and then added to a solution of $FeCl_2$ (0.100 g, 0.789 mmol) in 5 mL of 1:4 methanol/THF. Although a yellow precipitate formed immediately, the solution was allowed to stir for 12 hours at room temperature. The yellow precipitate was collected via filtration over a fritted glass filter, and washed with THF and then diethyl ether, yielding the iron complex as a yellow solid (0.209g, 73% yield). Electronic absorption, $\lambda_{max}$ (MeOH)/nm ($\epsilon/M^{-1}cm^{-1}$): 260 (4362), 376 (546). Selected IR bands (KBr, $cm^{-1}$): 1310 (C=$O_{sym}$), ~1580 (C=$O_{asym}$).

Preparation of [PSH][$Fe^{III}(N_2O_1py)(Cl)_3$]: In an inert atmosphere ($N_2$) glovebox, the $H_2N_2O_1py$ ligand (0.201 g, 0.684 mmol) was dissolved along with two equivalents of proton sponge (0.293 g, 1.37 mmol) in 5 mL 1:4 methanol/THF, and then added to a solution of anhydrous $FeCl_3$ (0.100 g, 0.616 mmol) in 5 mL of 1:4 methanol/THF. A yellow precipitate formed immediately, but the solution was allowed to stir for 12 hours at room temperature. The yellow precipitate was collected via filtration over a fritted glass filter, and washed with THF and then diethyl ether, yielding the iron complex as a yellow solid (0.209g, 73% yield). Electronic absorption, $\lambda_{max}$ (MeOH)/nm ($\epsilon/M^{-1}cm^{-1}$): 340 (3622). Selected IR bands: (KBr, $cm^{-1}$): 1350 (C=$O_{sym}$), ~1650 (C=$O_{asym}$).

Potentiometric Titration of [$H_2N_2O_1py$]$^+$

To a 250 mL volumetric flask was added 0.2080 g of the [$H_2N_2O_1py$][$C_2O_2F_3$] and ~50 mL distilled $H_2O$. A burette was charged with 0.0504 M NaOH. The ligand solution was slowly titrated with the base as the pH was constantly monitored. Titration continued until the pH stabilized at ~pH=13.

Cyclic Voltammetry

Cyclic voltammetry was performed inside an inert atmosphere ($N_2$) box, with degassed DMSO as the solvent and tetra-N-butylammonium hexafluorophosphate as the supporting electrolyte (0.2M). The ferrocenium/ferrocene couple was used as an internal reference; reduction potential values were corrected by assigning the ferrocenium/ferrocene couple to 0.64 V versus NHE (Zanello, P. *Inorganic Electrochemistry*; The Royal Society of Chemistry: Cambridge, 2003). Chloride titration experiments were performed by collecting CV data after the addition of one and two 50 μL aliquots of 204 mM [$NEt_4$][Cl] to 3.0 mL of 3.4 mM [$Fe^{II}(N_2O_1py)(Cl)_2$]$^-$ (concentration determined using flame atomic absorption spectroscopy) and correcting the potential with reference to the ferrocenium/ferrocene couple.

Chloride Elemental Analysis of [$Fe^{II}(N_2O_1py)(Cl)_2$]$^-$ and [$Fe^{III}(N_2O_1py)(Cl)_3$]$^-$ In an inert ($N_2$) atmosphere dry box, 1.00 mL solutions of [$Fe^{II}(N_2O_1py)(Cl)_2$]$^-$ and [$Fe^{III}(N_2O_1py)(Cl)_3$]$^-$ were prepared with respective concentrations of 10.38 mM (1.038× $10^{-5}$ mol) and 16.30 mM (1.630×$10^{-5}$ mol) (concentration determined using flame atomic absorption spectroscopy) in dry, degassed methanol. Five equivalents of silver nitrate were added to each solution which produced insoluble silver chloride. After 15 minutes, the solutions were centrifuged and then decanted. The precipitates were washed by the addition of methanol (~1 mL) to each, followed by centrifugation and solvent removal. After five washings, the solids were dried at 30° C. in a vacuum oven overnight before obtaining their final masses. [$Fe^{II}(N_2O_1py)(Cl)_2$]$^-$: yield of AgCl (2.6 mg, 1.53×$10^{-5}$ M); [$Fe^{III}(N_2O_1py)(Cl)_3$]$^-$: yield of AgCl (7.6 mg, 4.47×$10^{-5}$ M). These results are summarized in Table 10.

TABLE 10

| Chloride elemental analysis | |
| --- | --- |
| Complex | Cl equivalents |
| Fe(II) | 1.47 |
| Fe(III) | 2.74 |

$O_2$ Reactivity of Ferrous Complexes

[$Fe^{II}(N_2O_1py)(Cl)_2$]$^-$: A 1.0 mM $_{[PSH][Fe}{}^{II}(N_2O_1py)(Cl)_2$] solution was prepared in dry, degassed methanol in an inert ($N_2$) atmosphere glovebox. The solution was transferred to an anaerobic UV/vis cell and sealed. An initial spectrum was obtained of the ferrous complex, and then the solution was exposed to the air. Spectra were recorded every minute for the first two minutes and then every 5-30 minutes after that for seven hours. The absorbance was monitored at 350 nm to follow formation of the oxidized complex.

[$Fe^{II}(N_2O_1py)(\alpha KG)$]: A 1.0 mM [PSH][$Fe^{II}(N_2O_1py)(Cl)_2$] solution was prepared in dry, degassed methanol in an inert ($N_2$) atmosphere glovebox with a total volume of 3.0 mL. Five molar equivalents of solid sodium α-ketoglutarate (2.6 mg, 15.0 µmoles) were added. This solution was then transferred to an anaerobic UV/vis cell and sealed. An initial spectrum was obtained of the ferrous complex, and then the solution was exposed to the air. Spectra were collected every minute for the first 30 minutes and then every 5-20 minutes after that for 2 hours. The absorbance was monitored at 315 nm to follow formation of the oxidized complex.

Determination of formaldehyde concentration: Nash assay (Nash, T. *Biochemical Journal* 1953, 55, 416-21)

Preparation of Nash reagent: Ammonium acetate (15.42 g, 0.20 moles), glacial acetic acid (300 µL, 5 mmol) and acetylacetone (200 µL, 2 mmol) were dissolved in deionized water to give a 100 mL solution.

Preparation of formaldehyde standard: Paraformaldehyde (7.8 mg, 0.26 mmol) and 2M NaOH(aq) (1.00 mL, 2 mmol) were dissolved in distilled MeOH to give a 500 mL solution. Standards were prepared by diluting the formaldehyde solution to 500 µL, followed by the addition of Nash Reagent (500 µL) to give a series of 1.00 mL solutions with a concentration rang of 0.00-0.22 mM. The solutions were incubated at 42° C. for 60 min. and then the electronic absorbance at 412 nm was measured using UV/Vis spectroscopy for each solution to obtain a standard curve.

$O_2$ reactivity in methanol: In an inert atmosphere ($N_2$) glovebox, a 3.00 mL solution of $[Fe^{II}(N_2O_1py)(Cl)_2]^-$ (1.0-100 µM) was prepared in dry, degassed methanol. Five equivalents [Na][αKG] was added and the vial was removed from the glovebox and exposed to dioxygen via an $O_2$-filled balloon. The reaction was allowed to stir for 60 min. A 500 µL aliquot was removed and added to 500 µL of Nash Reagent. The solution was allowed to incubate at 42° C. for 60 min. and then the absorbance at 412 nm was measured using UV/Vis spectroscopy. The concentration of formaldehyde was calculated using the standard curve.

Electron Paramagnetic Resonance (EPR) Characterization of $[Fe^{II}(N_2O_2py)(NO)(Cl)_2]^-$ and $[Fe^{III}(N_2O_2py)(Cl)_3]^-$ Samples were prepared in an inert ($N_2$) atmosphere dry box. A 3.15 mM solution of $[Fe^{II}(N_2O_1py)(Cl)_2]^-$ and a 2.07 mM solution of $[Fe^{II}(N_2O_1py)(Cl)_3]^-$ were prepared in dry, degassed MeOH (concentrations determined using flame atomic absorption spectroscopy). The solutions were transferred to Schlenk flasks and a Schlenk line was used to evacuate the head space of each flask followed by introduction of NO gas (99+%). The flasks was evacuated and transferred to the dry box, where 400 µL of each solution were transferred to EPR tubes which were then frozen in liquid $N_2$ and stored in an $N_2$-cooled shipping dewar until analysis.

Computational Details

Method and Basis Set

All calculations were carried out using the Gaussian 09 software package (Revision B.01). Initial rough geometry optimizations were performed using unrestricted Hartree-Fock with the 6-31 g basis set. The converged configurations were then optimized using the unrestricted B3LYP method of hybrid DFT, which includes Becke's three-parameter exchange functional (B3) and the Lee, Yang and Parr (LYP) correlation (Becke, A. D. *Physical Review A* 1988, 38, 3098-100; Becke, A. D. *Journal of Chemical Physics* 1992, 96, 2155-60; Becke, A. D. *Journal of Chemical Physics* 1992, 97, 9173-77; Becke, A. D. *Journal of Chemical Physics* 1993, 98, 5648-52; Lee, C. T.; Yang, W. T.; Parr, R. G. *Physical Review B* 1988, 37, 785-89; Vosko, S. H.; et al., *Canadian Journal of Physics* 1980, 58, 1200-11). The valence triple-ζ 6-311+G(d,p) basis set was used, which includes polarization functions on all atoms and diffuse functions on non-hydrogen atoms. The iron complexes were all calculated as high-spin.

Geometry and Optimization

The initial geometry of the $H_2O$-bound $N_2O_1py$ αKG adduct (C in FIG. 59) was obtained by replacing the dimethyl amine group of the configuration 1b with a pyridine ring. Removal of αKG from the optimized geometry gave the initial geometry of the $[Fe^{II}(N_2O_1py)(H_2O)_3]$ configuration. The initial geometry of the $N_2O_1py$-medial configuration (A in FIG. 59) was obtained using Gaussview 5.0.

Solvation Model

Solvation effects were handled using the self-consistent reaction field (SCRF) approach as implemented by Gaussian 09 using the default IEF-PCM method. Dimethylsulfoxide, with a dielectric constant of 46.8, was used as the solvent.

Results and Discussion

Ligand and Complex Syntheses

Figure 58:
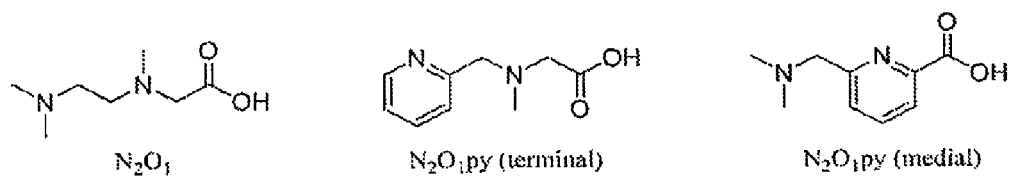
FIG. 58 is a set of chemical structures illustrating the incorporation of a pyridine group in the terminal and medial positions of the N$_2$O$_1$ ligand.

The $[Fe^{II}(N_2O_1)(αKG)]$ complex described herein has demonstrated the ability of an N,N,O-donor ligand bound in a facial manner to be capable of $O_2$ activation and catalytic activity. The complex can be modified through the incorporation of a pyridine group, as it would maintain the N,N,O coordination environment, but would also provide an aromatic ring, allowing for a variety of synthetic possibilities through the modulation of aromatic substituents. Two possibilities were considered that would introduce a pyridyl functionality while also preserving the two-carbon separation between the coordinated N,N, and O atoms (FIG. 58). However, incorporation of the pyridine group in the medial position would not allow for facial coordination. The pyridyl N atom and the α C atoms are all $sp^2$ hybridized in this configuration, forcing linear alignment with the β carbon atoms. This strain would be expected to force meridional coordination of the ligand. DFT studies were used to predict the structural properties of the ferrous complexes of these ligands, however, geometry optimization of the $[Fe^{II}(N_2O_1py\text{-medial})(H_2O)_3]$ configuration, with the ligand forced into a facial binding mode failed.

Figure 59:
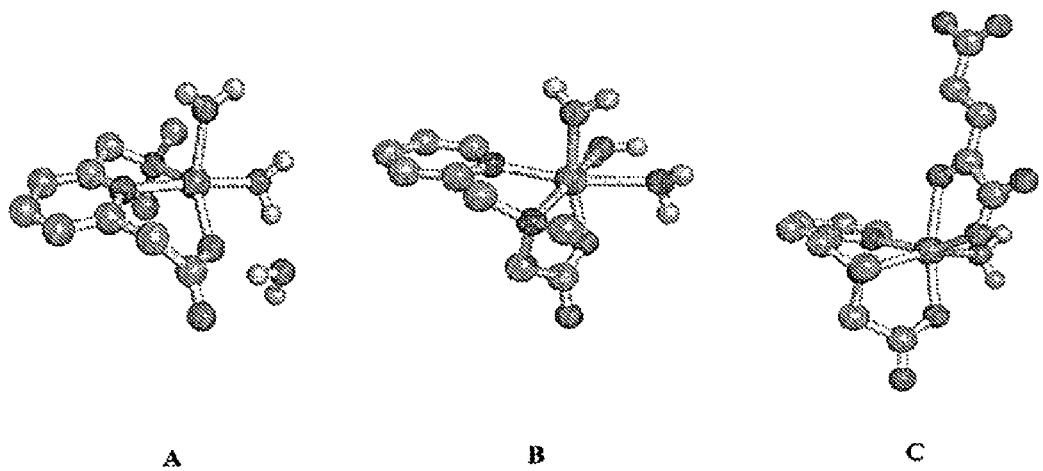
FIG. 59 is a set of geometry optimized configurations of A) fac-[Fe$^{II}$(N$_2$O$_1$py-medial)(H$_2$O)$_3$], showing the displacement of an H$_2$O ligand and formation of a distorted square pyramidal geometry, B) fac-[Fe$^{II}$(N$_2$O$_1$-terminal)(H$_2$O)$_3$] and C) fac-[Fe$^{II}$(N$_2$O$_1$-terminal)(αKG)(H$_2$O)].
Figure 60:
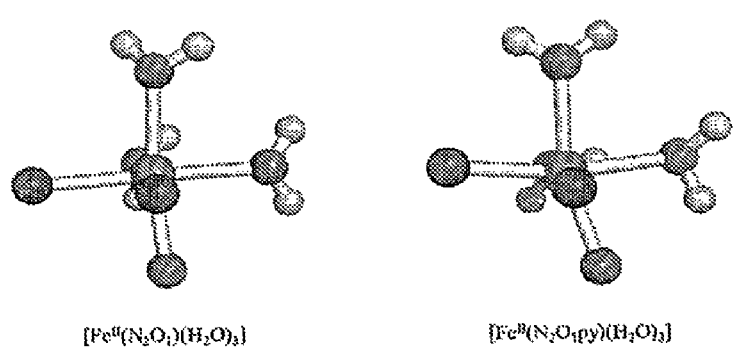
FIG. 60 is a set of skeleton structures of [Fe$^{II}$(N$_2$O$_1$)(H$_2$O)$_3$] and [Fe$^{II}$(N$_2$O$_1$py)(H$_2$O)$_3$] showing the increase in distortion of the octahedral geometry with the incorporation of a pyridyl group in the ligand.

The addition of another methylene group in-between the pyridyl and carboxylate groups allowed for convergence to a five-coordinate, distorted square pyramidal structure where an $H_2O$ ligand had been displaced (FIG. 59). This suggests that even with the increased mobility of the carboxylate group, provided by the addition of the methylene, facial coordination is an unfavorable configuration for the ligand with the pyridyl group in the medial position. Incorporation of the pyridyl group in the terminal position of $N_2O_1$ allowed convergence using uB3LYP/6-311+g(d,p) to a geometry with the ligand bound in a facial manner (B in FIG. 59). However, the pyridine ring does introduce strain in the ligand that causes the octahedral geometry to be quite distorted when compared to the $[Fe^{II}(N_2O_1)(H_2O)_3]$ configuration (FIG. 60 and Table 11). This is most noticeable upon inspection of the $N_{py}$-Fe—$O_{carb}$ angle of $[Fe^{II}(N_2O_1py)(H_2O)_3]$ compared to the $N_{dimethyl}$-Fe—$O_{carb}$ angle of $[Fe^{II}(N_2O_1)(H_2O)_3]$. Nevertheless, the $sp^3$ hybridized methylamine forces the carboxylate group to bind cis to the pyridine group rather that trans, giving facial coordination as opposed to meridional.

TABLE 11

Select bond lengths and bond angles of [Fe$^{II}$(N$_2$O$_1$py)(H$_2$O)$_3$] and [Fe$^{II}$(N$_2$O$_1$py)(H$_2$O)$_3$].

| [Fe$^{II}$(N$_2$O$_1$py)(H$_2$O)$_3$] | | [Fe$^{II}$(N$_2$O$_1$)(H$_2$O)$_3$] | |
|---|---|---|---|
| Select Bond Lengths (Å) | | Select Bond Lengths (Å) | |
| Fe—N$_{py}$ | 2.18 | Fe—N$_{dimethyl}$ | 2.29 |
| Fe—N$_{methyl}$ | 2.27 | Fe—N$_{methyl}$ | 2.28 |
| Fe—O$_{carb}$ | 2.01 | Fe—O$_{carb}$ | 2.03 |
| Select Bond Angles | | Select Bond Angles | |
| N$_{py}$—Fe—N$_{methyl}$ | 76.9 | N$_{dimethyl}$—Fe—N$_{methyl}$ | 81.9 |
| N$_{methyl}$—Fe—O$_{carb}$ | 79.2 | N$_{methyl}$—Fe—O$_{carb}$ | 79.7 |
| N$_{py}$—Fe—O$_{carb}$ | 110.1 | N$_{dimethyl}$—Fe—O$_{carb}$ | 92.0 |
| N$_{py}$—N$_{methyl}$—O$_{carb}$ | 77.2 | N$_{dimethyl}$—N$_{methyl}$—O$_{carb}$ | 65.3 |

Additional simulations of the αKG adduct found a converged octahedral geometry with the α-keto acid bound in a bidentate manner and the ligand bound facially.

These simulations show the requirement for an sp3 hybridized N-donor in the central position of the ligand for facial coordination and guide efforts towards the synthesis of next generation ligands.

Figure 61:
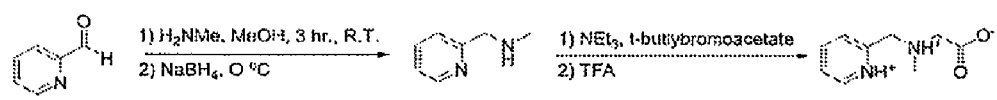
FIG. 61 is a diagram that illustrates the preparation of H$_2$N$_2$O$_1$py$^+$.

The N$_2$O$_1$py ligand was synthesized from pyridinecarboxyladehyde via reductive amination with methylamine and borohydride to give the methanamine. Subsequent reaction with t-butyl bromoacetate in the presence of triethylamine gave the t-butyl protected form of the ligand. Deprotection was accomplished by stirring with trifluoroacetic acid to give the trifluoroacetate salt of N$_2$O$_1$py (FIG. 61).

Figure 62:
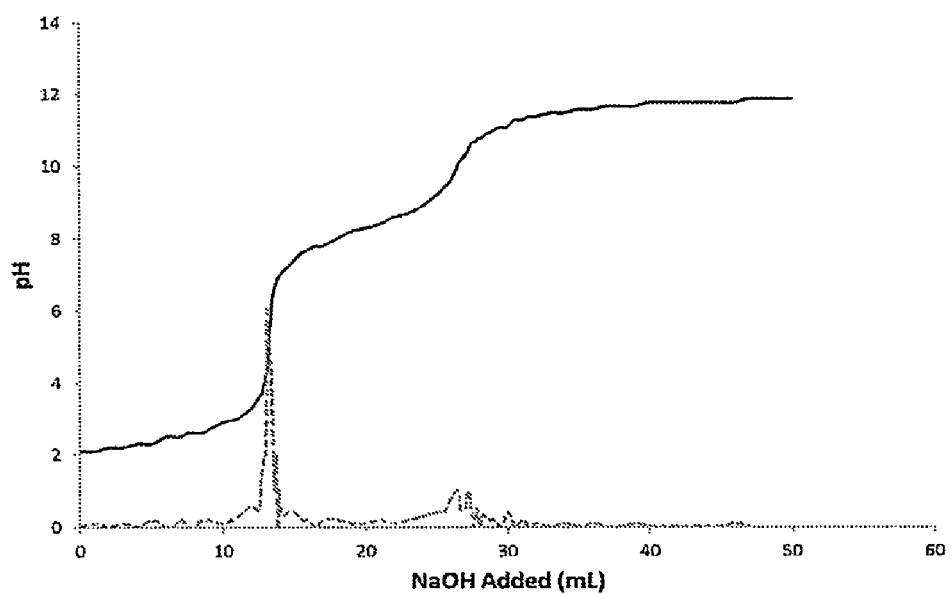
FIG. 62 is potentiometric titration of the H$_2$N$_2$O$_1$py$^+$ ligand (solid line) and derivative plot (dashed line).

Attempts to deprotect with HCl gave a hydroscopic oil that was less amenable to store and handle than the solid TFA salt. The number of protonated functional groups was determined by performing a potentiometric titration with sodium hydroxide (FIG. 62). Two acidic protons were detected suggesting that two of three functional groups of the ligand are protonated.

Based on estimated pK$_a$ values (carboxylic acid ~4.8; pyridinium ~5.2; tertiary ammonium ~10), it is proposed that the carboxylic acid is deprotonated and that the ligand exists as a zwitterion.

Figure 63:
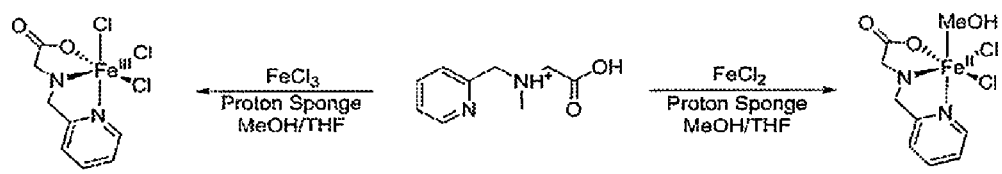
FIG. 63 is a diagram that illustrates the preparation of ferrous and ferric complexes.

Preparation of the ferrous and ferric complexes was achieved by addition of the ligand to the iron salts (FeCl$_2$ and FeCl$_3$, respectively) in the presence of 2 equivalents of proton sponge (FIG. 63). 1:4 MeOH:THF was required for the dissolution of the reagents and slow precipitation of the iron complexes.

Electronic Spectroscopy

Figure 64:
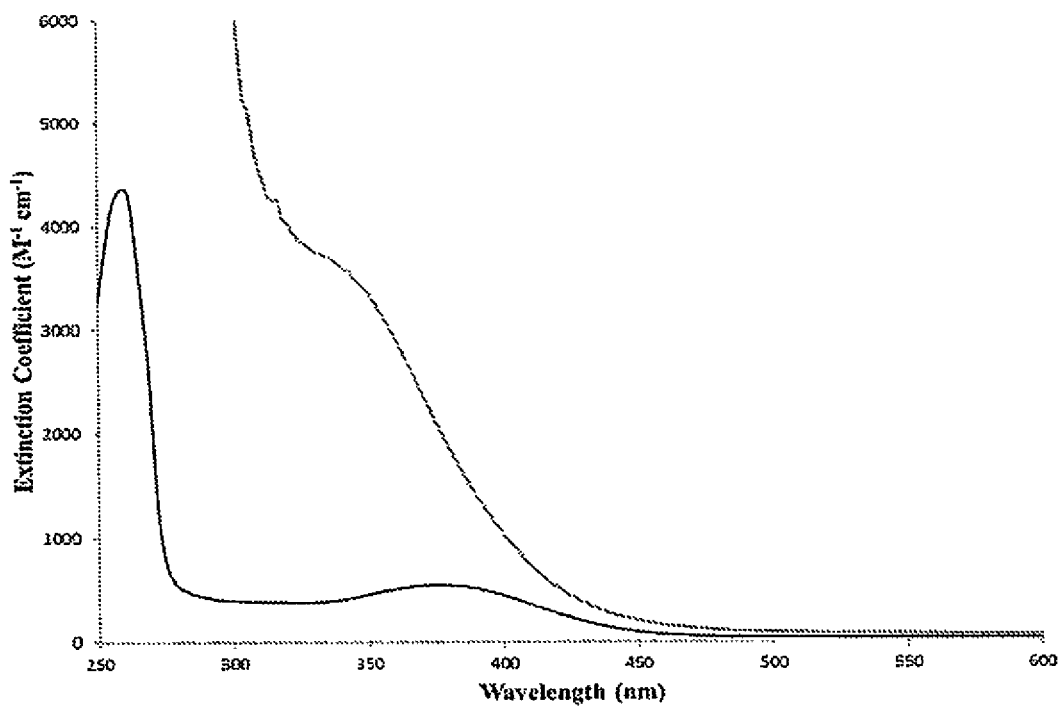
FIG. 64 are UV/vis spectra of [Fe$^{II}$(N$_2$O$_1$py)(Cl)$_2$]$^-$ (black) and [Fe$^{III}$(N$_2$O$_1$py)(Cl)$_3$]$^-$ (blue).

The UV/vis spectra of [Fe$^{II}$(N$_2$O$_1$py)(Cl)$_2$]$^-$ shows peaks at 260 nm and 376 nm with extinction coefficients of 4362 and 546 M$^{-1}$ cm$^{-1}$, respectively (FIG. 64). The higher energy transition at 260 nm can be attributed to a pyridyl π→π* transition, which has been observed in ferrous complexes with pyridyl ligands ([Fe$^{II}$(bipy)$_3$]$^{2+}$ shows a π→π* transition at 246 nm which has been ascribed to an intraligand transition) (Bryant, G.; et al., *Australian Journal of Chemistry* 1971, 24, 257-73). The peak at 376 nm is most likely due to a Fe$^{II}$-to-pyridine MLCT transition. Similar transitions have been observed in ferrous complexes with pyridine-based ligand sets (Chiou, Y.-M.; Que, L. *Journal of the American Chemical Society* 1995, 117, 3999-4013; Bryant, G.; et al., *Australian Journal of Chemistry* 1971, 24, 257-73; Borovik, A. S.; et al., *Journal of the American Chemical Society* 1989, 111, 6183-95). These two transitions characterize the complex as a ferrous species, with the pyridine-based ligand bound. Other expected transitions cannot be detected using UV/vis spectroscopy. LMCT transitions between the Cl ligands and the ferrous center are typically too high in energy, and are masked by intense ligand based transitions, for UV/vis analysis, and Fe$^{II}$ d→d transitions are too low in energy for detection.

The UV/vis spectrum of [Fe$^{III}$(N$_2$O$_1$py)(Cl)$_3$]$^-$ exhibits a single peak as a shoulder, centered at 340 nm with an extinction coefficient of 3622 cm$^{-1}$. This peak is consistent with a Cl$^-$→Fe$^{III}$ LMCT transition, and has been observed in other Fe complexes containing Cl$^-$ as a ligand, including the first generation N$_2$O$_1$ ferric complex, which exhibited a LMCT transition at 339 nm with an extinction coefficient of 3800 cm$^{-1}$ (Cappillino, P. J.; et al., *Dalton Trans* 2012, 41, 5662-77).

Figure 65:
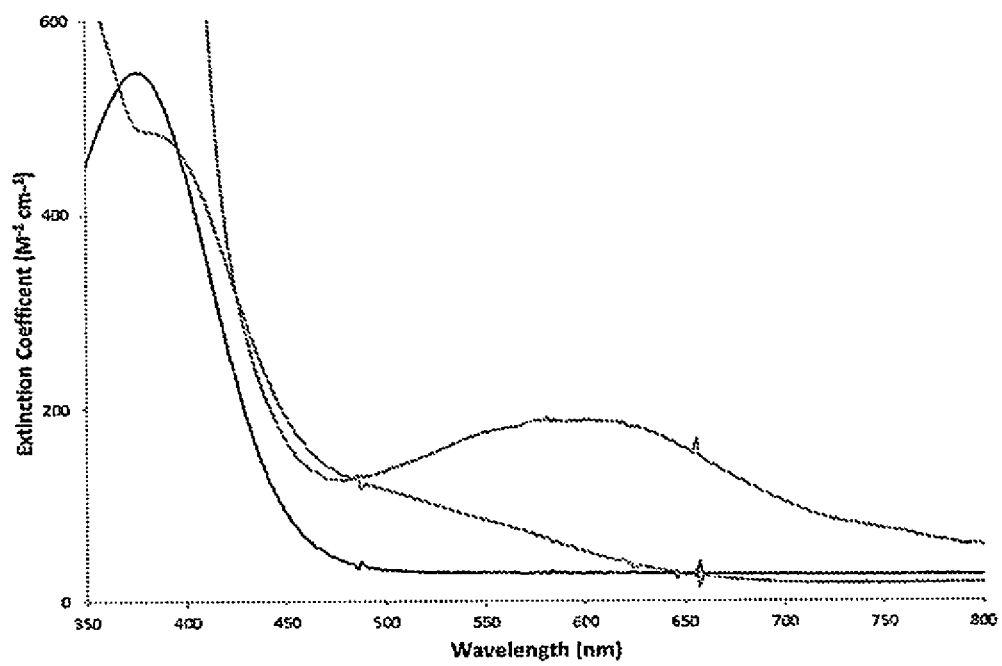
FIG. 65 are UV/vis spectra of [Fe$^{II}$(N$_2$O$_1$py)(Cl)$_2$]$^-$ (black), the αKG adduct (red) and BF adduct (blue).

The binding of α-keto acids to [Fe$^{II}$(N$_2$O$_1$py)(Cl)$_2$]$^-$ was studied using UV/vis, which aside from characterizing the electronic transitions associated with these adducts, also provided useful structural information pertaining to the ferrous complex. The fac-N$_2$O$_1$py ligand is useful as a structural model for non-heme iron oxygenase enzymes because of the facial coordination of the ligand, and the 1:1 Fe:ligand bonding mode. Analysis of the UV/vis spectra of the αKG and BF adducts of [Fe$^{II}$(N$_2$O$_1$py)(Cl)$_2$]$^-$ reveal a chromophore that is consistent with the bidentate binding of the α-keto acids (FIG. 65).

Studies of an Fe$^{II}$-TPA BF adduct (see FIG. 55 for structure of TPA) found a difference in absorption between coordinating and non-coordinating solvents (Chiou, Y.-M.; Que, L. *Journal of the American Chemical Society* 1995, 117, 3999-4013). In coordinating solvents (MeCN and MeOH), the typical Fe$^{II}$-TPA UV/vis spectrum was observed, whereas in non-coordinating solvents (DCM), a broad band between 550 and 610 nm$^{-1}$ was observed, along with the peak at 385 cm$^{-1}$, typically associated with Fe$^{II}$-TPA complexes. These broad bands were attributed to Fe$^{II}$-to-BF MLCT transitions that only appear when the BF ligand is bound in a bidentate manner. Monodentate coordination, caused by the presence of coordinating solvent ligands, leads to no feature in the UV/vis spectrum. In fact, variable-temperature variable-field magnetic circular dichroism (VTVH-MCD) studies on the ferrous active site of clavaminate synthase found a larger ground state splitting of the ferrous site with αKG bound ($\Delta^5T_{2g}$~−1000 cm$^{-1}$) than without ($\Delta^5T_{2g}$~−400 cm$^{-1}$) which suggests Fe$^{II}$-αKG π back-bonding to the metal center. The interaction was characterized as an Fe d→αKG carbonyl π* transition which helps to explain why no electronic spectral feature is observed upon monodentate binding of αKG. The αKG and BF adducts of the ferrous N$_2$O$_1$py complex have absorption features that are similar to those found for other adducts, as well as αKG dependent enzymes, and are consistent with bidentate coordination of the these α-keto acids (Table 12).

TABLE 12

Electronic absorbance features of αKG-dependent enzymes and N$_2$O$_1$ and N$_2$O$_1$py αKG and BF adducts.

| Fe$^{II}$ Center | α-keto acid | $\lambda_{max}$, nm (ε, M$^{-1}$ cm$^{-1}$) |
|---|---|---|
| TauD | αKG | 530 (140) |
| CAS | αKG | 500 (365) |
| P4H | αKG | 520 (250) |
| AlkB | αKG | 560 (1258) |
| TfdA | αKG | 530 (180) |
| HPPD | αKG | 500 (190) |
| N$_2$O$_1$ | αKG | 500 (125) |
| | BF | 625 (225) |

TABLE 12-continued

Electronic absorbance features of αKG-dependent enzymes
and N₂O₁ and N₂O₁py αKG and BF adducts.

| $Fe^{II}$ Center | α-keto acid | $\lambda_{max}$, nm (ε, M⁻¹ cm⁻¹) |
|---|---|---|
| N₂O₁py | αKG | 510 (110) |
|  | BF | 600 (188) |

This suggests that there are at least two open sites available for the binding of α-keto acids and confirms the 1:1 Fe:ligand coordination mode, as opposed to the bis (tridentate) binding motif with a 2:1 Fe:ligand ratio. Additionally, this implies that the electronic environment of the αKG adduct of the ferrous N₂O₁py complex is similar to those of the mononuclear non-heme iron enzymes that utilize αKG in their O₂ activation reactions. The presence of all six isomers is anticipated, although their relative energy distributions may not be the same.

Infrared Spectroscopy

Figure 66:
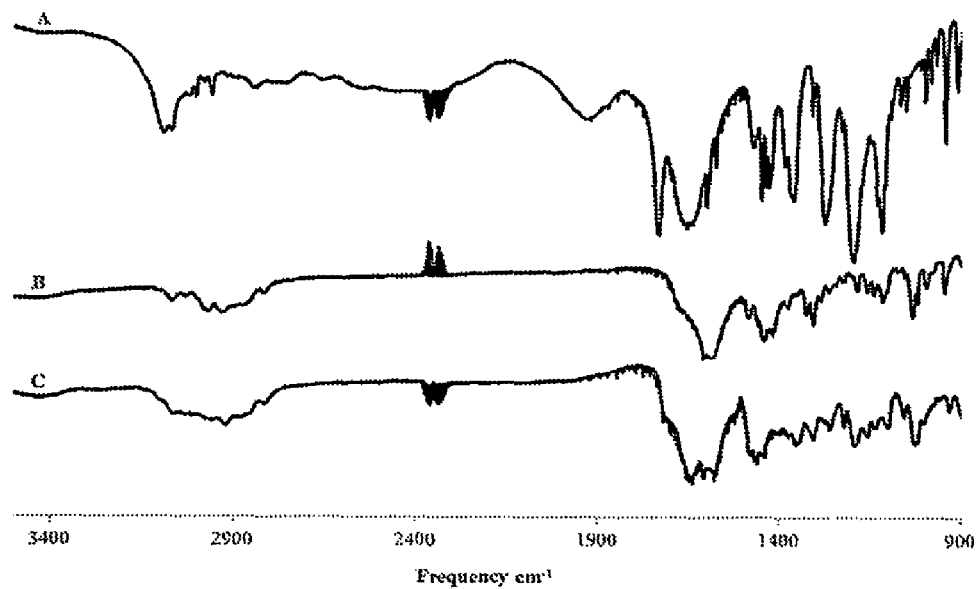
FIG. 66 are IR spectra of the H$_2$N$_2$O$_1$py$^+$ ligand (A), [Fe$^{II}$(N$_2$O$_1$py)(Cl)$_2$]$^-$ (B) and [Fe$^{III}$(N$_2$O$_1$py)(Cl)$_3$]$^-$ (C).

The IR spectrum of the H₂N₂O₁py ligand shows a band representing the asymmetric stretching of the C=O bond as an absorbance at 1730 cm⁻¹ (A in FIG. 66). Additionally, a broad absorbance centered at 3080 cm⁻¹ is observed, consistent with the presence of a carboxylic acid. This broad feature overlaps with weak features that arise from the alkyl and aromatic C—H bonds in the region of 2800-3070 cm⁻¹. Additional evidence of the heteroaromatic is the cluster of peaks in the region of 1500-1850 cm⁻¹, arising from the C—C and C—N bonds of the pyridyl group. A cluster of peaks in the region of 1120-1450 cm⁻¹ most likely arise from the C—O stretching on C—O—H bending modes of the acid, however, these peaks could not be independently assigned. There is also a broad band centered around 2400 cm⁻¹ that can be attributed to the trialkyl ammonium of the [H₂N₂O₁py]⁺ salt.

The coordination of the ligand to $Fe^{II}$ and $Fe^{III}$ expectedly results in the loss of the broad feature at 3080 cm⁻¹, due to loss of the O—H functionality, as well as loss of the broad ammonium band at 2400 cm⁻¹. For the iron complexes, the asymmetric C=O stretches are difficult to identify due to overlap with the aromatic C—C and C—N band, however, they appear to have shifted to lower frequencies when compared to the ligand, consistent with deprotonation of the acid. For [$Fe^{II}$(N₂O₁py)(Cl)₂]⁻, the symmetric stretch of the C=O bond appears at 1310 cm⁻¹ (B in FIG. 66), and at ~1350 cm⁻¹ (C in FIG. 66) for the ferric complex. The difference between the symmetric and asymmetric stretching frequencies of a carboxylate that is bound to a metal center has been shown to be significant in identifying the mode of binding (Cappillino, P. J., et al., *Dalton Trans* 2012, 41, 5662-77; Deacon, G. B.; Phillips, R. J. *Coordination Chemistry Reviews* 1980, 33, 227-50).

The monodentate coordination of an acetate to a metal ion typically has a frequency difference between these bands of >200 cm⁻¹, while bridging and chelating acetate ligands have a much smaller difference in frequencies (<150 cm⁻¹). Despite being unable to identify the exact value of the asymmetric absorbance, it does appear that the features for the ferrous and ferric complexes appear near 1600 cm⁻¹, suggesting a monodentate coordination mode of the acetate residue in both.

EPR Spectroscopy

Figures 67A, 67B, 67C:
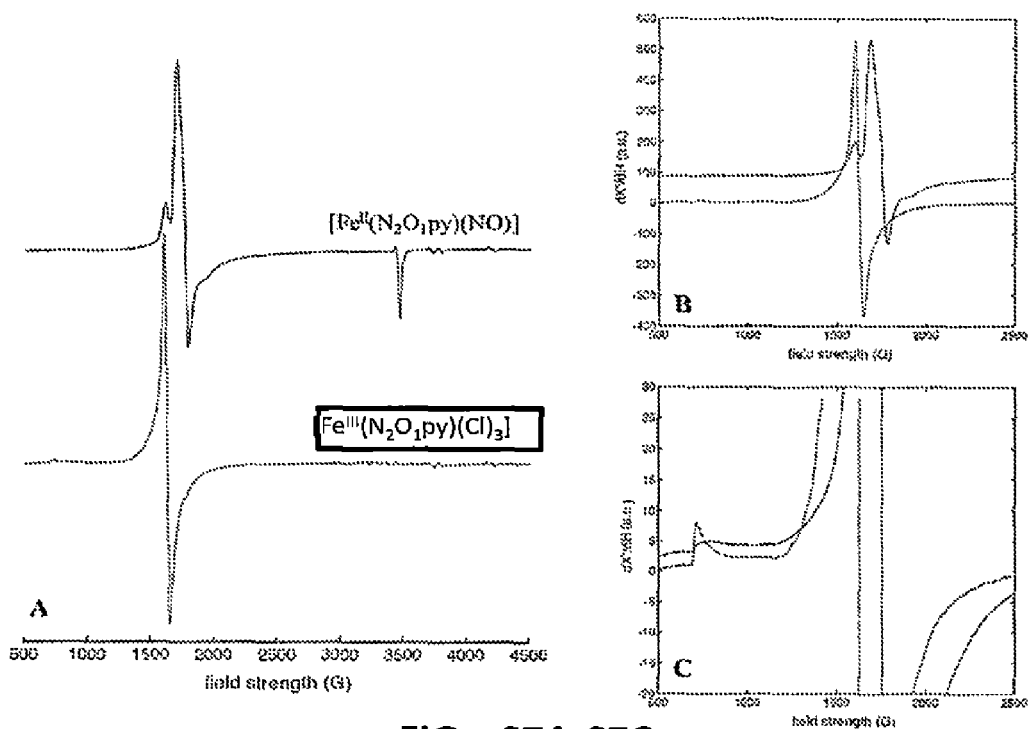
FIGS. 67A-67C are EPR spectra of [Fe$^{III}$(N$_2$O$_1$)(Cl)$_3$] (red) and [Fe$^{II}$(N$_2$O$_1$py)(NO)] (black) (67A). Highlight of the g~4 region (67B) and g~9 region (67C) of the spectra.

Iron(III) complexes lend themselves to EPR analysis due to their paramagnetic nature (half spin) in both the low and high spin states. An octahedral complex with a ferric center has five electrons, giving an S=5/2 spin state or an S=1/2 spin state. However, octahedral ferrous complexes are typically considered EPR inactive (non-kramers system), and cannot be easily studied using typical EPR approaches. Because of this, the NO ligand, containing an unpaired electron, is often used, which upon binding to a high spin ferrous center to provides an EPR active adduct with a distinct signal (denoted as [FeNO]⁷. This adduct has been studied extensively, and is best described as a high spin $Fe^{III}$ (S=5/2) antiferromagnetically coupled to an NO⁻ (S=1), to give an S=3/2 spin system (Brown, C. A.; et al., *Journal of the American Chemical Society* 1995, 117, 715-32). The EPR spectra of the ferrous-NO and ferric N₂O₁py species are shown in FIGS. 67A-67C. The spectrum for [$Fe^{III}$(N₂O₁py)(Cl)₃] is shown in FIG. 67A (red), and shows a g=4.3 signal which is consistent with a high-spin $Fe^{III}$ center. A weak, low-field feature at g=9.6 is also observed. These signals are similar to those found for [$Fe^{III}$(N₂O₁)(Cl)₃]. The low field (g=9.6) feature can be attributed to the lowest energy Kramers doublet with the low amplitude being suggestive of a zero-field splitting constant with a small value (Cappillino, P. J.; et al., *Dalton Trans* 2012, 41, 5662-77). The EPR spectrum for [$Fe^{II}$(N₂O₁py)(NO)] is shown in FIG. 67A (black) and shows a signal that is consistent with an [FeNO] (Shan, X.; Que Jr, L. *Journal of Inorganic Biochemistry* 2006, 100, 421-33), which implies a high-spin center antiferromagnetically coupled to the NO ligand. FIG. 67B focuses on the signals of the two complexes at g~4, and shows that the extra signal in the g=4 region of the [$Fe^{II}$(N₂O₁py)(NO)] spectrum aligns well with the positive lobe of the $Fe^{III}$ g=4.3 feature in the spectrum of [$Fe^{III}$(N₂O₁py)(Cl)₃].

FIG. 67C focuses on the g~9 region of the spectra and shows the presence of a high-spin $Fe^{III}$ center in the spectrum of [$Fe^{II}$(N₂O₁py)(NO)], which shows a faint amount of the g=9.6 signal, confirming the presence of ferric contaminant Cyclic Voltammetry (CV)

Figure 68:
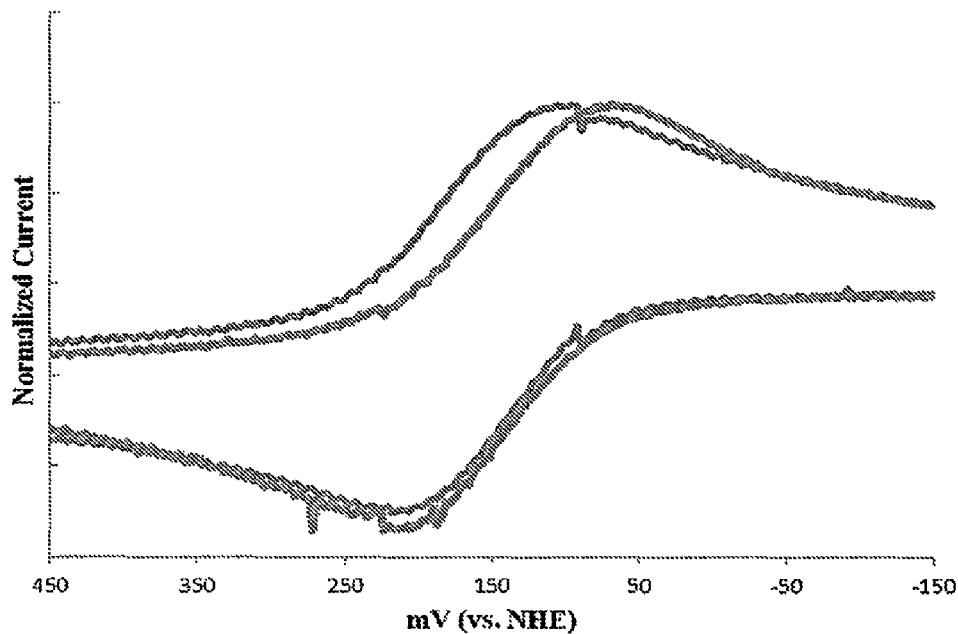
FIG. 68 are cyclic voltammograms of [Fe$^{II}$(N$_2$O$_1$)(Cl)$_3$]$^{2-}$ (blue) and [Fe$^{III}$(N$_2$O$_1$py)(Cl)$_3$]$^{2-}$ (red). Potentials calculated vs. NHE.

The cyclic voltammograms of [$Fe^{II}$(N₂O₁)(Cl)₃]²⁻ and [$Fe^{III}$(N₂O₁Py)(Cl)₃]²⁻ are shown in FIG. 68 and a comparison of their redox potentials with those of $Fe^{II}$ and $Fe^{III}$ N₂O₁ are shown in Table 13.

TABLE 13

Comparison of ferrous and ferric redox properties of the N₂O₁py and N₂O₁ ligand systems in the absence and presence of 1 and 2 equivelents of halide.

|  | N₂O₁py | | N₂O₁ |
|---|---|---|---|
|  | $E_{1/2}$ | ΔE | $E_{1/2}$ |
| $Fe^{III}$ | +189 | 128 | +136 |
| $Fe^{II}$ | +216 | 96 | +159 |
| $Fe^{II}$ + 1 eq. [NEt4]Cl | +202 | 104 | +131 |
| $Fe^{II}$ + 2 eq. [NEt4]Cl | +188 | 113 | +123 |

It can be seen that the redox potentials for the two complexes are close (~50 mV, see Table 13) suggesting that the incorporation of a pyridine group into the ligand has a minimal effect on the electronic properties of the iron center, which is interesting as this is typically not expected in the field of bioinorganic chemistry. Typically, ligand design for active site model compounds focuses on replicating the histidine residue with a pyridine of imdazole ring. However, this CV data demonstrates the ability of an alkyl amine to model the electronic properties of an iron center with the same effect as an aromatic amine. Additionally, these redox results imply that the reactivity properties of the pyridyl complex with $O_2$, relative to those of [$Fe^{II}(N_2O_1)(Cl)_2$], should not be effected by the redox properties of the metal. Considering the initial steps of the activation of $O_2$ involve bond formation and the one-electron transfer between iron and dioxygen, analysis suggests that $K_{eq}$ should not be dramatically impacted (Table 14). In both cases, the equilibrium lies far to the side of the reactants suggesting that the differences between the two ligands should not affect the initial reaction with or reduction of $O_2$. However, this does not imply that overall reactivity will happen with similar rates, or that the same mechanism is followed by both complexes.

TABLE 14

Gibbs free energies and equilibrium constants calculated using the equations shown in Chapter 2.

| | $\Delta G°/kJ$ | $K_{eq}$ |
|---|---|---|
| $N_2O_1$ | 45 | $1.1 \times 10^{-8}$ |
| $N_2O_1py$ | 50 | $1.7 \times 10^{-9}$ |

A similar observation is observed in the redox properties of [$Fe^{II}(N_2O_1py)$] as found for [$Fe^{II}(N_2O_1)$], where a significant difference in the redox potential of the $Fe^{II}$ and $Fe^{III}$ complexes of $N_2O_1py$ is observed, which would not be expected based on the nearly reversible nature of the $Fe^{II/III}$ couple (vide infra). However, addition of halide to the sample solution caused a decrease in the redox potential (see Table 13), with two equivalents of halide bringing the redox potential to that of the ferric complex, suggesting an identical electrochemically active species in solution. This behavior solution speciation suggests that $Fe^{II}$ loses $Cl^-$ in solution faster than $Fe^{II}$ in solution, giving a different electroactive $Fe^{II}$ species due to solvation effects, because the lability of chloride ligands coordinated to a ferrous center would be expected to have exchange rates greater than the time-scale of the CV experiment. This effect on the redox potential caused by the addition of halide is consistent with quantitative analysis of $Cl^-$ for [$Fe^{II}(N_2O_1py)$] and [$Fe^{III}(N_2O_1py)$] complexes.

Figure 69:
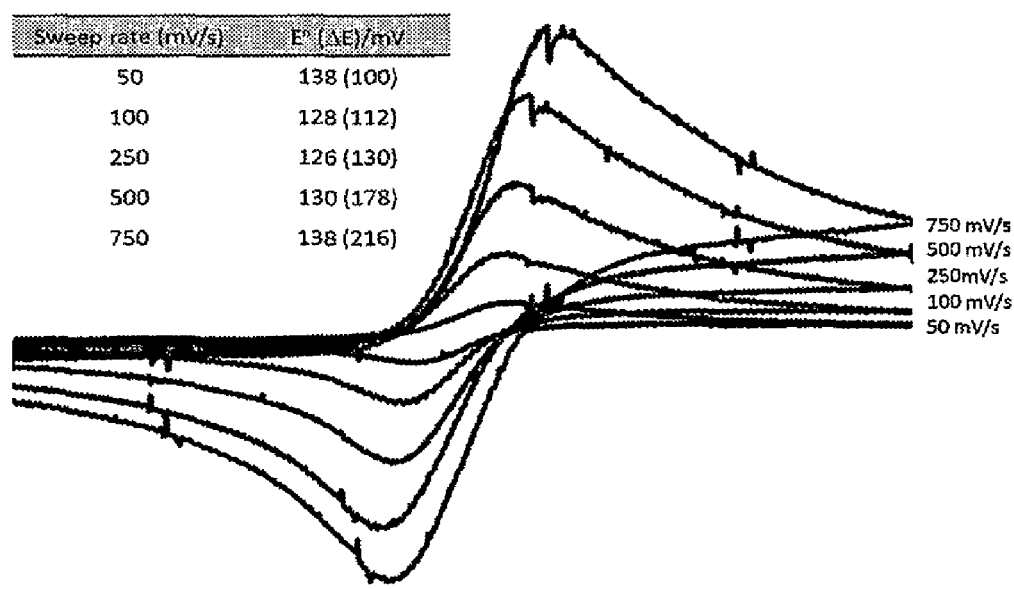
FIG. 69 are cyclic voltammograms demonstrating dependence of total current on sweep rate for $[Fe^{II}(N_2O_1py)Cl_2]^-$, with sweep rates of 50, 100, 250, 500 and 750 mV/s. Table shows the redox r potential (vs. NHE) at each sweep rate.

Within the Nernst diffusion layer, or region next to the electrode, the concentration gradient of the redox species is nearly linear, and the ratio of concentration of product to concentration of reactant is given by the Nernst equation. It follows that as the potential is scanned, the concentration of reactant will decrease which increases the concentration gradient. This results in a current that is proportional to the gradient at the electrode surface. Larger sweep rates decrease the timescale of the experiment, and therefore decrease the relaxation time of the concentration gradient, which has the effect of increasing the current relative to smaller sweep rates. The potential sweep rate dependence shows that [$Fe^{II}(N_2O_1py)Cl_2$]$^-$ has reversible qualities, with the peak current density increasing with increasing sweep rate, meaning that the redox system remains in near equilibrium (FIG. 69).

Figure 70:
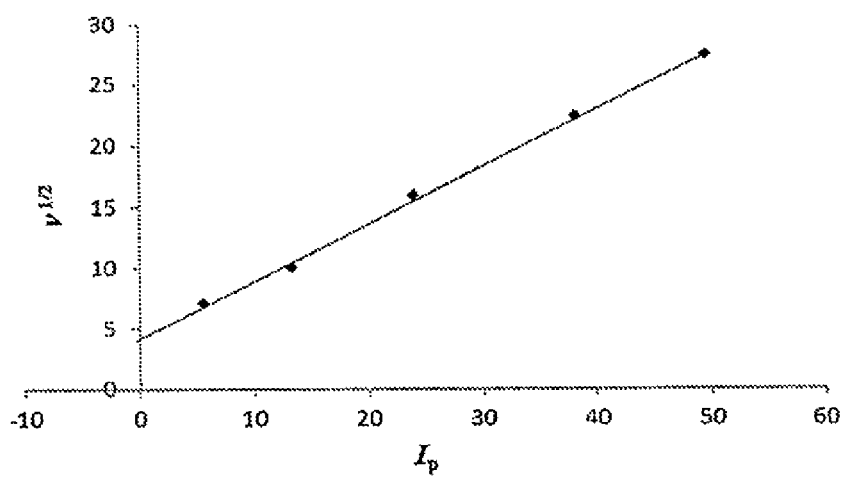
FIG. 70 is a graph of $v^{1/2}$ vs. $I_p$ with best linear fit.

However, not all criteria are met for a reversible process. Primarily, $\Delta E$ is high relative to reversible processes. Also, a plot of the peak current density as a function of the square root of sweep rate is linear, which is indicative of a reversible electrochemical process, but a linear fit of the plot does not pass through the origin (FIG. 70). In other terms, $I_p/v^{1/2}$ is not a constant, which is considered to be a diagnostic test for reversibility.

These results suggest that the redox process of the $Fe^{II/III}$ couple of this complex is nearly reversible, but does not meet the requirements to be considered a perfectly reversible process. Nevertheless, the results do suggest that both redox partners are stable and that the electron transfer process is fast.

Reactivity with $O_2$

Figure 71:
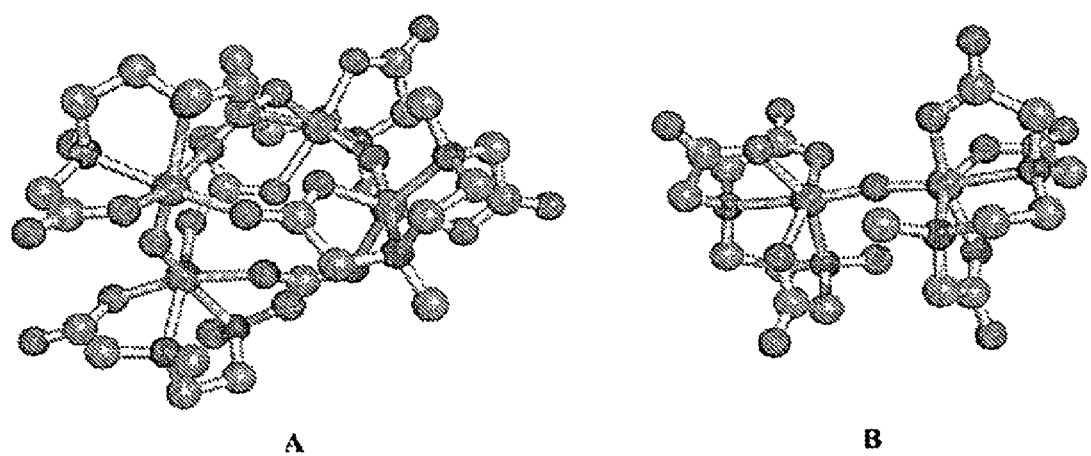
FIG. 71 are illustrations of X-ray crystal structures of the ferric μ-oxo tetramer (A) and the ferric μ-oxo dimer (B) that result from the reactions of $[Fe^{II}(N_2O_2)]$ and $[Fe^{II}(N_2O_3)]$ with $O_2$, respectively. Created using Pymol.

Exposure of [$Fe^{II}(N_2O_1py)(Cl)_2$]$^-$ to $O_2$ in methanol leads to the formation of a chromophore at 350 nm, which has been tentatively assigned as being due to the generation of an $Fe^{III}$—O—$Fe^{III}$, diferric oxo species. This absorbance feature is within the range (300-400 nm) typically associated with oxo-bridged diferric units and is similar in energy to the peak observed upon reaction of [$Fe^{II}(N_2O_1)(Cl)_2$] with dioxygen (335 nm), as well as the peaks observed in $O_2$ reactivity studies on [$Fe^{II}(N_2O_2)$] and [$Fe^{II}(N_2O_3)$] complexes (Kurtz, D. M. Chemical Reviews 1990, 90, 585-606; Cappillino, P. J., et al., Dalton Trans 2012, 41, 5662-77). In the case of these two ferrous complexes, x-ray crystal structures were obtained of the final dioxygen reacted products (FIG. 71).

These structures confirm the observed chromophores of these two species as arising from the formation of an $Fe^{III}$—O—$Fe^{III}$ center, and provides additional support for the assignment of the chromophore in the case of the $N_2O_1py$ system. Dioxygen uptake studies found a 4:1 Fe:$O_2$ reaction ratio for the [$Fe^{II}(N_2O_1)(Cl)_2$], [$Fe^{II}(N_2O_2)$] and [$Fe^{II}(N_2O_3)$] complexes, which is similar to results obtained by Balch et. al., suggesting that these three ferrous species react with $O_2$ via a Balch-type mechanism (Chin, D.-H., et al., Journal of the American Chemical Society 1980, 102, 4344-50).

Effect of αKG on Rate of Reaction with $O_2$

The rate of reaction of the ferrous complex with $O_2$ to form the diferric oxo-bridged product is quite slow (>7 hrs.). If the formation of this μ-oxo species occurs in a similar manner as that found in Fe-porphyrin autoxidation reactions, via a Balch-type mechanism, the relatively slow reaction kinetics would be expected based on the redox properties of the metal center (Chiou, Y.-M.; Que, L. Journal of the American Chemical Society 1995, 117, 3999-4013). The initial step in this mechanism is the 1-electron reduction of $O_2$ by the ferrous center to form an $Fe^{III}$-superoxide, which reacts with another ferrous center to form a diferric peroxide-bridging species. Homolytic cleavage gives two $Fe^{IV}$=O intermediates that each react with two additional equivalents of $Fe^{II}$ to give two $Fe^{III}$—O—$Fe^{III}$ product molecules. This mechanism involves a 4:1 Fe:$O_2$ reactant ratio, which was found to be the ratio of reactants in the case of [$Fe^{II}(N_2O_1)(Cl)_2$] in its reaction with $O_2$. However, dioxygen uptake studies are needed to confirm a similar reactant ratio in the $N_2O_1py$ system. Nevertheless, it is reasonable to propose a mechanism that begins with $O_2$ reduction. The relatively high redox potential of [$Fe^{II}(N_2O_1py)(Cl)_3$] (188 mV) leads to an equilibrium constant that predicts the reaction of the complex with $O_2$ lies mostly to the side of the reactants. Considering the next step in the reaction ($Fe^{III}$—O—O—$Fe^{III}$ formation in the case of the Balch mechanism) is dependent on the concentration of the product(s) of the first step ($Fe^{III}$—$O_2^-$), the overall rate of the reaction would be slow if the concentration of $Fe^{III}$—$O_2^-$ was small, as predicted by the value of $K_{eq}$ (Table 14). However, this could be mechanistically overcome if the rate of the reaction of $Fe^{III}$—$O_2^-$ to form product(s) were not dependent on its concentration, such as an intramolecular process. This is discussed in more detail below. If the slow rate of the reaction of [$Fe^{II}(N_2O_1py)(Cl)_2$] with $O_2$ is in fact due to its high redox potential, it would be expected that decreasing its redox potential would increase its rate of reaction with $O_2$.

Figure 72:
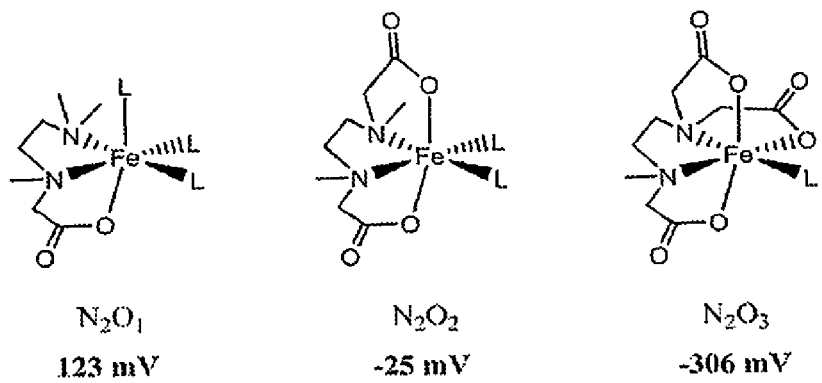
FIG. 72 illustrates the structures of iron complexes of the $N_2O_1$, $N_2O_2$ and $N_2O_3$ ligands, with L representing Cl⁻ and MeOH labile ligands. Redox potentials are vs. NHE and were obtained in the presence of two equivalents of chloride.

Previous studies found an $O_2$ reactivity trend consistent with this argument with the three ferrous complexes containing $N_2O_1$, $N_2O_2$ and $N_2O_3$ coordination motifs (FIG. 72).

A trend in decreasing redox potential with increasing carboxylate ligation was observed which was attributed to the increase in metal-ligand covalency, and thus electron density on the iron center, upon replacement of the labile chloride ligand(s) by the carboxylate residue(s) (FIG. 72). It was also observed that the rate of reactivity of the respective complex with $O_2$ increased as the number of coordinated carboxylate residues increased. These trends were considered to be related in a transitive manner and it was proposed that the observed trend in increased sensitivity to $O_2$ upon increased carboxylate ligation is due to a decrease in redox potential.

It was found that in the $N_2O_1$ system, the binding of αKG increased the rate with which the respective diferric μ-oxo product formed upon reaction with $O_2$, occurring in minutes as opposed to ~6 hrs. This was proposed to be due to the formation of an $N_2O_3$-type coordination mode. However, the calculated redox potentials of the $N_2O_1$, $N_2O_2$, $N_2O_3$ and $N_2O_1$-αKG complexes suggests that the coordination of αKG does not decrease the redox potential of the iron center by enough to account for the increased $O_2$ sensitivity. This was corroborated by the experimental determination of the $N_2O_1$-BF adduct ($E_{1/2}$=60 mV), which showed a modest decrease in redox potential. It has therefore been proposed that the increased rate in product formation is due to the coupling of the $Fe^{III}$-superoxide formation step (which has a small $K_{eq}$) with the following step(s) in the reaction mechanism, effectively removing the $Fe^{III}$-superoxide and driving its formation forward. Considering the proposed mechanism of TauD, an intramolecular attack of the superoxide on the C2 carbon of αKG, followed by an irreversible intramolecular rearrangement/decarboxylation step would serve as an effective concentration independent way to overcome the small $K_{eq}$ value of the initial $O_2$ reduction step.

Figure 73:
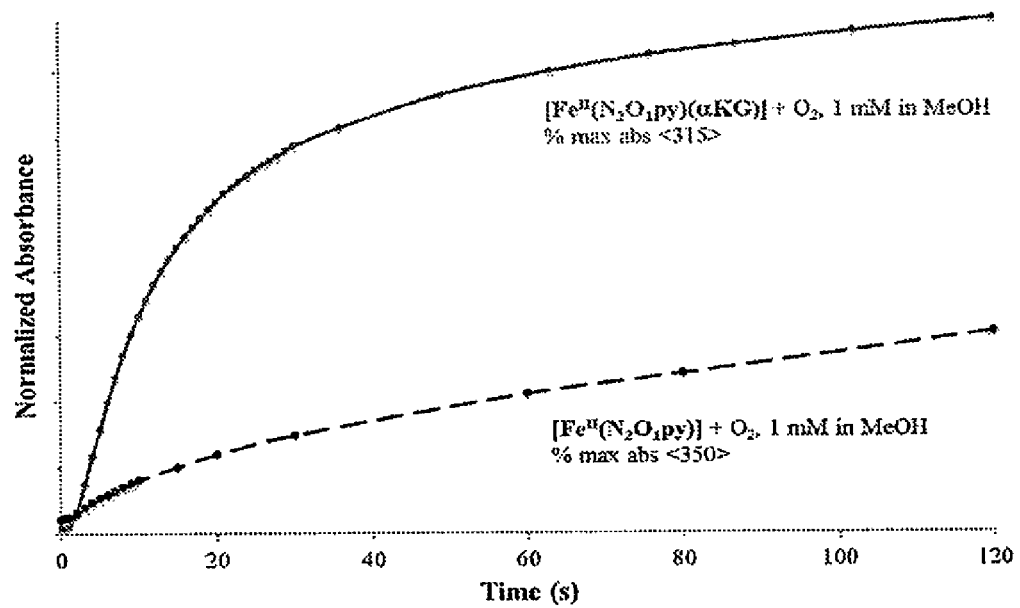
FIG. 73 is a graph of normalized maximum absorbance of the product chromophore of $[Fe^{II}(N_2O_1py)]$ (350 nm) and $[Fe^{II}(N_2O_1py)(\alpha KG)]$ (315 nm) upon reaction with $O_2$.

The incorporation of the pyridine ring appears to have little effect on this observed trend. Formation of the $[Fe^{II}(N_2O_1py)(αKG)]$ adduct generates a highly dioxygen-sensitive iron center that reacts with $O_2$ to form a product with a chromophore at 315 nm. As discussed, this electronic absorption is within the range expected for a μ-oxo bridged diferric species. The formation of the diferric oxo-bridged product that forms in the reaction of $[Fe^{II}(N_2O_1py)(Cl)_2]^-$ with $O_2$ takes >7 hrs. However, the αKG adduct fully reacts with $O_2$ within minutes (FIG. 73).

Figure 74:
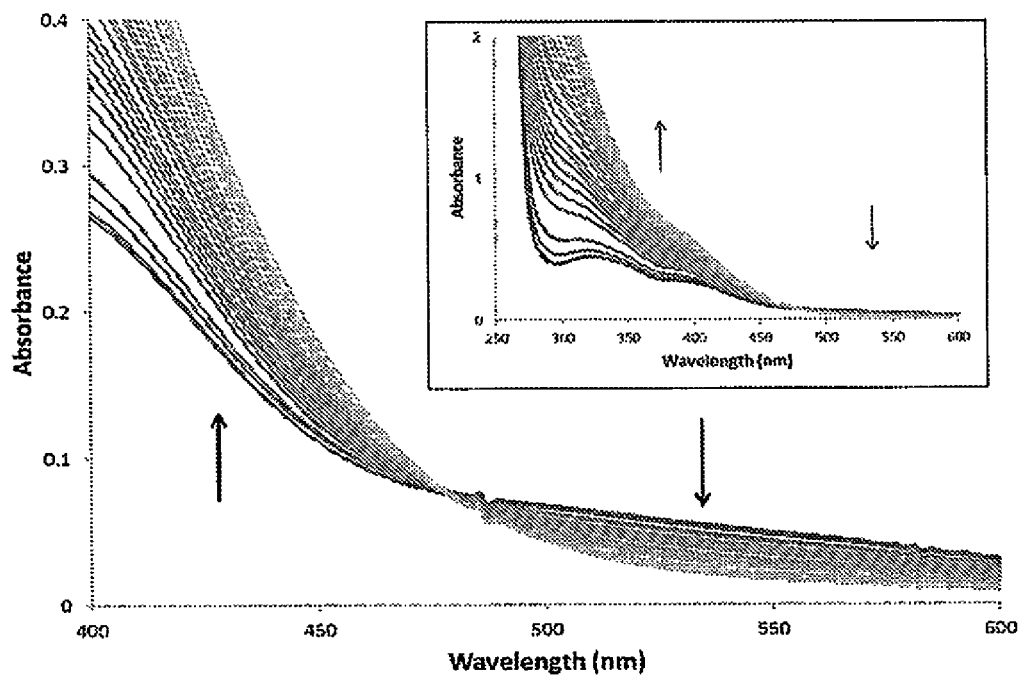
FIG. 74 are UV/vis spectrum of the oxidation of $[Fe^{II}(N_2O_1py)(\alpha KG)]$ (inset), focusing in on the isosbestic point.

From this trend it is clear that the incorporation of the pyridine group into the $N_2O_1$ ligand framework has very little effect on its rate of reaction with dioxygen. The reaction of $[Fe^{II}(N_2O_1py)(αKG)]^-$ with $O_2$ to from this product happens as a clean transformation, as indicated by the observation of an isosbestic point at 478 nm in the UV/vis spectra over the course of the reaction (FIG. 74). This suggests that the reaction proceeds from the ferrous complex to a single spectroscopically observable product.

Methanol Oxidation by $[Fe^{II}(N_2O_1py)(αKG)]$

The catalytic activity of the $[Fe^{II}(N_2O_1py)(αKG)]$ complex in the presence of $O_2$ was studied in the presence of the methanol solvent/substrate. Solutions of varying concentrations of iron catalyst were prepared in methanol and an excess of αKG was added before exposing to $O_2$. The oxidation of methanol was observed by use of the Nash assay, which allows for a concentration determination of formaldehyde. This chemistry was also observed in the $N_2O_1$ system, further demonstrating the lack of any significant effect on the properties of the complex with the pyridine group present. For the $N_2O_1py$ system, the oxidation of methanol was shown to be catalytic, capable of producing 33 equivalents of formaldehyde per iron center at 1.0 μM. The catalytic activity was found to be significantly reduced as the concentration of the iron complex was increased. This is evidence of the competing reaction pathways available for the reactive intermediate species to follow.

Figure 57:
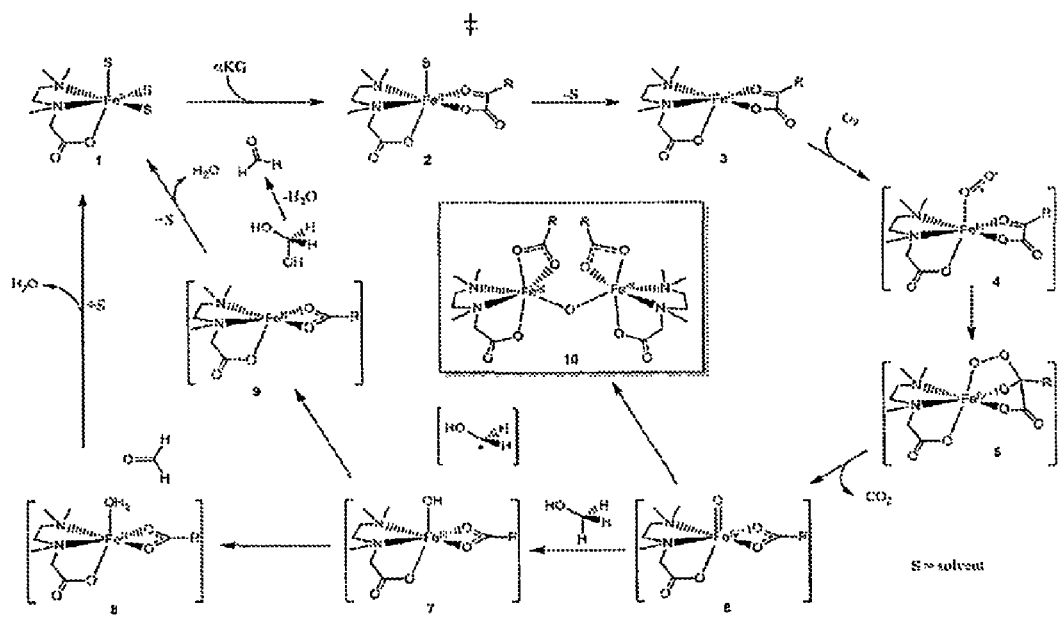
FIG. 57 is a diagram that illustrates a proposed catalytic mechanism of the reaction of [Fe$^{II}$(N$_2$O$_1$)(Cl)$_2$]$^-$ with O$_2$ in the presence of αKG (‡only one isomer of six possible isomers is shown).
Figure 75:
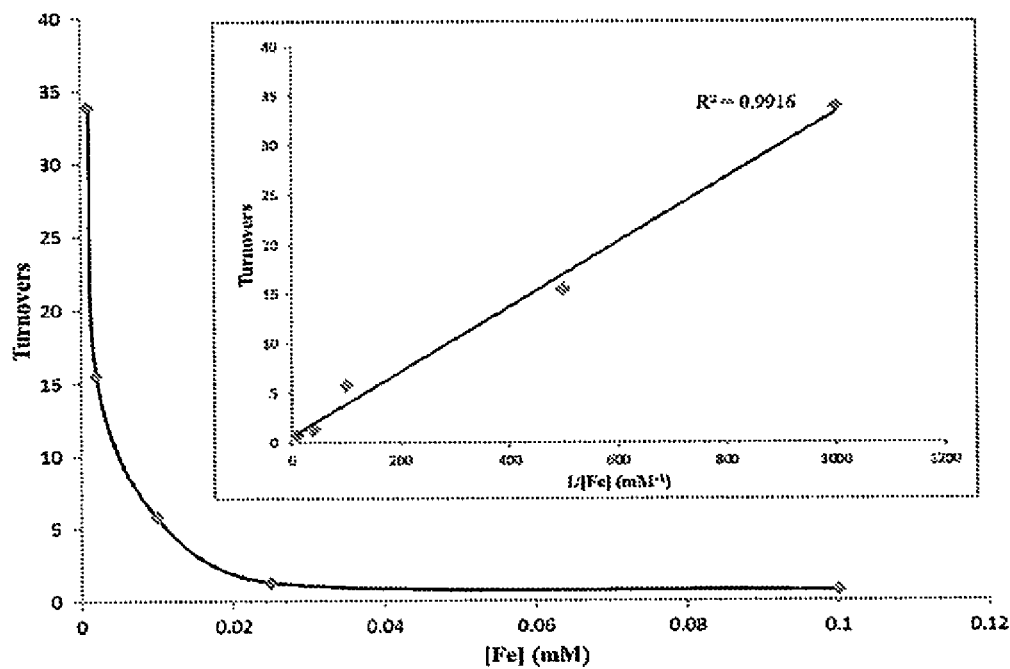
FIG. 75 is a graph that demonstrates dependence of turnover number on concentration of the catalyst and the inverse of catalyst concentration (inset).

This intermediate, which is proposed to be a metal-based oxidant, could react with the substrate methanol to produce formaldehyde, or react with another ferrous center to produce a differic γ-oxo species (see FIG. 57). This is a catalytic 'dead end', and effectively decreases the amount of active catalyst in solution, eventually leading to the quenching of the catalytic complex. The concentration dependent rate of μ-oxo formation would be expected to increase as the concentration of the ferrous complex were increased, which would lead to fewer catalytic reactions and a decrease in the amount of formaldehyde generated. FIG. 75 shows the decrease of the turnover number (equivalents of formaldehyde produced per equivalent of iron) from 33 to 0.7, as the concentration of iron complex is increased from 1 μM to 100 μM. The figure inset shows a plot of turnovers vs. 1/[Fe] is linear. This data also suggests that the observed reactivity is not due to radical based chemistry, where an inverse relationship between catalyst concentration and turnover number would not be expected.

Although the reactivity properties between the $N_2O_1$ and $N_2O_1py$ systems are quite similar, higher turnover numbers have been observed for $N_2O_1$ at the same concentrations of the catalysts. The reason for this difference is not completely understood at this time. However, identical reactivity properties would not necessarily be expected, as there are slight differences in the electronic properties of the two complexes and thus, potential differences in the rates of methanol oxidation and μ-oxo formation. Also, the aromatic ring of the $N_2O_1py$ system may serve as an additional substrate in solution. This intermolecular oxidation, along with μ-oxo formation, may be facilitated by π-stacking interactions, which may act as an attractive force between the $N_2O_1py$ ferrous complexes. This would not occur in the $N_2O_1$ system, which lacks an aromatic ring.

Conclusions

A ferrous complex has been synthesized that is based on an $N_2O_1$-type ligand with a pyridyl functionality that has been shown to bind to αKG and react with $O_2$ at room temperature and standard pressure, and catalytically oxidize methanol to formaldehyde. The inverse dependence of catalyst concentration on turnover number was found to be linear, suggesting a non-radical pathway and providing evidence of a competing irreversible autoxidation pathway that quenches the catalyst. This system shares many similarities in structure, electronics and reactivity to the previously studied $N_2O_1$ system, providing a second-generation catalyst with similar biological implications. Also, it demonstrates that the electronic differences between coordinated aliphatic and aromatic amines are not great enough to dramatically alter the properties of the iron complex. This is important when considering the structure/function dynamic in modeling chemistry. The electronic nature of the metal center in an enzyme active site is dictated by a number of factors aside from the first coordination sphere, implying the design of a small molecule with similar electronic properties most likely depends on more than the structure of the bound ligands. Both the $N_2O_1$ and $N_2O_1py$ systems provide the correct facial coordination mode, and bind to the iron center in a 1:1 ratio. Both ligands tune the redox potentials of the iron centers to within a similar range. Both ferrous complexes of the two ligands bind αKG in a bidentate manner to provide more $O_2$-sensitive metal centers that are capable of catalytically activating $O_2$ to form metal-based oxidants which are able to oxidize methanol to formaldehyde.

The observed catalytic behavior of [Fe$^{II}$(N$_2$O$_1$)(Cl)$_2$]$^-$ has led to a large series of reactivity, kinetic and computational studies in an effort to further understand the mechanistic details of its reaction with $O_2$. Additionally, spectroscopic studies are underway that will result in the characterization of the intermediates observed in kinetic studies. This complex has been proposed to react with $O_2$ in a very similar manner as the mononuclear ferrous site of TauD, suggesting that these studies may provide insight into enzyme function. Furthermore, the potential of this system as a useful catalyst for difficult oxidation reactions has been demonstrated which has led to interest in this complex as an applied catalyst for use in industrial purposes or fine chemical processes.

Figure 76:
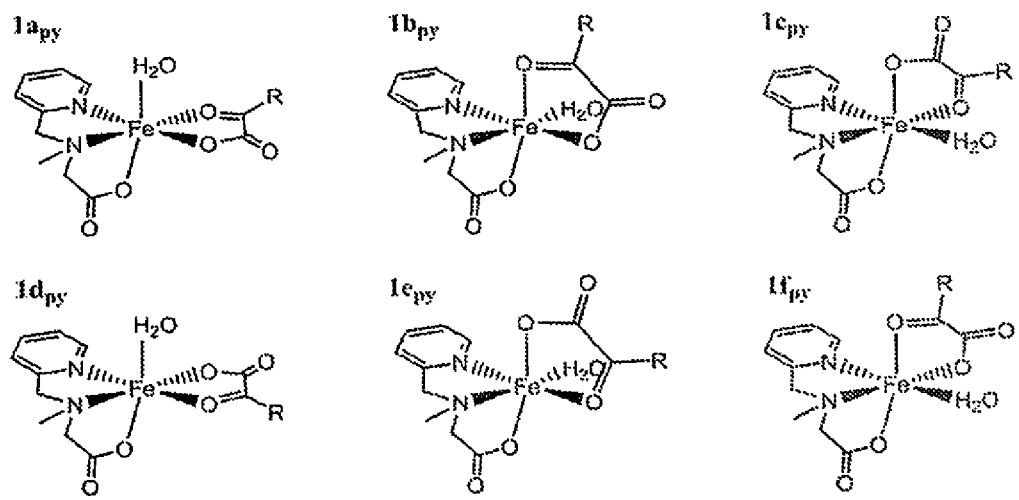
FIG. 76 illustrates the six possible isomers of $[Fe^{II}(N_2O_1py)(\alpha KG)(H_2O)]$.

The introduction of the aromatic group opens up a plethora of synthetic possibilities that allows for the tailoring of this catalytic system for desired purposes. The observation of catalytic activity is important, as it shows that this ligand modification has not drastically effected electronic and reactivity properties of the iron center, verifying its viability as a useful complex for $O_2$ activation. However, depending on the orientation of the pyridine ring relative to the coordinated αKG ligand, and the site of the proposed oxo formation, the reactivity properties of the αKG adduct with $O_2$ could potentially be impacted by the addition of para substituents on the aromatic ring. As with the [Fe$^{II}$(N$_2$O$_1$)(αKG)] complex, six possible isomers are expected due to the three facial open sites available for coordination by the asymmetric bidentate αKG ligand (FIG. 76). It can be seen that (1a$_{ps}$) and (1d$_{py}$) have a configuration with the pyridine ring and the αKG ligand in the same plane, so their π clouds may interact through their interaction with the iron center. If so, it may be possible to alter the π cloud of the pyridine ring with para substituents, which may in turn impact the π* cloud of the αKG chelate. The αKG π* cloud is mechanistically important, as it accepts an electron from the Fe(III)-superoxide to form the peroxide bridge in the proposed mechanism. FIG. 76 shows that the open site resides trans to the pyridine ring in the structures of (1c$_{py}$) and (1f$_{py}$). Considering the open site is where the proposed oxo forms, it may be possible to alter the electronic/reactivity properties of the Fe(IV)-oxo by modifying the electronic properties of the aromatic ring with para substituents. DFT simulations can provide insights into the possible effect of para substituents on the pyridine ring, and its impact on the electronic properties of the αKG and proposed oxo ligands.

Example 3

Functionalization of the N$_2$O$_1$py Ligand

The N$_2$O$_1$py ligand was synthesized to provide a chelate with similar coordination properties as the N$_2$O$_1$ ligand, with a tridentate 2-nitrogen-1-oxygen facial binding motif The aryl group provided by the N$_2$O$_1$py ligand has allowed for the addition of substituents that can tailor the solubility properties of the iron complex and offer the ability to immobilize the complex via click chemistry with the target being the prevention of catalyst diffusion, thereby inhibiting dimerization. Synthetic efforts that were focused on the functionalization of the aryl N$_2$O$_1$py ligand are discussed herein. The ligand was functionalized with a chloride in the para position of the aromatic ring that allows for substitution with a variety of substituents that may alter the solubility properties of the complex as well as the redox properties of the iron center. The para position of the aromatic ring has also been functionalized with an acetylene group, and ferrous complex prepared with this ligand has been attached to azidomethyl polystyrene by use of click chemistry methods.

General Methods

All reagents and solvents used were purchased from commercial sources and used as received unless otherwise noted. Prior to use, methanol (Pharmco-Aaper) was distilled over magnesium metal, dimethyl sulfoxide (Fisher Scientific) was distilled over calcium hydride, triethylamine was distilled over sodium metal and unstabilized dichloromethane (Fisher Scientific) was distilled over calcium hydride. Ferrocene was purified by sublimation for use as a reference for electrochemical analyses. All manipulations involving ferrous complexes were carried out in an inert atmosphere glovebox (M. Braun, Stratham, N.H.) with distilled and thoroughly degassed solvents. IR spectra were collected using a Thermo Nicolet AVATAR 330-FT-IR. Cyclic voltammetry experiments were performed using a Princeton Applied Research model 273 potentiostat with a glassy carbon working electrode, a silver wire reference electrode and a platinum wire counter electrode. NMR spectra were recorded at 25° C. using a Varian spectrometer operating at 400 MHz with all chemical shifts referenced to SiMe$_4$. Iron concentrations were determined using a Varian AA240Z Atomic Absorption Spectrometer. The syntheses of azidomethyl polystyrene, alk1, alk2-alk3, alk4-alk5, alk6, alk? and C11-C14 were adapted from previously published methods (He, Y.; Cai, C. *Chemical Communications* 2011, 47, 12319-21; Zaman, N., et al., *Tetrahedron Letters* 2008, 49, 7274-75; Jones, R. C., et al., *Tetrahedron* 2009, 65, 7474-81; Dubs, M. J., et al., Google Patents: 2007; Ladouceur, S., et al., *Synthesis-Stuttgart* 2011, 3604-11; Cappillino, P. J., et al., *Dalton Trans* 2012, 41, 5662-77).

Ligand and Metal Complex Synthesis

Preparation of N$_2$O$_1$-alkyne ligand and ferrous complex

Synthesis of 2-methyl-4-nitropyridine 1-oxide (alk1): 2-methylpyridine 1-oxide (10.0 g, 91.6 mmol) was dissolved in H$_2$SO$_4$ (32%, 50 mL) and then cooled to 0° C. before the slow addition of NaNO$_3$ (8.56 g, 0.100 mol). Once fully dissolved, the reaction was heated to 100° C. and allowed to stir for 2 hrs. The reaction was cooled to room temperature and then poured into cold H$_2$O (20 mL) before being made basic with K$_2$CO$_3$. A yellow precipitate formed which was collected via vacuum filtration. The solid was dissolved in CH$_2$Cl$_2$ (50 mL), dried over anhydrous MgSO$_4$ and concentrated via a rotary evaporator to give the product as a yellow solid (8.75 g, 56.8 mmol, 62%). 1H NMR (400 MHz, DMSO) δ 8.47 (d, J=8.0 Hz, 1H), 8.43 (d, J=4.0 Hz, 1H), 8.10 (dd, J=8.0 Hz, 1H), 2.43 (s, 3H). $^{13}$C NMR (400 MHz, DMSO) δ 149.78 ($^{Ar}$C), 141.19 ($^{Ar}$C), 139.93 ($^{Ar}$C), 120.84 ($^{Ar}$C), 118.48 ($^{Ar}$C), 17.13 (CH$_3$).

Synthesis of 2-methyl-4-bromopyridine 1-oxide (alk2): 2-methyl-4-nitropyridine 1-oxide (2.08 g, 13.0 mmol) was dissolved in glacial acetic acid (30.0 mL). The solution was heated to ~55° C. and then acetyl bromide (30.0 mL) was added in portions while maintaining the temperature. The solution was allowed to reflux at 120° C. for 2.5 hrs. After cooling to room temperature, the reaction was quenched by pouring into ~20 mL cold water. Potassium carbonate was added to the solution until slightly basic and then the product was extracted with four portions of CH$_2$Cl$_2$. The organic phases were collected, washed once with a saturated solution of sodium bicarbonate, dried over anhydrous magnesium sulfate, and concentrated to give the product as an orange oil (1.98 g, 10.5 mmol, 81% yield). $^1$H NMR (400 MHz, CDCl$_3$) δ 8.50 (d, J=8.0 Hz, 1H), 7.38 (d, J=4.0 Hz, 1H), 7.25 (dd, J=8.0 Hz, 1H), 2.47 (s, 3H). $^{13}$C NMR (400 MHz, CDCl$_3$) δ 150.35 ($^{Ar}$C), 140.03 ($^{Ar}$C), 129.36 ($^{Ar}$C), 126.79 ($^{Ar}$C), 118.35 ($^{Ar}$C), 17.72 (CH$_3$).

Synthesis of (4-bromopyridin-2-yl)methanol (alk3): In a three-neck flask, 2-methyl-4-bromopyridine 1-oxide (1.98 g, 10.5 mmol) was dissolved in in CH$_2$Cl$_2$ (35.0 mL). The solution was cooled down to 0° C. and purged with N$_2$ gas. Trifluoroacetic anhydride (7.3 mL, 52.5 mmol) was added via addition funnel over the course of 15 min. The reaction was allowed to stir at 45° C. for 14 hrs. The solution was cooled to room temperature and then concentrated via a rotary evaporator to an orange oil. The oil was dissolved in CH$_2$Cl$_2$ (40.0 mL) and 2M NaOH (25.0 mL) was added. The biphasic mixture was allowed to stir for 9 hrs. The organic phase was collected, and the product was further extracted from the aqueous phase with three portions of CH$_2$Cl$_2$. The combined organic phases were washed with saturated NaCl, dried over anhydrous magnesium sulfate and concentrated via a rotary evaporator (1.46 g, 7.76 mmol, 74%). $^1$H NMR (400 MHz, CDCl$_3$) δ 8.29 (d, J=4.0 Hz, 1H), 7.43 (d, J=4.0 Hz, 1H), 7.31 (dd, J=8.0 Hz, 1H), 4.68 (s, 2H). $^{13}$C NMR (400 MHz, CDCl$_3$) δ 161.00 ($^{Ar}$C), 149.33 ($^{Ar}$C), 133.56 ($^{Ar}$C), 125.75 ($^{Ar}$C), 123.93 ($^{Ar}$C), 63.93 (CH$_2$).

Synthesis of 4-bromo-2-(chloromethyl)pyridine (alk4): (4-bromo-pyridin-2-yl)methanol (1.46 g, 7.76 mmol) was dissolved in CH$_2$Cl$_2$ (30.0 mL). Thionyl chloride (1.59 g, 13.4 mmol) was added and the reaction stirred at room temperature for 1 hour, at which point the reaction was found to be complete by TLC. Saturated Na$_2$CO$_3$ (30.0 mL) was added and the organic phase was collected. The product was extracted from the aqueous phase with three portions of CH$_2$Cl$_2$. The organic phases were combined, washed with saturated NaCl, dried over anhydrous MgSO$_4$ and concentrated to an orange oil via a rotary evaporator (1.27 g, 6.15 mmol, 79%). $^1$H NMR (400 MHz, DMSO) δ 8.45 (d, J=8.0 Hz, 1H), 7.83 (d, J=4.0 Hz, 1H), 7.63 (dd, J=8.0 Hz, 1H), 4.75 (s, 2H). $^{13}$C NMR (400 MHz, DMSO) δ 158.52 ($^{Ar}$C), 151.14 ($^{Ar}$C), 133.17 ($^{Ar}$C), 126.90 ($^{Ar}$C), 126.72 ($^{Ar}$C), 46.37 (CH$_2$).

Synthesis of 1-(4-bromopyridin-2-yl)-N-methylmethanamine (alk5): 4-bromo-2-(chloromethyl)pyridine (1.27 g, 6.15 mmol) was dissolved in isopropanol (20.0 mL). Methylamine (15 mL, 40% aqueous solution) was added and the reaction stirred for 12 hrs. The volume was reduced to ~5 mL and then was taken up in a mixture of CHCl$_3$ (20.0 mL) and saturated Na$_2$CO$_3$ (20.0 mL). The organic phase was collected and the product was extracted from the aqueous phase with three portions of CHCl$_3$. The combined organic phases were washed with saturated NaCl, dried over MgSO$_4$, and reduced to an orange oil (1.05 g, 5.55 mmol, 90%). $^1$H NMR (400 MHz, DMSO) δ 8.35 (d, J=4.0 Hz, 1H), 7.65 (d, J=4.0 Hz, 1H), 7.49 (dd, J=8.0 Hz, 1H), 3.71 (s, 2H), 2.25 (s, 3H). $^{13}$C NMR (400 MHz, DMSO) δ 163.10 ($^{Ar}$C), 150.53 ($^{Ar}$C), 132.89 ($^{Ar}$C), 125.33 ($^{Ar}$C), 125.02 ($^{Ar}$C), 56.52 (CH$_2$), 36.07 (CH$_3$).

Synthesis of tert-butyl N-((4-bromopyridin-2-yl)methyl)-N-methylglycinate (alk6): 1-(4-bromopyridin-2-yl)-N-methylmethanamine (1.05 g, 5.55 mmol) was dissolved in CH$_3$CN (15.0 mL) and then triethylamine (6.8 g, 67.2 mmol) was added. The reaction was heated to 80° C. and allowed to stir for 45 min. After cooling to 0° C., teat-butyl bromoacetate (3.28 g, 16.8 mmol) was added via syringe over a 2 min. time period causing the formation of a white precipitate. The solution was heated to 80° C. and allowed to stir for 20 hrs, during which time, the precipitate re-dissolved. The reaction was cooled to 0° C. and the resultant precipitate was removed via vacuum filtration. The filtrate was reduced to an oil via a rotary evaporator and then dissolved in CH$_3$CN (30.0 mL). The crude product was extracted with four portions of 2M HCl (30.0 mL) with each portion being immediately made basic by the addition of 7M KOH (20.0 mL). The product was extracted from the combined aqueous phases with four portions of ethyl acetate (30.0 mL). The combined organic phases were washed with saturated NaCl, dried over anhydrous MgSO$_4$, and reduced to an oil (1.36 g, 4.31 mmol, 77%). $^1$H NMR (400 MHz, CDCl$_3$) δ 8.29 (d, J=8.0 Hz, 1H), 7.68 (d, J=4.0 Hz, 1H), 7.28 (dd, J=8.0 Hz, 1H), 3.78 (s, 2H), 3.22 (s, 2H), 2.36 (s, 3H), 1.42 (s, 9H).

Synthesis of tert-butyl N-methyl-N-((4-((trimethylsilypethynyl)pyridine-2-yl)methyl)glycinate (alk7): tert-butyl N-((4-bromopyridin-2-yl)methyl)-N-methylglycinate (0.700 g, 2.23 mmol) was dissolved in freshly distilled triethylamine (5.6 mL). CuI (4.2 mg, 0.022 mmol) and Pd(PPh$_3$)$_4$ (12.8 mg, 0.011 mmol) were added and reaction mixture was freeze-pump-thawed three times. Trimethylsilylacetylene (328 mg, 3.36 mmol) was added via syringe and the reaction was allowed to stir at 70° C. under an N$_2$ atmosphere for 24 hrs. After cooling to room temperature, H$_2$O (~20 mL) was added followed by the addition of dilute HCl to adjust the pH to ~7. The product was extracted using three portions of CH$_2$Cl$_2$ (20 mL), and the combined organic phases were collected and filtered through a celite pad via vacuum filtration, washed with saturated NaCl, dried over anhydrous MgSO$_4$, and concentrated to an oil (640 mg, 1.82 mmol, 81%). $^1$HNMR (400 MHz, DMSO) δ 8.47 (d, J=4.0 Hz, 1H), 7.47 (d, J=4.0 Hz, 1H), 7.28 (dd, J=8.0 Hz, 1H), 3.73 (s, 2H), 3.24 (s, 2H), 2.27 (s, 3H), 1.42 (s, 9H), 0.25 (s, 9H).

Synthesis of N-((4-ethynylpyridin-2-yl)methyl)-N-methylglycine (alk8): Deprotection of the t-butyl group of tert-butyl N-methyl-N-((4-((trimethylsilyl)ethynyl)pyridine-2-yl)methyl)glycinate was carried out by stirring g1 (0.64 g, 1.82 mmol) in trifluoroacetic acid (~25 mL) for 2 hrs. The reaction was concentrated and triturated six times with THF (5 mL portions) to the give the trifluoroacetate salt. Deprotection of the TMS group was carried out by dissolving the salt in MeOH and adding K$_2$CO$_3$ (0.50 g, 3.64 mmol). The reaction stirred at room temperate for 2 hrs. The solution was neutralized with 2M HCl and then extracted with three portions of ethyl acetate. The organic phases were reduced to give the product as a dark oil (330 mg, 1.62 mmol, 89%). $^1$H NMR (400 MHz, DMSO) δ 8.75 (d, J=4.0 Hz, 1H), 7.71 (d, J=4.0 Hz, 1H), 7.62 (dd, J=8.0 Hz, 1H), 4.81 (s, 1H), 3.58 (s, 2H), 4.24 (s, 2H), 2.93 (s, 3H).

Synthesis of [C$_6$H$_{16}$N][Fe$^{II}$(N$_2$O$_1$-alkyne)(MeOH)(Cl)$_2$]: The trifluoroacetate salt of the N$_2$O$_1$-alkyne ligand (0.200 g, 0.514 mmol) was dissolved along with two equivalents of triethylamine (0.104 g, 1.03 mmol) in 5 mL of a 1:4 methanol/THF mixture, and then added to a solution of FeCl$_2$ (0.059 g, 0.463 mmol) in 5 mL of 1:4 methanol/THF. A dark brownish-red precipitate formed immediately and the solution was allowed to stir for 12 hours at room temperature. The dark precipitate was collected via filtration over a fritted glass filter, and washed with THF and then diethyl ether, yielding the trialkylammonium salt of the iron complex as a dark solid (0.155 g, 0.350 mmol, 68% yield).

Preparation of N$_2$O$_1$py-polystyrene Resin

Synthesis of azidomethyl polystyrene: Merrifield resin (2.0 g, 1.2 mmol chloride per gram of resin) was stirred with DMSO (20 mL). NaN$_3$ (780 mg, 12 mmol) was added and the slurry was allowed to stir at 70° C. for 48 hrs. The reaction was allowed to cool to room temperature and the resin was removed via vacuum filtration and washed with DMSO (3×5 mL) and then alternatingly with MeOH (5×5 mL) and $CH_2Cl_2$ (5×5 mL) before being allowed to air dry. Selected IR bands (KBr, $cm^{-1}$): 2090 ($N_3$).

Synthesis of $N_2O_1$py-polystyrene via 'click' chemistry: The $[C_6H_{16}N][Fe^{II}(N_2O_1\text{-alkyne})(MeOH)(Cl)_2]$ complex (0.531 g, 1.2 mmol) was dissolved in solvent mix of 1:1 $H_2O$/MeOH (3.0 mL) and then added to a slurry of azidomethyl polystyrene (1.0 g) in MeOH (5.0 mL). CuI (0.046 g, 0.240 mmol) was added and the solution stirred for 48 hrs. at room temperature. The resin was removed via vacuum filtration and washed with MeOH (6×3 mL), THF (6×3 mL) and diethyl ether (6×3 mL) before being collected as a dark powder.

Preparation of $N_2O_1$py-Cl Ligand

Synthesis of methyl 4-chloropicolinate (Cl2): 2-picolinic acid (15.0 g, 0.120 mol) was dissolved in thionyl chloride (50 mL). NaBr (2.00 g, 20.0 mmol) was added and the reaction stirred at 75° C. for 20 hrs. The thionyl chloride was removed resulting in dark oil which was triturated with toluene (2×10 mL) and then left under vacuum for 1 hour to ensure the removal of the thionyl chloride. Toluene (100 mL) was added and the solution was cooled to 0° C. before the addition of MeOH (20 mL), which was added slowly resulting in the precipitation of product. The mixture stirred at room temperature for 30 min. and then the white precipitate was collected via vacuum filtration and washed with toluene (5×10 mL). The solid was dissolved in $H_2O$ (200 mL) and ethyl acetate (100 mL) was added. The aqueous phase was neutralized by the addition of $Na_2CO_3$. The organic phase was collected and the product was further extracted from the aqueous phase with ethyl acetate (3×50 mL). The organic phases were collected, washed once with saturated NaCl, dried over anhydrous $MgSO_4$ and concentrated to a yellow solid (13.2 g, 77.0 mmol, 64%). $^1$HNMR (400 MHz, DMSO) δ 8.67 (d, J=8.0 Hz, 1H), 8.03 (d, J=4.0 Hz, 1H), 7.79 (dd, J=8.0 Hz, 1H), 3.71 (s, 2H), 3.88 (s, 3H). $^{13}$C NMR (400 MHz, DMSO) δ 164.58 (C=O), 151.62 ($^{Ar}$C), 149.48 ($^{Ar}$C), 144.49 ($^{Ar}$C), 127.74 ($^{Ar}$C), 125.27 ($^{Ar}$C), 53.17 ($CH_3$).

Synthesis of (4-chloropyridin-2-yl)methanol (Cl2): Cl1 (0.750 g, 4.37 mmol) was dissolved in freshly distilled MeOH (5.0 mL) and THF (2.5 mL), and the solution was cooled to 0° C. $CaCl_2$ (1.90 g, 17.1 mmol) was added and the solution stirred for 5 min. before the slow addition of $NaBH_4$ (0.330 g, 8.73 mmol) causing the evolution of $H_2$ gas. The reaction was allowed to stir at 0° C. for 2 hrs. and then warmed up to room temperature, at which point, reaction completion was confirmed by TLC analysis. $H_2O$ (30 mL) was added and the product was extracted with ethyl acetate (3×10 mL). The organic phases were collected, dried over anhydrous $MgSO_4$ and concentrated to a white solid (0.509 g, 3.55 mmol, 81%). $^1$H NMR (400 MHz, DMSO) δ 8.44 (d, J=4.0 Hz, 1H), 7.49 (d, J=4.0 Hz, 1H), 7.36 (dd, J=8.0 Hz, 1H), 5.54 (s, 1H), 4.45 (s, 2H). $^{13}$C NMR (400 MHz, DMSO) δ 164.74 ($^{Ar}$C), 150.57 ($^{Ar}$C), 143.87 ($^{Ar}$C), 122.44 ($^{Ar}$C), 120.47 ($^{Ar}$C), 64.16 ($CH_2$).

Synthesis of 4-chloro-2-(chloromethyl)pyridine (Cl3): Cl2 (0.500 g, 3.48 mmol) was dissolved in freshly distilled $CH_2Cl_2$ (23 mL) and thionyl chloride (0.530 g, 4.45 mmol) was added. The reaction stirred at room temperature for 2 hrs, at which point, reaction completion was confirmed by TLC analysis. A saturated aqueous solution of $Na_2CO_3$ (30 mL) was added and the solution stirred for 10 min. The product was extracted with $CH_2Cl_2$ (3×50 mL). The organic phases were collected, dried of anhydrous $MgSO_4$ and concentrated to give the product (0.415 g, 2.56 mmol, 74%). $^1$H NMR (400 MHz, DMSO) δ 8.53 (d, J=4.0 Hz, 1H), 7.69 (d, J=4.0 Hz, 1H), 7.50 (dd, J=8.0 Hz, 1H), 4.76 (s, 2H). $^{13}$C NMR (400 MHz, DMSO) δ 158.73 ($^{Ar}$C), 151.32 ($^{Ar}$C), 144.03 ($^{Ar}$C), 123.93 ($^{Ar}$C), 123.78 ($^{Ar}$C), 46.43 ($CH_2$).

Synthesis of 1-(4-chloropyridin-2-yl)-N-methylmethanamine (Cl4): Cl3 (0.451 g, 2.56 mmol) was dissolved in isopropyl alcohol (7.0 mL) and aqueous methylamine (4.7 mL, 40%) was added. The reaction was allowed to stir at room temperature for 16 hrs. and was then concentrated to an oil. A saturated solution of aqueous $Na_2CO_3$ (15 mL) was added and the product was extracted with $CHCl_3$ (3×10 mL). The organic phases were collected, dried over anhydrous $MgSO_4$ and concentrated to give the product (0.209 g, 1.34 mmol, 52%). $^1$H NMR (400 MHz, DMSO) δ 8.44 (d, J=4.0 Hz, 1H), 7.51 (d, J=4.0 Hz, 1H), 7.36 (dd, J=8.0 Hz, 1H), 3.75 (s, 2H), 2.26 (s, 3H). $^{13}$C NMR (400 MHz, DMSO) δ 163.26 ($^{Ar}$C), 150.70 ($^{Ar}$C), 143.63 ($^{Ar}$C), 122.39 ($^{Ar}$C), 121.98 ($^{Ar}$C), 62.45 ($CH_2$), 25.93 ($CH_3$).

Synthesis of 2-(methyl(4-chloropyridine-1-ium-2-ylmethyl)ammonio)acetate tri-fluoroacetate (Cl5): In a round bottom flask, 1-(4-chloropyridin-2-yl)-N-methylmethanamine (0.451 g, 2.90 mmol) was added to a solution of triethylamine (3.45 g, 34.1 mmol) and freshly distilled MeCN (8 mL). The solution was refluxed at 80° C. for 45 minutes before being cooled to 0° C., at which point t-butyl bromoacetate (1.26 mL, 8.52 mmol) was added slowly via pipette. A white precipitate ($NH_4Br$) formed that dissolved back into solution as the reaction was brought back to reflux and allowed to stir at 80° C. for 20 hours. The reaction was cooled to 0° C. and the precipitate was removed via vacuum filtration through a fritted glass funnel. The filtrate was reduced via rotary evaporator yielding an orange solid that was dissolved in 20 mL $CH_2Cl_2$ and extracted with 4×20 mL portions of 2M HCl. Each 20 mL fraction of HCl was immediately collected into a flask cooled to 0° C., containing 40 mL of 7M KOH to prevent unwanted hydrolysis of the t-butyl group. The aqueous phases were collected and the product was extracted with 4×20 mL of ethyl acetate. The organic phases were collected and washed twice with 20 mL of sat. $K_2CO_3$, dried over $MgSO_4$ and then reduced via a rotary evaporator to yield the t-butyl protected form of the ligand as a brown oil. Deprotection was performed by dissolving the oil in 20 mL of concentrated trifluoroacetic acid and stirring for 3 hours. The trifluoroacetic acid was removed under high vacuum, and the remaining oil was triturated six times with THF. The product was dissolved in a minimal amount of THF and recrystallized by the addition of diethyl ether as a white solid (0.517 g, 1.57 mmol, 54% yield). $^1$H NMR (400 MHz, DMSO) δ 8.61 (d, J=8.0 Hz, 1H), 7.71 (d, J=4.0 Hz, 1H), 7.61 (dd, J=8.0 Hz, 1H), 4.44 (s, 2H), 4.06 (s, 2H), 2.79 (s, 3H). $^{13}$C NMR (400 MHz, DMSO) δ 163.26 ($^{Ar}$C), 150.70 ($^{Ar}$C), 143.63 ($^{Ar}$C), 122.39 ($^{Ar}$C), 121.98 ($^{Ar}$C), 62.45 ($CH_2$), 25.93 ($CH_3$).

Figure 77:
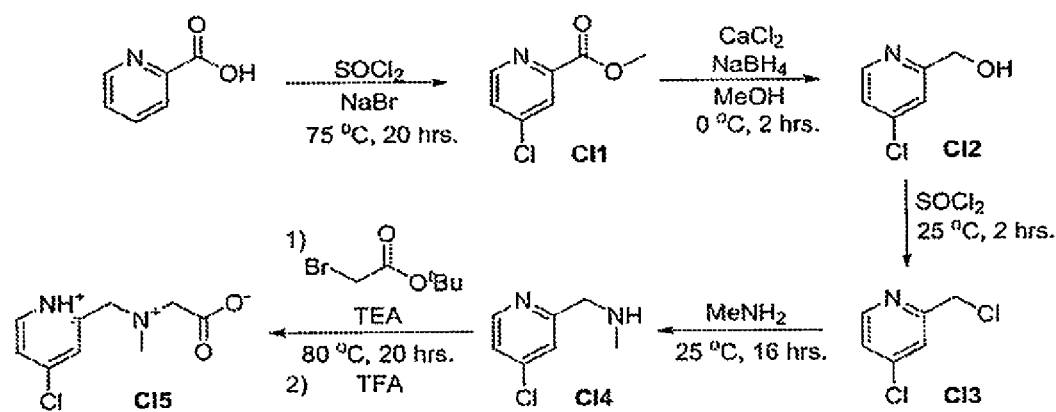
FIG. 77 is a diagram that illustrates the synthesis of the $N_2O_1py$-Cl ligand.

The $N_2O_1$py-Cl ligand as a precursor: The preparation of the $N_2O_1$py-Cl ligand (C15) was achieved by first converting picolinic acid to methyl 4-chloropicolinate by using sodium bromide as a catalyst (FIG. 77). Very low yields resulted in the absence sodium bromide, even when the reaction was refluxed for three days. Reduction of the ester, followed by reaction with thionyl chloride gave Cl3, which was reacted with methyl amine to give Cl4. Reaction with tert-butyl bromoacetate gave the protected form of the ligand, which was deprotected using trifluoroacetic acid to produce the trifluoracetate salt of the ligand as a powder. Using hydrochloric acid for the deprotection resulted in hydroscopic oil that proved more difficult to work with.

Based on its similarities with the $H_2N_2O_1py$, ligand, the $N_2O_1py$-Cl ligand is likely to exist in solution as the zwitterion.

Figure 79:
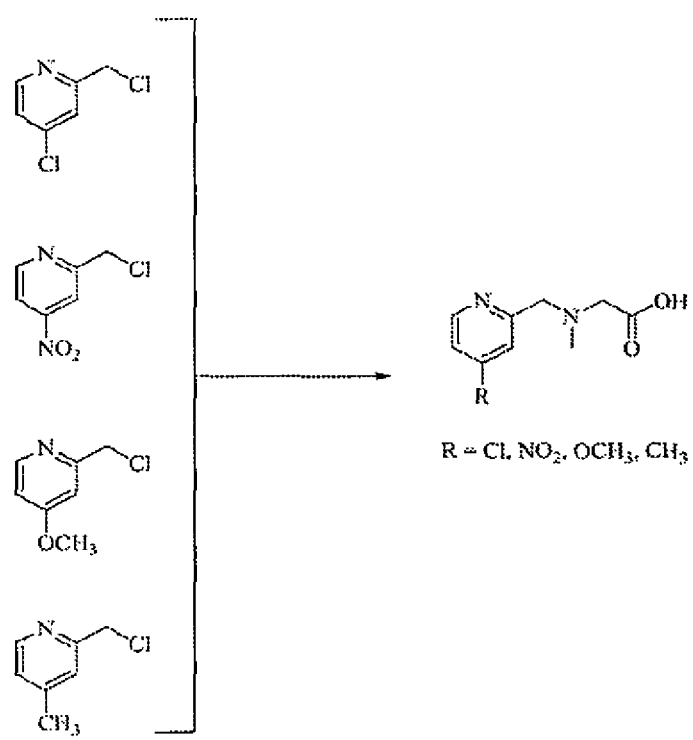
FIG. 79 is a diagram that illustrates a proposed synthetic route to four derivatives of the $N_2O_1py$ ligand.

The $N_2O_1py$-Cl ligand provides the same coordination mode as the $N_2O_1py$ ligand. The addition of the chloride in the para position of the aromatic group allows for substitution reactions that may lead to a variety of substituents in that position. This is important for two reasons. First, the addition of substituents that consist of organic soluble groups may facilitate in the dissolution of the metal complex coordinating the ligand. The first generation catalyst, $[Fe^{II}(N_2O_1)(Cl)_2(MeOH)]$, is soluble in protic solvents, but only slightly soluble in DMF and DMSO (Cappillino, P. J., et al., Dalton Trans 2012, 41, 5662-77; Thesis of Tarves, P. C., Boston University, 2012). The complex is insoluble in other outlined for the $N_2O_1py$-Cl (Cl3 to Cl5, FIG. 77) species outlined herein (FIG. 79). The preparation of iron complexes based on these $N_2O_1py$ derivatives could be utilized in a redox study to determine the effect of the electron donating/ withdrawing properties on the electronics of the metal center. A 'redox series' of $[Fe^{II}(p\text{-}X\ N_2O_1py)]$ complexes could be useful in mechanistic studies to identify the steps that are dependent on the redox properties of iron. Additionally, altering the redox activity of the complex may affect the build-up curves associated with the intermediate(s) dependent on these redox properties in such a way that spectroscopic analysis of these intermediates becomes feasible.

Alternatively, derivatives of the $N_2O_1$-py ligand substituted with alkoxy groups in the para position of the aromatic ring can be prepared using Scheme 2 below.

Scheme 2: Synthesis of Substituted $N_2O_1$-py ligand

Figure 78:
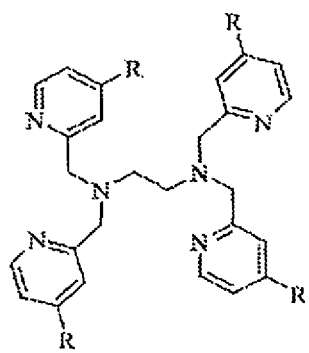
FIG. 78 illustrates the structure of derivatives of the TPEN ligand.

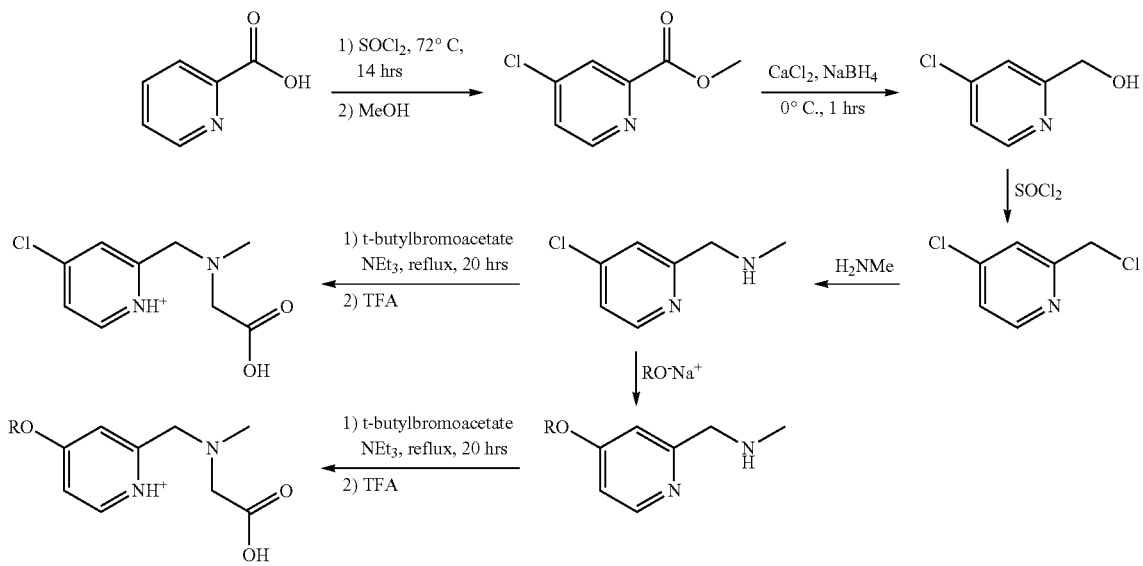

common polar and nonpolar aprotic solvents, including $CH_3CN$, $CH_2Cl_2$, THF, $Et_2O$, toluene and ethyl acetate. The second generation $N_2O_1py$-based catalyst has very similar solubility properties. Solubility in other solvents is desirable as it would allow for a variety of substrates to be used in the analysis of the reactivity properties of these complexes over a range of concentrations. Second, the addition of electron donating/withdrawing groups in the para position of the aromatic ring may allow for the tuning of the redox properties of the iron center. This effect has been observed in the case of $[Fe^{II}(TPEN)]$ (TPEN=tetrakis-N,N,N',N'-(2-pyridyl-methyl)ethylenediamine) derivatives with a variety of para substituents (FIG. 78) (Tamura, M., et al., Chemical and Pharmaceutical Bulletin (Tokyo) 2000, 48, 1514-8). Cyclic voltammetry experiments of ferrous complexes based on the five derivatives of the TPEN ligand shown in FIG. 78 found that electron-donating groups made the redox potentials less positive and electron-withdrawing groups made the redox potentials more positive.

Similar synthetic protocols as those used by Tamura et. al. (Tamura, M., et al., Chemical and Pharmaceutical Bulletin (Tokyo) 2000, 48, 1514-8) could be used to prepare the precursor compounds that could result in derivatives of the $N_2O_1py$ ligand, in conjunction with the synthetic procedures Immobilization of the $N_2O_1py$ catalyst: The catalytic properties of the $[Fe^{II}(N_2O_1)(\alpha KG)(MeOH)]$ complex demonstrate the potential of this system as a useful catalyst in a variety of oxidative transformations. However, the dimerization of the proposed high-oxidant reactive intermediate with another ferrous center leads to the formation of a highly stable diferric μ-oxo species. This catalytic degradation pathway is an issue that needs to be overcome to increase the number of turnovers, and develop this catalytic system in a way that makes its reactivity properties useful for fine chemical and industrial applications. Towards this end, a common approach would be the functionalization of the ligand with groups that contain a large amount of steric bulk. This synthetic tactic effectively creates a cavity for the iron center and inhibits the dimerization of two complex molecules by preventing close contact between the metal centers. This would be effective in preventing μ-oxo formation, however, the design of a ligand that creates enough steric bulk to inhibit dimerization, but still allows for the binding of an α-keto acid and the interaction with substrate would be a challenge. Because this catalyst utilizes the natural coenzyme in its reaction with dioxygen, the exposure of the iron center is necessary.

The tactic that has been proposed to prevent the dimerization of the $[Fe^{II}(N_2O_1)(\alpha KG)(MeOH)]$ catalyst is the immobilization of the complex via a ligand functional group. This was one of the reasons for the development of the $N_2O_1py$ ligand, as the aryl ring provides a synthetic platform for the incorporation of a variety of structural modifications.

Figure 80:
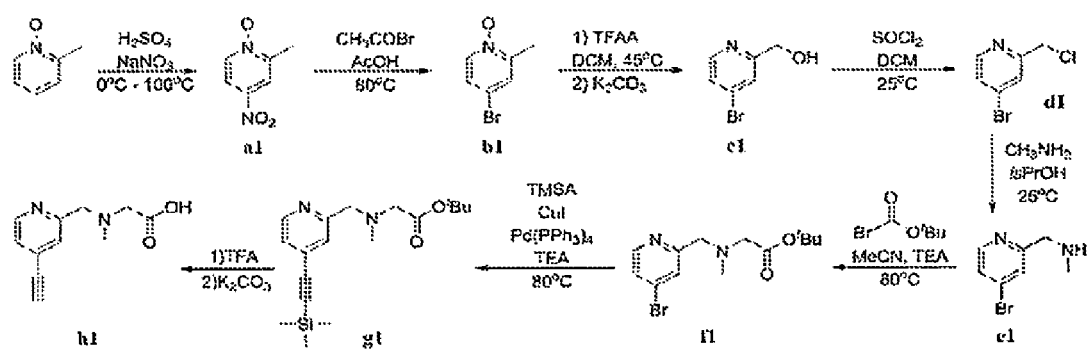
FIG. 80 is a diagram that illustrates the preparation of the $N_2O_1py$-alkyne ligand.

The synthetic procedure for a modified $N_2O_1py$ derivative has been developed that incorporates an acetylene group in the para position of the $N_2O_1py$ aromatic ring (FIG. 80). The ligand was synthesized by preparing the tent-butyl ester form of the p-Br $N_2O_1$ derivative, and then substituting the bromo group with trimethylsilylacetylene via a Sonagashira coupling reaction. Deprotection of the carboxylic acid and the acetylene resulted in the $N_2O_1py$ ligand with a terminal alkyne functional group.

Figure 81:
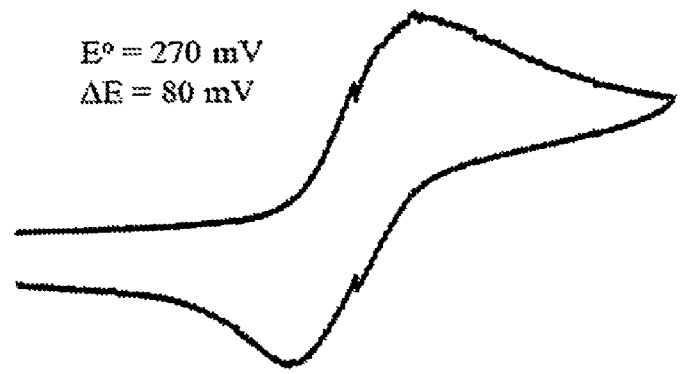
FIG. 81 is a cyclic voltammogram for $[Fe^{II}(N_2O_1py$-alkyne)]$.

Synthesis of ferrous complex using this ligand was achieved by reaction of the $N_2O_1$-alkyne ligand with $FeCl_2$ in the presence of base. Cyclic voltammetry (FIG. 81) showed that this complex is monomeric in solution, with a redox potential equal to 270 mV.

Table 15 shows a comparison of the redox potential to those of the $N_2O_1$ and $N_2O_1py$ systems, determined using cyclic voltammetry with tetrabutylammonium tetrfluoroborate as the supporting electrolyte, in DMSO, with a glassy carbon working electrode. It should be noted that these redox potentials were determined in the absence of excess halide, and further CV studies will be performed in the presence of excess halide for all derivatives of the $N_2O_1py$ system.

TABLE 15

Experimental redox properties of ferrous complexes of the $N_2O_1$, $N_2O_1py$ and $N_2O_1py$-alkyne systems.

| Complex | $E_{1/2}$ (mV) |
|---|---|
| [$Fe^{II}(N_2O_1)$] | 159 |
| [$Fe^{II}(N_2O_1py)$] | 216 |
| [$Fe^{II}(N_2O_1py$-alkyne)] | 270 |

It can be seen in Table 15 that the redox properties of the metal center are only somewhat (~110 mV) affected by the three different ligand environments. This suggests that the initial reaction with $O_2$ may not be significantly altered by these differences in ligands.

Figure 82:
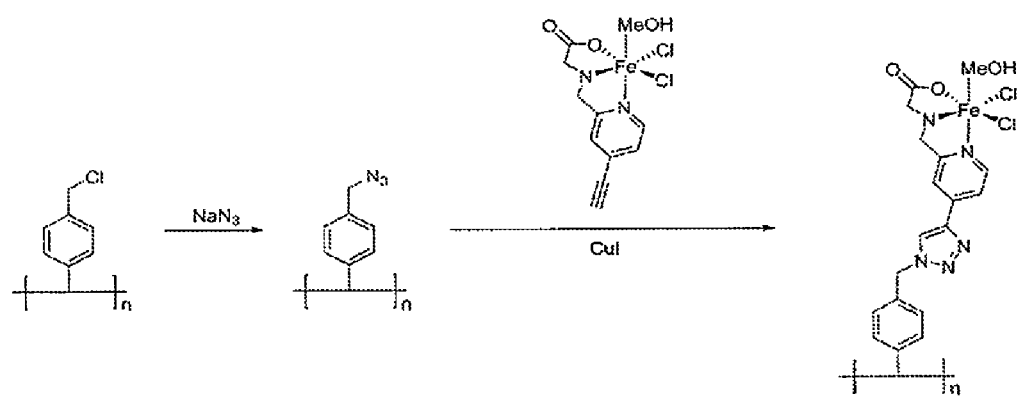
FIG. 82 is a diagram that illustrates the preparation of $[Fe^{II}(N_2O_1py)]$-functionalized polystyrene.

The terminal alkyne present in the para position of the $N_2O_1py$-alkyne ligand presents the necessary functionality for 'click' reactions between the [$Fe^{II}(N_2O_1py$-alkyne)] complex and azido functionalized materials. The reaction of this complex with azidomethyl polystyrene was carried out, establishing a synthetic protocol for the immobilization of [$Fe^{II}(N_2O_1py)$] to a solid support (FIG. 82).

Figure 83:
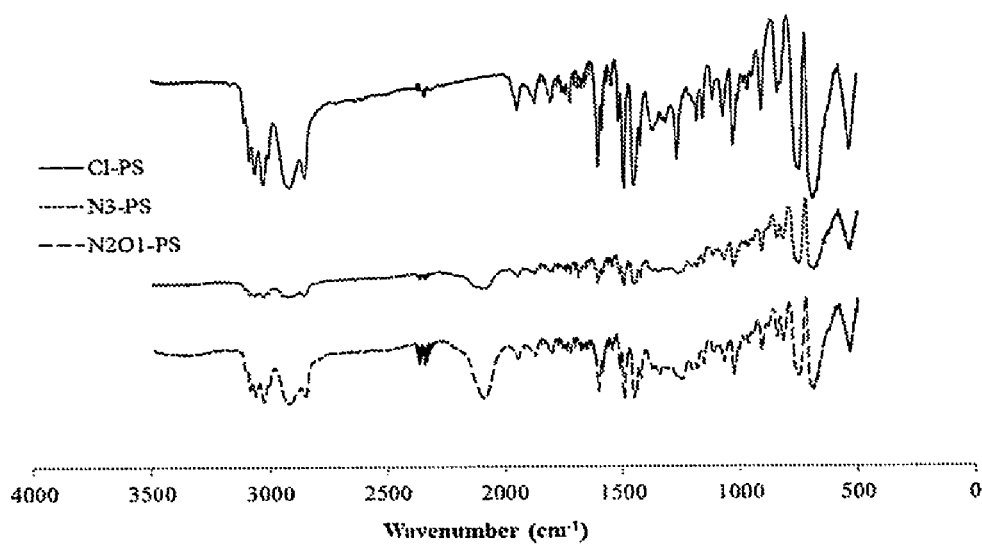
FIG. 83 are IR spectra of chloromethyl, azidomethyl and $[Fe^{II}(N_2O_1py)]$-functionalized polystyrene. Samples were prepared as KBr pellets.

The preparation of the azidomethyl polystyrene resin was followed using IR spectroscopy, where a distinct signal is detected at ~2050 cm$^{-1}$ due to the vibrational frequency of the azido group. However, reaction of the azide-functionalized material did not result in the total loss of this feature in the IR spectrum (FIG. 83). Atomic absorption spectroscopy was used to determine the moles of iron per gram of polystyrene for the three functionalized supports (chloromethyl, azidomethyl and [$Fe^{II}(N_2O_1py)$]-functionalized polystyrene). This was performed by degrading a sample of each in concentrated nitric acid, and using AA to determine the resultant iron concentration. It was found that no iron was present in samples of chloromethyl and azidomethyl polystyrene, but an appreciable amount of iron was present in the sample of the [$Fe^{II}(N_2O_1py)$]-functionalized polystyrene. It was calculated that 71% conversion of the original Cl groups by iron complex had taken place (the chloromethyl polystyrene reagent contained 1.2 mmol Cl/gram of resin, and AA determined 0.852 mmol Fe/gram of resin for the [$Fe^{II}(N_2O_1py)$]-functionalized polystyrene). Further AA analyses of the chloromethyl and azidomethyl polystyrene resins were performed after stirring a sample of each with $FeCl_2$ and it was found that no iron was present, suggesting that the presence of iron in the sample of the [$Fe^{II}(N_2O_1py)$]-functionalized polystyrene, was due to the 'click' reaction between the ligand and the azide.

Further analytical studies provided support for the presence of at least two open sites available for the binding of a bidentate chelate. The addition of bathophenanthroline to a solution of [$Fe^{II}(N_2O_1py$-alkyne)] and a slurry of [$Fe^{II}(N_2O_1py)$]-functionalized polystyrene each resulted in a similar deep red color (the solution of [$Fe^{II}(N_2O_1py$-alkyne)] turned red and the solid [$Fe^{II}(N_2O_1py)$]-functionalized polystyrene turned red). Bathophenanthroline forms a red chromophore when it binds to a ferrous center in a bidentate manner, allowing it to serve as an indicator for the presence of at least two binding sites. This is important, as it suggests that immobilization of the complex should not impact its interaction with αKG and $O_2$.

The reactivity of the immobilized complex was analyzed by exposing the resin to $O_2$ in the presence of five equivalents of αKG and 500 equivalents of cyclohexene. Gas chromatography was used to quantify the resultant oxidation products of cyclohexene (cyclohexene epoxide, cyclohexenol and cyclohexenone). However, the resin was found to be ineffective in the oxidation of cyclohexene vs. control reactions. It is proposed that this may be due to two primary reasons. Firstly, the loading of the complex on the polystyrene resin may be too high. The loading needs to be low enough that the immobilized complex molecules are too far apart to interact. Secondly, polystyrene resins are known to swell in many solvents (Brandrup, J., Immergut, E. H. Polymer Handbook; 2 ed.; John Wiley and Sons, Inc.: New York, 1975). The reaction with cyclohexene took place in a 5:95 DMF:$CH_2Cl_2$ solvent mixture. Polystyrene has a swelling volume of 5.6 mL/g in DMF and 8.3 mL/g in $CH_2Cl_2$. Swelling is expected to change the properties of the surface area of the polystyrene beads which may cause the iron sites to become less accessible.

These synthetic protocols can be used to prepare $N_2O_1py$-functionalized resins with lower loading capacities, and more predictable surface behavior in aprotic solvents. Polystyrene resins with a higher degree of crosslinking may minimize the swelling effects in solvents that are conducive to reactivity studies. Other organic resins, with a range of swelling properties have been developed, including resins based on polyethylene glycol (PEG), such as Tentagel, which is a PEG-polystyrene hybrid. The use of organic resins has been the initial focus due to their lack of functional groups that could coordinate to the iron center, thereby removing the open sites needed for αKG binding. The linker formed using the 'click reaction' discussed above with the $N_2O_1py$-alkyne ligand would not be expected to provide enough flexibility to allow for the iron complex to interact with the resin surface, however, swelling may cause the resin surface to be close enough to the immobilized catalyst to potentially interact as a substrate. Silica based solid supports, such as functionalized silicon dioxide beads and mesoporous glass may also be considered. A variety of resins or beads can be analyzed to find a solid support that most effectively immobilizes the iron complex with a low loading capacity, does not interact with the iron center, and is inert to chemical oxidation.

EPR spectroscopy can be useful in characterizing the electronic structure of the NO-adduct of the immobilized iron complex. The EPR signal for the immobilized complex should be able to be fit with the fitting parameters used for the EPR data corresponding to the [Fe(N$_2$O$_1$py)(NO)] and [Fe(N$_2$O$_1$py)(αKG)(NO)] complexes. 'Click' chemistry is a well-known process that is used in chemistry and biochemistry, and as discussed, a variety of solid supports are available.

Figure 84A:
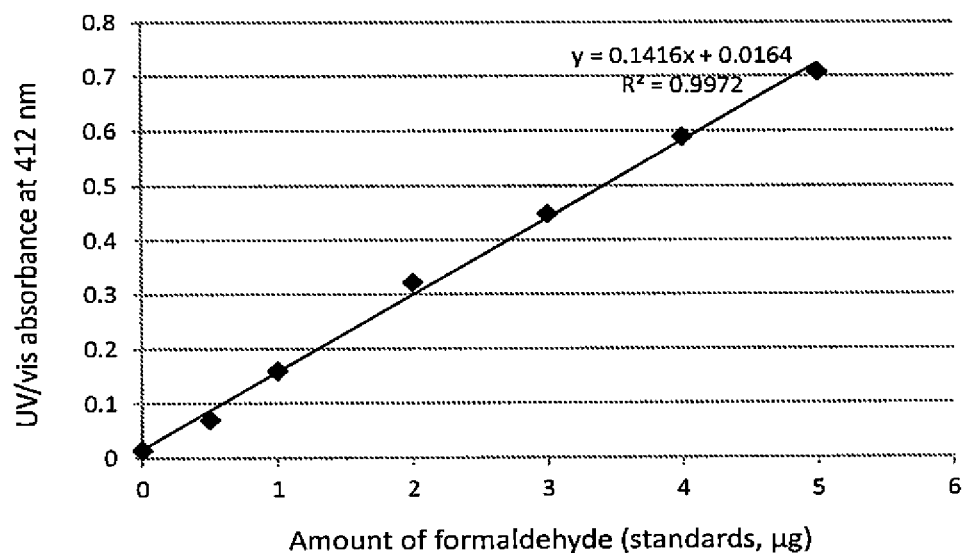
FIG. 84A is a graph of calibration curve that correlates absorption spectrum based formaldehyde assay with standards.
Figure 84B:
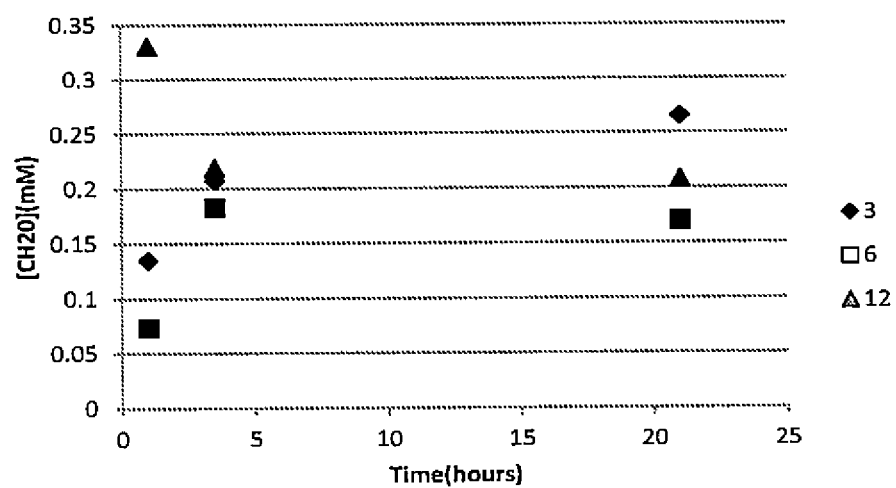
FIG. 84B is a graph of formaldehyde concentration as a function of reaction time in reactions catalyzed by a heterogeneous catalyst. The numbers 3, 6, 12 refer to the time allowed for the linking reaction that links the alkyne-substituted homogeneous catalyst to the resin to generate the heterogeneous catalyst.

Experiments were performed to observe the oxidation of methanol to formaldehyde catalyzed by catalysts bound to a resin (Table 16, FIGS. 84A-84B). The experimental data show that production of formaldehyde stops, but can be made to continue by washing the resin with solvent and starting the reaction again (Table 16). This suggests that the product (formaldehyde) binds to the catalyst on the resin and poisons it. Washing removes the formaldehyde and allows the catalyst to regain its catalytic activity. These data show that the same mode of homogeneous solution-based catalyst inactivation (irreversible dimer formation) is not occurring, as the catalytic activity can be regained after washing, which would not be the case if irreversible dimer inactivation occurred.

$C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl. In other embodiments, utilizing an $R_1$-moiety that contains an alkyne (or a protected alkyne group) in the modular ligand synthesis (Scheme 3) followed by $R_2$- and $R_3$-moieties selected for their steric/solubility/substrate directing characteristics, can generate a chiral environment at the resin-bound iron catalyst necessary for asymmetric catalysis.

Scheme 3: Modular Ligand Synthesis

Revised N$_2$O$_1$ Synthesis

A.

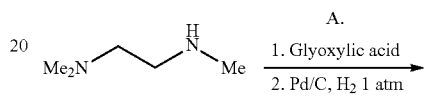

TABLE 16

Catalyst bound to resin regains activity after washing the resin

| time | Resin | A412 | ppm[CH2O] diluted | ppm[CH2O] | mM[CH2O] | mmol Fe | [Fe]mM | |
|---|---|---|---|---|---|---|---|---|
| 1 | 3 h | 0.28839 | 2.020252542 | 4.04050508 | 0.1346835 | 0.000358 | 0.071535 | 3.709336 |
| 1 | 6 h | 0.15766 | 1.097018079 | 2.19403616 | 0.07313454 | 0.000338 | 0.0675 | 2.517526 |
| 1 | 12 h | 0.70363 | 4.952738418 | 9.90547684 | 0.33018256 | 0.000253 | 0.050592 | 4.109328 |
| 3.5 | 3 h | 0.44236 | 3.107611299 | 6.2152226 | 0.20717409 | | | |
| 3.5 | 6 h | 0.38983 | 2.736636723 | 5.47327345 | 0.18244245 | | | |
| 3.5 | 12 h | 0.46758 | 3.285718644 | 6.57143729 | 0.21904791 | | | |
| 21 | 3 h | 0.56592 | 3.980210169 | 7.96042034 | 0.26534734 | | | |
| 21 | 6 h | 0.36326 | 2.54899548 | 5.09799096 | 0.16993303 | | | |
| 21 | 12 h | 0.4439 | 3.118487006 | 6.23697401 | 0.20789913 | | | |
| | | | −0.0164 | −0.0328 | −0.0010933 | | | |
| 1.5 | 3 h | 0.91203 | 6.424489831 | 12.8489797 | 0.42829932 | 0.000289 | 0.096334 | 4.445992 |
| 1 | 6 h wash | 0.16066 | 1.11820452 | 2.23640904 | 0.07454697 | 0.000338 | 0.0675 | 1.1044 |
| 4 | 3 h | 0.93216 | 6.566650847 | 13.1333017 | 0.43777672 | 0.000289 | 0.096334 | 4.544373 |
| 28 | 3 h | 1.0197 | 7.184871186 | 14.3697424 | 0.47899141 | 0.000289 | 0.096334 | 4.972205 |
| 28 | 6 h wash | 0.82139 | 5.784376836 | 11.5687537 | 0.38562512 | 0.000338 | 0.0675 | 5.712965 |
| 48 | 3 h | 0.95514 | 6.728938983 | 13.457878 | 0.44859593 | | | |
| 48 | 6 h wash | 0.577 | 4.058458757 | 8.11691751 | 0.27056392 | | | |

Example 4

Improved Synthesis of the N$_2$O$_1$ Ligand and Analogs

An alternative two-step synthesis for the N$_2$O$_1$ ligand was devised which allows generation of gram quantities of ligand with an overall isolated, recrystallized yield of 72% (see Scheme 3). Scheme 3 also depicts a synthetic route for enhancing the solubility of catalyst-ligand complexes by enabling the selection of three independent R groups in the ligand. As stated earlier, although alkane oxidation catalysis can be observed when using mixed solvent systems, it is important to improve the solubility of the catalyst to reasonable levels. This synthetic approach allows independent modification of each of the nitrogen centers in a stepwise manner so that three distinct side chains can be introduced. Each of $R_1$, $R_2$, and $R_3$ can be independently selected from any of the possible substituents through $R^{19}$ discloses herein for Formula (I). For example, each of $R_1$, $R_2$, and $R_3$ can be independently H, optionally substituted linear or branched -continued

72%

Literature References:
A. Vaid et al, Synthesis (2013). 45, 1534.

N$_2$O$_1$ "Catalyst-Pocket" Synthesis

A.

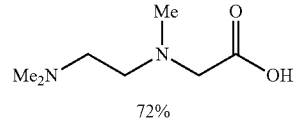

B.

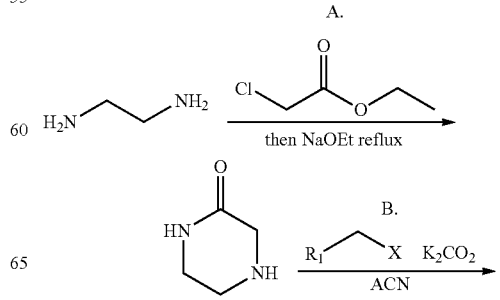

-continued

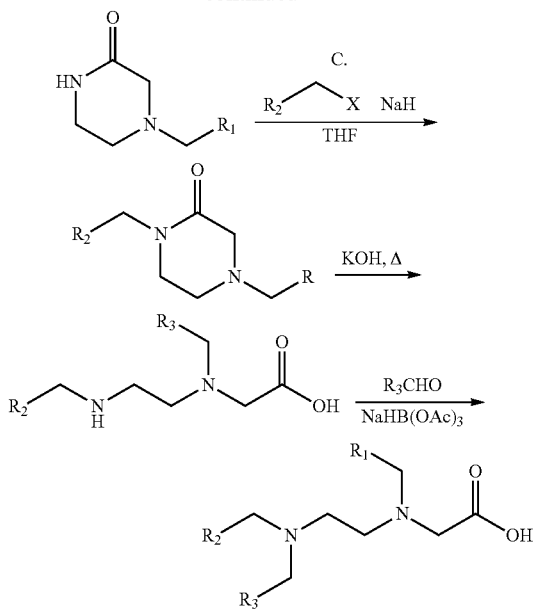

Literature References:
A. 1) Korch et al. Angew, Chem. Int. Ed, (2015), 54, 179, 2) US Patent 2005/0222166 A1
B. 1) Korch et al. Angew, Chem. Int. Ed, (2015), 54, 179, 2) Patent: WO2012/154676
C. Miserazzi et al, Tetrahedron Lett. (2011) 52, 448.

As demonstrated herein, $[Fe^{II}(N_2O_1py)(MeOH)_3]^+$ can be linked to a substituted polystyrene resin via a terminal alkyne linker on the pyridine-containing catalyst through the use of Click chemistry to produce $[Fe_{II}(N_2O_{1py})]$-functionalized polystyrene (see Example 3, FIG. 82). The iron(II) complex on this modified resin was observed to bind a bidentate ligand (bidentate bathophenanthroline coordination induces an intense an intense color change), indicating the availability of at least two open or exchangeable sites. This modified resin is capable of converting MeOH to formaldehyde in the presence of α-KG and $O_2$ in a batch mode (resin sitting in solution). Appropriate control reactions showed no activity in the absence of either α-ketoglutarate or iron(II). While turnover numbers were modest (8 per Fe based on AA analysis), if the resin was washed, the catalyst retained its low-level of activity (8-10 turnovers for second and third rounds of catalysis) unlike the homogeneous catalyst that once inactivated remains so due to irreversible dimer formation.

In another embodiment, the aliphatic tridentate N,N,O-ligand system can be functionalized and linked to a solid support. Scheme 4 shows an embodiment wherein the saturated ligand backbone $N_2O_1$ of the active homogeneous catalyst is functionalized to link it to resin through standard azide-alkyne cycloaddition coupling methodology (Click Chemistry). This ligand will enable the fully active catalyst to be linked to a wide range of commercially available resins/supports (e.g., silica, alumina, polystyrene, aerogels, controlled-pore glass, PEGA, etc.) and numerous other solid phase supports that have played a key role in organic synthetic efforts over the past two decades. By this approach, parameters can be controlled such as permeability (degree of crosslinking), swelling characteristics, linker length and rigidity, and level of loading to assess access to the Fe(II) center of α-keto acids, oxygen, and substrates.

Scheme 4. Synthesis for Linking Aliphatic Ligand $N_2O_1$ Resin-linker Synthesis

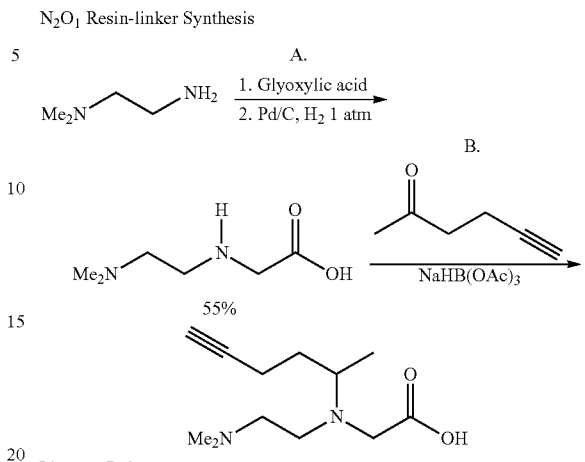

Literature References:
A. Vaid et al. Synthesis (2013), 45, 1534.
B. Tojino et al. J. Am. Chem. Soc. (2006), 128, 7712 (Just a reference for reductive amination of a homopropargylic ketone)

EPR spectra of the NO/α-KG adducts of these resin bound forms of the complexes can be compared with their homogeneous solution states to ensure that the appropriate ligand environment is preserved. Furthermore, synthetic $C_1,C_2$-$^{13}C$-labelled α-KG can be used with the NO bound form to the $Fe^{II}$ centers (generating an S=3/2 EPR spectrum with coupling from the two $^{13}C$ centers) and will verify the requisite coordination mode for activity. In addition, the resin bound form of the catalyst (in presence/absence of α-KG, presence/absence of NO) can also be characterized by Mössbauer spectroscopy and compared witht he homogenous version of the catalyst.

What is claimed is:

1. A reaction mixture comprising
an oxidation catalyst comprising a metal ion complexed with an α-keto acid and a tridentate N,N,O-ligand;
a solvent, wherein the solvent is in contact with the oxidation catalyst; and
a substrate dissolved in the solvent, wherein the solvent and the substrate are different; and wherein the solvent is a polar or polar aprotic solvent.

2. The reaction mixture of claim 1, wherein the tridentate N,N,O-ligand is of Formula (I):

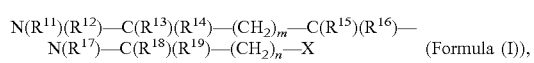

wherein:

$R^{11}$ and $R^{12}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{11}$ and $R^{12}$ together with the N they are attached to form an optionally substituted heteroaryl or an optionally substituted heterocyclyl;

$R^{13}$ and $R^{14}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{11}$ and $R^{13}$ together with the N and C they are attached to form an optionally substituted heteroaryl or an optionally substituted heterocyclyl, or $R^{12}$ and $R^{14}$ together form a double bond between the N and C, or $R^{13}$ and $R^{14}$ together with the C they are attached to form an optionally substituted cyclyl, optionally substituted heterocyclyl, optionally substituted aryl or optionally substituted heteroaryl;

$R^{15}$ and $R^{16}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{13}$ and $R^{15}$ together with the carbons they are attached to form an optionally substituted cyclyl, optionally substituted heterocyclyl, optionally substituted aryl or optionally substituted heteroaryl, or $R^{14}$ and $R^{16}$ form a double bond between the carbons they are attached to, or $R^{15}$ and $R^{16}$ together with the C they are attached to form an optionally substituted cyclyl, optionally substituted heterocyclyl, optionally substituted aryl or optionally substituted heteroaryl, or $R^{11}$ and $R^{15}$ together with the N and C they are attached to form an optionally substituted heterocyclyl or optionally substituted heteroaryl;

$R^{17}$ is H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{15}$ and $R^{17}$ together with the carbon and nitrogen they are attached to form an optionally substituted heteroaryl or an optionally substituted heterocyclyl, or $R^{16}$ and $R^{17}$ together form a double bond between the N and C, or $R^{13}$ and $R^{17}$ together with the carbon and nitrogen they are attached to form an optionally substituted heteroaryl or an optionally substituted heterocyclyl;

$R^{18}$ and $R^{19}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{17}$ and $R^{18}$ together with the N and C they are attached to form an optionally substituted heteroaryl or an optionally substituted heterocyclyl, or $R^{17}$ and $R^{19}$ together form a double bond between the N and C, or $R^{18}$ and $R^{19}$ together with the C they are attached to form an optionally substituted cyclyl, optionally substituted heterocyclyl, optionally substituted aryl or optionally substituted heteroaryl, or $R^{15}$ and $R^{18}$ together with the carbons they are attached to form an optionally substituted heterocyclyl or optionally substituted heteroaryl, or $R^{13}$ and $R^{18}$ together with the carbons they are attached to form an optionally substituted heterocyclyl or optionally substituted heteroaryl, or $R^{11}$ and $R^{18}$ together with the carbons they are attached to form an optionally substituted heterocyclyl or optionally substituted heteroaryl;

or one of $R^{11}$, $R^{12}$, $R^{13}$, $R^{14}$, $R^{15}$, $R^{16}$, $R^{17}$, $R^{18}$, $R^{19}$ is a solid support linked to Formula (I) with a linker;

X is an oxygen containing moiety;

n is 0, 1, 2, 3, or 4; and m is 0, 1, 2, 3, or 4.

3. The reaction mixture of claim 2, wherein X is $CO_2H$ or $CO_2^-$.

4. The reaction mixture of claim 1, wherein the tridentate N,N,O-ligand is $N(CH_3)_2CH_2CH_2N(CH_3)CH_2C(O)O$; or

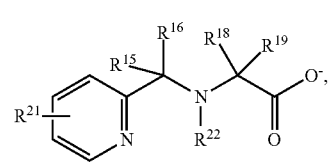

(Formula (IIa))

wherein $R^{21}$ is a solid support linked to the pyridine ring via a linker, an electron-withdrawing group, an electron donating group, absent, or $OR^{23}$ (where $R^{23}$ is an electron donating group, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or a solid support linked to O via a linker); and $R^{22}$ is H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl; $R^{15}$ and $R^{16}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{15}$ and $R^{16}$ together with the C they are attached to form an optionally substituted cyclyl, optionally substituted heterocyclyl, optionally substituted aryl or optionally substituted heteroaryl; $R^{18}$ and $R^{19}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{18}$ and $R^{19}$ together with the C they are attached to form an optinally substituted cyclyl, optionally substituted heterocyclyl, optionally substituted aryl or optionally substituted heteroaryl; or

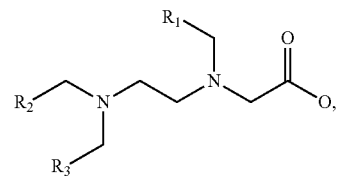

wherein $R_1$, $R_2$, and $R_3$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl.

5. The reaction mixture of claim, 1 wherein the tridentate N,N,O-ligand is linked to a solid support.

6. The reaction mixture of claim 1, wherein the α-keto acid is selected from the group consisting of α-ketoglutarate, benzoylformate, and pyruvate.

7. The reaction mixture of claim 1, wherein the reaction is selected from the group consisting of hydrocarbon hydroxylation, alkene epoxidation/alkyne oxygenation, arene epoxidation, aromatic hydroxylation, NIH shift, N-dealkylation, S-dealkylation, O-dealkylation, N-hydroxylation, N-oxidation, S-oxidation, oxidative deamination, oxidative dehalogenation, alcohol and aldehyde oxidations, dehydrogenation, dehydrations, reductive dehalogenation, N-oxide reduction, epoxide reduction, reductive β-scission of alkyl peroxides, NO reduction, isomerizations, and oxidative C—C bond cleavage.

8. A method for oxidizing a C—H bond, the method comprising:
contacting a molecule having the C—H bond with a metal complex comprising a metal ion complexed with a tridentate N,N,O-ligand in the presence of an α-keto acid and a solvent; and wherein the solvent is a polar or polar aprotic solvent.

9. The method of claim 8, wherein the tridentate N,N,O-ligand is of Formula (I):

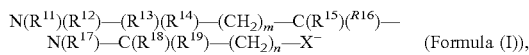

wherein:
- $R^{11}$ and $R^{12}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{11}$ and $R^{12}$ together with the N they are attached to form an optionally substituted heteroaryl or an optionally substituted heterocyclyl;
- $R^{13}$ and $R^{14}$ are independently H, optionally substituted linear or branched $C_1$-$C_{10}$ alkyl, optionally substituted linear or branched $C^2$-$C_{10}$ alkenyl, optionally substituted linear or branched $C^2$-$C_{10}$ alkynyl, optionally substituted cyclyl, optionally substituted heterocyclyl, optionally substituted aryl or optionally substituted heteroaryl, or $R^{11}$ and $R^{13}$ together with the N and C they are attached to form an optionally substituted heteroaryl or an optionally substituted heterocyclyl, or $R^{12}$ and $R^{14}$ together form a double bond between the N and C, or $R^{13}$ and $R^{14}$ together with the C they are attached to form an optionally substituted cyclyl, optionally substituted heterocyclyl, optionally substituted aryl or optionally substituted heteroaryl;
- $R^{15}$ and $R^{16}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{13}$ and $R^{15}$ together with the carbons they are attached to form an optionally substituted cyclyl, optionally substituted heterocyclyl, optionally substituted aryl or optionally substituted heteroaryl, or $R^{14}$ and $R^{16}$ form a double bond between the carbons they are attached to, or $R^{15}$ and $R^{16}$ together with the C they are attached to form an optionally substituted cyclyl, optionally substituted heterocyclyl, optionally substituted aryl or optionally substituted heteroaryl, or $R^{11}$ and $R^{15}$ together with the N and C they are attached to form an optionally substituted heterocyclyl or optionally substituted heteroaryl;
- $R^{17}$ is H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{15}$ and $R^{17}$ together with the carbon and nitrogen they are attached to form an optionally substituted heteroaryl or an optionally substituted heterocyclyl, or $R^{16}$ and $R^{17}$ together form a double bond between the N and C, or $R_{13}$ and $R^{17}$ together with the carbon and nitrogen they are attached to form an optionally substituted heteroaryl or an optionally substituted heterocyclyl;
- $R^{18}$ and $R^{19}$ are independently H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or $R^{17}$ and $R^{18}$ together with the N and C they are attached to form an optionally substituted heteroaryl or an optionally substituted heterocyclyl, or $R^{17}$ and $R^{19}$ together form a double bond between the N and C, or $R^{18}$ and $R^{19}$ together with the C they are attached to form an optionally substituted cyclyl, optionally substituted heterocyclyl, optionally substituted aryl or optionally substituted heteroaryl, or $R^{15}$ and $R^{18}$ together with the carbons they are attached to form an optionally substituted heterocyclyl or optionally substituted heteroaryl, or $R^{13}$ and $R^{18}$ together with the carbons they are attached to form an optionally substituted heterocyclyl or optionally substituted heteroaryl, or $R^{11}$ and $R^{18}$ together with the carbons they are attached to form an optionally substituted heterocyclyl or optionally substituted heteroaryl;
- or one of $R^{11}$, $R^{12}$, $R^{13}$, $R^{14}$, $R^{15}$, $R^{16}$, $R^{17}$, $R^{18}$, $R^{19}$ is a solid support linked to Formula (I) with a linker;
- X is an oxygen containing moiety;
- n is 0, 1, 2, 3, or 4; and
- m is 0, 1, 2, 3, or 4.

10. The method of claim 9, wherein X is $CO_2H$ or $CO_2^-$.

11. The method of claim 8, wherein the tridentate N,N,O-ligand is $N(CH_3)_2CH_2CH_2N(CH_3)CH_2C(O)O$; or

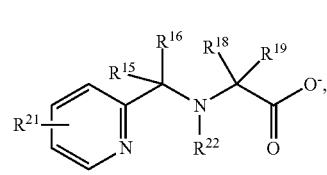

(Formula (IIa))

wherein $R^{21}$ is a solid support linked to the pyridine ring via a linker, an electron-withdrawing group, an electron donating group, absent, or $OR^{23}$ (where $R^{23}$ is an electron donating group, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl, or a slid support linked to O via a linker); and $R^{22}$ is H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl or optionally substituted heteroaryl; $R^{15}$ and $R^{16}$ are independently H, optionally substituted linear or branched C₁-C₁₀ alkyl, optionally substituted linear or branched C₂-C₁₀ alkenyl, optionally substituted linear or branched C₂-C₁₀ alkynyl, optionally substituted cyclyl, optionally substituted heterocyclyl, optionally substituted aryl or optionally substituted heteroaryl, or $R^{15}$ and $R^{16}$ together with the C they are attached to form an optionally substituted cyclyl, optionally substituted heterocyclyl, optionally substituted aryl or optionally substituted heteroaryl; $R^{18}$ and $R^{19}$ are independently H, optionally substituted linear or branched C₁-C₁₀ alkyl, optionally substituted linear or branched C₂-C₁₀ alkenyl, optionally substituted linear or branched C₂-C₁₀ alkynyl, optionally substituted cyclyl, optionally substituted heterocyclyl, optionally substituted aryl or optionally substituted heteroaryl, or $R^{18}$ and $R^{19}$ together with the C they are attached to form an optionally substituted cyclyl, optionally substituted heterocyclyl, optionally substituted aryl or optionally substituted heteroaryl; or

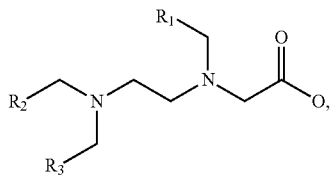

wherein $R_1$, $R_2$, and $R_3$ are independently H, optionally substituted linear or branched C₁-C₁₀ alkyl, optionally substituted linear or branched C₂-C₁₀ alkenyl, optionally substituted linear or branched C₂-C₁₀ alkynyl, optionally substituted cyclyl, optionally substituted heterocyclyl, optionally substituted aryl or optionally substituted heteroaryl.

12. The method of claim 8, wherein the tridentate N,N,O-ligand is linked to a solid support.

13. The method of claim 8, wherein the metal complex has a concentration in the range of 0.1 μM to 10 μM.

14. The method of claim 8, wherein the α-keto acid is selected from the group consisting of α-ketoglutarate, benzoylformate, and pyruvate.

15. A method of catalyzing a reaction, the method comprising contacting a substrate with a metal complex comprising a metal ion complexed with a tridentate N,N,O-ligand in the presence of an α-keto acid and a solvent; and wherein the solvent is a polar or polar aprotic solvent.

16. An oxidation catalyst of Formula III:

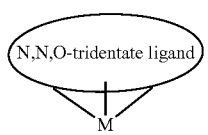

Formula III wherein:
M is a metal ion; and

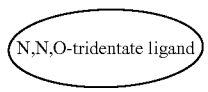

is a N,N,O-tridentate ligand, wherein the tridentate N,N,O-ligand is of Formula (I):

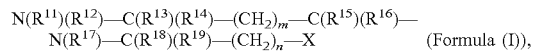

wherein:
$R^{11}$ and $R^{12}$ are independently H, unsubstituted linear or branched C₁-C₁₀ alkyl, optionally substituted linear or branched C₂-C₁₀ alkenyl, optionally substituted linear or branched C₂-C₁₀ alkynyl, optionally substituted cyclyl, optionally substituted heterocyclyl, optionally substituted aryl or optionally substituted heteroaryl, or $R^{11}$ and $R^{12}$ together with the N they are attached to form an optionally substituted heteroaryl or an optionally substituted heterocyclyl;

$R^{13}$ and $R^{14}$ are independently H, optionally substituted linear or branched C₁-C₁₀ alkyl, optionally substituted linear or branched C₂-C₁₀ alkenyl, optionally substituted linear or branched C₂-C₁₀ alkynyl, optionally substituted cyclyl, optionally substituted heterocyclyl, optionally substituted aryl or optionally substituted heteroaryl, or $R^{11}$ and $R^{13}$ together with the N and C they are attached to form an optionally substituted heteroaryl or an optionally substituted heterocyclyl, or $R^{12}$ and $R^{14}$ together form a double bond between the N and C, or $R^{13}$ and $R^{14}$ together with the C they are attached to form an optionally substituted cyclyl, optionally substituted heterocyclyl, optionally substituted aryl or optionally substituted heteroaryl;

$R^{15}$ and $R^{16}$ are independently H, optionally substituted linear or branched C₁-C₁₀ alkyl, optionally substituted linear or branched C₂-C₁₀ alkenyl, optionally substituted linear or branched C₂-C₁₀ alkynyl, optionally substituted cyclyl, optionally substituted heterocyclyl, optionally substituted aryl or optionally substituted heteroaryl, or $R^{13}$ and $R^{15}$ together with the carbons they are attached to form an optionally substituted cyclyl, optionally substituted heterocyclyl, optionally substituted aryl or optionally substituted heteroaryl, or $R^{14}$ and $R^{16}$ form a double bond between the carbons they are attached to, or $R^{15}$ and $R^{16}$ together with the C they are attached to form an optionally substituted cyclyl, optionally substituted heterocyclyl, optionally substituted aryl or optionally substituted heteroaryl, or $R^{11}$ and $R^{15}$ together with the N and C they are attached to form an optionally substituted heterocyclyl or optionally substituted heteroaryl;

$R^{17}$ is H, linear or branched C₁-C₁₀ alkyl, optionally substituted linear or branched C₂-C₁₀ alkenyl, optionally substituted linear or branched C₂-C₁₀ alkynyl, optionally substituted cyclyl, optionally substituted heterocyclyl, optionally substituted aryl or optionally substituted heteroaryl, or $R^{15}$ and $R^{17}$ together with the carbon and nitrogen they are attached to form an optionally substituted heteroaryl or an optionally substituted heterocyclyl, or $R^{16}$ and $R^{17}$ together form a double bond between the N and C, or $R^{13}$ and $R^{17}$ together with the carbon and nitrogen they are attached to form an optionally substituted heteroaryl or an optionally substituted heterocyclyl;

$R^{18}$ and $R^{19}$ are independently H, optionally substituted linear or branched C₁-C₁₀ alkyl, optionally substituted linear or branched C₂-C₁₀ alkenyl, optionally substituted linear or branched C₂-C₁₀ alkynyl, optionally substituted cyclyl, optionally substituted heterocyclyl, optionally substituted aryl or optionally substituted heteroaryl, or $R^{17}$ and $R^{18}$ together with the N and C they are attached to form an optionally substituted heteroaryl or an optionally substituted heterocyclyl, or $R^{17}$ and $R^{19}$ together form a double bond between the N and C, or $R^{18}$ and $R^{19}$ together with the C they are attached to form an optionally substituted cyclyl, optionally substituted heterocyclyl, optionally substituted aryl or optionally substituted heteroaryl, or $R^{15}$ and $R^{18}$ together with the carbons they are attached to form an optionally substituted heterocyclyl or optionally substituted heteroaryl, or $R^{13}$ and $R^{18}$ together with the carbons they are attached to form an optionally substituted heterocyclyl or optionally substituted heteroaryl, or $R^{11}$ and $R^{18}$ together with the carbons they are attached to form an optionally substituted heterocyclyl or optionally substituted heteroaryl;

or one of $R^{11}$, $R^{12}$, $R^{13}$, $R^{14}$, $R^{15}$, $R^{16}$, $R^{17}$, $R^{18}$, $R^{19}$ is a solid support linked to Formula (I) with a linker;

X is an oxygen containing moiety;

n is 0, 1, 2, 3, or 4; and m is 0, 1, 2, 3, or 4, provided that the N,N,O tridentate ligand is not $N(CH_3)_2CH_2CH_2N(CH_3)CH_2C(O)O^-$.

* * * * *